United States Patent
Gillespie et al.

(10) Patent No.: US 7,452,894 B2
(45) Date of Patent: Nov. 18, 2008

(54) PURINE DERIVATIVES AS PURINERGIC RECEPTOR ANTAGONISTS

(75) Inventors: Roger John Gillespie, Wokingham (GB); Joanne Lerpiniere, Wokingham (GB); Claire Elizabeth Dawson, Wokingham (GB); Suneel Gaur, Wokingham (GB); Robert Mark Pratt, Wokingham (GB); Gemma Caroline Stratton, Wokingham (GB); Scott Murray Weiss, Wokingham (GB)

(73) Assignee: Vernalis Research Limited, Wokinham (GB)

( * ) Notice: Subject to any disclaimer, the term of this patent is extended or adjusted under 35 U.S.C. 154(b) by 114 days.

(21) Appl. No.: 10/250,941

(22) PCT Filed: Jan. 10, 2002

(86) PCT No.: PCT/GB02/00076

§ 371 (c)(1),
(2), (4) Date: Nov. 13, 2003

(87) PCT Pub. No.: WO02/055521

PCT Pub. Date: Jul. 18, 2002

(65) Prior Publication Data

US 2004/0102459 A1 May 27, 2004

(30) Foreign Application Priority Data

Jan. 10, 2001 (GB) .................... 0100623.8

(51) Int. Cl.
- C07D 473/34 (2006.01)
- C07D 473/30 (2006.01)
- A61K 31/52 (2006.01)
- A61K 31/522 (2006.01)
- A61P 25/16 (2006.01)
- A61P 25/14 (2006.01)
- C07D 473/40 (2006.01)

(52) U.S. Cl. ............................. 514/263.22; 514/263.23; 544/265; 544/277

(58) Field of Classification Search ................ 544/264, 544/265, 277, 276; 514/263.22, 263.23, 514/263.24, 263.21, 263.2
See application file for complete search history.

(56) References Cited

U.S. PATENT DOCUMENTS

| | | |
|---|---|---|
| 6,197,788 B1 | 3/2001 | Fletcher et al. |
| 6,583,156 B1 | 6/2003 | Gillespie et al. |
| 6,608,085 B1 | 8/2003 | Gillespie et al. |
| 6,787,541 B1 | 9/2004 | Gillespie et al. |

FOREIGN PATENT DOCUMENTS

| EP | 0 992 510 A | 4/2000 |
|---|---|---|
| EP | 1 221 444 A1 | 7/2002 |
| EP | 1 300 147 A1 | 4/2003 |
| WO | WO 94/17803 A | 8/1994 |
| WO | WO 99/01454 A1 | 1/1999 |
| WO | WO 99/48903 A | 9/1999 |
| WO | WO 01/02400 A | 1/2001 |

OTHER PUBLICATIONS

Wolff, Manfred E. "Burger's Medicinal Chemistry, 5ed, Part I", John Wiley & Sons, 1995, pp. 975-977.*
Banker, G. S. et al, "Modern Pharmaceutics, 3ed.", Marcel Dekker, New York, 1996, pp. 451 and 596.*
Kulisevsky, Jaime; Barbanoj, Manel; Gironell, Alexandre; Antonijoan, Rosa; Casas, Miquel; Pascual-Sedano, Berta, Clinical Neuropharmacology. 25(1):25-31, Jan./Feb. 2002, abstract only.*

(Continued)

Primary Examiner—Mark L Berch
(74) Attorney, Agent, or Firm—Foley & Lardner LLP

(57) ABSTRACT

Use of a compound of formula (I) wherein $R_1$ is selected from alkyl, aryl, alkoxy, aryloxy, 0thioalkyl, thioaryl, CN, halo, $NR_5R_6$, $NR_4COR_5$, $NR_4CONR_5R_6$, $NR_4CO_2R_7$ and $NR_4SO_2R_7$; $R_2$ is selected from N, O or S-containing heteroaryl groups, wherein the heteroaryl group is attached via an unsaturated carbon atom which is adjacent to one or two N, O or S-heteroatom(s), other than ortho, ortho-disubstituted heteroaryl groups; $R_3$ is selected from H, alkyl, $COR_8$, $CONR_9R_{10}$, $CONR_8NR_9R_{10}$, $CO_2R_{11}$ and $SO_2R_{11}$; $R_4$, $R_5$ and $R_6$ are independently selected from H, alkyl and aryl or where $R_5$ and $R_6$ are in an ($NR_5R_6$) group then $R_5$ and $R_6$ may be linked to form a heterocyclic ring; $R_7$ is selected from alkyl and aryl; $R_8$, $R_9$ and $R_{10}$ are independently selected from H, alkyl and aryl, or $R_9$ and $R_{10}$ may be linked to form a heterocyclic ring, or where $R_8$, $R_9$ and $R_{10}$ are in a ($CONR_8NR_9R_{10}$) group, $R_8$ and $R_9$ may be linked to form a heterocyclic group; and $R_{11}$, is selected from alkyl and aryl, or a pharmaceutically acceptable salt thereof or prodrug thereof, in the treatment or prevention of a disorder in which the blocking of purine receptors, particularly adenosine receptors and more particularly $A_{2A}$ receptors, may be beneficial, particularly wherein said disorder is a movement disorder such as Parkinson's disease or said disorder is depression, cognitive or memory impairment, acute or chronic pain, ADHD or narcolepsy, or for neuroprotection in a subject; compounds of formula (I) for use in therapy; and novel compounds of formula (I) per se.

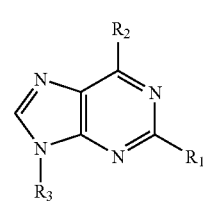

(I)

31 Claims, No Drawings

OTHER PUBLICATIONS

Morelli, Micaela, Experimental Neurology, 184, 20-23, 2003.*
Tuite, Paul et al, Expert. Opin. Investig. Drugs, 12, 1335-1352, 2003.*
Bibbiani, F. et al, Experimental Neurology, 184, 285-294, 2003.*
Spiros Konitsiotis, Expert. Opin. Investig. Drugs, 14, 377-392 2005.*
Anonymous, Drug and Therapeutic Bulletin, 35, pp. 36-40, 1999.*
LeWitt, Peter A., Pharmacotherapy, 20, pp. 26S-32S, 2000.*
Weiss, S. M.; Benwell, K.; Cliffe, I. A.; Gillespie, R. J.; Knight, A. R.; Lerpiniere, J.; Misra, A.; Pratt, R. M.; Revell, D.; Upton, R.; Dourish, C. T., Neurology, 61(11, Suppl. 6), S101-S106 (English) 2003.*
Hirao, Ichiro; Mitsui, Tsuneo; Kimoto, Michiko; Harada, Yoko; Yokoyama, Shigeyuki, Nucleic Acids Research Supplement, 3(3rd Iternational Symposium on Nucleic Acids Chemistry [and] 30th Symposium on Nucleic Acids Chemistry in Japan, 2003), 215-216.*
Akira Matsuda, "Invitation", Hokkaido University, Sapporo Japan, [online] Nov. 18, 2004, [retrieved on Jul. 21, 2005]. Retrieved from the Internet, <http://www.hokudai.ac.jp/pharma/yakka/inacs.html>.*
Loscher W.,.Epilepsy Res. Jun. 2002;50(1-2):105-23.*
Jennifer L. Hellier, Peter R. Patrylo, Ping Dou, Michelle Nett, Gregory M. Rose, and F. Edward Dudek, J. Neurosci. 1999, 19(22):10053-10064.*
Wenning GK, Granata R, Puschban Z, Scherfler C, Poewe W., J Neural Transm Suppl. 1999;55:103-13, Medline abstract PMID: 10335497.*
Rebecca J. Carter et al ,The Journal of Neuroscience, Apr. 15, 1999, 19(8):3248-3257.*
Yanamoto H, Nagata I, Niitsu Y, Xue JH, Zhang Z, Kikuchi H., Evaluation of MCAO stroke models in normotensive rats: standardized neocortical infarction by the 3VO technique, Exp Neurol. Aug. 2003;182(2):261-74.*
Osborne NN, Chidlow G, Layton CJ, Wood JP, Casson RJ, Melena J., Optic nerve and neuroprotection strategies.Eye. Nov. 2004;18(11):1075-84.*
Jenner, Peter, Expert Opin. Investig. Drugs, 14(6), 2005, pp. 729-738.*
McKenzie, Thomas C. and Epstein, Joseph W., J. Org. Chem., 47, 1982, 4881-4884.*
Alarcon et al., "Diaminoupurine-acridine Heterodimers for Specific Recognition of Abasic Site Containing DNA. Influence on the Biological Activity of the Position of the Linker on the Purine Ring," Bioorg. Med. Chem. Lett. (2001), vol. 11, pp. 1855-1858, XP002192660.
Alarcon et al., "2-Amino-6-(1,2,4-triazol-4-yl)-purine: a useful intermediate in the synthesis of 9-alkylguanines," Tetrahedron Letters (2000), vol. 41, pp. 7211-7215, XP002192661.
Gunderson, "6-Chlorpuines and Organostannanes in Palladium Catalyzed Cross Coupling Reactions," Tetrahedron Letters (1994), vol. 35, No. 19, pp. 3155-3158, XP001061830.
Skalski et al., "Photophysical properties of pyridinlum salts derived from purine bases," Can J. Chem. (1990), vol. 68, No. 12, pp. 2164-2170, XP001061835.
Jaskolski et al., "Structure of N-(2-Amino-6-purinyl) pyridinium Chloride Dihydrate," Acta Cyrstallogr., Sect. C: Cryst. Struct. Commun. (1987), vol. C43, No. 11, pp. 2110-2113, XP001058066.
Strappaghetti et al., "Adenosince receptors: synthesis, structure-activity relationships and biological activity of new 6-amino purine derivatives," Eur. J. Med. Chem. (1998), vol. 33, pp. 501-508, XP002192662.
Cesnek, et al., Collect. Czech. Chem. Commun., (2000), pp. 1357-1373, 65(9).
Bakkestuen, et al., Bioorg. Med. Chem. Lett. (2000), pp. 1207-1210, 10(11).
Hocek, et al., Collect. Czech. Chem. Commun. (1997), pp. 136-146 61(1).
Langll, et al., Tetrahedron, (1996), pp. 5625-5638, 52(15).
McKenzie, et al., J. Org. Chem. (1982), pp. 4881-4884, 47(25).
Nair, et al., J. Org. Chem. (1982), pp. 4520-4524, 47(23).
Muresan, et al., Theochem (1995), pp. 161-171, 342.
Nair, et al., J. Org. Chem. (1984), pp. 4340-4344, 49(23).
Havelkova, et al., Synlett, (1999), pp. 1145-1147, (7).
Nolsoe, et al., Acta Chem. Scand. (1999), pp. 366-372, 53(5).
Gundersen, Acta Chem. Scand, (1996), pp. 462-465, 50(5).
Estep, et al., J. Med. Chem., (1995), pp. 2582-2595, 38(14).
Gundersen, et al., Tetrahedron Lett., (1995), pp. 1945-1948, 36(11).
Gundersen, et al., Tetrahedron, (1994), pp. 9743-9756, 50(32).
Nair, et al., Magn. Reson. Chem., (1987), pp. 937-940, 25(11),.
Robev, et al., Dokl. Bolg. Akad. Nauk, (1978), pp. 1131-1134, 31(9).
Prasad, et al., Tetrahedron, (1997), pp. 7237-7254, 53(21).
Stevenson, et al., Tetrahedron Lett., (1996), pp. 8375-8378, 37(46).
Hamamichi, et al., Heterocycles, (1990), pp. 321-326, 31(2).
Hamamichi, et al., J. Heterocycl. Chem., (1990), pp. 835-838, 27(4).
Pendergast, et al., J. Chem. Soc. Perkin Trans. 1, (1973), pp. 2759-2763, (22).
Kim, et al., Arch. Pharmacal Res., (1998), pp. 458-464, 21(4).
(Abstract only) Bailey et al., "Changes in spinal δ- and κ-opioid systems in mice deficient in the A2A receptor gene", Journal of Neuroscience, vol. 22, No. 21, 2002 (pp. 9210-9220).
(Abstract only) Bara-Jimenez et al., "Adenosine A2A receptor antagonist treatment of Parkinson's disease", Neurology, vol. 61, No. 3, 2003 (pp. 293-296).
Bastia et al., "Effects of $A_1$ and $A_{2A}$ adenosine receptor ligands in mouse acute models of pain", Neuroscience Letters 328, 2002 (pp. 241-244).
Behan et al., "Enhanced neuronal damage by co-administration of quinolinic acid and free radicals, and protection by adenosine $A_{2A}$ receptor antagonists", British Hournal of Pharmacology, vol. 135, 2002 (pp. 1435-1442).
Bertorelli et al., "Effects of Selective Agonists and Antagonists for $A_1$ or $A_{2A}$ Adenosine Receptors on Sleep-Waking Patterns in Rats", Drug Development Research, vol. 37, 1996 (pp. 65-72).
(Abstract only) Chase et al., "Translating $A_{2A}$ antagonist KW6002 from animal models to parkinsonian patients", Neurology , vol. 61, (11, Suppl. 6), (pp. S107-S111).
Dall'lgna et al., "Neuroprotection by caffeine and adenosine $A_{2A}$ receptor blockade of β-amyloid neurotoxicity", British Journal of Pharmacology, vol. 138, 2003 (pp. 1207-1209).
Fredholm, et al., "Actions of Caffeine in the Brain with Special References to Factors That Contribute to Its widespread Use", Pharmacological Reviews, vol. 51, No. 1, 1999 (pp. 83-133).
Garfinkel, et al., "Responses to Methylphenidate and Varied Doses of Caffeine in Children with Attention Deficit Disorder", Can. J. Psychiatry, vol. 26, No. 6, Oct. 1981 (pp. 395-401).
González-Benitez et al., "Regulation of glycogen metabolism in hepatocytes through adenosine receptors. Role of $Ca^{2+}$and cAMP", European Journal of Pharmacology, vol. 437, 2002 (pp. 105-111).
(Abstract only) Hauser et al., "Randomized trial of the adenosine A2A receptor antagonist istradefylline in advanced PD", Neurology, vol. 61, No. 3, 2003 (pp. 297-303).
Hess, "Recent advances in adenosine receptor antagonist research", Review, Monthly Focus: Central and Peripheral Nervous Systems, 2001 (pp. 1533-1561).
Ikeda et al., "Neuroprotection by adenosine $A_{2A}$ receptor blockade in experimental models of Parkinson's disease", Journal of Neurochemistry, vol. 80, No. 2, Jan. 2002 (pp. 262-270).
(Abstract only) Kase, "New aspects of physiological and pathophysiological functions of adenosine A2A receptor in basal ganglia", Biochemistry, vol. 65, No. 7, 2001 (pp. 1447-1457).
Kopf et al., "Adenosine and memory storage: effect of $A_1$ and $A_2$ receptor antagonists", Psychopharmacology, vol. 146, No. 2, Sep. 11, 1999 (pp. 214-219).
(Abstract only) Ledent et al., "Aggressiveness, hypoalgesia and high blood pressure in mice lacking the adenosine A2a receptor", Nature, vol. 388(6643), Aug. 14, 1997 (pp. 674-678).
Li et al., "Differing Roles of Adenosine Receptor Subtypes in Retinal Ischemia-Reperfusion Injury in the Rat", Exp. Eye Res. , vol. 68, 1999 (pp. 9-17).
Mally et al., "Potential of Adenosine $A_{2A}$ Receptor Antagonists in the Treatment of Movement Disorders", CNS Drugs, vol. 10, No. 5, Nov. 1998 (pp. 311-320).
Monopoli et al., "Blockade of adenosine $A_{2A}$ receptors by SCH 58261 results in neuroprotective effects in cerebral ischaemia in rats", Neuropharmacology, vol. 9, No. 17, Dec. 1, 1998 (pp. 3955-3959).

Monopoli et al., "Cardiovascular Pharamacology of the $A_{2A}$ Adenosine Receptor Antagonist, SCH 58261, in the Rat", *The Journal of Pharmacology and Experimental Therapeutics*, vol. 285, No. 1, 1998 (pp. 9-15).

Ongini et al., "Dual Actions of $A_{2A}$ Adenosine Receptor Antagonists on Motor Dysfunction and Neurodegenerative Processes", *Drug Development Research*, vol. 52, No. ½, 2001 (pp. 379-386).

Popoli et al., "Blockade of Striatal Adenosine $A_{2A}$ Receptor Reduces, through a Presynaptic Mechanism, Quinolinic Acid-Induced Excitotoxicity: Possible Relevance to Neuroprotective Interventions in Neurodegenerative Diseases of the Striatum", *The Journal of Neuroscience*, vol. 22, No. 5, Mar. 1, 2002 (pp. 1967-1975).

Satoh et al., "Involvement of adenosine $A_{2A}$ receptor in sleep promotion", *European Journal of Pharmacology*, vol. 351, 1998 (pp. 155-162).

Scammell et al., "An Adenosine A2a Agonist Increases Sleep and Induces FOS in Ventrolateral Preoptic Neurons", *Neuroscience*, vol. 107 No. 4, 2001 (pp. 653-663).

Schechter, M.D. et al., "Objectively Measured Hyperactivity—II. Caffeine and Amphetamine Effects", *J. Clin. Pharmacol.*, vol. 25, 1985 (pp. 276-280).

Stone et al., "Neuroprotection by $A_{2A}$ Receptor Antagonists", *Drug Development Research*, vol. 52 No. ½, 2001 (pp. 323-330).

Svenningsson, P. et al., "Distribution, Biochemistry and Function of Striatal Adenosine $A_{2A}$ Receptors", *Progress in Neurobiology*, vol. 59, 1999 (pp. 355-396).

(Abstract only) Urade et al., "Sleep regulation in adenosine $A_{2A}$ receptor-deficient mice", *Neurology*, vol. 61(11, Suppl. 6), 2003 (pp. S94-S96).

(Abstract only) Varani et al., "Aberrant $A_{2A}$ receptor function in peripheral blood cells in Huntington's disease", *FASEB Journal*, vol. 17, No. 14, 2003 (pp. 2148-2150).

Varani et al., "Adenosine $A_{2A}$ Antagonists and Huntington's disease", *Colloque Scientifique sur le Café*, 2001 19th (pp. 51-58).

El Yacoubi et al., "Adenosine $A_{2A}$ receptor antagonists are potential antidepressants: evidence based on pharmacology and $A_{2A}$ receptor knockout mice", *British Journal of Pharmacology*, vol. 134, No. 1, 2001 (pp. 68-77).

* cited by examiner

PURINE DERIVATIVES AS PURINERGIC RECEPTOR ANTAGONISTS

The present invention relates to purine derivatives and their use in therapy. In particular, the present invention relates to the treatment of disorders in which the reduction of purinergic neurotransmission could be beneficial. The invention relates in particular to blockade of adenosine receptors and particularly adenosine $A_{2A}$ receptors, and to the treatment of movement disorders such as Parkinson's disease.

Movement disorders constitute a serious health problem, especially amongst the elderly sector of the population. These movement disorders are often the result of brain lesions. Disorders involving the basal ganglia which result in movement disorders include Parkinson's disease, Huntington's chorea and Wilson's disease. Furthermore, dyskinesias often arise as sequelae of cerebral ischaemia and other neurological disorders.

There are four classic symptoms of Parkinson's disease: tremor, rigidity, akinesia and postural changes. The disease is also commonly associated with depression, dementia and overall cognitive decline. Parkinson's disease has a prevalence of 1 per 1,000 of the total population. The incidence increases to 1 per 100 for those aged over 60 years. Degeneration of dopaminergic neurones in the substantia nigra and the subsequent reductions in interstitial concentrations of dopamine in the striatum are critical to the development of Parkinson's disease. Some 80% of cells from the substantia nigra need to be destroyed before the clinical symptoms of Parkinson's disease are manifested.

Current strategies for the treatment of Parkinson's disease are based on transmitter replacement therapy (L-dihydroxyphenylacetic acid (L-DOPA)), inhibition of monoamine oxidase (e.g. Deprenyl®), dopamine receptor agonists (e.g. bromocriptine and apomorphine) and anticholinergics (e.g. benztrophine, orphenadrine). Transmitter replacement therapy in particular does not provide consistent clinical benefit, especially after prolonged treatment when "on-off" symptoms develop, and this treatment has also been associated with involuntary movements of athetosis and chorea, nausea and vomiting. Additionally current therapies do not treat the underlying neurodegenerative disorder resulting in a continuing cognitive decline in patients. Despite new drug approvals, there is still a medical need in terms of improved therapies for movement disorders, especially Parkinson's disease. In particular, effective treatments requiring less frequent dosing, effective treatments which are associated with less severe side-effects, and effective treatments which control or reverse the underlying neurodegenerative disorder, are required.

Blockade of $A_2$ adenosine receptors has recently been implicated in the treatment of movement disorders such as Parkinson's disease (Richardson, P. J. et al., *Trends Pharmacol. Sci.* 1997, 18, 338-344) and in the treatment of cerebral ischaemia (Gao, Y. and Phillis, J. W., *Life Sci.* 1994, 55, 61-65). The potential utility of adenosine $A_{2A}$ receptor antagonists in the treatment of movement disorders such as Parkinson's Disease has recently been reviewed (Mally, J. and Stone, T. W., *CNS Drugs*, 1998, 10, 311-320).

Adenosine is a naturally occurring purine nucleoside which has a wide variety of well-documented regulatory functions and physiological effects. The central nervous system (CNS) effects of this endogenous nucleoside have attracted particular attention in drug discovery, owing to the therapeutic potential of purinergic agents in CNS disorders (Jacobson, K. A. et al., *J. Med. Chem.* 1992, 35, 407-422). This therapeutic potential has resulted in considerable recent research endeavour within the field of adenosine receptor agonists and antagonists (Bhagwhat, S. S.; Williams, M. *Exp. Opin. Ther. Patents* 1995, 5,547-558).

Adenosine receptors represent a subclass ($P_1$) of the group of purine nucleotide and nucleoside receptors known as purinoreceptors. The main pharmacologically distinct adenosine receptor subtypes are known as $A_1$, $A_{2A}$, $A_{2B}$ (of high and low affinity) and $A_3$ (Fredholm, B. B., et al., *Pharmacol. Rev.* 1994, 46, 143-156). The adenosine receptors are present in the CNS (Fredholm, B. B., *News Physiol. Sci.*, 1995, 10, 122-128).

The design of $P_1$ receptor-mediated agents has been reviewed (Jacobson, K. A., Suzuki, F., *Drug Dev. Res.*, 1997, 39, 289-300; Baraldi, P. G. et al., *Curr. Med Chem.* 1995, 2, 707-722), and such compounds are claimed to be useful in the treatment of cerebral ischemia or neurodegenerative disorders, such as Parkinson's disease (Williams, M. and Burnstock, G. *Purinergic Approaches Exp. Ther.* (1997), 3-26. Editor: Jacobson, Kenneth A.; Jarvis, Michael F. Publisher: Wiley-Liss, New York, N.Y.)

It has been speculated that xanthine derivatives such as caffeine may offer a form of treatment for attention-deficit hyperactivity disorder (ADHD). A number of studies have demonstrated a beneficial effect of caffeine on controlling the symptoms of ADHD (Garfinkel, B. D. et al., *Psychiatry*, 1981, 26, 395-401). Antagonism of adenosine receptors is thought to account for the majority of the behavioural effects of caffeine in humans and thus blockade of adenosine $A_{2A}$ receptors may account for the observed effects of caffeine in ADHD patients. Therefore a selective $A_{2A}$ receptor antagonist may provide an effective treatment for ADHD but without the unwanted side-effects associated with current therapy.

Adenosine receptors have been recognised to play an important role in regulation of sleep patterns, and indeed adenosine antagonists such as caffeine exert potent stimulant effects and can be used to prolong wakefulness (Porkka-Heiskanen, T. et al., *Science*, 1997, 276, 1265-1268). Recent evidence suggests that a substantial part of the actions of adenosine in regulating sleep is mediated through the adenosine $A_{2A}$ receptor (Satoh, S., et al., *Proc. Natl. Acad. Sci.*, USA, 1996). Thus, a selective $A_{2A}$ receptor antagonist may be of benefit in counteracting excessive sleepiness in sleep disorders such as hypersomnia or narcolepsy.

It has recently been observed that patients with major depression demonstrate a blunted response to adenosine agonist-induced stimulation in platelets, suggesting that a dysregulation of $A_{2A}$ receptor function may occur during depression (Berk, M. et al, 2001, *Eur. Neuropsychopharmacol.* 11, 183-186). Experimental evidence in animal models has shown that blockade of $A_{2A}$ receptor function confers antidepressant activity (ElYacoubi, M et al. *Br. J. Pharmacol.* 2001, 134, 68-77). Thus, $A_{2A}$ receptor antagonists may offer a novel therapy for the treatment of major depression and other affective disorders in patients.

The pharmacology of adenosine $A_{2A}$ receptors has been reviewed (Ongini, E.; Fredholm, B. B. *Trends Pharmacol. Sci.* 1996, 17(10), 364-372). One potential underlying mechanism in the aforementioned treatment of movement disorders by the blockade of $A_2$ adenosine receptors is the evidence of a functional link between adenosine $A_{2A}$ receptors to dopamine $D_2$ receptors in the CNS. Some of the early studies (e.g. Ferre, S. et al., Stimulation of high-affinity adenosine $A_2$ receptors decreases the affinity of dopamine $D_2$ receptors in rat striatal membranes. *Proc. Natl. Acad. Sci. U.S.A.* 1991, 88, 7238-41) have been summarised in two more recent articles (Fuxe, K. et al., *Adenosine Adenine Nucleotides Mol. Biol. Integr. Physiol.*, [Proc. Int. Symp.], 5th (1995), 499-507. Editors: Belardinelli, Luiz; Pelleg, Amir. Publisher: Kluwer, Boston, Mass.; Ferre, S. et al., *Trends Neurosci.* 1997, 20, 482-487).

As a result of these investigations into the functional role of adenosine $A_{2A}$ receptors in the CNS, especially in vivo studies linking $A_2$ receptors with catalepsy (Ferre et al., *Neurosci. Lett.* 1991, 130, 162-4; Mandhane, S. N. et al., *Eur. J. Pharmacol.* 1997, 328, 135-141) investigations have been made into agents which selectively bind to adenosine $A_{2A}$ receptors as potentially effective treatments for Parkinson's disease.

While many of the potential drugs for treatment of Parkinson's disease have shown benefit in the treatment of movement disorders, an advantage of adenosine $A_{2A}$ antagonist therapy is that the underlying neurodegenerative disorder may also be treated. The neuroprotective effect of adenosine $A_{2A}$ antagonists has been reviewed (Ongini, E.; Adami, M.; Ferri, C.; Bertorelli, R., *Ann. N. Y. Acad. Sci.* 1997, 825 (Neuroprotective Agents), 30-48). In particular, compelling recent evidence suggests that blockade of $A_{2A}$ receptor function confers neuroprotection against MPTP-induced neurotoxicity in mice (Chen, J-F., *J. Neurosci.* 2001, 21, RC143). In addition, several recent studies have shown that consumption of dietary caffeine, a known adenosine $A_{2A}$ receptor antagonist, is associated with a reduced risk of Parkinson's disease in man (Ascherio, A. et al, *Ann Neurol.,* 2001, 50, 56-63; Ross G W, et al., *JAMA,* 2000, 283, 2674-9). Thus, $A_{2A}$ receptor antagonists may offer a novel treatment for conferring neuroprotection in neurodegenerative diseases such as Parkinson's disease.

Xanthine derivatives have been disclosed as adenosine $A_2$ receptor antagonists as useful for treating various diseases caused by hyperfunctioning of adenosine $A_2$ receptors, such as Parkinson's disease (see, for example, EP-A-565377).

One prominent xanthine-derived adenosine $A_{2A}$ selective antagonist is CSC [8-(3-chlorostyryl)caffeine] (Jacobson et al., *FEBS Lett.,* 1993, 323, 141-144).

Theophylline (1,3-dimethylxanthine), a bronchodilator drug which is a mixed antagonist at adenosine $A_1$ and $A_{2A}$ receptors, has been studied clinically. To determine whether a formulation of this adenosine receptor antagonist would be of value in Parkinson's disease an open trial was conducted on 15 Parkinsonian patients, treated for up to 12 weeks with a slow release oral theophylline preparation (150 mg/day), yielding serum theophylline levels of 4.44 mg/L after one week. The patients exhibited significant improvements in mean objective disability scores and 11 reported moderate or marked subjective improvement (Mally, J., Stone, T. W. *J. Pharm. Pharmacol.* 1994, 46, 515-517).

KF 17837 [(E)-8-(3,4-dimethoxystyryl)-1,3-dipropyl-7-methylxanthine] is a selective adenosine $A_{2A}$ receptor antagonist which on oral administration significantly ameliorated the cataleptic responses induced by intracerebroventricular administration of an adenosine $A_{2A}$ receptor agonist, CGS 21680. KF 17837 also reduced the catalepsy induced by haloperidol and reserpine. Moreover, KF 17837 potentiated the anticataleptic effects of a subthreshold dose of L-DOPA plus benserazide, suggesting that KF 17837 is a centrally active adenosine $A_{2A}$ receptor antagonist and that the dopaminergic function of the nigrostriatal pathway is potentiated by adenosine $A_{2A}$ receptor antagonists (Kanda, T. et al., *Eur. J. Pharmacol.* 1994, 256, 263-268). The structure activity relationship (SAR) of KF 17837 has been published (Shimada, J. et al., *Bioorg. Med. Chem. Lett.* 1997, 7, 2349-2352). Recent data has also been provided on the $A_{2A}$ receptor antagonist KW-6002 (Kuwana, Y et al., *Soc. Neurosci. Abstr.* 1997, 23, 119.14; and Kanda, T. et al., *Ann. Neurol.* 1998, 43(4), 507-513).

New non-xanthine structures sharing these pharmacological properties include SCH 58261 and its derivatives (Baraldi, P. G. et al., Pyrazolo[4,3-e]-1,2,4-triazolo[1,5-c]pyrimidine Derivatives: Potent and Selective $A_{2A}$ Adenosine Antagonists. *J. Med. Chem.* 1996, 39, 1164-71). SCH 58261 (7-(2-phenylethyl)-5-amino-2-(2-furyl)-pyrazolo-[4,3-e]-1,2,4-triazolo[1,5-c]pyrimidine) is reported as effective in the treatment of movement disorders (Ongini, E. *Drug Dev. Res.* 1997, 42(2), 63-70) and has been followed up by a later series of compounds (Baraldi, P. G. et al., *J. Med Chem.* 1998, 41(12), 2126-2133).

The foregoing discussion indicates that a potentially effective treatment for movement disorders in humans would comprise agents which act as antagonists at adenosine $A_{2A}$ receptors.

It has now been found that purine derivatives, which are structurally unrelated to known adenosine receptor antagonists, exhibit unexpected antagonist binding affinity at adenosine ($P_1$) receptors, and in particular at the adenosine $A_{2A}$ receptor. Such compounds may therefore be useful for the treatment of disorders in which the blocking of purine receptors, particularly adenosine receptors and more particularly adenosine $A_{2A}$ receptors, may be beneficial. In particular such compounds may be suitable for the treatment of movement disorders, such as disorders of the basal ganglia which result in dyskinesias. Disorders of particular interest in the present invention include Parkinson's disease, Alzheimer's disease, spasticity, Huntington's chorea and Wilson's disease.

Such compounds may also be particularly suitable for the treatment of depression, cognitive or memory impairment including Alzheimer's disease, acute or chronic pain, ADHD, narcolepsy or for neuroprotection.

According to the present invention there is provided the use of a compound of formula (I):

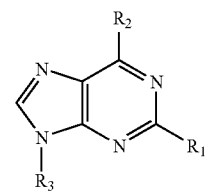

wherein $R_1$ is selected from alkyl, aryl, alkoxy, aryloxy, thioalkyl, thioaryl, CN, halo, $NR_5R_6$, $NR_4COR_5$, $NR_4CONR_5R_6$, $NR_4CO_2R_7$ and $NR_4SO_2R_7$;

$R_2$ is selected from N, O or S-containing heteroaryl groups, wherein the heteroaryl group is attached via an unsaturated carbon atom which is adjacent to one or two N, O or S-heteroatom(s), other than ortho,ortho-disubstituted heteroaryl groups;

$R_3$ is selected from H, alkyl, $COR_8$, $CONR_9R_{10}$, $CONR_8NR_9R_{10}$, $CO_2R_{11}$ and $SO_2R_{11}$;

$R_4$, $R_5$ and $R_6$ are independently selected from H, alkyl and aryl or where $R_5$ and $R_6$ are in an ($NR_5R_6$) group then $R_5$ and $R_6$ may be linked to form a heterocyclic group;

$R_7$ is selected from alkyl and aryl;

$R_8$, $R_9$ and $R_{10}$ are independently selected from H, alkyl and aryl, or $R_9$ and $R_{10}$ may be linked to form a heterocyclic group, or where $R_8$, $R_9$ and $R_{10}$ are in a ($CONR_8NR_9R_{10}$) group, $R_8$ and $R_9$ may be linked to form a heterocyclic group, and $R_{11}$ is selected from alkyl and aryl, or a pharmaceutically acceptable salt thereof or prodrug thereof, in the manufacture of a medicament for the treatment or prevention of a disorder in which the blocking of purine receptors, particularly adenosine receptors and more particularly $A_{2A}$ receptors, may be beneficial.

As used herein, the term "alkyl" means a branched or unbranched, cyclic or acyclic, saturated or unsaturated (i.e., alkenyl or alkynyl) hydrocarbyl radical which may be substituted or unsubstituted. Where cyclic, the alkyl group is preferably $C_3$ to $C_{12}$, more preferably $C_5$ to $C_{10}$, more preferably $C_5$, $C_6$ or $C_7$. Where acyclic, the alkyl group is preferably $C_1$ to $C_{10}$, more preferably $C_1$ to $C_6$, more preferably methyl, ethyl, propyl (n-propyl or isopropyl), butyl (n-butyl, isobutyl or tertiary-butyl) or pentyl (including n-pentyl and iso-pentyl), more preferably methyl. It will be appreciated therefore that the term "alkyl" as used herein includes alkyl (branched or unbranched), alkenyl (branched or unbranched), alkynyl (branched or unbranched), cycloalkyl, cycloalkenyl and cycloalkynyl.

As used herein, the term "lower alkyl" means methyl, ethyl, propyl (n-propyl or isopropyl) or butyl (n-butyl, isobutyl or tertiary-butyl).

As used herein, the term "aryl" means an aromatic group, such as phenyl or naphthyl (preferably phenyl), or a heteroaromatic group containing one or more heteroatom(s) preferably selected from N, O and S, such as pyridyl, pyrrolyl, quinolinyl, furanyl, thienyl, oxadiazolyl, thiadiazolyl, thiazolyl, oxazolyl, isoxazolyl, pyrazolyl, triazolyl, imidazolyl, pyrimidinyl, indolyl, pyrazinyl or indazolyl.

As used herein, the term "heteroaryl" means an aromatic group containing one or more heteroatom(s) preferably selected from N, O and S, such as pyridyl, pyrrolyl, quinolinyl, furanyl, thienyl, oxadiazolyl, thiadiazolyl, thiazolyl, oxazolyl, isoxazolyl, pyrazolyl, triazolyl, imidazolyl, pyrimidinyl, indolyl, pyrazinyl or indazolyl.

As used herein, the term "non-aromatic heterocyclyl" means a non-aromatic cyclic group containing one or more heteroatom(s) preferably selected from N, O and S, such as a cyclic amino group (including aziridinyl, azetidinyl, pyrrolidinyl, piperidyl, piperazinyl, morpholinyl) or a cyclic ether (including tetrahydrofuranyl).

As used herein, the term "alkoxy" means alkyl-O—. As used herein, the term "aryloxy" means aryl-O—.

As used herein, the term "halogen" means a fluorine, chlorine, bromine or iodine radical.

As used herein, the term "ortho,ortho-disubstituted heteroaryl groups" refers to heteroaryl groups which are substituted in both ortho positions of the heteroaryl group relative to the point of attachment of the heteroaryl group to the purine ring.

As used herein, the term "prodrug" means any pharmaceutically acceptable prodrug of a compound of the present invention.

Where any of $R_1$ to $R_{20}$ is selected from alkyl, alkoxy and thioalkyl, in accordance with formula (I) as defined above, then that alkyl group, or the alkyl group of the alkoxy or thioalkyl group, may be substituted or unsubstituted. Where any of $R_1$ to $R_{20}$ are selected from aryl, aryloxy and thioaryl, in accordance with formula (I) as defined above, then said aryl group, or the aryl group of the aryloxy or thioaryl group, may be substituted or unsubstituted. Where $R_5$ and $R_6$, or $R_9$ and $R_{10}$, or $R_8$ and $R_9$, or $R_{14}$ and $R_{15}$, are linked to form a heterocyclic group in accordance with formula (I) as defined above, then said heterocyclic ring may be substituted or unsubstituted. Where substituted, there will generally be 1 to 3 substituents present, preferably 1 substituent. Substituents are selected from the group consisting of:

carbon-containing groups selected from the group consisting of
  alkyl,
  aryl, (e.g. substituted and unsubstituted phenyl, including (alkyl)phenyl, (alkoxy)phenyl and halophenyl),
  arylalkyl; (e.g. substituted and unsubstituted benzyl, including alkylbenzyl);
halogen atoms and halogen containing groups selected from the group consisting of
  haloalkyl (e.g. trifluoromethyl),
  haloaryl (e.g. chlorophenyl);
oxygen containing groups selected from the group consisting of
  alcohols (e.g. hydroxy, hydroxyalkyl, hydroxyaryl, (aryl)(hydroxy)alkyl),
  ethers (e.g. alkoxy, aryloxy, alkoxyalkyl, aryloxyalkyl, alkoxyaryl, aryloxyaryl),
  aldehydes (e.g. carboxaldehyde),
  ketones (e.g. alkylcarbonyl, arylcarbonyl, alkylcarbonylalkyl, alkylcarbonylaryl, arylcarbonylalkyl, arylcarbonylaryl, arylalkylcarbonyl, arylalkylcarbonylalkyl, arylalkylcarbonylaryl)
  acids (e.g. carboxy, carboxyalkyl, carboxyaryl),
  acid derivatives selected from the group consisting of
    esters
    (e.g. alkoxycarbonyl, aryloxycarbonyl, alkoxycarbonylalkyl, aryloxycarbonylalkyl, alkoxycarbonylaryl, aryloxycarbonylaryl, alkylcarbonyloxy, alkylcarbonyloxyalkyl),
    amides
    (e.g. aminocarbonyl, mono- or di-alkylaminocarbonyl, cyclicaminocarbonyl, aminocarbonylalkyl, mono- or di-alkylaminocarbonylalkyl, arylaminocarbonyl or arylalkylaminocarbonyl, alkylcarbonylamino, arylcarbonylamino, arylalkylcarbonylamino, alkylcarbonylaminoalkyl, arylcarbonylaminoalkyl or arylalkylcarbonylaminoalkyl),
    carbamates
    (eg. alkoxycarbonylamino, aryloxycarbonylamino, arylalkyloxycarbonylamino, aminocarbonyloxy, mono- or di-alkylaminocarbonyloxy, arylaminocarbonyloxy or arylalkylaminocarbonyloxy)
    and ureas
    (eg. mono- or di-alkylaminocarbonylamino, arylaminocarbonylamino or arylalkylaminocarbonylamino);
nitrogen containing groups selected from the group consisting of
  amines (e.g. amino, mono- or dialkylamino, cyclicamino, arylamino, aminoalkyl, mono- or dialkylaminoalkyl),
  azides,
  nitriles (e.g. cyano, cyanoalkyl),
  nitro;
  sulfonamides (e.g. aminosulfonyl, mono- or di-alkylaminosulfonyl, mono- or di-arylaminosulfonyl, alkyl- or aryl-sulfonylamino, alkyl- or aryl-sulfonyl(alkyl)amino, alkyl- or aryl-sulfonyl(aryl)amino)
sulfur containing groups selected from the group consisting of
  thiols, thioethers, sulfoxides, and sulfones
  (e.g. alkylthio, alkylsulfinyl, alkylsulfonyl, alkylthioalkyl, alkylsulfinylalkyl, alkylsulfonylalkyl, arylthio, arylsulfinyl, arylsulfonyl, arylthioalkyl, arylsulfinylalkyl, arylsulfonylalkyl);
heterocyclic groups containing one or more, preferably one, heteroatom,
  (e.g. thienyl, furanyl, pyrrolyl, imidazolyl, pyrazolyl, thiazolyl, isothiazolyl, oxazolyl, oxadiazolyl, thiadiazolyl, aziridinyl, azetidinyl, pyrrolidinyl, pyrrolinyl, imidazolidinyl, imidazolinyl, pyrazolidinyl, tetrahydrofuranyl, pyranyl, pyronyl, pyridyl, pyrazinyl, pyridazinyl, piperidyl, hexahydroazepinyl, piperazinyl, morpholinyl, thianaphthyl, benzofuranyl, isobenzofuranyl, indolyl, oxyindolyl, isoindolyl, indazolyl, indolinyl, 7-azaindolyl, benzopyranyl, coumarinyl, isocoumarinyl, quinolinyl, isoquinolinyl, naphthridinyl, cinnolinyl, quinazolinyl, pyridopyridyl, benzoxazinyl, quinoxalinyl, chromenyl, chromanyl, isochromanyl, phthalazinyl and carbolinyl); and silicon-containing groups selected from the group consisting of silanes (e.g. trialkylsilyl); and $R_{12}$ wherein: $R_3$ may include alkyl substituted by a substituent $R_{12}$, wherein $R_{12}$ is selected from the group consisting of hydroxy, alkoxy, dialkylamino, $NH_2$, aryloxy, CN, halo, cycloalkyl, aryl, non-aromatic heterocyclyl, $CO_2R_{13}$, $CONR_{14}R_{15}$, $CONR_9R_{10}$, $CONR_8NR_9R_{10}$, $C(=NR_{13})NR_{14}R_{15}$, $NR_{13}COR_{14}$, $NR_{13}CO_2R_{11}$, triallcylsilyl, and phthalimido, wherein: (a) $R_{13}$, $R_{14}$ and $R_{15}$ are selected from the group consisting of hydrogen, alkyl, and aryl, or (b) where $R_1$, and $R_{15}$ are in an $(NR_{14}R_{15})$group, $R_{14}$ and $R_{15}$ may be linked to form a heterocyclic ring.

Where any of $R_1$ to $R_{20}$ is selected from aryl or from an aryl-containing group such as aryloxy or arylthio, preferred substituent group(s) are selected from halogen, alkyl (substituted or unsubstituted; and where substituted particularly from alkoxyalkyl, hydroxyalkyl, aminoalkyl and haloalkyl), hydroxy, alkoxy, CN, $NO_2$, amines (including amino, mono- and di-alkylamino), alkoxycarbonyl, aminocarbonyl, carboxamido, sulfonamido, alkoxycarbonylamino and aryl, and particularly from unsubstituted alkyl, substituted alkyl (including alkoxyalkyl and aminoalkyl), halogen and amines.

In one embodiment, where any of $R_1$ to $R_{20}$ is directly substituted by an alkyl substituent group, or by an alkyl-containing substituent group (such as alkoxy or alkylcarbonylamino for example), then the alkyl moiety of the substituent group directly attached to any of $R_1$ to $R_{20}$ may be further substituted by the substituent groups hereinbefore described and particularly by halogen, hydroxy, alkoxy, CN, amines (including amino, mono- and di-allyl amino) and aryl.

In a further embodiment, where any of $R_1$ to $R_{20}$ is directly substituted by an aryl substituent group, or by an aryl-containing substituent group (such as aryloxy or arylaminocarbonylamino for example), then the aryl moiety of the substituent group directly attached to any of $R_1$ to $R_{20}$ may be further substituted by the substituent groups hereinbefore described and particularly by halogen, alkyl (substituted or unsubstituted; and where substituted particularly from alkoxyalkyl, hydroxyalkyl, aminoalkyl and haloalkyl), hydroxy, alkoxy, CN, $NO_2$, amines (including amino, mono- and di-alkylamino), alkoxycarbonyl, aminocarbonyl, carboxamido, sulfonamido, alkoxycarbonylamino and aryl. In a further embodiment, said aryl moiety is substituted by halogen, alkyl (including $CF_3$), hydroxy, alkoxy, CN, amines (including amino, mono- and di-alkyl amino) and $NO_2$. In a further embodiment, said aryl moiety is substituted by unsubstituted alkyl, substituted alkyl particularly alkoxyalkyl and aminoalkyl), halogen and amines.

The terms "directly substituted" and "directly attached", as used herein, mean that the substituent group is bound directly to any of $R_1$ to $R_{20}$ without any intervening divalent atoms or groups.

In the compounds of formula (I), $R_1$ is selected from alkyl (including haloalkyl (such as $CF_3$), branched alkyl, cycloalkyl and arylalkyl), aryl (including heteroaryl), alkoxy, aryloxy, thioalkyl, thioaryl, halo, CN, $NR_5R_6$ (including $NH_2$), $NR_4COR_5$, $NR_4CONR_5R_6$, $NR_4CO_2R_{7\,and\,NR4}SO_2R_7$.

In a preferred embodiment, $R_1$ is selected from $NR_5R_6$ (including $NH_2$), alkoxy, thioalkyl and alkyl.

In a particularly preferred embodiment, $R_1$ is selected from $NR_5R_6$ (including $NH_2$), and is preferably $NH_2$.

Where $R_1$ is selected from alkyl, preferably $R_1$ is selected from $C_{1-6}$ alkyl, more preferably from saturated $C_{1-6}$ alkyl and more preferably from lower alkyl.

Where $R_1$ is selected from alkoxy and thioalkyl, preferably the alkyl moiety of said thioalkyl or alkoxy group is selected from $C_{1-6}$ alkyl, more preferably from saturated $C_{1-6}$ alkyl and more preferably from lower alkyl.

Where $R_1$ is selected from halo, preferably $R_1$ is selected from chloro.

Where $R_1$ is selected from $NR_5R_6$, preferably at least one and more preferably both of $R_5$ and $R_6$ are hydrogen.

In one embodiment, $R_1$ is selected from $NR_4COR_5$, $NR_4CONR_5R_6$, $NR_4CO_2R_7$ and $NR_4SO_2R_7$, and $R_4$ is selected from H and alkyl, and more preferably hydrogen.

In a preferred embodiment, $R_2$ is selected from furyl (including 2-furyl), thienyl (including 2-thienyl), pyridyl (including 2-pyridyl), thiazolyl (including 2- and 5-thiazolyl), pyrazolyl (including 3-pyrazolyl), triazolyl (including 4-triazolyl), pyrrolyl (including 2-pyrrolyl) and oxazolyl (including 5-oxazolyl). In a further embodiment, $R_2$ is selected from 2-furyl, 2-thienyl, 2-thiazolyl, 2-pyridyl, 3-pyrazolyl, 2-pyrrolyl, 4-triazolyl and 5-oxazolyl. In a further preferred embodiment, $R_2$ is selected from furyl, thienyl, pyridyl, thiazolyl and pyrazolyl, and particularly from 2-furyl, 2-thienyl, 2-thiazolyl, 2-pyridyl and 3-pyrazolyl. In a further embodiment, $R_2$ is selected from furyl, thienyl and pyridyl, preferably 2-furyl, 2-thienyl and 2-pyridyl, and more preferably from 2-furyl.

In the compounds of formula (I), where $R_2$ is substituted heteroaryl, it is preferred that the substituent group(s) are not present in the ortho position relative to the point of attachment of the heteroaryl group to the purine moiety. As used herein, reference to ortho-substitution of the $R_2$ group means the ortho positions of the $R_2$ group relative to the point of attachment of $R_2$ to the pyrimidine moiety of formula (I).

In a preferred embodiment, $R_2$ is an unsubstituted heteroaryl group.

In the compounds of formula (I), $R_3$ is selected from H, substituted and unsubstituted alkyl (including saturated alkyl, alkenyl, alkynyl, branched and unbranched alkyl, and cyclic and acyclic allyl), $COR_8$, $CONR_9R_{10}$, $CONR_8NR_9R_{10}$, $CO_2R_{11}$ and $SO_2R_{10}$.

In a preferred embodiment, $R_3$ is selected from H, alkyl and $CONR_9R_{10}$.

In a particularly preferred embodiment, $R_3$ is selected from H, substituted alkyl and $CONR_9R_{10}$. In an alternative embodiment, $R_3$ is selected from alkyl (substituted or unsubstituted) and $CONR_9R_{10}$, preferably substituted alkyl and $CONR_9R_{10}$. Wherein $R_3$ is substituted alkyl, said substituted alkyl is preferably selected from arylalkyl (including heteroarylalkyl) and allyl substituted by $CONR_9R_{10}$, and more preferably from arylalkyl (including heteroarylalkyl), and more preferably from arylmethyl (including heteroarylmethyl).

Where $R_3$ is selected from $COR_8$, $R_8$ is preferably selected from alkyl (including cycloalkyl) and aryl (including heteroaryl), preferably from saturated $C_{1-6}$ alkyl (including cycloalkyl) and aryl.

Where $R_3$ is selected from $CONR_9R_{10}$, it is preferred that $R_9$ and $R_{10}$ are selected from H, $C_{1-6}$ alkyl and aryl, and preferably from H, $C_{1-6}$ saturated alkyl (including cycloalkyl)

and aryl, and more preferably from H, lower alkyl and aryl. Preferably one of $R_9$ and $R_{10}$ is hydrogen. Where $R_9$ or $R_{10}$ is aryl, it is preferred that said aryl is substituted or unsubstituted phenyl. Where $R_9$ or $R_{10}$ is lower alkyl, said lower alkyl may be substituted by hydroxy, halo, alkoxy, dialkylamino, substituted or unsubstituted aryl, preferably by substituted or unsubstituted aryl (including heteroaryl), more preferably by substituted and unsubstituted phenyl, thienyl, furyl and pyridyl, and more preferably by substituted phenyl, thienyl, furyl and pyridyl.

In a preferred embodiment, $R_3$ is $CONR_9R_{10}$, $R_9$ is H and $R_{10}$ is selected from $C_{1-6}$ saturated alkyl, preferably saturated lower alkyl and preferably methyl, preferably substituted by substituted or unsubstituted aryl (including heteroaryl), more preferably substituted by phenyl, thienyl, furyl and pyridyl.

Where $R_3$ is selected from $CO_2R_{11}$, preferably $R_{11}$ is selected from $C_{1-6}$ alkyl, preferably saturated $C_{1-6}$ alkyl, preferably saturated $C_{1-6}$ alkyl, and more preferably lower alkyl, optionally substituted by one or more (preferably one) substituent group preferably selected from aryl.

Where $R_3$ is selected from $SO_2R_{11}$, it is preferred that $R_{11}$ is selected from $C_{1-6}$ alkyl (including cycloalkyl and alkenyl) and aryl (including heteroaryl). Where $R_3$ is $SO_2R_{11}$ and $R_{11}$ is aryl, the aryl group may be substituted or unsubstituted, preferably substituted, and preferably substituted by lower alkyl or halo groups.

Where $R_3$ is selected from alkyl, in one embodiment $R_3$ is selected from acyclic alkyl (substituted or unsubstituted). In a further embodiment, $R_3$ is selected from substituted or unsubstituted $C_{1-6}$ alkyl (preferably acyclic, and including alkenyl and alkynyl), preferably from substituted or unsubstituted $C_{1-6}$ saturated alkyl and alkenyl (preferably acyclic), more preferably from substituted or unsubstituted $C_{1-6}$ saturated alkyl (preferably acyclic), preferably substituted or unsubstituted lower alkyl, more preferably from substituted or unsubstituted methyl, ethyl and propyl (n-propyl or isopropyl) groups, and more preferably from substituted or unsubstituted methyl.

In a preferred embodiment, $R_3$ is selected from substituted alkyl, preferably mono-substituted alkyl where said substituent(s) is/are represented by $R_{12}$. Preferably, $R_{12}$ is selected from hydroxy, alkoxy, dialkylamino, $NH_2$, aryloxy, CN, halo, cycloalkyl, aryl (including heteroaryl), non-aromatic heterocyclyl, $CO_2R_{13}$, $CONR_{14}R_{15}$, $CONR_8NR_9R_{10}$, $C(=NR_{13})NR_{14}R_{15}$, $NR_{13}COR_{14}$, $NR_{13}CO_2R_{11}$, tialkylsilyl and phthalimido, wherein $R_{13}$, $R_{14}$ and $R_{15}$ are selected from hydrogen, alkyl and aryl, or where $R_{14}$ and $R_{15}$ are in an ($NR_{14}R_{15}$)group, $R_{14}$ and $R_{15}$ may be linked to form a heterocyclic ring. Preferably, $R_{12}$ is selected from aryl (including heteroaryl) and $CONR_{14}R_{15}$, and preferably from aryl (including heteroaryl).

Where $R_{12}$ is $CONR_{14}R_{15}$, it is preferred that $R_{14}$ and $R_{15}$ are selected from H, $C_{1-6}$ alkyl and aryl, preferably from H, $C_{1-6}$ saturated alkyl (including cycloalkyl and arylalkyl (including heteroaryl)) and aryl (including heteroaryl) and more preferably from H, lower alkyl and aryl. Preferably one of $R_{14}$ and $R_{15}$ is hydrogen.

In one embodiment, $R_{12}$ is $CONR_{14}R_{15}$ and $R_{14}$ and/or $R_{15}$ are selected from alkyl substituted by one or more, preferably one, substituent group(s) selected from hydroxy, alkoxy and dialkylamino.

Where $R_{12}$ is selected from aryl (including heteroaryl), the aryl group may be unsubstituted or substituted, and is preferably substituted. In a preferred embodiment, $R_{12}$ is selected from mono-, di- or tri-substituted aryl (including heteroaryl) groups. Where $R_{12}$ is heteroaryl, $R_{12}$ is preferably selected from mono or bicyclic heteroaryl groups, more preferably from pyridyl (including 2-pyridyl, 3-pyridyl and 4-pyridyl, preferably 2-pyridyl), indolyl (including 2-indolyl, 3-indolyl, 4-indolyl, 5-indolyl, 6-indolyl and 7-indolyl), furyl (including 2-furyl and 3-furyl, preferably 2-furyl), thienyl (including 2-thienyl and 3-thienyl, preferably 2-thienyl), isoindolyl, indolinyl, isoxazolyl, oxazolyl, thiazolyl, pyrazinyl, pyrimidinyl, quinolinyl, benzoxadiazolyl, benzothiadiazolyl, benzotriazolyl, indazolyl, benzodioxolyl and dihydrobenzofuranyl, more preferably from pyridyl (preferably 2-pyridyl), indolyl, furyl (preferably 2-furyl) and thienyl (preferably 2-thienyl), and most preferably from pyridyl (preferably 2-pyridyl), furyl (preferably 2-furyl) and thienyl (preferably 2-thienyl). Preferably, $R_{12}$ is selected from phenyl, thienyl, furyl and pyridyl, more preferably from phenyl, 2-thienyl, 2-furyl and 2-pyridyl In a preferred embodiment, $R_{12}$ is phenyl.

In one embodiment, $R_{12}$ is selected from mono-, di- or tri-substituted aryl (including heteroaryl) groups represented by the formula $Ar(R_{18})_a(R_{19})_b(R_{20})_c$ wherein Ar is an aryl (including heteroaryl) group, preferably selected from the preferred aryl groups described above for $R_{12}$; wherein $R_{18}$, $R_{19}$ and $R_{20}$ are substituent group(s), the same or different; and wherein a, b and c are 0 or 1 such that $a+b+c \geq 1$.

The substituent groups $R_{18}$, $R_{19}$ and $R_{20}$ may be selected from any of the substituent groups described herein above.

In a preferred embodiment, $R_{18}$, $R_{19}$ and $R_{20}$ are selected from $NR_5R_6$ (including $NH_2$, and $NHR_5$) alkyl (substituted or unsubstituted; preferably $C_{1-6}$ acyclic alkyl), alkoxy (including fluoroalkoxy), halogen (including F, Cl, Br and I), $NO_2$, CN, hydroxy, NHOH, CHO, $CONR_5R_6$, $CO_2R_5$, $NR_4COR_5$ (preferably $NHCOR_5$), $NR_4CO_2R_7$ (preferably $NHCO_2R_7$), $NR_4SO_2R_7$ (preferably $NHSO_2R_7$), $OCO_2R_7$ and aryl (including heteroaryl).

In a more preferred embodiment, $R_{18}$, $R_{19}$ and $R_{20}$ are selected from $NR_5R_6$ (including $NH_2$ and $NHR_5$), alkyl (substituted or unsubstituted; and preferably $C_{1-6}$ acyclic saturated alkyl) and halogen (preferably F or Cl, particularly F).

In a particularly preferred embodiment, $R_{18}$, $R_{19}$ and $R_{20}$ are selected from $NR_5R_6$ (including $NH_2$ and $NHR_5$, preferably $NH_2$) and alkyl (substituted or unsubstituted; preferably $C_{1-4}$ acyclic saturated alkyl).

Where $R_{18}$, $R_{19}$ and $R_{20}$ are selected from substituted alkyl, said alkyl is preferably selected from alkoxyalkyl, hydroxyalkyl, aminoalkyl (including $NH_2$-alkyl, mono-alkylaminoalkyl and di-alkylaminoalkyl), haloalkyl (particularly fluoroalkyl (including $CF_3$)), cyanoalkyl, alkylthioalkyl, alkylcarboxyaminoalkyl, alkoxycarbonylaminoalkyl and alkylsulfonylamino, more preferably from alkoxyalkyl, hydroxyalkyl, aminoalkyl and haloalkyl (particularly fluoroalkyl (including $CF_3$)) and most preferably from alkoxyalkyl and aminoalkyl.

In one embodiment, particularly where $R_{12}$ is aryl, preferably phenyl, the substituent groups $R_{18}$, $R_{19}$ and $R_{20}$ are selected from lower alkyl, hydroxy, lower alkoxy, amino (including $NH_2$, mono- and di-alkylamino), $NO_2$, CN, amido, aminocarbonyl (including mono- and di-alkylaminocarbonyl), sulfonamido or halo group(s). In a further embodiment $R_{12}$ is aryl, preferably phenyl, substituted by $NR_{16}SO_2R_{17}$ wherein $R_{16}$ is selected from H, alkyl and aryl and preferably H, and $R_{17}$ is selected from alkyl and aryl, preferably from $C_{1-6}$ saturated alkyl and aryl (including heteroaryl). $R_{17}$ may be unsubstituted or substituted, for instance by alkyl or hydroxy.

In the compounds of formula (I) $R_4$, $R_5$, $R_6$, $R_8$, $R_9$, $R_{10}$, $R_{13}$, $R_{14}$ and $R_{15}$ are independently selected from H, substituted and unsubstituted alkyl (including saturated alkyl, alkenyl, alkenyl, branched and unbranched alkyl, and cyclic and acyclic alkyl) and substituted and unsubstituted aryl (including heteroaryl), or where $R_5$ and $R_6$ are in an $(NR_5R_6)$ group then $R_5$ and $R_6$ may be linked to form a heterocyclic group, or where $R_9$ and $R_{10}$ are in an $(NR_9R_{10})$ group then $R_9$ and $R_{10}$ may be linked to form a heterocyclic group, or where $R_8$, $R_9$ and $R_{10}$ are in a $(CONR_8NR_9R_{10})$ group, $R_8$ and $R_9$ may be linked to form a heterocyclic group, or where $R_{14}$ and $R_{15}$ are in an $(NR_{14}R_{15})$group, $R_{14}$ and $R_{15}$ may be linked to form a heterocyclic group. Preferably, $R_4$, $R_{13}$ and $R_{16}$ are independently selected from H and alkyl.

In the compounds of formula (I), $R_7$, $R_{11}$, and $R_{17}$ are independently selected from substituted and unsubstituted alkyl (including saturated alkyl, alkenyl, alkenyl, branched and unbranched alkyl and cyclic and acyclic alkyl) and substituted and unsubstituted aryl (including heteroaryl).

Where $R_4$, R, $R_6$, $R_7$, $R_{13}$ and $R_{16}$ are independently selected from alkyl (substituted or unsubstituted), said alkyl group is preferably selected from $C_{1-6}$ alkyl, and preferably from $C_{1-6}$ saturated alkyl and $C_{1-6}$ alkenyl. In one embodiment, $R_4$ to $R_7$, $R_{13}$ and $R_{16}$ are selected from $C_{1-6}$ saturated alkyl, preferably lower alkyl.

Where $R_4$, $R_5$, $R_6$, $R_7$, $R_{13}$ and $R_{16}$ are independently selected from substituted alkyl (including saturated alkyl, alkenyl and alkynyl), the one or more substituent group(s) are preferably selected from cycloalkyl, substituted and unsubstituted aryl (including heteroaryl), non-aromatic heterocyclyl, hydroxy, alkoxy and dialkylamino.

Where $R_5$ and $R_6$, or $R_9$ and $R_{10}$, or $R_8$ and $R_9$, or $R_{14}$ and $R_{15}$, in accordance with the definitions herein, are linked to form a heterocyclic ring, said heterocyclic ring may be saturated, partially unsaturated or aromatic, and is preferably saturated. Said heterocyclic ring preferably is a 5, 6 or 7-membered ring, preferably a 5 or 6-membered ring, and may contain one or more further heteroatoms preferably selected from N, O and S heteroatoms.

In a particularly preferred embodiment of the invention, the compounds of formula (I) are selected from those compounds wherein $R_1$ is $NH_2$, $R_2$ is 2-furyl and $R_3$ is arylalkyl (including heteroarylalkyl), particularly arylmethyl (including heteroarylmethyl).

In a particularly preferred embodiment of the invention, the compounds of the present invention are selected from:
N,N-Dimethyl-6-(2-furyl)-1H-purine-2-amine;
6-(2-Furyl)-1H-purine-2-amine;
6-(2-Furyl)-2-methylthio-1H-purine;
2-Amino-N-benzyl-6-(2-furyl)-9H-purine-9-carboxamide;
2-Amino-N-n-butyl-6-(2-furyl)-9H-purine-9-carboxamide;
2-Amino-6-(2-furyl)-N-(4-methoxybenzyl)-9H-purine-9-carboxamide;
2-Amino-6-(2-furyl)-N-(4-methylbenzyl)-9H-purine-9-carboxamide;
2-Amino-N-(2-chlorobenzyl)-6-(2-furyl)-9H-purine-9-carboxamide;
(1S)-2-Amino-6-(2-furyl)-N-(1-phenylethyl)-9H-purine-9-carboxamide;
2-Amino-6-(2-furyl)-N-(3-methylbenzyl)-9H-purine-9-carboxamide;
2-Amino-6-(2-furyl)-N-n-pentyl-9H-purine-9-carboxamide;
6-(2-Furyl)-9-(1-phenyl-1-propene-3-yl)-9H-purine-2-amine;
6-(2-Furyl)-9-(3-phenylpropyl)-9H-purine-2-amine;
2-Amino-N-(4-fluorobenzyl)-6-(2-furyl)-9H-purine-9-carboxamide;
2-Amino-N-(3,4-dichlorobenzyl)-6-(2-furyl)-9H-purine-9-carboxamide;
6-(2-Furyl)-9-(4-isopropylbenzyl)-9H-purine-2-amine;
2-Amino-6-(2-furyl)-N-(2-phenylethyl)-9H-purine-9-carboxamide;
2-Amino-N-(2,4-dichlorobenzyl)-6-(2-furyl)-9H-purine-9-carboxamide;
Benzyl 2-amino-6-(2-furyl)-9H-purine-9-carboxylate;
N-Benzyl-2-methoxy-6-(2-furyl)-9H-purine-9-carboxamide;
2-Amino-N-benzyl-6-(2-furyl)-N-methyl-9H-purine-9-carboxamide;
9-(3-Chlorobenzyl)-6-(2-furyl)-9H-purine 2-amine;
6-(2-Furyl)-9-(3-methylbenzyl)-9H-purine-2-amine;
6-(2-Furyl)-9-(4-methylbenzyl)-9H-purine-2-amine;
2-Amino-N-(3-chlorophenyl)-6-(2-furyl)-9H-purine-9-acetamide;
9-(2-Fluorobenzyl)-6-(2-furyl)-9H-purine-2-amine;
6-(2-Furyl)-9-(4-trifluoromethylbenzyl)-9H-purine-2-amine;
9-(4-Bromophenyl)sulphonyl-6-(2-furyl)-9H-purine-2-amine;
6-(2-Furyl)-9-(2-phenylethenyl)sulphonyl-9H-purine-2-amine;
6-(2-Furyl)-9-(3-(3-pyridyl)propyl)-9H-purine-2-amine;
9-(3-Aminobenzyl)-6-(2-furyl)-9H-purine-2-amine;
6-(2-Furyl)-9-(3-methoxybenzyl)-9H-purine-2-amine;
2-Amino-6-(2-furyl)-N-(2-furylmethyl)-9H-purine-9-carboxamide;
2-Amino-6-(2-furyl)-N-(2-thienylmethyl)-9H-purine-9-carboxamide;
9-(4-Methylbenzyl)-6-(5-methyl-2-furyl)-9H-purine-2-amine;
9-(2,6-Difluorobenzyl)-6-(2-furyl)-9H-purine-2-amine;
6-(2-Furyl)-9-(6-methyl-2-pyridyl)methyl-9H-purine-2-amine;
6-(2-Furyl)-9-(2-(1-methyl-1H-imidazol-4-ylsulphonylamino)benzyl)-9H-purine-2-amine;
9-(5-Chloro-2-thienylmethyl)-6-(2-furyl)-9H-purine-2-amine;
9-(2-Fluorobenzyl)-6-(4-methyl-2-thiazolyl)-9H-purine-2-amine; and
9-(2-Fluoro-5-nitrobenzyl)-6-(2-furyl)-9H-purine-2-amine.

Where chiral the compounds of the formula (I) may be in the form of a racemic mixture of pairs of enantiomers or in enantiomerically pure form.

The present invention may be employed in respect of a human or animal subject, more preferably a mammal, more preferably a human subject.

According to a further aspect of the present invention there is provided a method of treating or preventing a disorder in which the blocking of purine receptors, particularly adenosine receptors and more particularly adenosine $A_{2A}$ receptors, may be beneficial, the method comprising administration to a subject in need of such treatment an effective dose of a compound of formula (I) or a pharmaceutically acceptable salt or prodrug thereof.

The disorder may be caused by the hyperfunctioning of the purine receptors.

The disorders of particular interest are those in which the blocking of purine receptors, partiucularly adenosine receptors and more particularly adenosine $A_{2A}$ receptors, may be beneficial. These may include movement disorders such as Parlinson's disease, drug-induced Parkinsonism, post-encephalitic Parkinsonism, Parkinsonism induced by poisoning (for example MPTP, manganese, carbon monoxide) and post-traumatic Parkinson's disease (punch-drunk syndrome).

Other movement disorders in which the blocking of purine receptors, may be of benefit include progressive supernuclear palsy, Huntingtons disease, multiple system atrophy, corticobasal degeneration, Wilsons disease, Hallerrorden-Spatz disease, progressive pallidal atrophy, Dopa-responsive dystonia-Parkinsonism, spasticity or other disorders of the basal ganglia which result in abnormal movement or posture. The present invention may also be effective in treating Parkinson's with on-off phenomena; Parldnson's with freezing (end of dose deterioration); and Parkinson's with prominent dyskinesias.

The compounds of formula (I) may be used or administered in combination with one or more additional drugs useful in the treatment of movement disorders, such as L-DOPA or a dopamine agonist, the components being in the same formulation or in separate formulations for administration simultaneously or sequentially.

Other disorders in which the blocking of purine receptors, particularly adenosine receptors and more particularly adenosine $A_{2A}$ receptors may be beneficial include acute and chronic pain; for example neuropathic pain, cancer pain, trigeminal neuralgia, migraine and other conditions associated with cephalic pain, primary and secondary hyperalgesia, inflammatory pain, nociceptive pain, tabes dorsalis, phantom limb pain, spinal cord injury pain, central pain, post-herpetic pain and HIV pain; affective disorders including mood disorders such as bipolar disorder, seasonal affective disorder, depression, manic depression, a typical depression and monodepressive disease; central and peripheral nervous system degenerative disorders including corticobasal degeneration, demyelinating disease (multiple sclerosis, disseminated sclerosis), Freidrich's ataxia, motoneurone disease (amyotrophic lateral sclerosis, progressive bulbar atrophy), multiple system atrophy, myelopathy, radiculopathy, peripheral neuropathy (diabetic neuropathy, tabes dorsalis, drug-induced neuropathy, vitamin deficiency), systemic lupus erythamatosis, granulomatous disease, olivo-ponto-cerebellar atrophy, progressive pallidal atrophy, progressive supranuclear palsy, spasticity; schizophrenia and related pyshoses; cognitive disorders including dementia, Alzheimers Disease, Frontotemporal dementia, multi-infarct dementia, AIDS dementia, dementia associated with Huntingtons Disease, Lewy body dementia, senile dementia, age-related memory impairment, cognitive impairment associated with dementia, Korsakoff syndrome, dementia pugilans; attention disorders such as attention-deficit hyperactivity disorder (ADHD), attention deficit disorder, minimal brain dysfunction, brain-injured child syndrome, hyperkinetic reaction childhood, and hyperactive child syndrome; central nervous system injury including traumatic brain injury, neurosurgery (surgical trauma), neuroprotection for head injury, raised intracranial pressure, cerebral oedema, hydrocephalus, spinal cord injury; cerebral ischaemia including transient ischaemic attack, stroke (thrombotic stroke, ischaemic stroke, embolic stroke, haemorrhagic stroke, lacunar stroke) subarachnoid haemorrhage, cerebral vasospasm, neuroprotection for stroke, peri-natal asphyxia, drowning, cardiac arrest, subdural haematoma; myocardial ischaemia; muscle ischaemia; sleep disorders such as hypersomnia and narcolepsy; eye disorders such as retinal ischaemia-reperfusion injury and diabetic neuropathy; cardiovascular disorders such as claudication and hypotension; and diabetes and its complications.

According to a further aspect of the present invention there is provided use of a compound of formula (I) or a pharmaceutically acceptable salt or prodrug thereof in the manufacture of a medicament for the treatment or prevention of movement disorders in a subject.

According to a further aspect of the invention there is provided a method of treating or preventing movement disorders comprising administration to a subject in need of such treatment an effective dose of a compound of formula (I) or a pharmaceutically acceptable salt or prodrug thereof.

According to a further aspect of the invention there is provided use of a compound of formula (I) or a pharmaceutically acceptable salt or prodrug thereof in the manufacture of a medicament for neuroprotection in a subject.

According to a further aspect of the invention there is provided a method of neuroprotection comprising administration to a subject in need of such treatment an effective dose of a compound of formula (I) or a pharmaceutically acceptable salt or prodrug thereof.

The medicament for or method of neuroprotection may be of use in the treatment of subjects who are suffering from or at risk from a neurodegenerative disorder, such as a movement disorder.

According to a further aspect of the invention, there is provided for use in therapy a compound of formula (I), or a pharmaceutically acceptable salt or prodrug thereof, other than:
(i) compounds wherein $R_1$ is halogen or aryl and $R_3$ is benzyl, and preferably other than compounds wherein $R_1$ is halogen or aryl; and
(ii) compounds wherein $R_3$ is H, $R_1$ is $NH_2$ and $R_2$ is thienyl, preferably other than compounds wherein $R_3$ is H and $R_1$ is $NH_2$, and preferably other than compounds wherein $R_3$ is H.

According to a further aspect of the invention, there is provided for use in therapy a compound of formula (I), or a pharmaceutically acceptable salt or prodrug thereof, other than:
(i) compounds wherein $R_1$ is halogen or aryl and $R_3$ is benzyl, and preferably other than compounds wherein $R_1$ is halogen or aryl; and
(ii) compounds wherein $R_3$ is H, $R_1$ is $NH_2$ and $R_2$ is thienyl, preferably other than compounds wherein $R_3$ is H and $R_2$ is thienyl, and preferably other than compounds wherein $R_2$ is thienyl.

In an alternative embodiment, there is provided for use in therapy a compound of formula (I), or a pharmaceutically acceptable salt or prodrug thereof, wherein:
$R_1$ is selected from $NR_5R_6$ (including $NH_2$), alkoxy, thioalkyl and alkyl, preferably wherein $R_1$ is selected from $NR_5R_6$, and more preferably wherein $R_1$ is $NH_2$, and
$R_3$ is-selected from alkyl and $CONR_9R_{10}$, preferably wherein $R_3$ is selected from substituted alkyl and $CONR_9R_{10}$, more preferably wherein $R_3$ is selected from substituted alkyl and $CONR_9R_{10}$ wherein said substituted alkyl is selected from arylalkyl (including heteroarylalkyl) and alkyl substituted by $CONR_9R_{10}$.

According to a further aspect of the present invention there is provided a compound of formula (I) or a pharmaceutically acceptable salt or prodrug thereof, per se, other than:
(i) compounds wherein $R_1$ is halogen or aryl and $R_3$ is benzyl, and preferably other than compounds wherein $R_1$ is halogen or aryl; and
(ii) compounds wherein $R_3$ is H, $R_1$ is $NH_2$ and $R_2$ is thienyl, preferably other than compounds wherein $R_3$ is H and $R_1$ is $NH_2$, and preferably other than compounds wherein $R_3$ is H.

According to a further aspect of the invention, there is provided a compound of formula (I), or a pharmaceutically acceptable salt or prodrug thereof, per se, other than:
(i) compounds wherein $R_1$ is halogen or aryl and $R_3$ is benzyl, and preferably other than compounds wherein $R_1$ is halogen or aryl; and
(ii) compounds wherein $R_3$ is H, $R_1$ is $NH_2$ and $R_2$ is thienyl, preferably other than compounds wherein $R_3$ is H and $R_2$ is thienyl, and preferably other than compounds wherein $R_2$ is thienyl.

In an alternative embodiment, there is provided a compound of formula (I), or a pharmaceutically acceptable salt or prodrug thereof, per se, wherein:

$R_1$ is selected from $NR_5R_6$ (including $NH_2$), alkoxy, thioalkyl and alkyl, preferably wherein $R_1$ is selected from $NR_5R_6$, and more preferably wherein $R_1$ is $NH_2$, and $R_3$ is selected from alkyl and $CONR_9R_{10}$, preferably wherein $R_3$ is selected from substituted alkyl and $CONR_9R_{10}$, more preferably wherein $R_3$ is selected from substituted alkyl and $CONR_9R_{10}$ wherein said substituted alkyl is selected from arylalkyl (including heteroarylalkyl) and alkyl substituted by $CONR_9R_{10}$.

According to a further aspect of the invention, there is provided a method of preparing the novel compounds of the present invention. Compounds of formula (I) may be prepared according to conventional synthetic methods, such as set out in Reaction Scheme 1.

Compounds of formula (1) where $R_3$ is alkyl substituted with $R_{12}$ wherein $R_{12}$ is $CO_2R_{13}$ or CN may be prepared from compounds of formula (2) by standard methods such as treatment with an appropriate substituted alkyl halide in the presence of a suitable base such as sodium hydride.

Compounds of formula (1) where $R_3$ is alkyl substituted with $R_{12}$ wherein $R_{12}$ is $NR_{13}COR_{14}$, $NR_{13}CO_2R_{17}$ or $NR_{13}SO_2R_{17}$ may be prepared from compounds of formula (1) where $R_3$ is alkyl substituted with $R_{12}$ wherein $R_{12}$ is $NHR_{13}$ by standard methods such as treatment with an appropriate acid chloride ($R_{14}COCl$), chloroformate ($ClCO_2R_{17}$) or sulphonyl chloride ($R_{17}SO_2Cl$) in the presence of a suitable base such as triethylamine.

Compounds of formula (1) where $R_3$ is alkyl substituted with $R_{12}$ wherein $R_{12}$ is $NR_{13}CONR_{14}R_{15}$ may be prepared from compounds of formula (1) where $R_3$ is alkyl substituted with $R_{12}$ wherein $R_{12}$ is $NHR_3$ by standard methods such as treatment with an appropriate isocyanate ($R_{14}NCO$ or $R_{15}NCO$) or carbamoyl chloride ($R_{14}R_{15}NCOCl$).

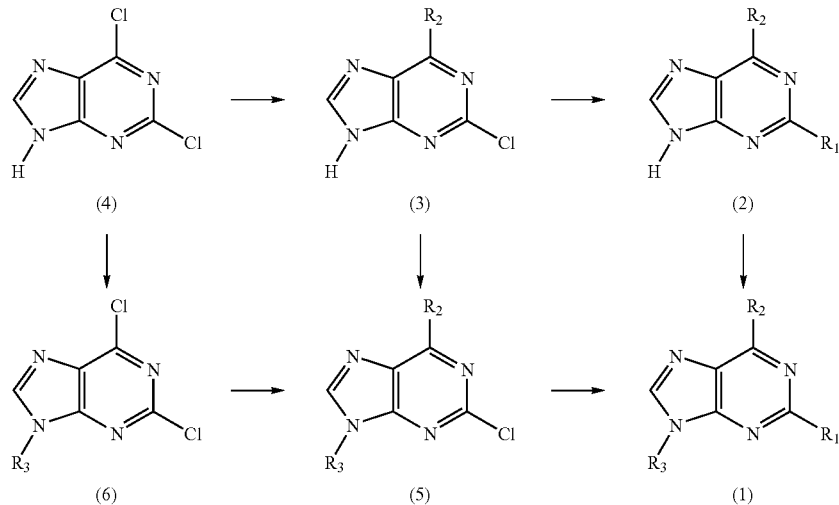

Reaction Scheme 1

Compounds of formula (1) where $R_3$ is alkyl (including arylalkyl, heteroarylalkyl and other substituted alkyl) may be prepared from a compound of formula (2) by standard methods such as reaction with an appropriate alkyl halide, or substituted alkyl halide in the presence of a suitable base such as sodium hydride.

Compounds of formula (1) where $R_3$ is alkyl substituted with $R_{12}$ wherein $R_{12}$ is $CONR_{14}R_{15}$ or $CONR_8NR_9R_{10}$ may be prepared from compounds of formula (1) where $R_3$ is alkyl substituted with $R_{12}$ wherein $R_{12}$ is $CO_2R_{13}$ by standard methods such as direct reaction with an appropriate amine or hydrazine or by initial hydrolysis of the ester group $CO_2R_{13}$ to a carboxylic acid followed by reaction with an appropriate amine or hydrazine in the presence of a standard coupling reagent such as DCC.

Compounds of formula (1) where $R_3$ is alkyl substituted with $R_{12}$ wherein $R_{12}$ is $C(=NR_{13})NR_{14}R_{15}$ may be prepared from compounds of formula (1) where $R_3$ is alkyl substituted with $R_{12}$ wherein $R_{12}$ is CN by standard methods such as treatment with an appropriate amine in the presence of trimethylaluminium.

Compounds of formula (1) where $R_3$ is alkyl substituted with $R_{12}$ wherein $R_{12}$ is $NHR_{13}$ may be prepared from compounds of formula (1) where $R_3$ is alkyl substituted with $R_{12}$ wherein $R_{12}$ is $NH_2$ by standard methods such as alkylation or reductive alkylation. Compounds of formula (1) where $R_3$ is alkyl substituted with $R_{12}$ wherein $R_{12}$ is $NH_2$ may be prepared from compounds of formula (1) where $R_3$ is alkyl substituted with $R_{12}$ wherein $R_{12}$ is phthalimide by standard methods such as treatment with hydrazine. Compounds of formula (1) where $R_3$ is alkyl substituted with $R_{12}$ wherein $R_{12}$ is phthalimide may be prepared from compounds of formula (2) by standard methods such as treatment with an appropriate substituted alkyl halide in the presence of a suitable base such as sodium hydride.

Compounds of formula (1) where $R_3$ is an ethyl group substituted in the β-position with an electron withdrawing group such as an ester, amide, ketone or nitrile group may be prepared from compounds of formula (2) by standard methods such as Michael addition with a suitable α,β-unsaturated ester, amide, ketone or nitrile. It will be appreciated by those skilled in the art that selection of an α,β-unsaturated ester, amide, ketone or nitrile which contained additional substituents would lead in an analogous way to compounds of formula (1) where $R_3$ is an ethyl group substituted in the β-position with an ester, amide, ketone or nitrile and additionally substituted elsewhere.

Compounds of formula (1) where $R_3$ is $CONR_9R_{10}$ or $CONR_8NR_9R_{10}$ may be prepared from compounds of formula (2) by standard methods such as treatment with an appropriate isocyanate ($R_9NCO$ or $R_{10}NCO$) or carbamoyl chloride ($R_9R_{10}NCOCl$, or $R_8R_9NR_{10}NCOCl$).

Compounds of formula (1) where $R_3$ is $COR_8$, $CO_2R_{11}$ or $SO_2R_{11}$ may be prepared from compounds of formula (2) by standard methods such as treatment with an appropriate acid chloride ($R_8COCl$), chloroformate ($ClCO_2R_{11}$) or sulphonyl chloride ($R_{11}SO_2Cl$) in the presence of a suitable base such as triethylamine.

Compounds of formula (2) where $R_1$ is alkoxy, aryloxy, alkylthio, arylthio, CN or $NR_5R_6$ may be prepared from compounds of formula (3) by standard methods such as nucleophilic displacement using an appropriate nucleophilic reagent such as an alcohol, thiol, cyanide or amine ($HN_5R_6$) in the presence of a suitable base if required.

Compounds of formula (3) may be prepared from the commercially available chloro compound of formula (4) by standard methods such as aryl or heteroaryl coupling reactions. Suitable aryl or heteroaryl coupling reactions would include reaction with an appropriate aryl or heteroaryl trialkylstannane derivative, an aryl or heteroarylboronic acid or boronic ester derivative, or an aryl or heteroarylzinc halide derivative in the presence of a suitable catalyst such as a palladium complex.

Compounds of formula (1) where $R_1$ is $NR_4CONR_5R_6$, wherein $R_4$ is H, may be prepared from compounds of formula (1) where $R_1$ is $NH_2$, by standard methods such as treatment with an appropriate isocyanate ($R_5NCO$ or $R_6NCO$) or carbamoyl chloride ($R_5R_6NCOCl$). Compounds of formula (1) where $R_1$ is $NR_4CONR_5R_6$, wherein $R_4$ is alkyl or aryl, may be prepared from compounds of formula (1) where $R_1$ is $NR_5R_6$, wherein one of $R_5$ and $R_6$ is alkyl or aryl and the other is H, by standard methods as described above.

Compounds of formula (1) where $R_1$ is $NR_4COR_5$, $NR_4CO_2R_7$ or $NR_4SO_2R_7$, wherein $R_4$ is H, may be prepared from compounds of formula (1) where $R_1$ is $NH_2$ by standard methods such as treatment with an appropriate acid chloride ($R_5COCl$), chloroformate ($ClCO_2R_7$) or sulphonyl chloride ($R_7SO_2Cl$) in the presence of a suitable base. Compounds of formula (1) where $R_1$ is $NR_4COR$, $NR_4CO_2R_7$ or $NR_4SO_2R_7$, wherein $R_4$ is alkyl or aryl, may be prepared from compounds of formula (1) where $R_1$ is $NR_5R_6$, wherein one of $R_5$ and $R_6$ is alkyl or aryl and the other is H, as described above.

Compounds of formula (1) where $R_1$ is $NH_2$ may be prepared from compounds of formula (1) where $R_1$ is $NR_5R_6$, wherein one of $R_5$ and $R_6$ is a protecting group and the other is H by standard methods such as treatment with TFA or Amberlyst-15. Suitable protecting groups would include 3,4-dimethoxybenzyl and THP.

Alternatively it may be advantageous to prepare compounds of formula (1) from compounds of formula (5) by standard methods such as nucleophilic displacement reactions as described above. Compounds of formula (5) are prepared either from compounds of formula (3) or from compounds of formula (6) by standard methods as described above. Compounds of formula (6) are prepared from compounds of formula (4) by standard methods as described above.

Compounds of formula (1) where $R_1$ is alkyl may be prepared from compounds of formula (5) by standard methods such as reaction with a suitable reagent such as a trialkylaluminium reagent preferably in the presence of a suitable catalyst such as a palladium catalyst.

Compounds of formula (1) where $R_1$ is aryl may be prepared from compounds of formula (5) by standard methods such as aryl coupling reaction as described above.

Alternatively compounds of formula (1) where $R_1$ is $NH_2$ may be prepared by standard methods such as those illustrated in Reaction Scheme 2.

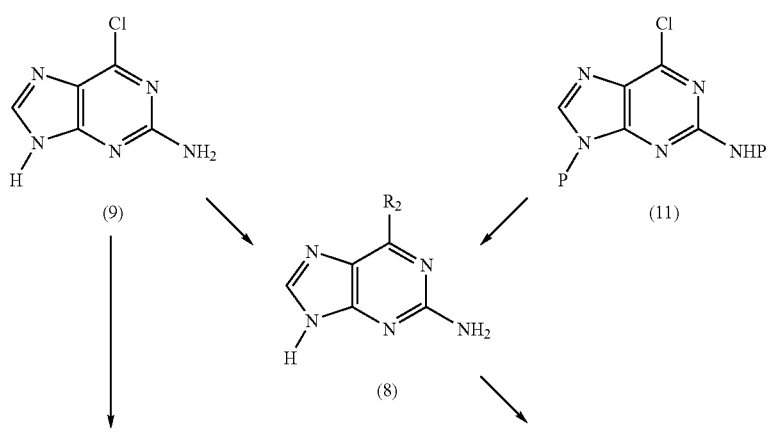

Reaction Scheme 2

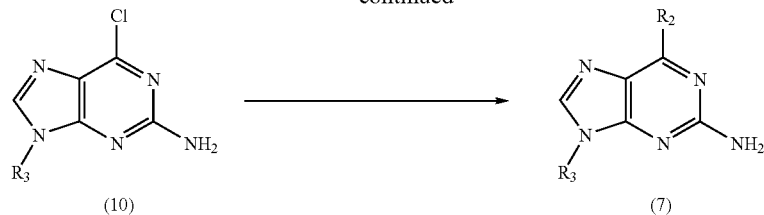

Compounds of formula (7) are prepared from compounds of formula (8) by standard methods such as those described above. Alternatively compounds of formula (7) are prepared from compounds of formula (10) by standard methods such as those described above. Compounds of formula (8) and formula (10) are prepared from the commercially available compound of formula (9) by standard methods such as those described above. In certain cases it may be advantageous to prepare compounds of formula (8) from compounds of formula (11) where P is a protecting group, for example THP. Compounds of formula (11) may be transformed into compounds of formula (8) by standard methods such as aryl coupling reactions as described above followed by removal of the protecting groups by standard methods such as treatment with Amberlyst-15. Compounds of formula (11) are either known in the literature or may be prepared by methods analogous to those reported in the literature.

Alternatively compounds of formula (1) where $R_1$ is alkyl or aryl are prepared by standard methods such as those illustrated in Reaction Scheme 3.

aryl are prepared from compounds of formula (12) where $R_1$ is alkyl or aryl by standard methods such as those described above. Compounds of formula (2) where $R_1$ is alkyl or aryl and compounds of formula (12) where $R_1$ is alkyl or aryl are prepared from compounds of formula (13) by standard methods such as those described above. Compounds of formula (13) where $R_1$ is alkyl or aryl are either known in the literature or may be prepared by methods analogous to those reported in the literature.

In the compounds of the present invention, where any of the groups $R_1$ to $R_{11}$ is an alkyl group or aryl group or where any of the groups $R_1$ to $R_{11}$ contains an alkyl or aryl substituent, the alkyl or aryl group may also be substituted. It will be appreciated by those skilled in the art that certain substituents on the alkyl or aryl groups mentioned above may be introduced directly as an integral part of the substituent $R_1$ to $R_{11}$ by using the synthetic methods described above. In other cases it may be advantageous to introduce certain substituents on the alkyl or aryl groups mentioned above by chemical transformation of other substituent groups. For example

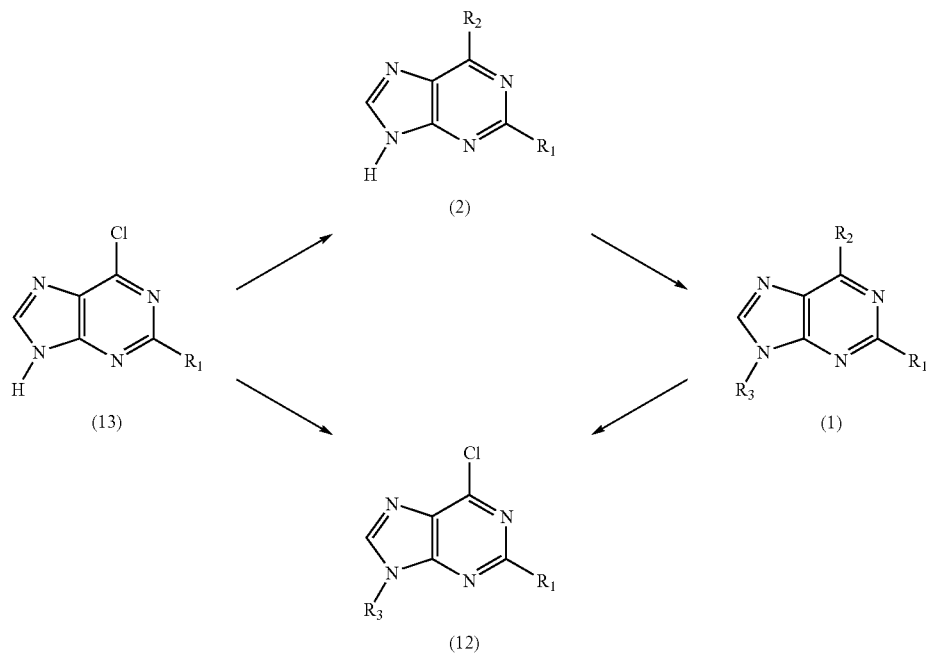

Compounds of formula (1) where $R_1$ is alkyl or aryl are prepared from compounds of formula (2) where $R_1$ is alkyl or aryl by standard methods such as those described above. Alternatively compounds of formula (1) where $R_1$ is alkyl or where the alkyl or aryl group mentioned above contains an amino substituent this may be converted to an alkylamino or dialkylamino group by standard methods such as alkylation or reductive alkylation, or to an amide, carbamate, urea or sulphonamide by standard methods such as those described above. Additionally, for example, where the alkyl or aryl group mentioned above contains a carboxylic ester substituent this may be converted to an amide or hydrazide derivative by standard methods such as reaction with an amine or hydrazine directly or in the presence of a catalyst such as $Me_3Al$ if required. It will be appreciated by those skilled in the art that substituents such as an amino group or a carboxylic ester group may also be transformed by standard methods to a wide range of additional substituent groups.

According to a further aspect of the invention, there is provided a pharmaceutical composition comprising a compound of formula (I) in combination with a pharmaceutically acceptable carrier or excipient and a method of making such a composition comprising combining a compound of the present invention with a pharmaceutically acceptable carrier or excipient.

The pharmaceutical compositions employed in the present invention comprise a compound of formula (I), or pharmaceutically acceptable salts or prodrugs thereof, and may also contain a pharmaceutically acceptable carrier and optionally other therapeutic ingredients known to those skilled in the art. The term, "pharmaceutically acceptable salts", refers to salts prepared from pharmaceutically acceptable non-toxic acids including inorganic acids and organic acids.

Where the compounds of formula (I) are basic, salts may be prepared from pharmaceutically acceptable non-toxic acids including inorganic and organic acids. Such acids include acetic, benzenesulfonic, benzoic, camphorsulfonic, citric, ethenesulfonic, fumaric, gluconic, glutamic, hippuric, hydrobromic, hydrochloric, isethionic, lactic, maleic, malic, mandelic, methanesulfonic, mucic, nitric, pamoic, pantothenic, phosphoric, succinic, sulfuric, tartaric, oxalic, p-toluenesulfonic and the like. Particularly preferred are hydrochloric, hydrobromic, phosphoric, and sulfuric acids, and most particularly preferred is the hydrochloride salt.

Any suitable route of administration may be employed for providing the patient with an effective dosage of a compound of formula (I). For example, oral, rectal, parenteral (intravenous, intramuscular), transdermal, subcutaneous, and the like may be employed. Dosage forms include tablets, troches, dispersions, suspensions, solutions, capsules, patches, and the like. The most suitable route in any given case will depend on the severity of the condition being treated. The most preferred route of administration is the oral route. The compositions may be conveniently presented in unit dosage form and prepared by any of the methods well known in the art of pharmacy.

In practical use, the compounds of formula (I) can be combined as the active ingredient in intimate admixture with a pharmaceutical carrier according to conventional pharmaceutical compounding techniques. The carrier may take a wide variety of forms depending on the form of preparation desired for administration, e.g. oral or parenteral (e.g. intravenous). In preparing the compositions for oral dosage form, any of the usual pharmaceutical media may be employed as carriers, such as, for example, water, glycols, oils, alcohols, flavouring agents, preservatives, colouring agents, and the like in the case of oral liquid preparations (such as suspensions, solutions and elixirs) or aerosols; or carriers such as starches, sugars, micro-crystalline cellulose, diluents, granulating agents, lubricants, binders, disintegrating agents, and the like may be used in the case of oral solid preparations such as, for example, powders, capsules, and tablets, with the solid oral preparations being preferred over the liquid preparations. The most preferred solid oral preparation is tablets.

Because of their ease of administration, tablets and capsules represent the most advantageous oral dosage unit form in which case solid pharmaceutical carriers are employed. If desired, tablets may be coated by standard aqueous or non-aqueous techniques.

In addition to the common dosage forms set out above, the compounds of formula (I) may also be administered by controlled release means and/or delivery devices such as those described in U.S. Pat. Nos. 3,845,770; 3,916,899; 3,536,809; 3,598,123; 3,630,200; 4,008,719; 4,687,660; and 4,769,027, the disclosures of which are hereby incorporated by reference.

Pharmaceutical compositions suitable for oral administration may be presented as discrete units such as capsules, cachets, or tablets, or aerosol sprays each containing a predetermined amount of the active ingredient as a powder or granules, a solution or a suspension in an aqueous liquid, an oil-in-water emulsion, or a water-in-oil liquid emulsion. Such compositions may be prepared by any of the methods of pharmacy, but all methods include the step of bringing the active ingredient into association with the carrier which constitutes one or more necessary ingredients. In general, the compositions are prepared by uniformly and intimately admixing the active ingredient with liquid carriers or finely divided solid carriers or both, and then, if necessary, shaping the product into the desired presentation.

For example, a tablet may be prepared by compression or moulding, optionally with one or more accessory ingredients. Compressed tablets may be prepared by compressing in a suitable machine the active ingredient in a free-flowing form such as powder or granules, optionally mixed with a binder, a lubricant, an inert diluent, and/or a surface active or dispersing agent. Moulded tablets may be made by moulding in a suitable machine a mixture of the powdered compound moistened with an inert liquid diluent.

The invention is further defined by reference to the following examples. It will be apparent to those skilled in the art that many modifications, both to materials and methods, may be practised without departing from the purpose and interest of this invention.

EXAMPLES

Synthetic Examples

The invention is illustrated with reference to the Examples set out in Table 1. The syntheses of the Examples are performed using the general Synthetic Methods set out hereinafter. The Method used for a given Example is noted in parentheses in column 1 of Table 1. Table 2 includes the analytical data for the compounds.

TABLE 1

| Example | Structure | Compound Name |
|---|---|---|
| 1 (A) | 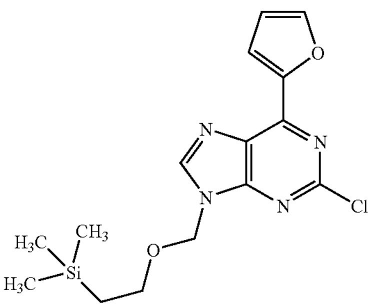 | 2-Chloro-6-(2-furyl)-9-(2-trimethylsilylethoxymethyl)-9H-purine |
| 2 (B) | 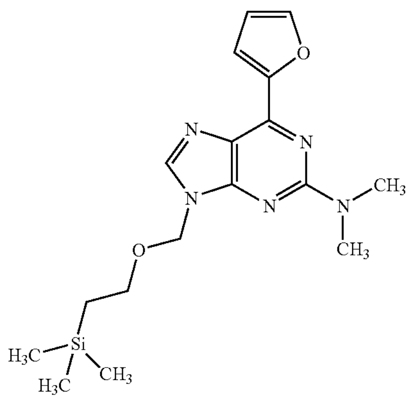 | N,N-Dimethyl-6-(2-furyl)-9-(2-trimethylsilylethoxymethyl)-9H-purine-2-amine |
| 3 (C) | 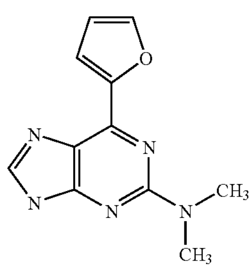 | N,N-Dimethyl-6-(2-furyl)-1H-purine-2-amine |
| 4 (B) | 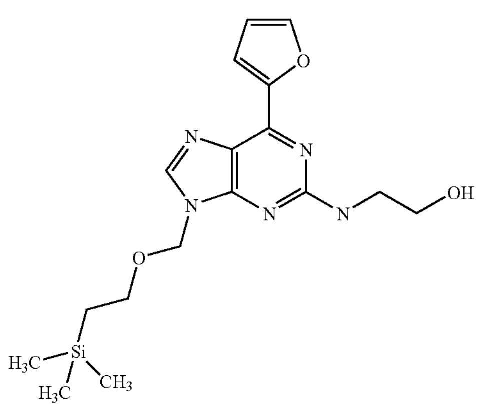 | 6-(2-Furyl)-N-(2-hydroxyethyl)-9-(2-trimethylsilylethoxymethyl)-9H-purine-2-amine |

TABLE 1-continued
| Example | Structure | Compound Name |
|---|---|---|
| 5 (C) | 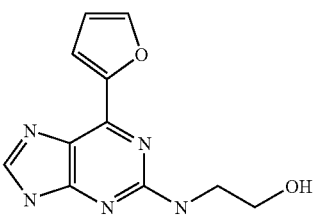 | N-(2-Hydroxyethyl)-6-(2-furyl)-1H-purine-2-amine |
| 6 (S) | 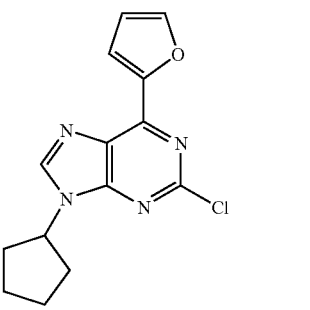 | 2-Chloro-9-cyclopentyl-6-(2-furyl)-9H-purine |
| 7 (A) | 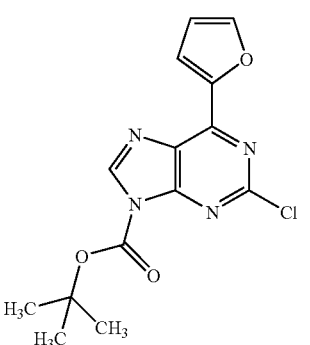 | tert-Butyl 2-chloro-6-(2-furyl)-9H-purine-9-carboxylate |
| 8 (A) | 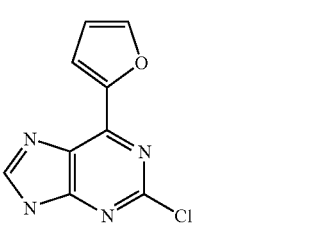 | 2-Chloro-6-(2-furyl)-1H-purine |
| 9 (B) | 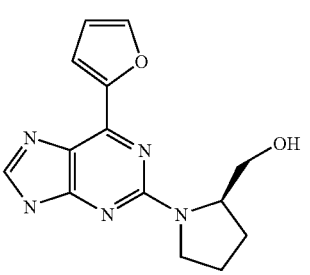 | (2R)-1-(6-(2-Furyl)-1H-purine-2-yl)-2-pyrrolidinemethanol |

TABLE 1-continued

| Example | Structure | Compound Name |
|---|---|---|
| 10 (B) | 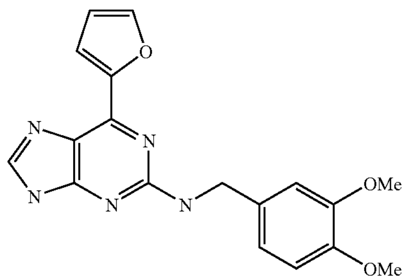 | N-(3,4-Dimethoxybenzyl)-6-(2-furyl)-1H-purine-2-amine |
| 11 (D) | 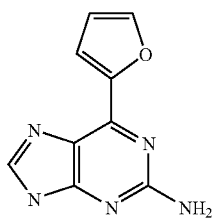 | 6-(2-Furyl)-1H-purine-2-amine |
| 12 (E) | 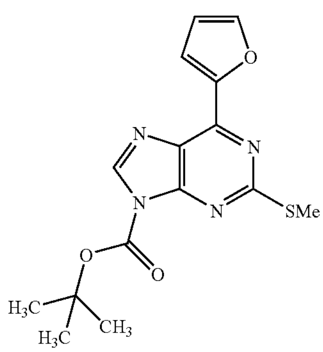 | tert-Butyl 6-(2-furyl)-2-methylthio-9H-purine-9 carboxylate |
| 13 (F) | 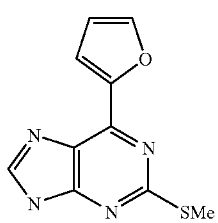 | 6-(2-Furyl)-2-methylthio-1H-purine |
| 14 (A) | 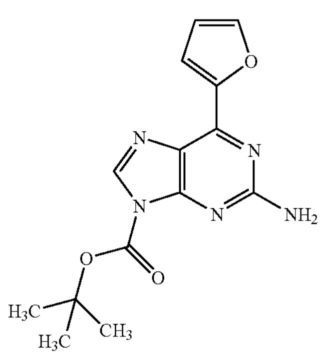 | tert-Butyl 2-amino-6-(2-furyl)-9H-purine-9-carboxylate |

TABLE 1-continued
| Example | Structure | Compound Name |
|---|---|---|
| 15 (B) | 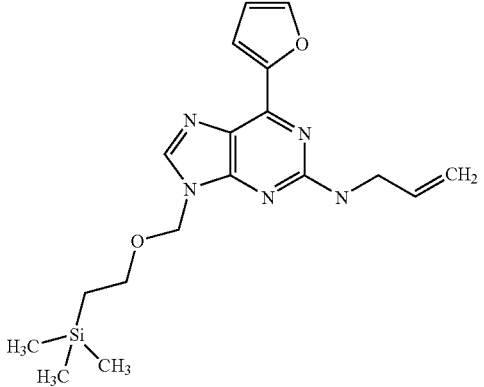 | N-Allyl-6-(2-furyl)-9-(2-trimethylsilylethoxymethyl)-9H-purine-2-amine |
| 16 (B) | 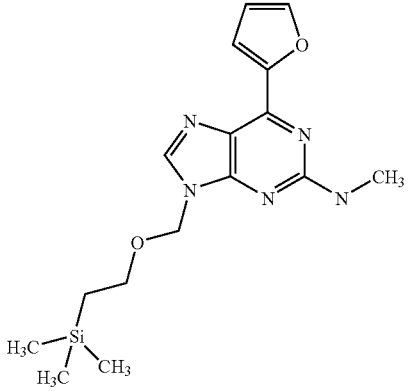 | 6-(2-Furyl)-N-methyl-9-(2-trimethylsilylethoxymethyl)-9H-purine-2-amine |
| 17 (C) | 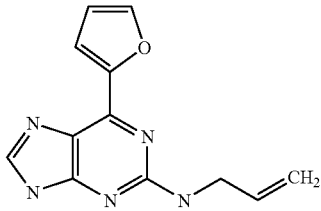 | N-Allyl-6-(2-furyl)-1H-purine-2-amine |
| 18 (C) | 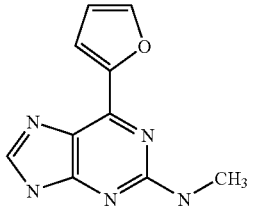 | 6-(2-Furyl)-N-methyl-1H-purine-2-amine |

TABLE 1-continued
| Example | Structure | Compound Name |
|---|---|---|
| 19 (A) | 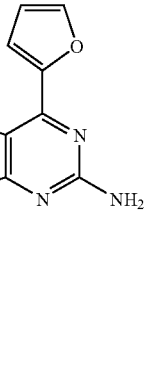 | 2-Amino-N-cyclohexyl-6-(2-furyl)-9H-purine-9-carboxamide |
| 20 (A) | 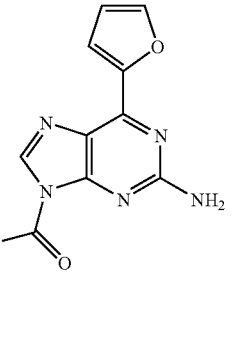 | 2-Methylpropyl 2-amino-6-(2-furyl)-9H-purine-9-carboxylate |
| 21 (A) | 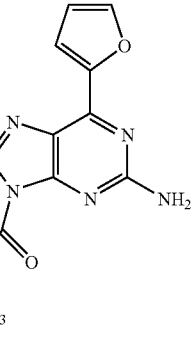 | 2-Amino-N-tert-butyl-6-(2-furyl)-9H-purine-9-carboxamide |
| 22 (A) | 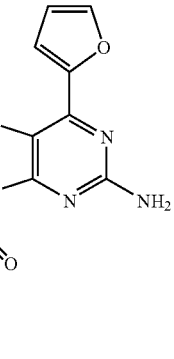 | Phenyl 2-amino-6-(2-furyl)-9H-purine-9-carboxylate |

TABLE 1-continued

| Example | Structure | Compound Name |
|---|---|---|
| 23 (A) | 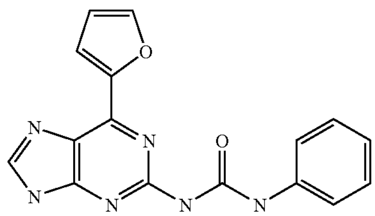 | N-(6-(2-Furyl)-1H-purine-2-yl)-N'-phenylurea |
| 24 (A) | 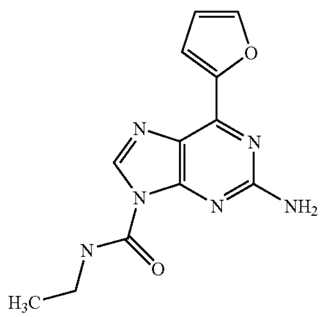 | 2-Amino-N-ethyl-6-(2-furyl)-9H-purine-9-carboxamide |
| 25 (A) | 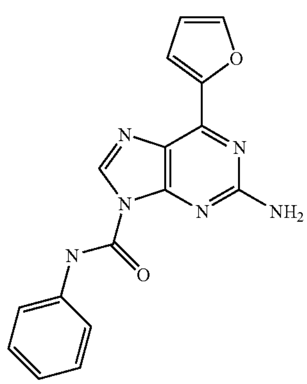 | 2-Amino-6-(2-furyl)-N-phenyl-9H-purine-9-carboxamide |
| 26 (G) | 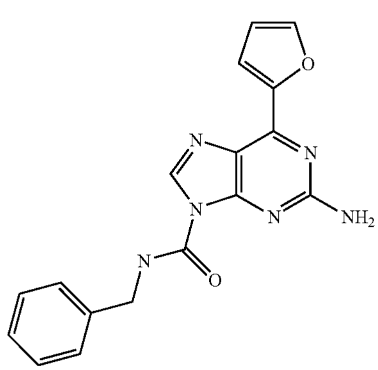 | 2-Amino-N-benzyl-6-(2-furyl)-9H-purine-9-carboxamide |

TABLE 1-continued

| Example | Structure | Compound Name |
|---|---|---|
| 27 (H) | 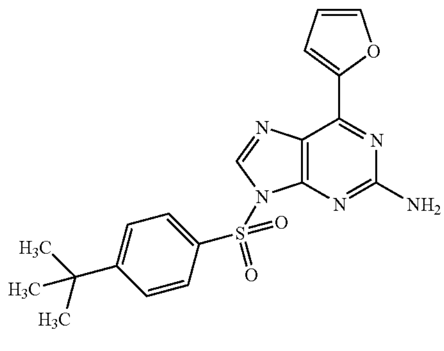 | 9-(4-tert-Butylphenylsulphonyl)-6-(2-furyl)-9H-purine-2-amine |
| 28 (H) | 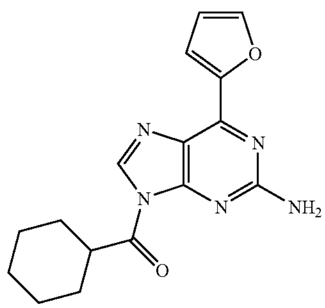 | 9-Cyclohexylcarbonyl-6-(2-furyl)-9H-purine-2-amine |
| 29 (I) | 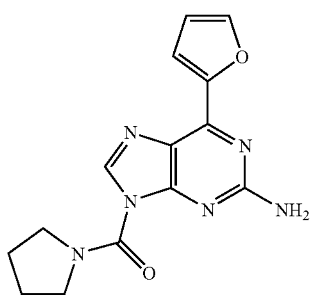 | 6-(2-Furyl)-9-(1-pyrrolidinylcarbonyl)-9H-purine-2-amine |
| 30 (G) | 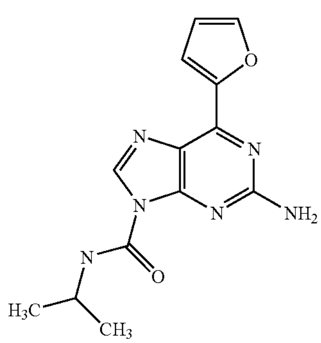 | 2-Amino-6-(2-furyl)N-isopropyl-9H-purine-9-carboxamide |

TABLE 1-continued

| Example | Structure | Compound Name |
|---|---|---|
| 31 (A) | 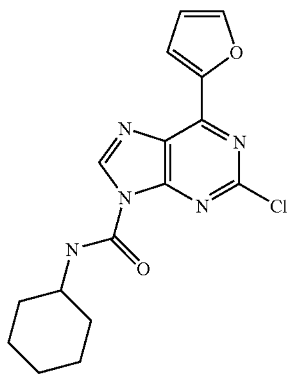 | 2-Chloro-N-cyclohexyl-6-(2-furyl)-9H-purine-9-carboxamide |
| 33 (H) | 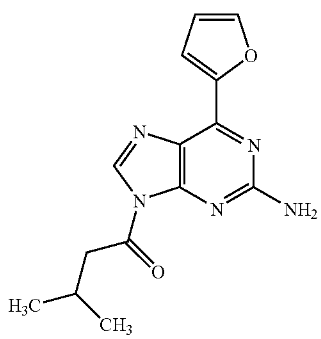 | 6-(2-Furyl)-9-(3-methylbutyryl)-9H-purine-2-amine |
| 34 (H) | 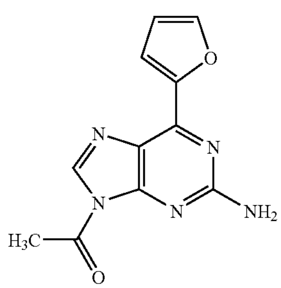 | 9-Acetyl-6-(2-furyl)-9H-purine-2-amine |
| 35 (G) | 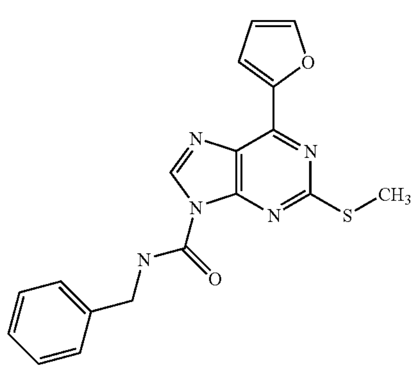 | N-Benzyl-6-(2-furyl)-2-methylthio-9H-purine-9-carboxamide |

TABLE 1-continued
| Example | Structure | Compound Name |
|---|---|---|
| 36 (G) | 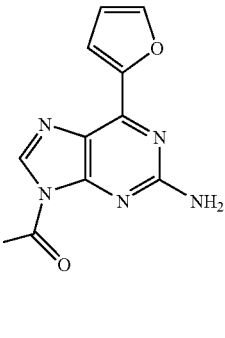 | 2-Amino-N-n-butyl-6-(2-furyl)-9H-purine-9-carboxamide |
| 37 (G) | 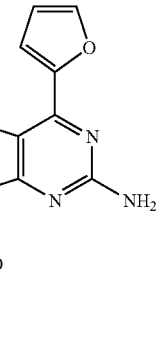 | 2-Amino-6-(2-furyl)-N-(4-methoxybenzyl)-9H-purine-9-carboxamide |
| 38 (G) | 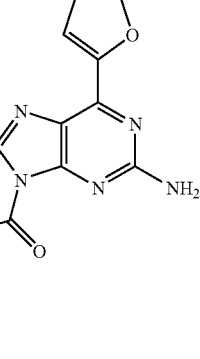 | 2-Amino-6-(2-furyl)-N-(4-methylbenzyl)-9H-purine-9-carboxamide |
| 39 (G) | 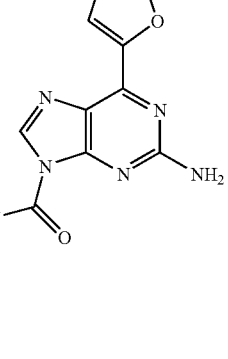 | 2-Amino-N-(2-chlorobenzyl)-6-(2-furyl)-9H-purine-9-carboxamide |

TABLE 1-continued
| Example | Structure | Compound Name |
|---|---|---|
| 40 (G) | 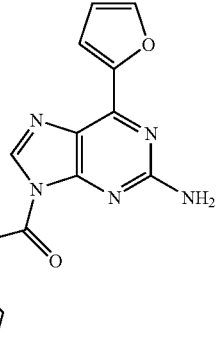 | 2-Amino-6-(2-furyl)-N-(l-naphthyl)-9H-purine-9-carboxamide |
| 41 (G) | 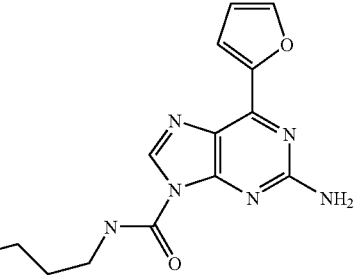 | 2-Amino-6-(2-furyl)-N-n-heptyl-9H-purine-9 carboxamide |
| 42 (G) | 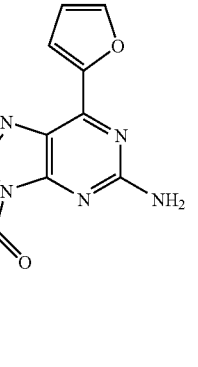 | 2-Amino-6-(2-furyl)-N-(2-methylphenyl)-9H-purine-9-carboxamide |
| 43 (G) | 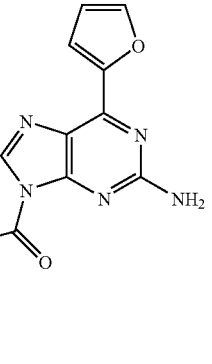 | 2-Amino-6-(2-furyl)-N-(3-methylphenyl)-9H-purine-9-carboxamide |

TABLE 1-continued
| Example | Structure | Compound Name |
|---|---|---|
| 44 (G) | 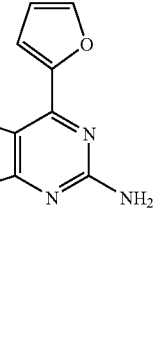 | 2-Amino-N-(2-chlorophenyl)-6-(2-furyl)-9H-purine-9-carboxamide |
| 45 (G) | 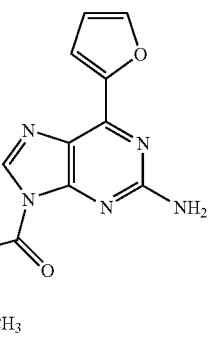 | (1S)-2-Amino-6-(2-furyl)-N-(1-phenyethyl)-9H-purine-9-carboxamide |
| 46 (G) | 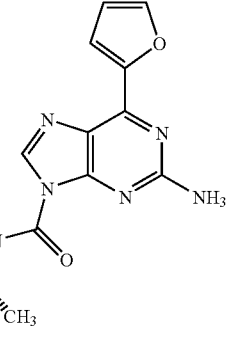 | (1R)-2-Amino-6-(2-furyl)-N-(1-phenylethyl)-9H-purine-9-carboxamide |
| 47 (G) | 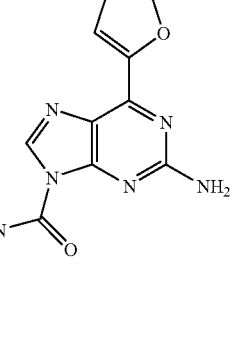 | 2-Amino-6-(2-furyl)-N-(3-methylbenzyl)-9H-purine-9-carboxamide |

TABLE 1-continued

| Example | Structure | Compound Name |
|---|---|---|
| 48 (G) | 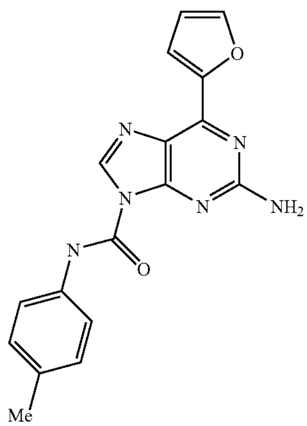 | 2-Amino-6-(2-furyl)-N-(4-methylphenyl)-9H-purine-9-carboxamide |
| 49 (G) | 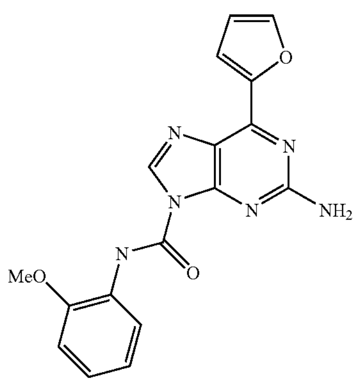 | 2-Amino-6-(2-furyl)-N-(2-methoxyphenyl)-9H-purine-9-carboxamide |
| 50 (G) | 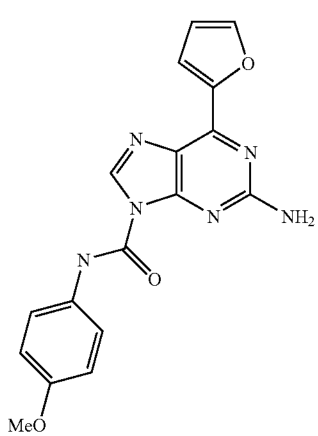 | 2-Amino-6-(2-furyl)-N-(4-methoxyphenyl)-9H-purine-9-carboxamide |

TABLE 1-continued
| Example | Structure | Compound Name |
|---|---|---|
| 51 (G) | 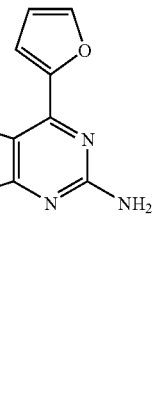 | 2-Amino-N-(4-chlorophenyl)-6-(2-furyl)-9H-purine-9-carboxamide |
| 52 (G) | 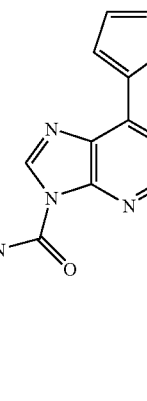 | 2-Amino-6-(2-furyl)-N-n-pentyl-9H-purine-9-carboxamide |
| 53 (G) | 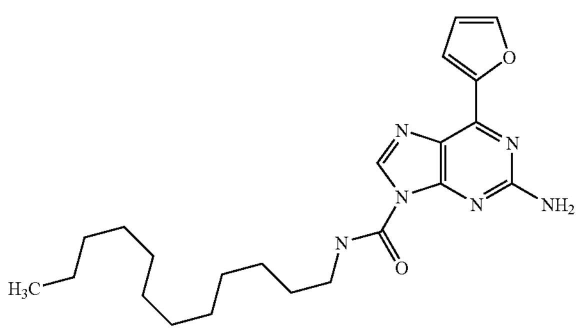 | 2-Amino-N-n-dodecyl-6-(2-furyl)-9H-purine-9-carboxamide |
| 54 (K) | 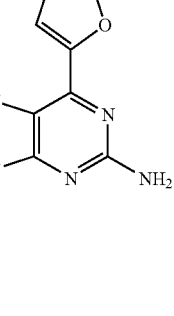 | 9-(2-Cyclohexylethyl)-6-(2-furyl)-9H-purine-2-amine |

TABLE 1-continued

| Example | Structure | Compound Name |
|---|---|---|
| 55 (G) | 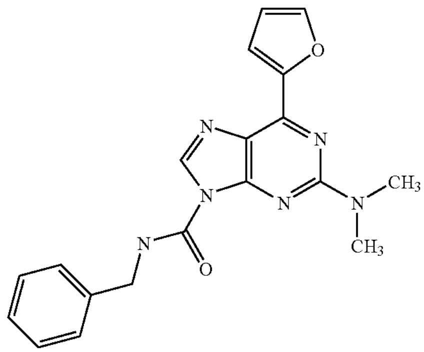 | N-Benzyl-2-dimethylamino-6-(2-furyl)-9H-purine-9-carboxamide |
| 56 (H) | 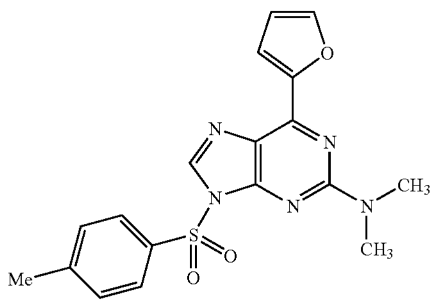 | N,N-Dimethyl-6-(2-furyl)-9-(4-methylphenylsulphonyl)-9H-purine-2-amine |
| 57 (K) | 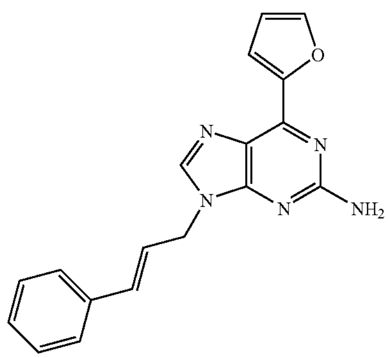 | 6-(2-Furyl)-9-(1-phenyl-1-propene-3-yl)-9H-purine-2-amine |
| 58 (K) | 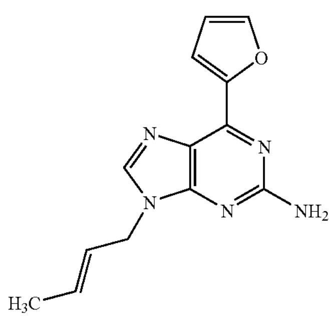 | 9-(But-2-ene-4-yl)-6-(2-furyl)-9H-purine-2-amine |

TABLE 1-continued
| Example | Structure | Compound Name |
|---|---|---|
| 59 (K) | 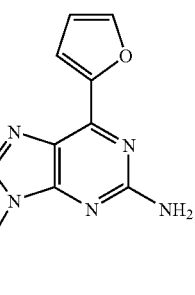 | 9-n-Butyl-6-(2-furyl)-9H-purine-2-amine |
| 60 (K) | 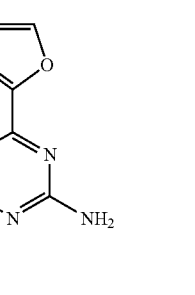 | 9-Cyclopentyl-6-(2-furyl)-9H-purine-2-amine |
| 61 (K) | 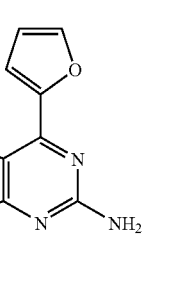 | 6-(2-Furyl)-9-isopropyl-9H-purine-2-amine |
| 62 (K) | 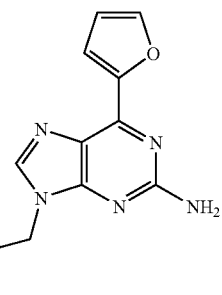 | 6-(2-Furyl)-9-(4-phenylbutyl)-9H-purine-2-amine |

TABLE 1-continued

| Example | Structure | Compound Name |
|---|---|---|
| 63 (K) | 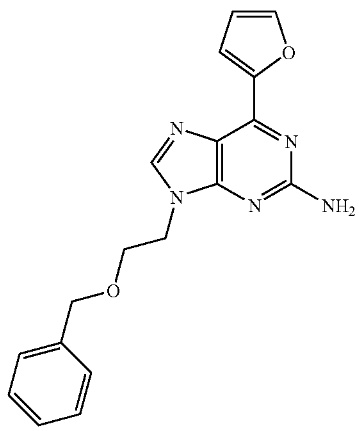 | 9-(2-Benzyloxyethyl)-6-(2-furyl)-9H-purine-2-amine |
| 64 (K) | 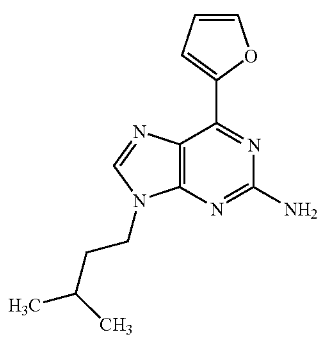 | 6-(2-Furyl)-9-(3-methylbutyl)-9H-purine-2-amine |
| 65 (K) | 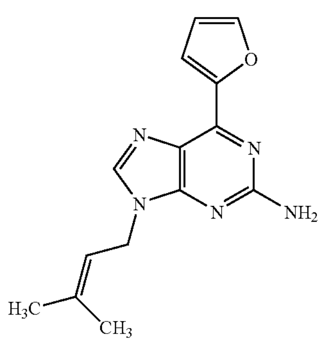 | 6-(2-Furyl)-9-(2-methyl-2-buten-4-yl)-9H-purine-2-amine |
| 66 (K) | 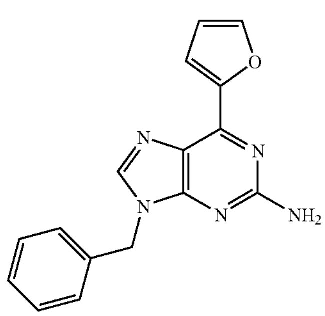 | 9-Benzyl-6-(2-furyl)-9H-purine-2-amine |

TABLE 1-continued

| Example | Structure | Compound Name |
|---|---|---|
| 67 (K) | 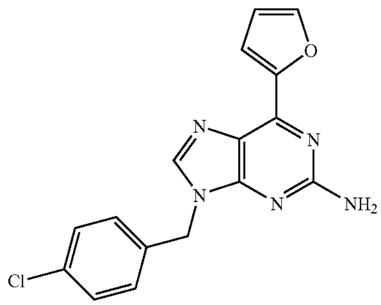 | 9-(4-Chlorobenzyl)-6-(2-furyl)-9H-purine-2-amine |
| 68 (K) | 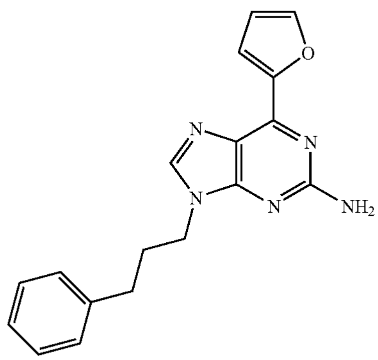 | 6-(2-Furyl)-9-(3-phenylpropyl)-9H-purine-2-amine |
| 69 (X) | 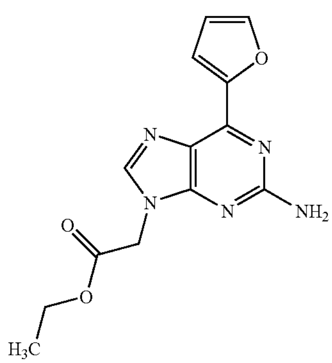 | Ethyl 2-amino-6-(2-furyl)-9H-purine-9-acetate |
| 70 (L) | 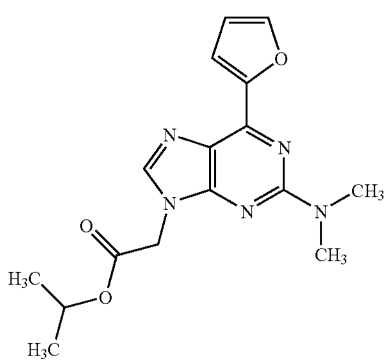 | Isopropyl 2-dimethylamino-6-(2-furyl)-9H-purine-9-acetate |

TABLE 1-continued
| Example | Structure | Compound Name |
|---|---|---|
| 71 (B) | 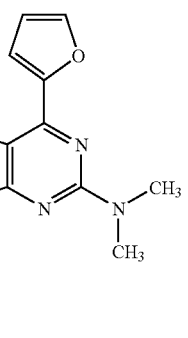 | Ethyl 2-dimethylamino-6-(2-furyl)-9H-purine-9-acetate |
| 72 (A) | 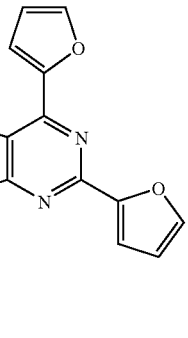 | Ethyl 2,6-bis(2-furyl)-9H-purine-9-acetate |
| 73 (M) | 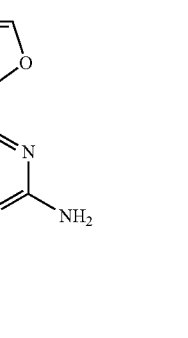 | 2-Amino-6-(2-furyl)-9H-purine-9-acetic acid |
| 74 (N) | 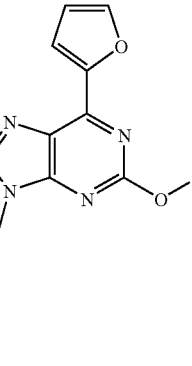 | 6-(2-Furyl)-2-methoxy-9-(2-trimethylsilylethoxymethyl)-9H-purine |

TABLE 1-continued

| Example | Structure | Compound Name |
|---|---|---|
| 75 (C) | 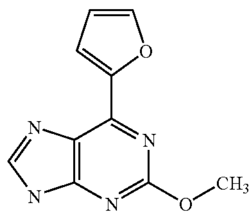 | 6-(2-Furyl)-2-methoxy-1H-purine |
| 76 (O) | 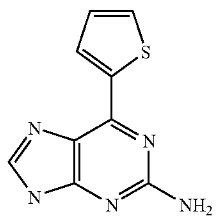 | 6-(2-Thienyl)-1H-purine-2-amine |
| 77 (G) | 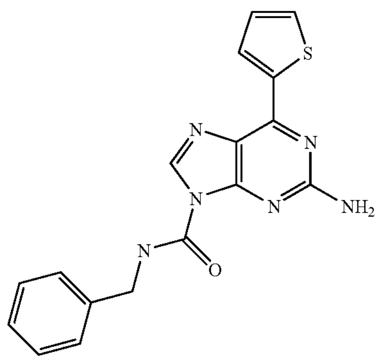 | 2-Amino-N-benzyl-6-(2-thienyl)-9H-purine-9-carboxamide |
| 78 (A) | 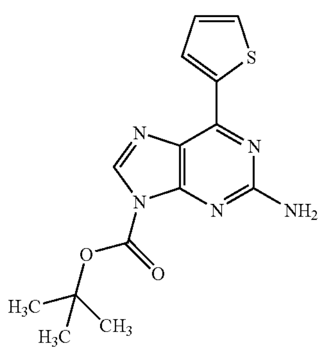 | tert-Butyl 2-amino-6-(2-thienyl)-9H-purine-9-carboxylate |
| 79 (G) | 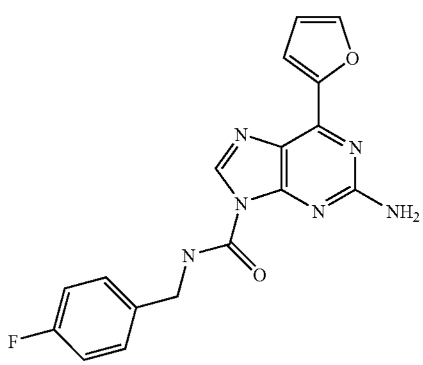 | 2-Amino-N-(4-fluorobenzyl)-6-(2-furyl)-9H-purine-9-carboxamide |

TABLE 1-continued
| Example | Structure | Compound Name |
|---|---|---|
| 80 (G) | 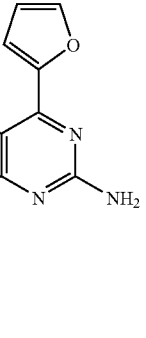 | 2-Amino-N-(3,4-dichlorobenzyl)-6-(2-furyl)-9H-purine-9-carboxamide |
| 81 (K) | 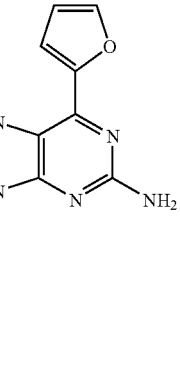 | 6-(2-Furyl)-9-(2-phenylethyl)-9H-purine-2-amine |
| 82 (K) | 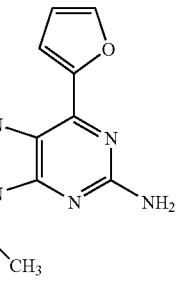 | 9-(1-(4-Fluorophenyl)ethyl)-6-(2-furyl)-9H-purine-2-amine |
| 83 (K) | 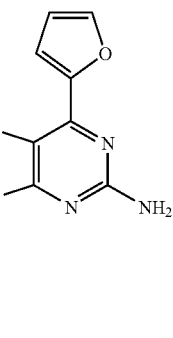 | 6-(2-Furyl)-9-(4-isopropylbenzyl)-9H-purine-2-amine |

TABLE 1-continued

| Example | Structure | Compound Name |
|---|---|---|
| 84 (K) | 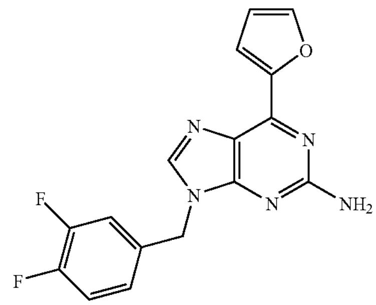 | 9-(3,4-Difluorobenzyl)-6-(2-furyl)-9H-purine-2-amine |
| 85 (P) | 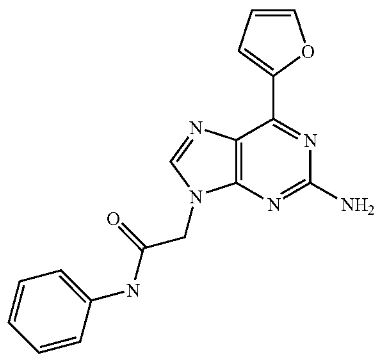 | 2-Amino-6-(2-furyl)-N-phenyl-9H-purine-9-acetamide |
| 86 (Q) | 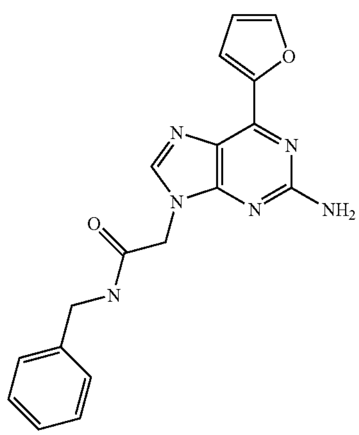 | 2-Amino-N-benzyl-6-(2-furyl)-9H-purine-9-acetamide |
| 87 (Q) | 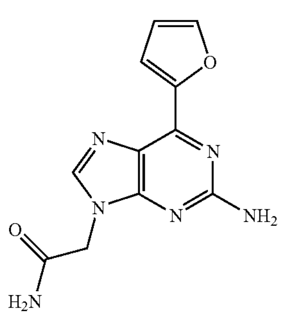 | 2-Amino-6-(2-furyl)-9H-purine-9-acetamide |

TABLE 1-continued

| Example | Structure | Compound Name |
|---|---|---|
| 88 (Q) | 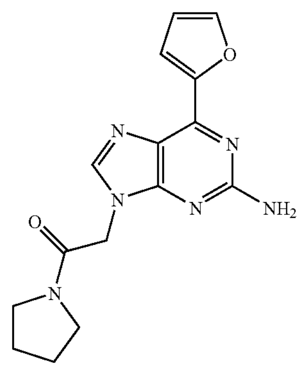 | 6-(2-Furyl)-9-(2-oxo-2-(1-pyrrolidinyl)ethyl)-9H-purine-2-amine |
| 89 (Q) | 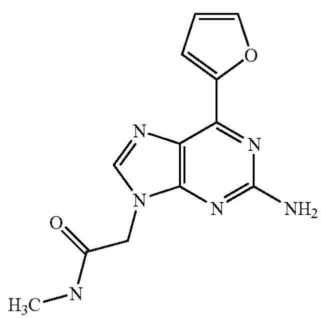 | 2-Amino-6-(2-furyl)-N-methyl-9H-purine-9-acetamide |
| 90 (R) | 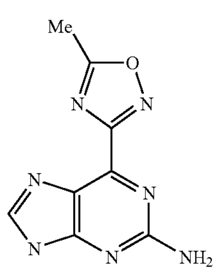 | 6-(5-Methyl-[1,2,4]-oxadiazol-3-yl)-1H-purine-2-amine |
| 91 (G) | 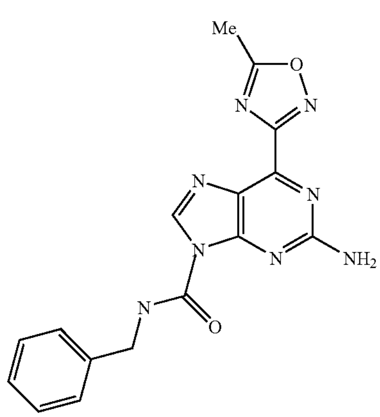 | 2-Amino-N-benzyl-6-(5-methyl-[1,2,4]-oxadiazol-3-yl)-9H-purine-9-carboxamide |

TABLE 1-continued
| Example | Structure | Compound Name |
|---|---|---|
| 92 (G) | 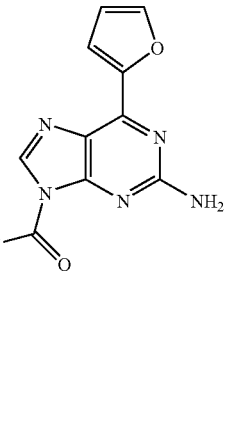 | 2-Amino-6-(2-furyl)-N-(2-phenylethyl)-9H-purine-9-carboxamide |
| 93 (G) | 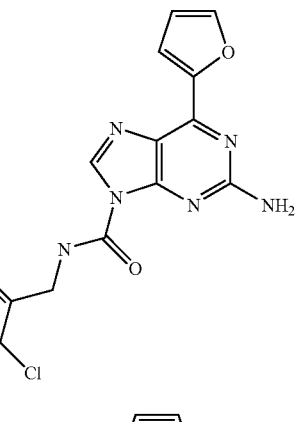 | 2-Amino-N-(2,4-dichlorobenzyl)-6-(2-furyl)-9H-purine-9-carboxamide |
| 94 (G) | 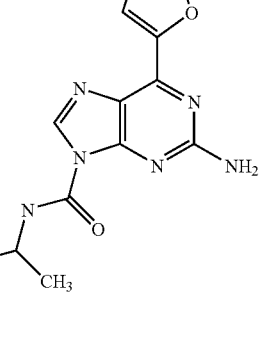 | (1RS)-2-Amino-6-(2-furyl)-N-(1-(1-naphthyl)ethyl)-9H-purine-9-carboxamide |
| 95 (G) | 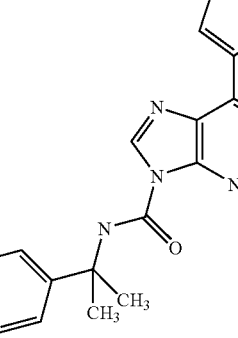 | 2-Amino-6-(2-furyl)-N-(2-(3-isopropenylphenyl)-2-propyl)-9H-purine-9-carboxamide |

TABLE 1-continued

| Example | Structure | Compound Name |
|---|---|---|
| 96 (Q) | 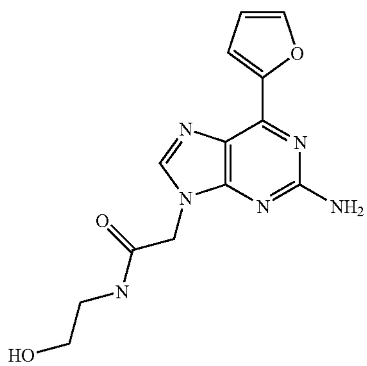 | 2-Amino-6-(2-furyl)-N-(2-hydroxyethyl)-9H-purine-9-acetamide |
| 97 (Q) | 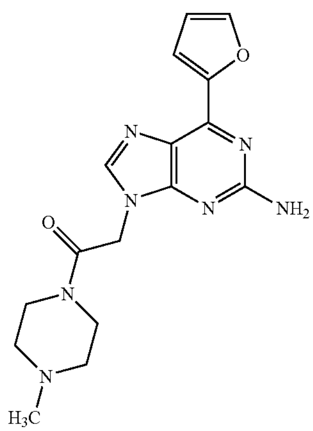 | 6-(2-Furyl)-9-(2-oxo-2-(4-methyl-1-piperazinyl)ethyl)-9H-purine-2-amine |
| 98 (G) | 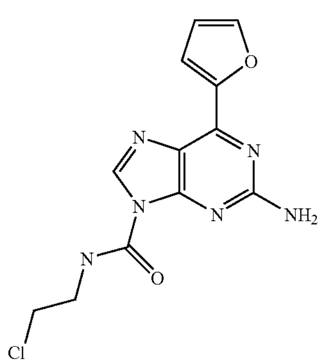 | 2-Amino-N-(2-chloroethyl)-6-(2-furyl)-9H-purine-9-carboxamide |
| 99 (G) | 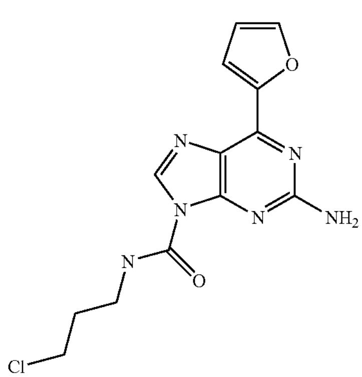 | 2-Amino-N-(3-chloropropyl)-6-(2-furyl)-9H-purine-9-carboxamide |

TABLE 1-continued

| Example | Structure | Compound Name |
|---|---|---|
| 100 (G) | 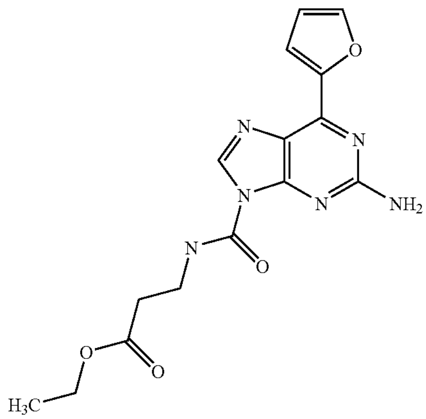 | Ethyl 3-(2-Amino-6-(2-furyl)-9H-purine-9-yl)carbonylaminopropionate |
| 101 (G) | 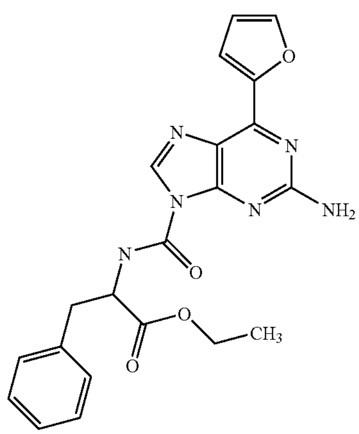 | Ethyl 2-(2-Amino-6-(2-furyl)-9H-purine-9-yl)carbonylamino-3-phenylpropionate |
| 102 (S) | 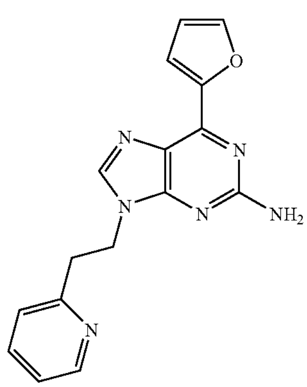 | 6-(2-Furyl)-9-(2-(2-pyridyl)ethyl)-9H-purine-2-amine |

TABLE 1-continued

| Example | Structure | Compound Name |
|---|---|---|
| 103 (S) | 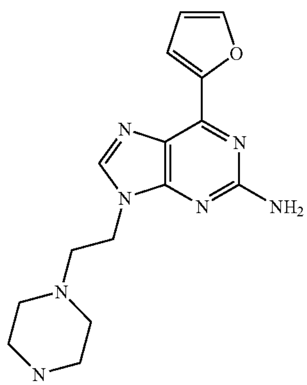 | 6-(2-Furyl)-9-(2-(1-piperazinyl)ethyl)-9H-purine-2-amine |
| 104 (S) | 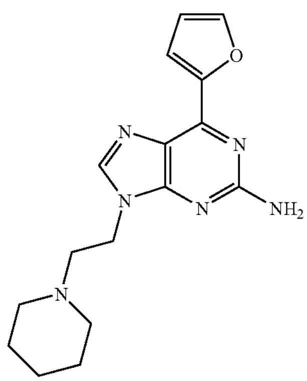 | 6-(2-Furyl)-9-(2-(1-piperidinyl)ethyl)-9H-purine-2-amine |
| 105 (S) | 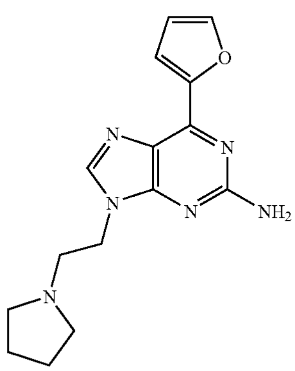 | 6-(2-Furyl)-9-(2-(1-pyrrolidinyl)ethyl)-9H-purine-2-amine |
| 106 (T) | 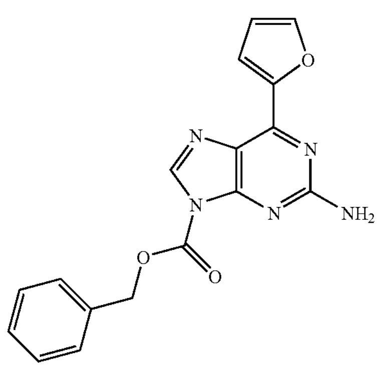 | Benzyl 2-amino-6-(2-furyl)-9H-purine-9-carboxylate |

TABLE 1-continued

| Example | Structure | Compound Name |
|---|---|---|
| 112 (G) | 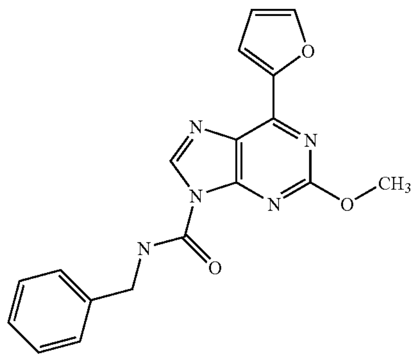 | N-Benzyl-2-methoxy-6-(2-furyl)-9H-purine-9-carboxamide |
| 113 (S) | 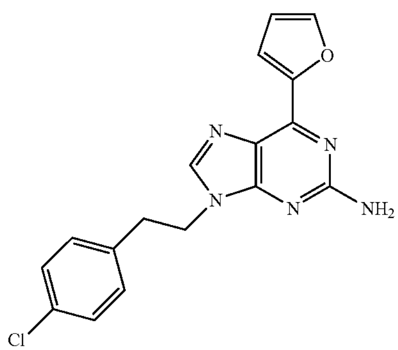 | 9-(2-(4-Chlorophenyl)ethyl)-6-(2-furyl)-9H-purine-2-amine |
| 114 (S) | 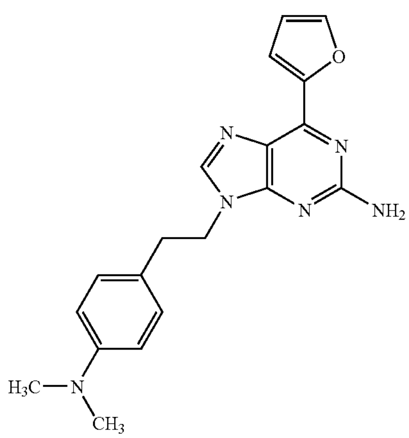 | 9-(2-(4-Dimethylaminophenyl)ethyl)-6-(2-furyl)-9H-purine-2-amine |
| 115 (S) | 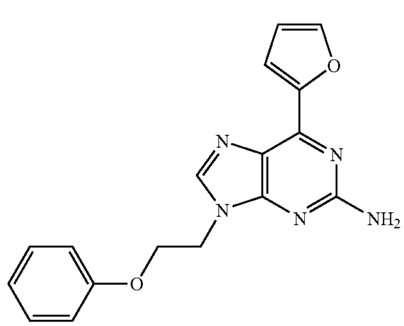 | 6-(2-Furyl)-9-(2-phenoxyethyl)-9H-purine-2-amine |

TABLE 1-continued

| Example | Structure | Compound Name |
|---|---|---|
| 116 (S) | 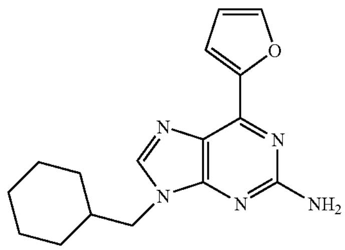 | 9-Cyclohexylmethyl-6-(2-furyl)-9H-purine-2-amine |
| 117 (S) | 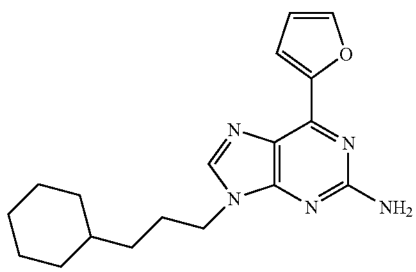 | 9-(3-Cyclohexylpropyl)-6-(2-furyl)-9H-purine-2-amine |
| 118 (I) | 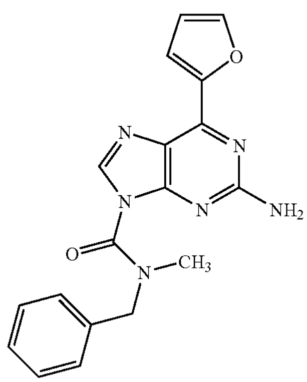 | 2-Amino-N-benzyl-6-(2-furyl)-N-methyl-9H-purine-9-carboxamide |
| 119 (Q) | 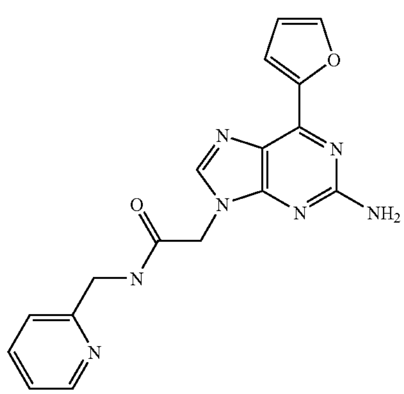 | 2-Amino-6-(2-furyl)-N-(2-pyridylmethyl)-9H-purine-9-acetamide |

TABLE 1-continued

| Example | Structure | Compound Name |
|---|---|---|
| 120 (O) | 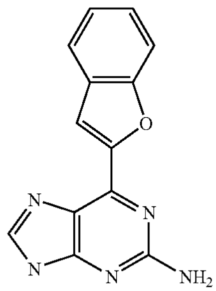 | 6-(Benzofuran-2-yl)-1H-purine-2-amine |
| 122 (Q) | 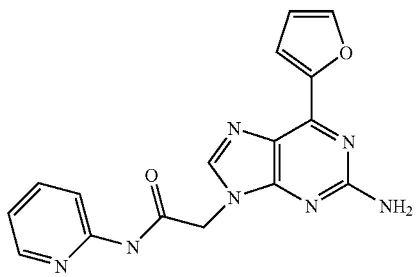 | 2-Amino-6-(2-furyl)-N-(2-pyridyl)-9H-purine-9-acetamide |
| 123 (Q) | 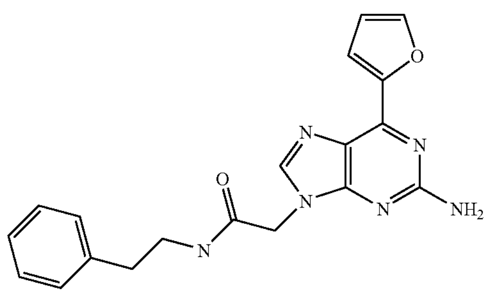 | 2-Amino-6-(2-furyl)-N-(2-phenylethyl)-9H-purine-9-acetamide |
| 124 (Q) | 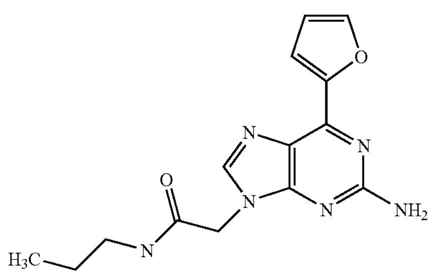 | 2-Amino-6-(2-furyl)-N-n-propyl-9H-purine-9-acetamide |
| 125 (S) | 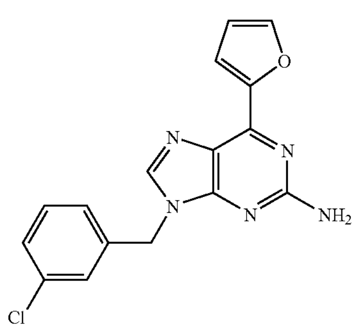 | 9-(3-Chlorobenzyl)-6-(2-furyl)-9H-purine-2-amine |

TABLE 1-continued
| Example | Structure | Compound Name |
|---|---|---|
| 126 (S) | 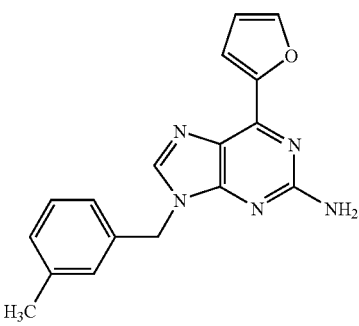 | 6-(2-Furyl)-9-(3-methylbenzyl)-9H-purine-2-amine |
| 127 (S) | 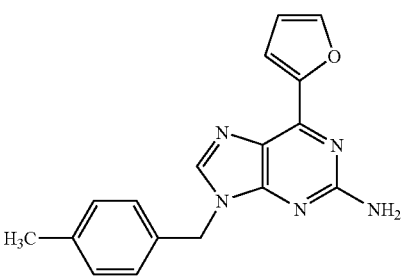 | 6-(2-Furyl)-9-(4-methylbenzyl)-9H-purine-2-amine |
| 128 (G) | 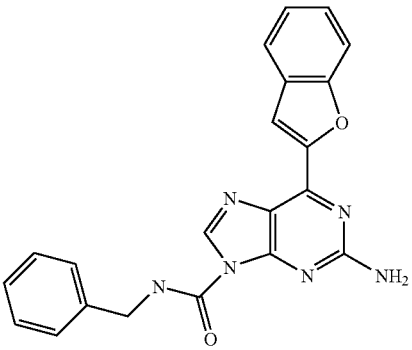 | 2-Amino-6-(benzofuran-2-yl)-N-benzyl-9H-purine-9-carboxamide |
| 129 (O) | 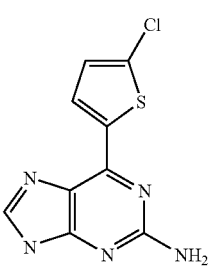 | 6-(5-Chloro-2-thienyl)-1H-purine-2-amine |

TABLE 1-continued
| Example | Structure | Compound Name |
|---|---|---|
| 130 (G) | 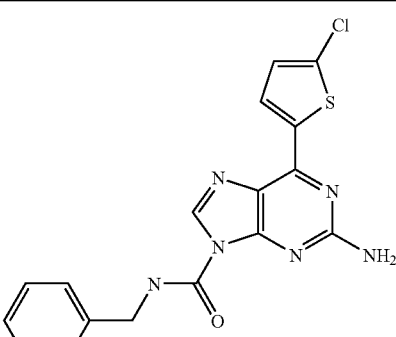 | 2-Amino-N-benzyl-6-(5-chloro-2-thienyl)-9H-purine-9-carboxamide |
| 131 (I) | 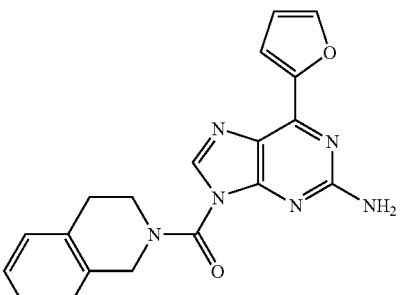 | 6-(2-Furyl)-9-(1,2,3,4-tetrahydroisoquinolin-2-ylcarbonyl)-9H-purine-2-amine |
| 132 (I) | 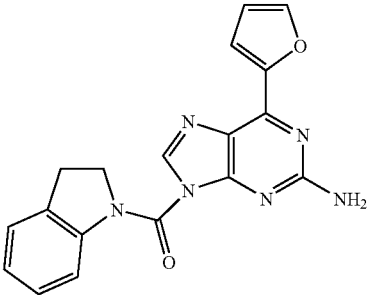 | 6-(2-Furyl)-9-(1-indolinylcartbonyl)-9H-purine-2-amine |
| 133 (A) | 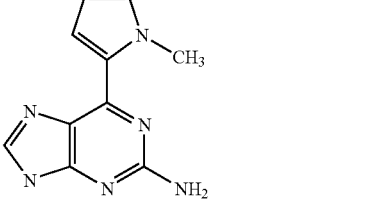 | 6-(1-Methyl-1H-pyrrol-2-yl)-1H-purine-2-amine |
| 134 (G) | 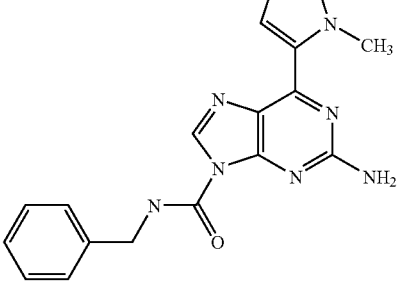 | 2-Amino-N-benzyl-6-(1-methyl-1H-pyrrol-2-yl)-9H-purine-9-carboxamide |

TABLE 1-continued

| Example | Structure | Compound Name |
|---|---|---|
| 137 (Y) | 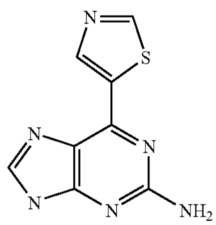 | 6-(5-Thiazolyl)-1H-purine-2-amine |
| 139 (G) | 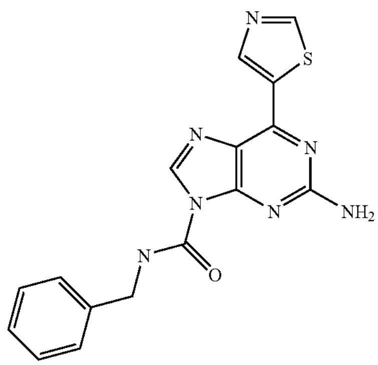 | 2-Amino-N-benzyl-6-(5-thiazolyl)-9H-purine-9-carboxamide |
| 140 (Q) | 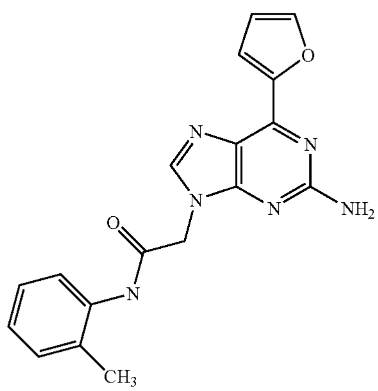 | 2-Amino-6-(2-furyl)-N-(2-methylphenyl)-9H-purine-9-acetamide |
| 141 (Q) | 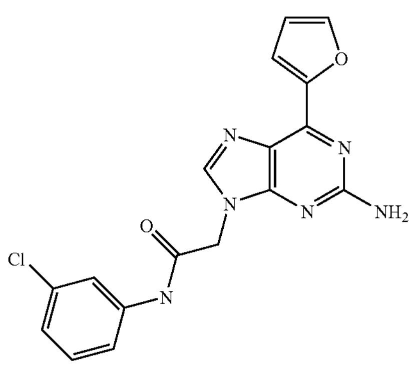 | 2-Amino-N-(3-chlorophenyl)-6-(2-furyl)-9H-purine-9-acetamide |

TABLE 1-continued
| Example | Structure | Compound Name |
|---|---|---|
| 142 (Q) | 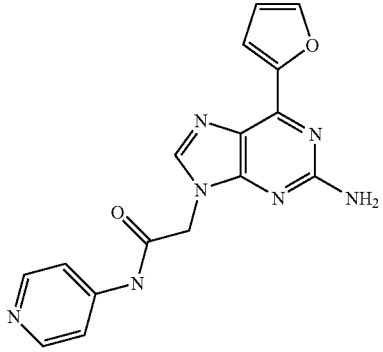 | 2-Amino-6-(2-furyl)-N-(4-pyridyl)-9H-purine-9-acetamide |
| 143 (Q) | 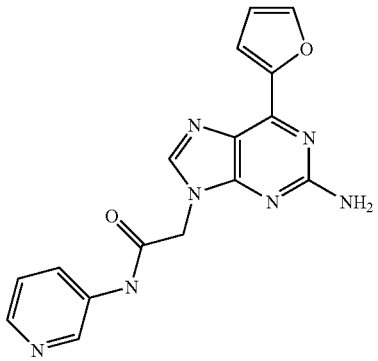 | 2-Amino-6-(2-furyl)-N-(3-pyridyl)-9H-purine-9-acetamide |
| 144 (Q) | 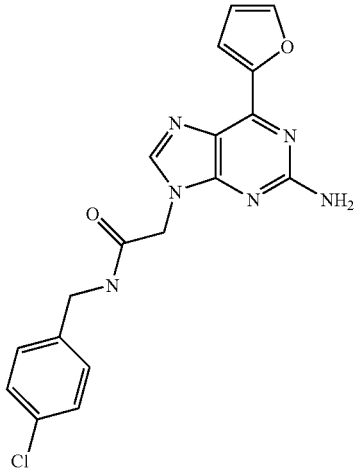 | 2-Amino-N-(4-chlorobenzyl)-6-(2-furyl)-9H-purine-9-acetamide |

TABLE 1-continued

| Example | Structure | Compound Name |
|---|---|---|
| 145 (Q) | 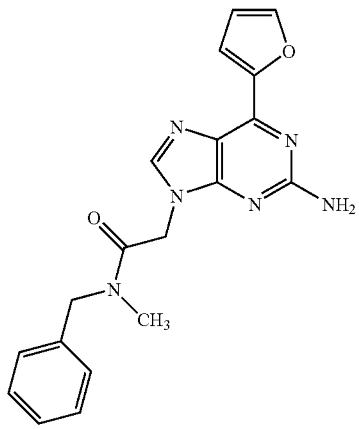 | 2-Amino-N-benzyl-6-(2-furyl)-N-methyl-9H-purine-9-acetamide |
| 146 (S) | 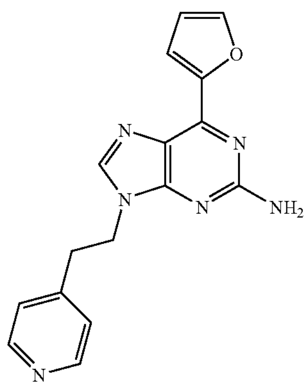 | 6-(2-Furyl)-9-(2-(4-pyridyl)ethyl)-9H-purine-2-amine |
| 147 (S) | 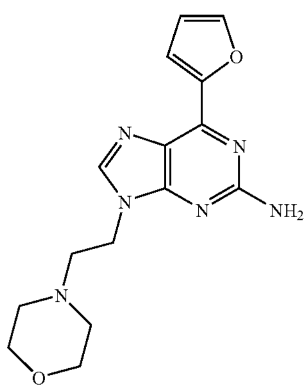 | 6-(2-Furyl)-9-(2-(4-morpholinyl)ethyl)-9H-purine-2-amine |
| 148 (S) | 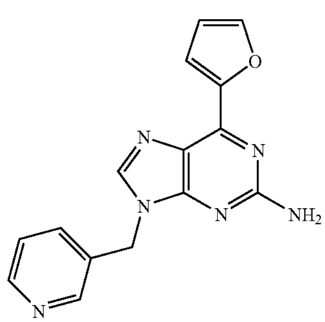 | 6-(2-Furyl)-9-(3-pyridylmethyl)-9H-purine-2-amine |

TABLE 1-continued

| Example | Structure | Compound Name |
|---|---|---|
| 150 (A) | 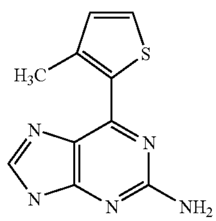 | 6-(3-Methyl-2-thienyl)-1H-purine-2-amine |
| 151 (AA) | 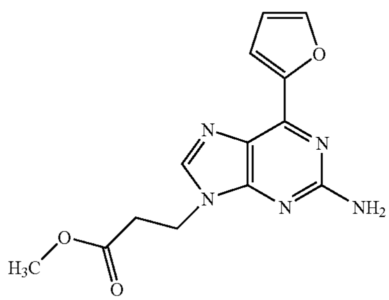 | Methyl 3-(2-amino-6-(2-furyl)-9H-purine-9-yl)propionate |
| 152 (M) | 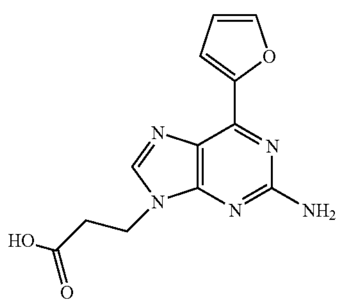 | 3-(2-Amino-6-(2-furyl)-9H-purine-9-yl)propionic acid |
| 153 (AB) | 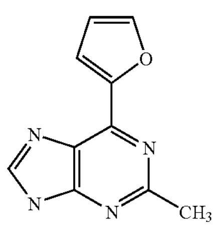 | 6-(2-Furyl)-2-methyl-1H-purine |
| 154 (G) | 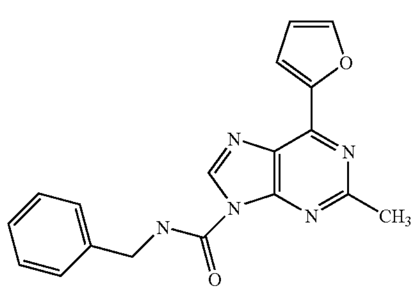 | N-Benzyl-6-(2-furyl)-2-methyl-9H-purine-9-carboxamide |

TABLE 1-continued

| Example | Structure | Compound Name |
|---|---|---|
| 155 (H) | 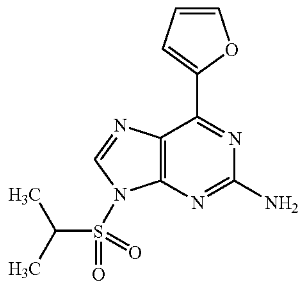 | 6-(2-Furyl)-9-isopropylsulphonyl-9H-purine-2-amine |
| 156 (AC) | 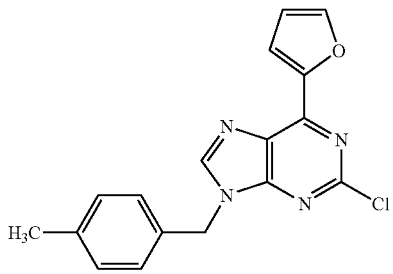 | 2-Chloro-6-(2-furyl)-9-(4-methylbenzyl)-9H-purine |
| 157 (AC) | 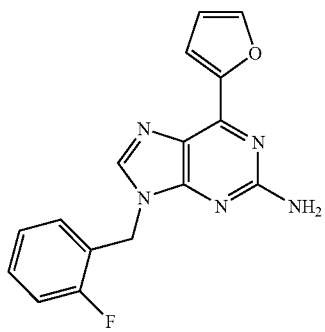 | 9-(2-Fluorobenzyl)-6-(2-furyl)-9H-purine-2-amine |
| 158 (AC) | 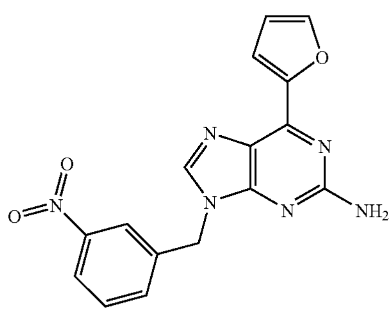 | 6-(2-Furyl)-9-(3-nitrobenzyl)-9H-purine-2-amine |
| 159 (AC) | 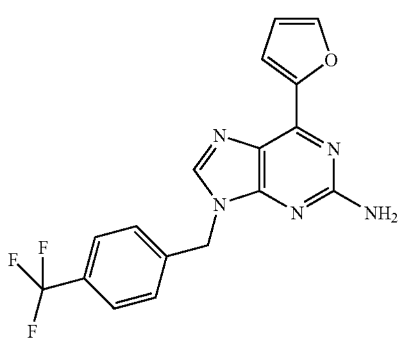 | 6-(2-Furyl)-9-(4-trifluoromethylbenzyl)-9H-purine-2-amine |

TABLE 1-continued
| Example | Structure | Compound Name |
|---|---|---|
| 160 (H) | 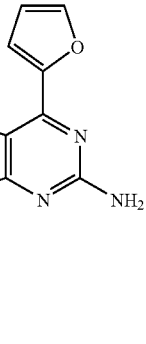 | 6-(2-Furyl)-9-(3-nitrophenyl)sulphonyl-9H-purine-2-amine |
| 161 (H) | 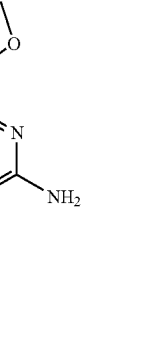 | 9-(2-Bromophenyl)sulphonyl-6-(2-furyl)-9H-purine-2-amine |
| 162 (H) | 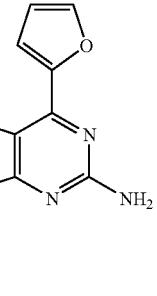 | 9-(4-Bromophenyl)sulphonyl-6-(2-furyl)-9H-purine-2-amine |
| 163 (H) | 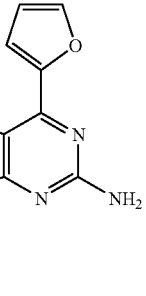 | 9-(4-Fluorophenyl)sulphonyl-6-(2-furyl)-9H-purine-2-amine |
| 164 (H) | 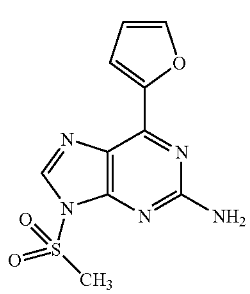 | 6-(2-Furyl)-9-methanesulphonyl-9H-purine-2-amine |

TABLE 1-continued

| Example | Structure | Compound Name |
|---|---|---|
| 165 (H) | 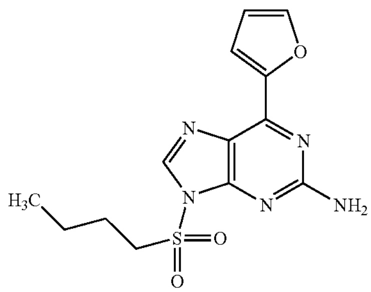 | 9-Butanesulphonyl-6-(2-furyl)-9H-purine-2-amine |
| 166 (H) | 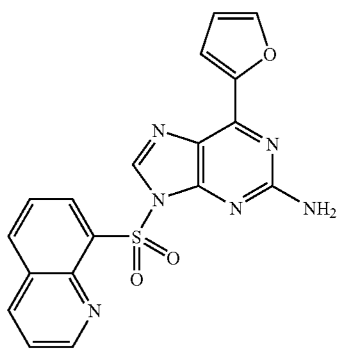 | 6-(2-Furyl)-9-(8-quinolinesulphonyl)-9H-purine-2-amine |
| 167 (H) | 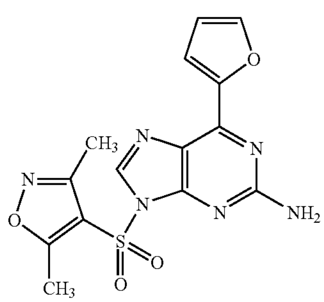 | 9-(3,5-Dimethylisoxazole-4-yl)sulphonyl-6-(2-furyl)-9H-purine-2-amine |
| 168 (H) | 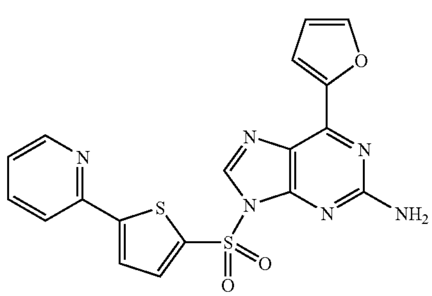 | 6-(2-Furyl)-9-(5-(2-pyridyl)-2-thienyl)sulphonyl-9H-purine-2-amine |

TABLE 1-continued

| Example | Structure | Compound Name |
|---|---|---|
| 169 (Q) | 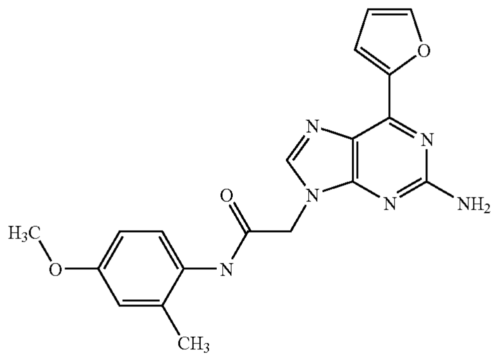 | 2-Amino-6-(2-furyl)-N-(4-methoxy-2-methylphenyl)-9H-purine-9-acetamide |
| 170 (Q) | 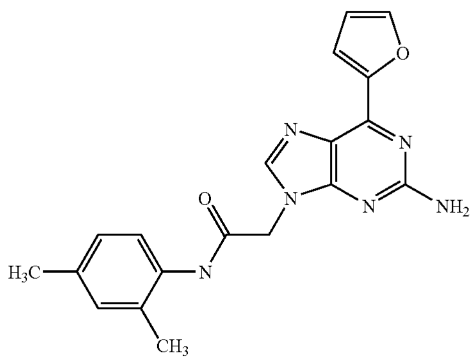 | 2-Amino-N-(2,4-dimethylphenyl)-6-(2-furyl)-9H-purine-9-acetamide |
| 171 (I) | 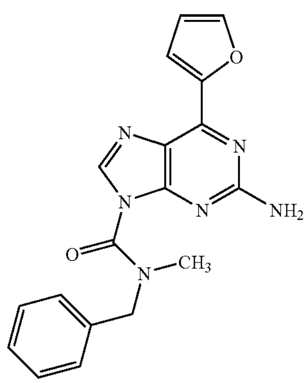 | N-Benzyl-N,2-dimethyl-6-(2-furyl)-9H-purine-9-carboxamide |
| 172 (AC) | 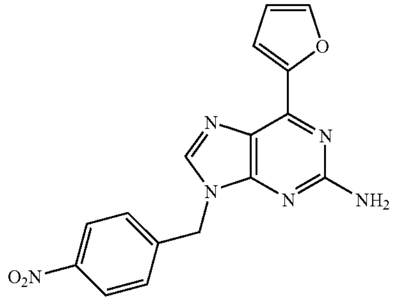 | 6-(2-Furyl)-9-(4-nitrobenzyl)-9H-purine-2-amine |

TABLE 1-continued
| Example | Structure | Compound Name |
|---|---|---|
| 173 (AH) | 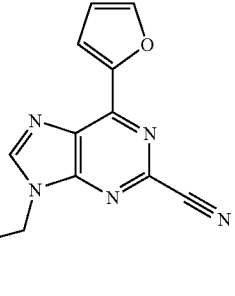 | 6-(2-Furyl)-9-(4-methylbenzyl)-9H-purine-2-carbonitrile |
| 174 (X) | 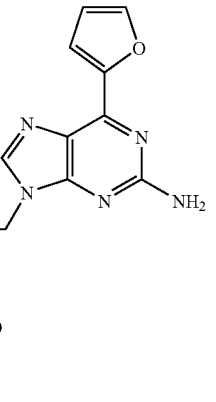 | 6-(2-Furyl)-9-(2-phthalimidoethyl)-9H-purine-2-amine |
| 175 (Q) | 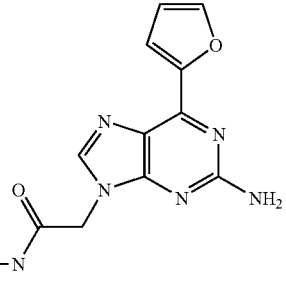 | 2-Amino-N-(4-chlorophenyl)-6-(2-furyl)-9H-purine-9-acetamide |
| 176 (Q) | 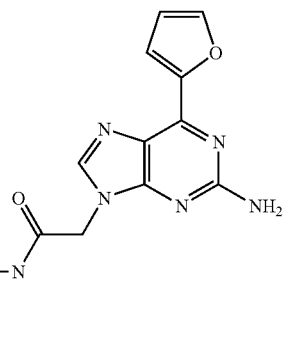 | 2-Amino-N-(3,4-dichlorophenyl)-6-(2-furyl)-9H-purine-9-acetamide |

TABLE 1-continued

| Example | Structure | Compound Name |
|---|---|---|
| 177 (AC) | 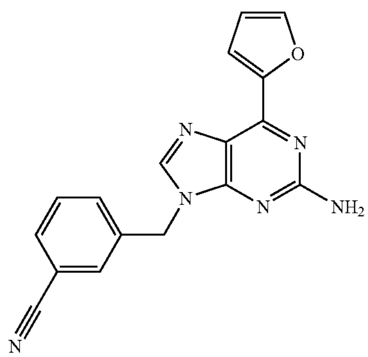 | 9-(3-Cyanobenzyl)-6-(2-furyl)-9H-purine-2-amine |
| 178 (AC) | 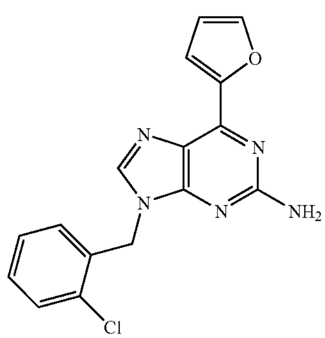 | 9-(2-Chlorobenzyl)-6-(2-furyl)-9H-purine-2-amine |
| 179 (H) | 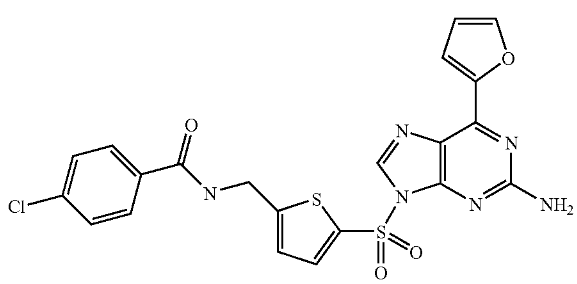 | N-(5-(2-Amino-6-(2-furyl)-9H-purine-9-ylsulphonyl)-2-thienylmethyl)-4-chlorobenzamide |
| 180 (H) | 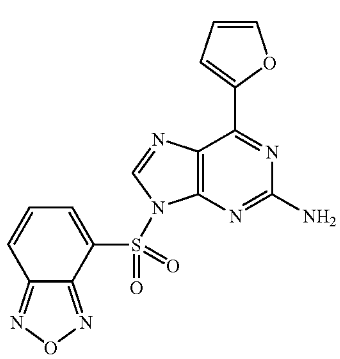 | 9-(2,1,3-Benzoxadiazol-4-yl)sulphonyl-6-(2-furyl)-9H-purine-2-amine |

TABLE 1-continued

| Example | Structure | Compound Name |
|---|---|---|
| 181 (H) | 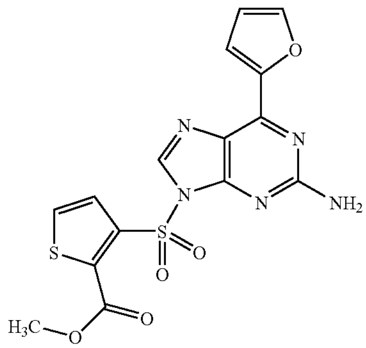 | Methyl 3-(2-amino-6-(2-furyl)-9H-purine-9-sulphonyl)thiophene-2-carboxylate |
| 182 (H) | 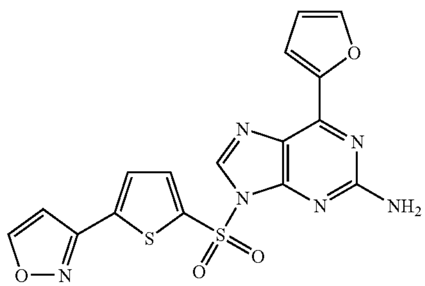 | 6-(2-Furyl)-9-(5-(isoxazol-3-yl)-2-thienyl)sulphonyl-9H-purine-2-amine |
| 183 (H) | 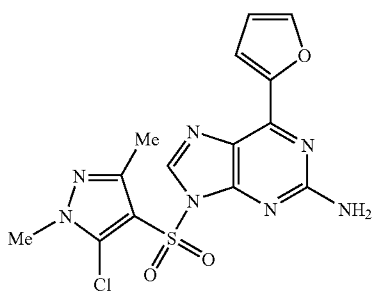 | 6-(2-Furyl)-9-(5-chloro-1,3-dimethyl-1H-pyrazol-4-yl)sulphonyl-9H-purine-2-amine |
| 184 (H) | 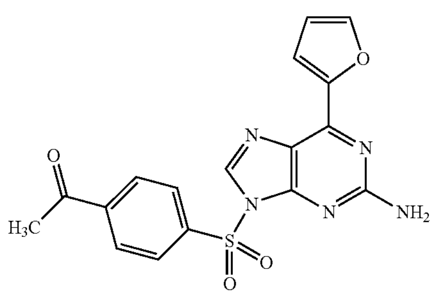 | 9-(4-Acetylphenylsulphonyl)-6-(2-furyl)-9H-purine-2-amine |
| 185 (H) | 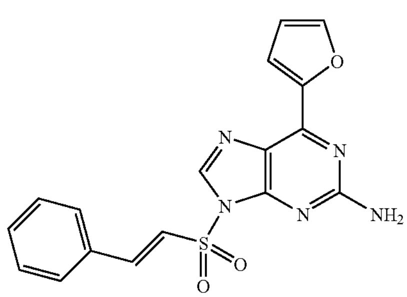 | 6-(2-Furyl)-9-(2-phenylethenyl)sulphonyl-9H-purine-2-amine |

TABLE 1-continued
| Example | Structure | Compound Name |
|---|---|---|
| 186 (H) | 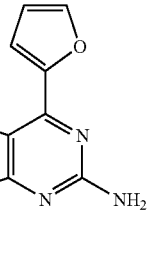 | 9-Ethanesulphonyl-6-(2-furyl)-9H-purine-2-amine |
| 187 (S) | 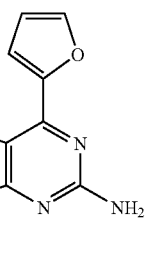 | 6-(2-Furyl)-9-(2-pyridylmethy)-9H-purine-2-amine |
| 188 (S) | 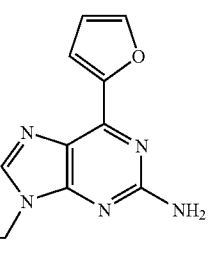 | 6-(2-Furyl)-9-(4-pyridylmethy)-9H-purine-2-amine |
| 189 (S) | 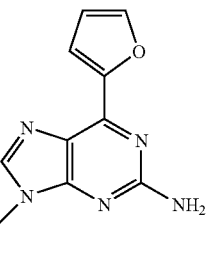 | 6-(2-Furyl)-9-(3-(3-pyridyl)propyl)-9H-purine-2-amine |
| 190 (S) | 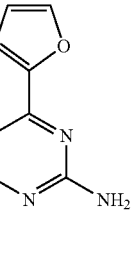 | 6-(2-Furyl)-9-(3-(4-pyridyl)propyl)-9H-purine-2-amine |

TABLE 1-continued
| Example | Structure | Compound Name |
|---|---|---|
| 191 (G) | 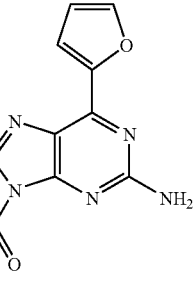 | 2-Amino-N-(1-(4-bromophenyl)ethyl)-6-(2-furyl)-9H-purine-9-carboxamide |
| 192 (AD) | 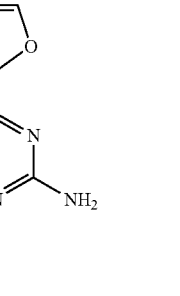 | 9-(3-Aminobenzyl)-6-(2-furyl)-9H-purine-2-amine |
| 193 (AC) | 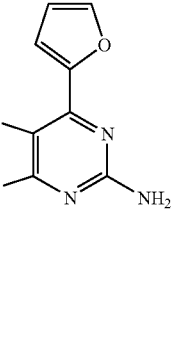 | Methyl 3-(2-amino-6-(2-furyl)-9H-purine-9-ylmethyl)benzoate |
| 194 (AC) | 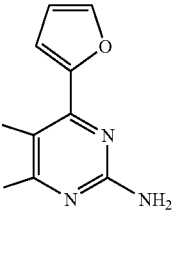 | 9-(4-Cyanobenzyl)-6-(2-furyl)-9H-purine-2-amine |
| 195 (Y) | 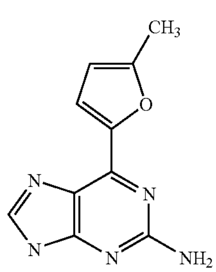 | 6-(5-Methyl-2-furyl)-1H-purine-2-amine |

| Example | Structure | Compound Name |
|---|---|---|
| 196 (H) | 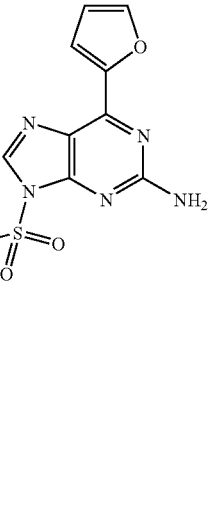 | 9-n-Decanesulphonyl-6-(2-furyl)-9H-purine-2-amine |
| 197 (AC) | 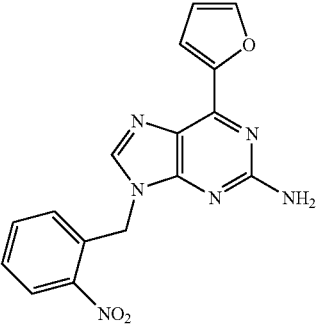 | 6-(2-Furyl)-9-(2-nitrobenzyl)-9H-purine-2-amine |
| 198 (AC) | 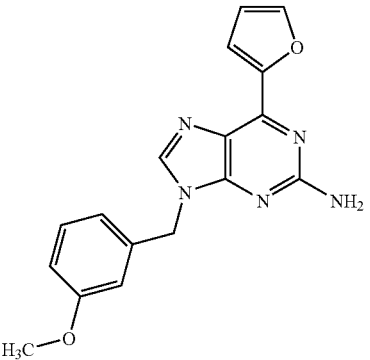 | 6-(2-Furyl)-9-(3-methoxybenzyl)-9H-purine-2-amine |

TABLE 1-continued
| Example | Structure | Compound Name |
|---|---|---|
| 199 (M) | 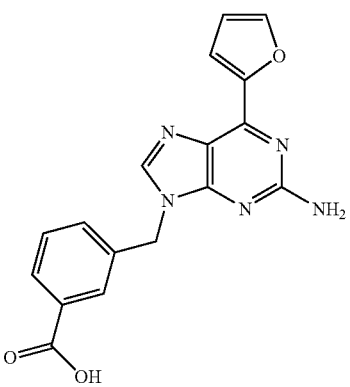 | 3-(2-Amino-6-(2-furyl)-9H-purine-9-ylmethyl)benzoic acid |
| 200 (B) | 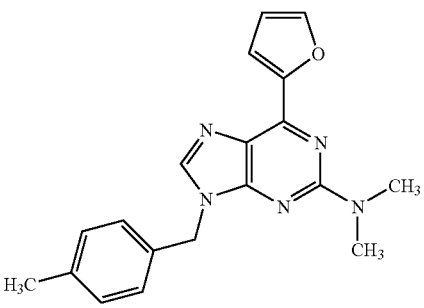 | N,N-Dimethyl-6-(2-furyl)-9-(4-methylbenzyl)-9H-purine-2-amine |
| 201 (G) | 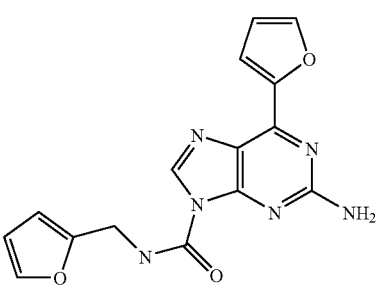 | 2-Amino-6-(2-furyl)-N-(2-furylmethyl)-9H-purine-9-carboxamide |
| 202 (G) | 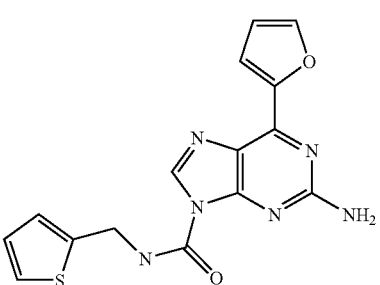 | 2-Amino-6-(2-furyl)-N-(2-thienylmethyl)-9H-purine-9-carboxamide |

TABLE 1-continued

| Example | Structure | Compound Name |
|---|---|---|
| 203 (AC) | 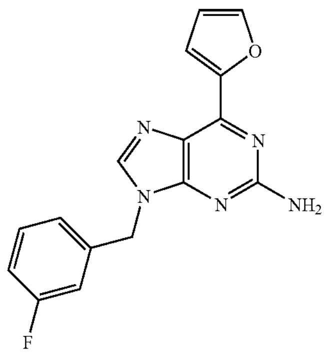 | 9-(3-Fluorobenzyl)-6-(2-furyl)-9H-purine-2-amine |
| 204 (G) | 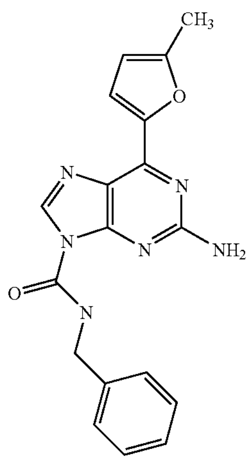 | 2-Amino-N-benzyl-6-(5-methyl-2-furyl)-9H-purine-9-carboxamide |
| 205 (AF) | 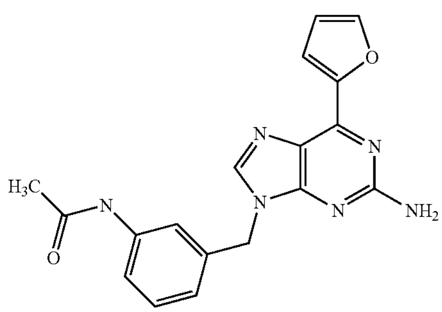 | 9-(3-Acetamidobenzyl)-6-(2-furyl)-9H-purine-2-amine |
| 206 (AC) | 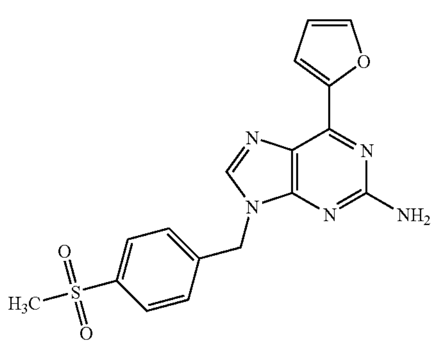 | 6-(2-Furyl)-9-(4-methanesulphonylbenzyl)-9H-purine-2-amine |

TABLE 1-continued

| Example | Structure | Compound Name |
|---|---|---|
| 207 (AD) | 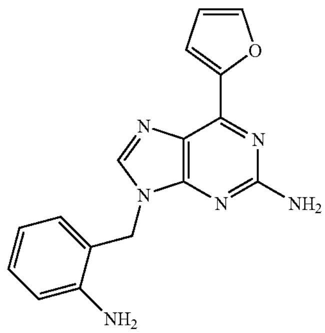 | 9-(2-Aminobenzyl)-6-(2-furyl)-9H-purine-2-amine |
| 208 (AC) | 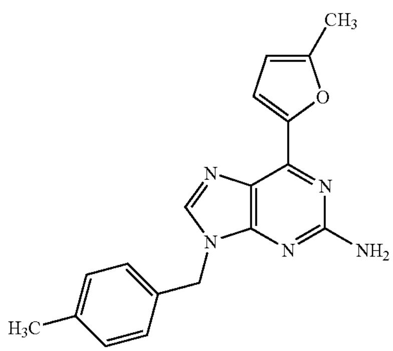 | 9-(4-Methylbenzyl)-6-(5-methyl-2-furyl)-9H-purine 2-amine |
| 209 (Y) | 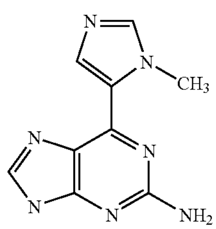 | 6-(1-Methyl-1H-imidazol-5-yl)-1H-purine-2-amine |
| 210 (AF) | 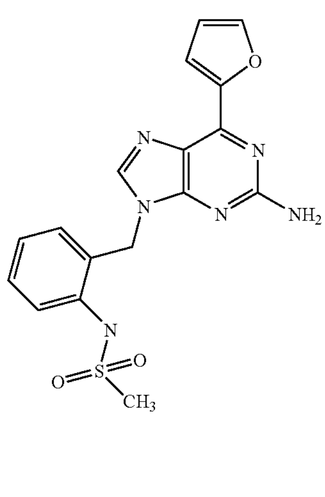 | 6-(2-Furyl)-9-(2-methanesulphonylaminobenzyl)-9H-purine-2-amine |

TABLE 1-continued

| Example | Structure | Compound Name |
|---|---|---|
| 211 (AC) | 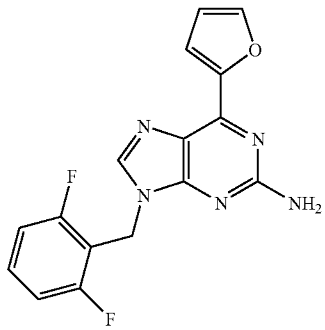 | 9-(2,6-Difluorobenzyl)-6-(2-furyl)-9H-purine-2-amine |
| 212 (S) | 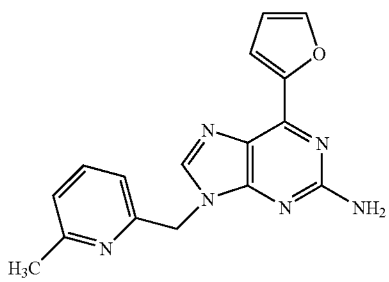 | 6-(2-Furyl)-9-(6-methyl-2-pyridyl)methyl-9H-purine-2-amine |
| 213 (S) | 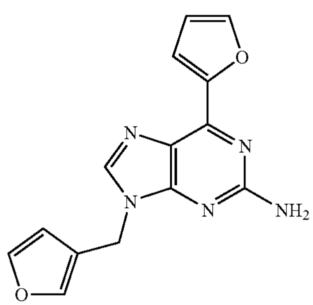 | 6-(2-Furyl)-9-(3-furylmethy)-9H-purine-2-amine |
| 214 (H) | 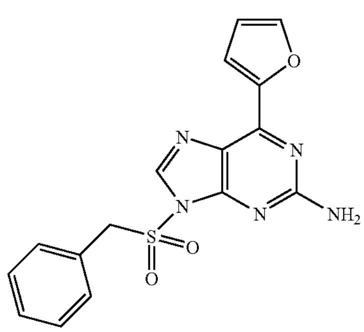 | 9-Benzylsulphonyl-6-(2-furyl)-9H-purine-2-amine |

TABLE 1-continued

| Example | Structure | Compound Name |
|---|---|---|
| 215 (AC) | 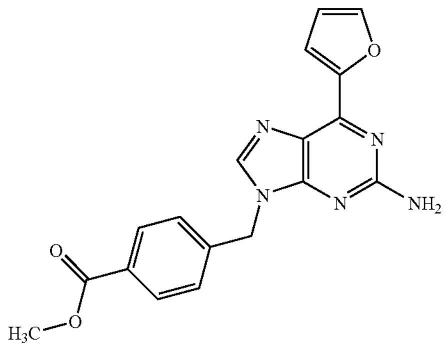 | Methyl 4-(2-amino-6-(2-furyl)-9H-purine-9-ylmethyl)benzoate |
| 216 (M) | 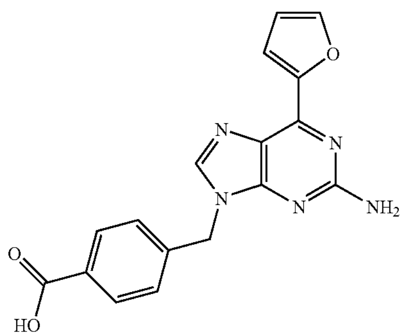 | 4-(2-Amino-6-(2-furyl)-9H-purine-9-ylmethyl)benzoic acid |
| 217 (AF) | 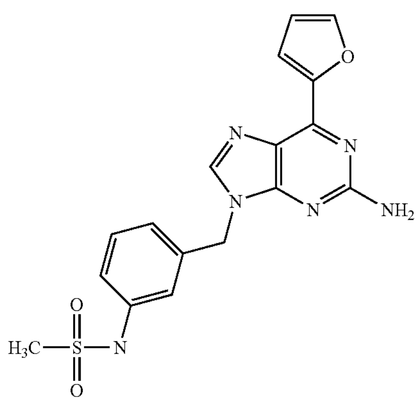 | 6-(2-Furyl)-9-(3-methanesulphonylaminobenzyl)-9H-purine-2-amine |
| 218 (Q) | 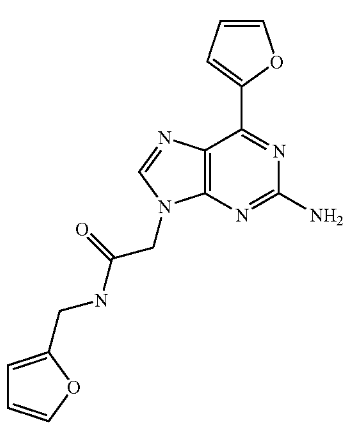 | 2-Amino-6-(2-furyl)-N-(2-furylmethyl)-9H-purine-9-acetamide |

TABLE 1-continued

| Example | Structure | Compound Name |
|---|---|---|
| 219 (AC) | 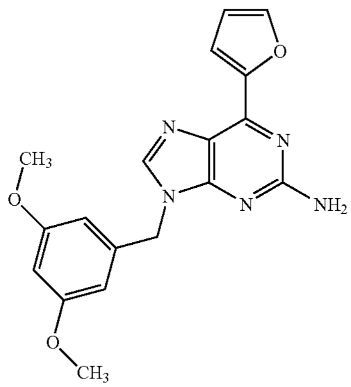 | 9-(3,5-Dimethoxybenzyl)-6-(2-furyl)-9H-purine-2-amine |
| 220 (AF) | 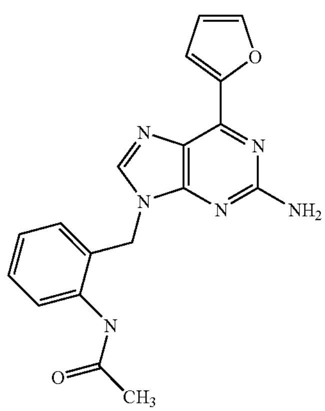 | 9-(2-Acetamidobenzyl)-6-(2-furyl)-9H-purine-2-amine |
| 221 (AG) | 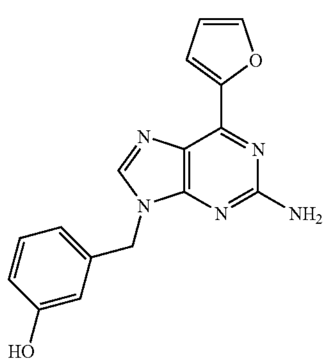 | 6-(2-Furyl)-9-(3-hydroxybenzyl)-9H-purine-2-amine |

TABLE 1-continued

| Example | Structure | Compound Name |
|---|---|---|
| 222 (S) | 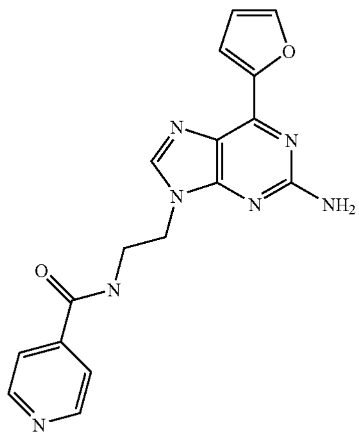 | N-(2-(2-Amino-6-(2-furyl)-9H-purine-9-yl)ethyl)-4-pyridinecarboxamide |
| 223 (S) | 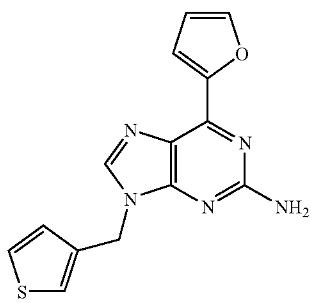 | 6-(2-Furyl)-9-(3-thienylmethyl)-9H-purine-2-amine |
| 224 (S) | 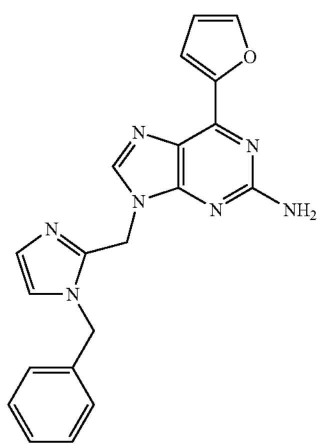 | 9-(1-Benzyl-1H-imidazol-2-ylmethyl)-6-(2-furyl)-9H-purine-2-amine |
| 225 (AD) | 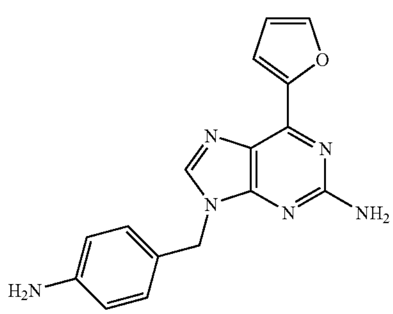 | 9-(4-Aminobenzyl)-6-(2-furyl)-9H-purine-2-amine |

TABLE 1-continued

| Example | Structure | Compound Name |
|---|---|---|
| 226 (P) | 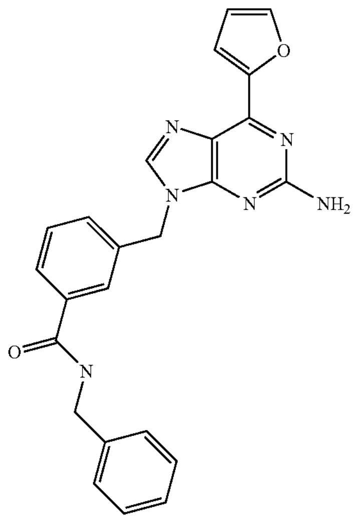 | 3-(2-Amino-6-(2-furyl)-9H-purine-9-ylmethyl)-N-benzylbenzamide |
| 227 (P) | 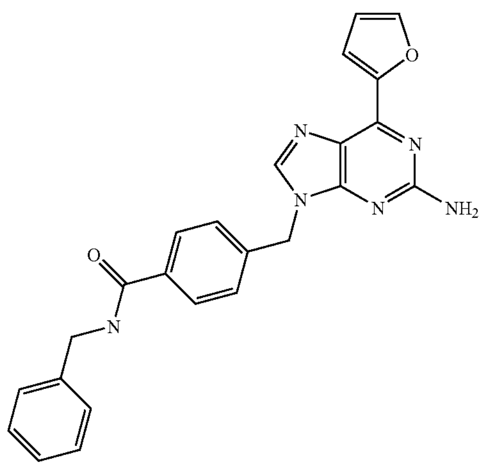 | 4-(2-Amino-6-(2-furyl)-9H-purine-9-ylmethyl)-N-benzylbenzamide |
| 228 (H) | 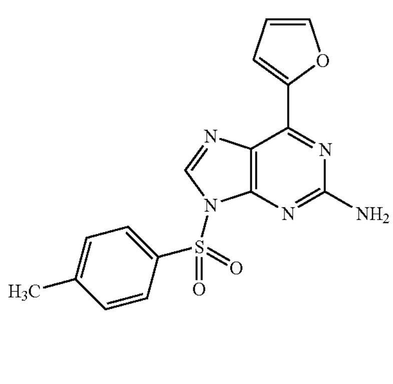 | 6-(2-Furyl)-9-(4-methylphenylsulphonyl)-9H-purine-2-amine |

TABLE 1-continued

| Example | Structure | Compound Name |
|---|---|---|
| 229 (AC) | 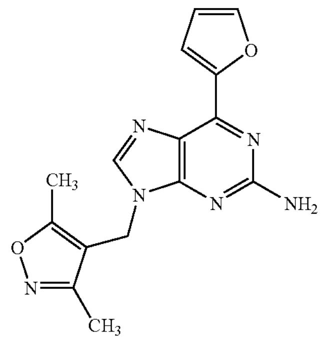 | 9-(3,5-Dimethylisoxazol-4-ylmethyl)-6-(2-furyl)-9H-purine-2-amine |
| 230 (P) | 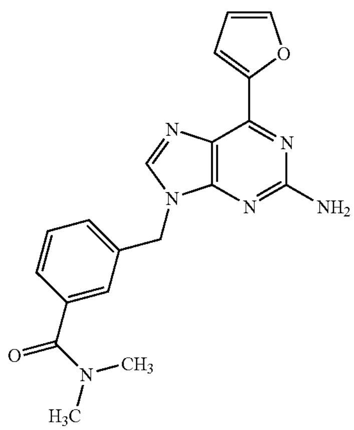 | 3-(2-Amino-6-(2-furyl)-9H-purine-9-ylmethyl)-N,N-dimethylbenzamide |
| 231 (Q) | 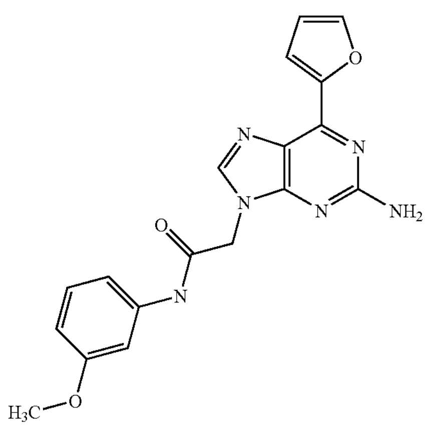 | 2-Amino-6-(2-furyl)-N-(3-methoxyphenyl)-9H-purine-9-acetamide |
| 232 (AF) | 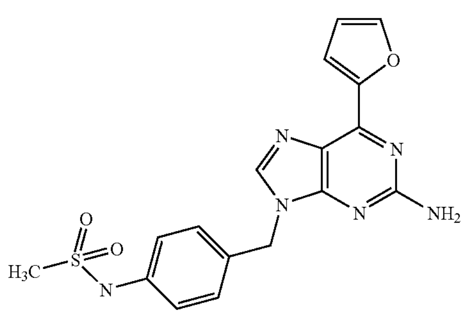 | 6-(2-Furyl)-9-(4-methanesulphonylaminobenzyl)-9H-purine-2-amine |

TABLE 1-continued

| Example | Structure | Compound Name |
|---|---|---|
| 233 (P) | 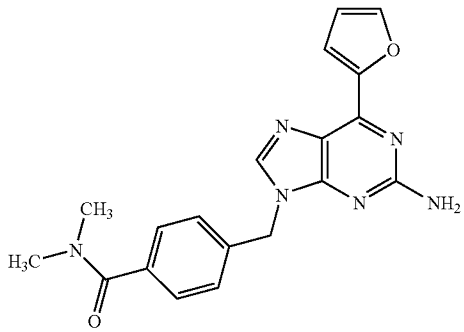 | 4-(2-Amino-6-(2-furyl)-9H-purine-9-ylmethyl)-N,N-dimethylbenzamide |
| 234 (AF) | 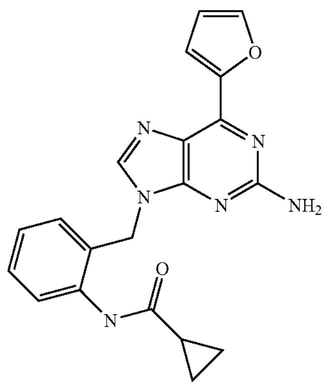 | N-(2-(2-Amino-6-(2-furyl)-9H-purine-9-ylmethyl)phenyl)cyclopropanecarboxamide |
| 235 (AF) | 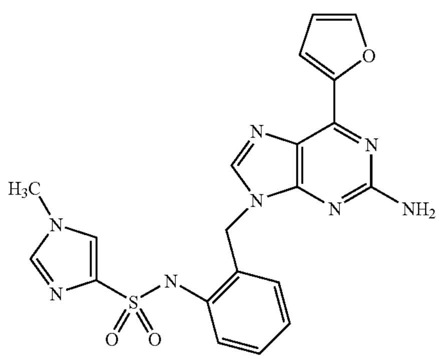 | 6-(2-Furyl)-9-(2-(1-methyl-1H-imidazol-4-ylsulphonylamino)benzyl)-9H-purine-2-amine |
| 236 (Q) | 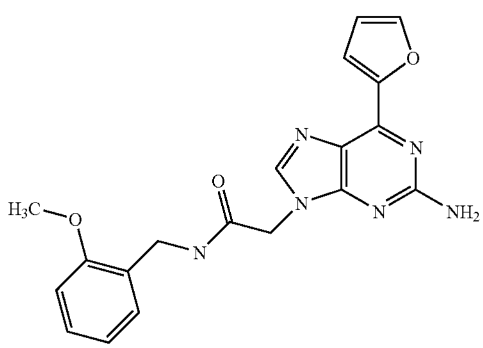 | 2-Amino-6-(2-furyl)-N-(2-methoxybenzyl)-9H-purine-9-acetamide |

TABLE 1-continued

| Example | Structure | Compound Name |
|---|---|---|
| 237 (Q) | 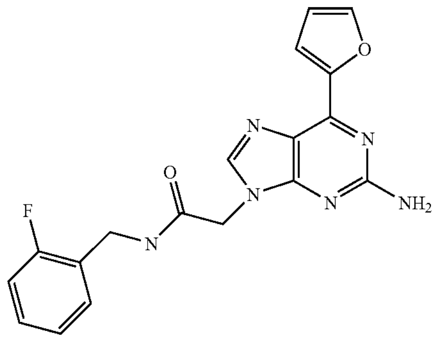 | 2-Amino-N-(2-fluorobenzyl)-6-(2-furyl)-9H-purine 9-acetamide |
| 238 (AF) | 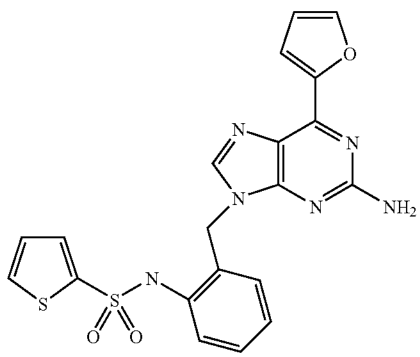 | 6-(2-Furyl)-9-(2-(2-thienylsulphonylamino)benzyl)-9H-purine-2-amine |
| 239 (AF) | 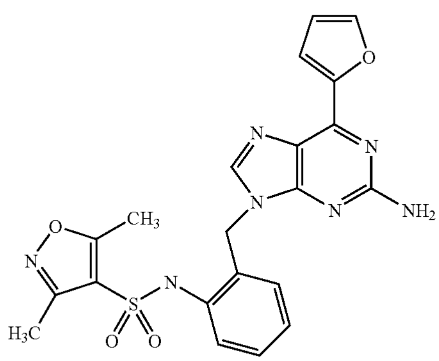 | 6-(2-Furyl)-9-(2-(3,5-dimethylisoxazol-4-ylsulphonylamino)benzyl)-9H-purine-2-amine |
| 240 (AC) | 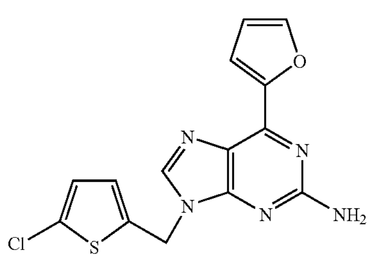 | 9-(5-Chloro-2-thienylmethyl)-6-(2-furyl)-9H-purine-2-amine |

TABLE 1-continued

| Example | Structure | Compound Name |
|---|---|---|
| 241 (Z) | 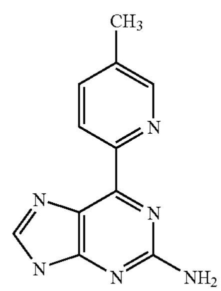 | 6-(5-Methyl-2-pyridinyl)-1H-purine-2-amine |
| 242 (AF) | 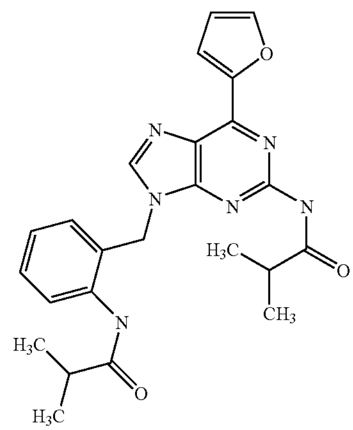 | N-(6-(2-Furyl)-9-(2-(2-methylpropanamido)benzyl)-9H-purine-2-yl)-2-methylpropanamide |
| 243 (AC) | 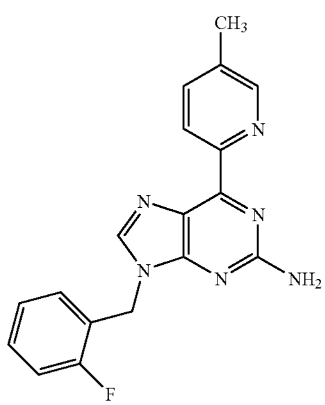 | 9-(2-Fluorobenzyl)-6-(5-methyl-2-pyridinyl)-9H-purine-2-amine |
| 244 (AJ) | 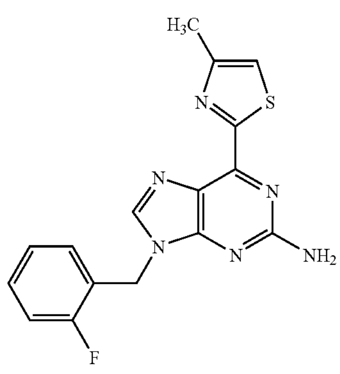 | 9-(2-Fluorobenzyl)-6-(4-methyl-2-thiazolyl)-9H-purine-2-amine |

TABLE 1-continued

| Example | Structure | Compound Name |
|---|---|---|
| 245 (AK) | 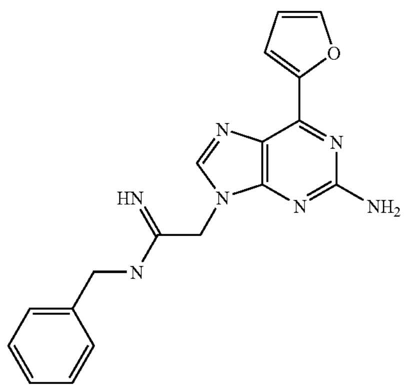 | 2-Amino-N-benzyl-6-(2-furyl)-9H-purine-9-acetimidamide |
| 246 (Q) | 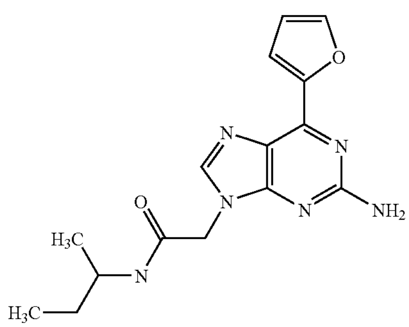 | 2-Amino-6-(2-furyl)-N-(1-methylpropyl)-9H-purine-9-acetamide |
| 247 (Q) | 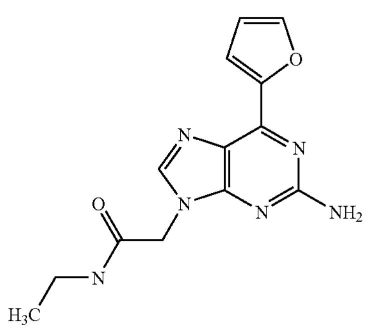 | 2-Amino-N-ethyl-6-(2-furyl)-9H-purine-9-acetamide |
| 248 (Q) | 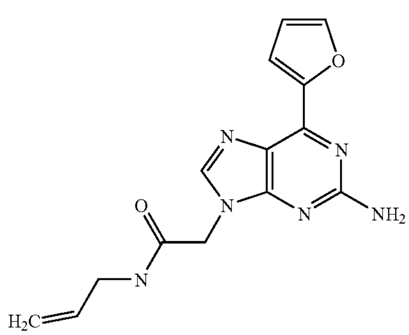 | N-Allyl-2-amino-6-(2-furyl)-9H-purine-9-acetamide |

TABLE 1-continued

| Example | Structure | Compound Name |
|---|---|---|
| 249 (Q) | 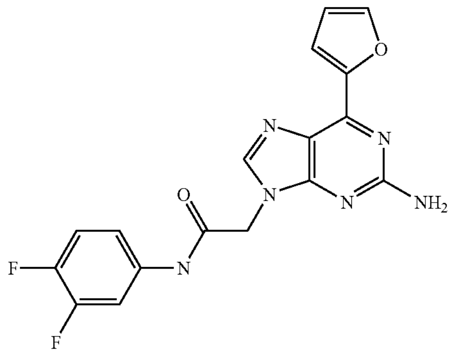 | 2-Amino-N-(3,4-difluorophenyl)-6-(2-furyl)-9H-purine-9-acetamide |
| 250 (AF) | 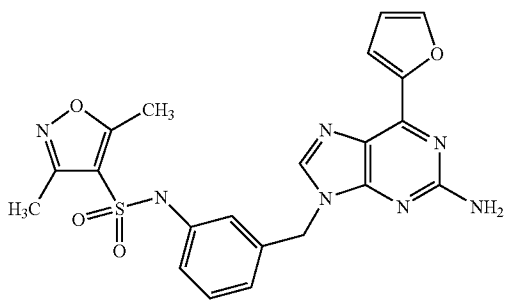 | 6-(2-Furyl)-9-(3-(3,5-dimethylisoxazol-4-ylsulphonylamino)benzyl)-9H-purine-2-amine |
| 251 (AL) | 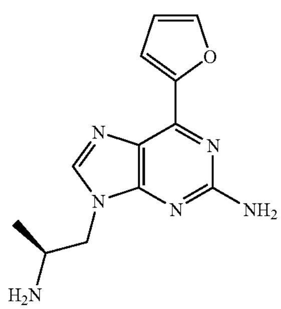 | (2S)-9-(2-Amino-1-propyl)-6-(2-furyl)-9H-purine-2-amine |
| 252 (Q) | 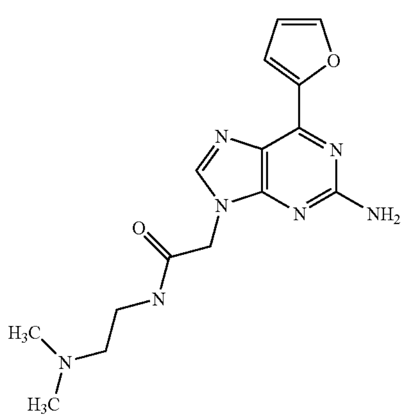 | 2-Amino-N-(2-dimethylaminoethyl)-6-(2-furyl)-9H-purine-9-acetamide |

TABLE 1-continued

| Example | Structure | Compound Name |
|---|---|---|
| 253 (AC) | 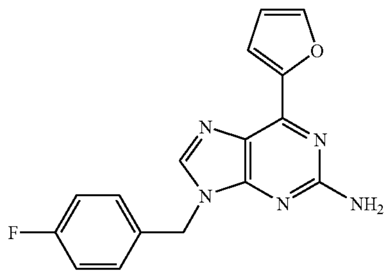 | 9-(4-Fluorobenzyl)-6-(2-furyl)-9H-purine-2-amine |
| 254 (AL) | 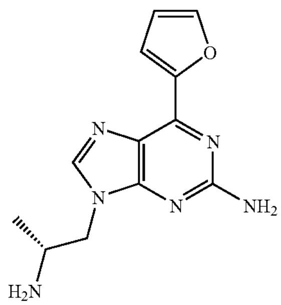 | (2R)-9-(2-Amino-1-propyl)-6-(2-furyl)-9H-purine-2-amine |
| 255 (X) | 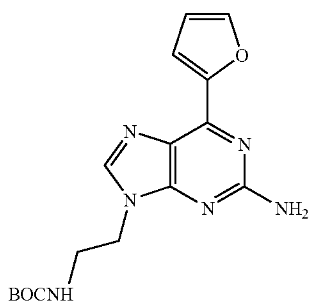 | 9-(2-(Butoxycarbonylamino)ethyl)-6-(2-furyl)-9H-purine-2-amine |
| 256 (AC) | 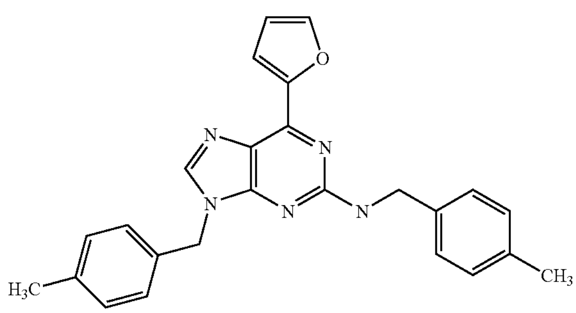 | N,9-Bis(4-methylbenzyl)-6-(2-furyl)-9H-purine-2-amine |
| 257 (F) | 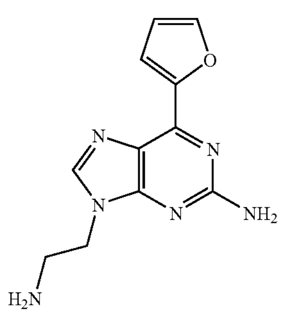 | 9-(2-Aminoethyl)-6-(2-furyl)-9H-purine-2-amine |

TABLE 1-continued

| Example | Structure | Compound Name |
|---|---|---|
| 258 (AC) | 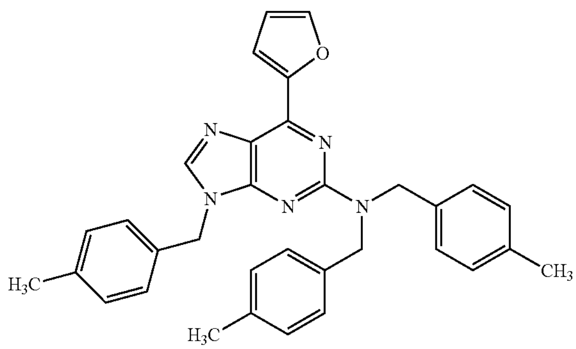 | 6-(2-Furyl)-N,N,9-tris(4-methylbenzyl)-9H-purine-2-amine |
| 259 (AC) | 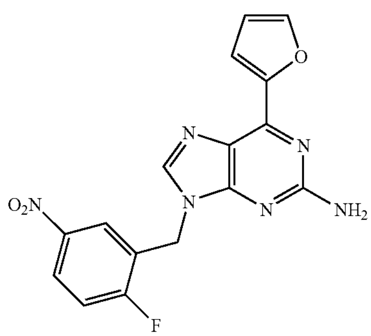 | 9-(2-Fluoro-5-nitrobenzyl)-6-(2-furyl)-9H-purine-2-amine |
| 260 (AG) | 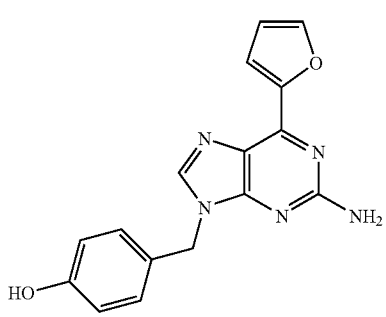 | 6-(2-Furyl)-9-(4-hydroxybenzyl)-9H-purine-2-amine |
| 261 (AC) | 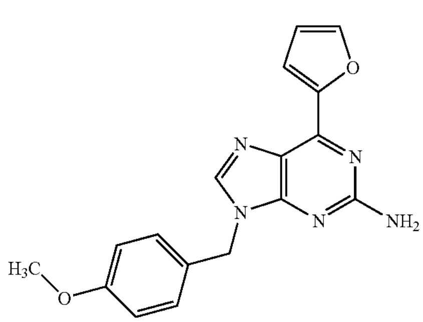 | 6-(2-Furyl)-9-(4-methoxybenzyl)-9H-purine-2-amine |

TABLE 1-continued

| Example | Structure | Compound Name |
|---|---|---|
| 262 (AM) | 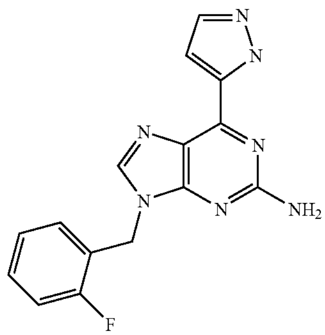 | 9-(2-Fluorobenzyl)-6-(1H-pyrazol-3-yl)-9H-purine-2-amine |
| 263 (AM) | 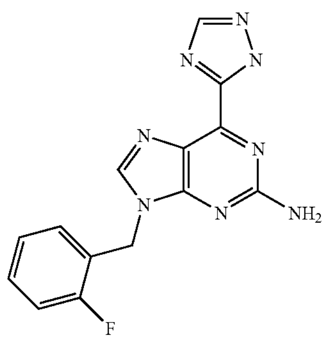 | 9-(2-Fluorobenzyl)-6-(1H-triazol-3-yl)-9H-purine-2-amine |
| 264 (AM) | 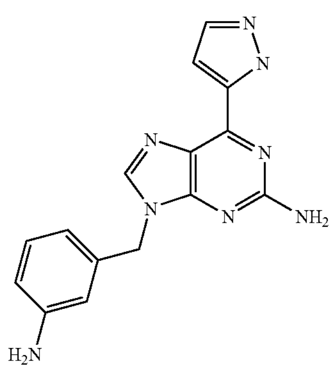 | 9-(3-Aminobenzyl)-6-(1H-pyrazol-3-yl)-9H-purine-2-amine |
| 265 (AO) | 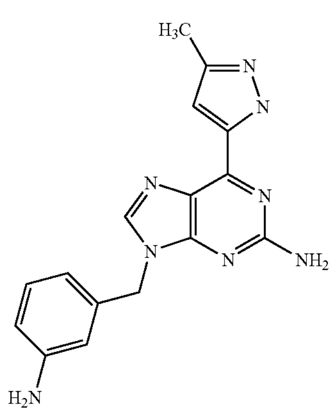 | 9-(3-Aminobenzyl)-6-(5-methyl-1H-pyrazol-3-yl)-1H-purine-2-amine |

TABLE 1-continued

| Example | Structure | Compound Name |
|---|---|---|
| 266 (AC) | 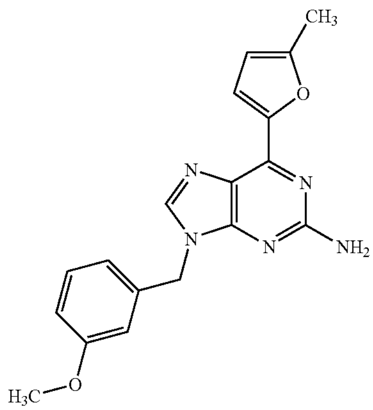 | 9-(3-Methoxybenzyl)-6-(5-methyl-2-furyl)-9H-purine-2-amine |
| 267 (AC) | 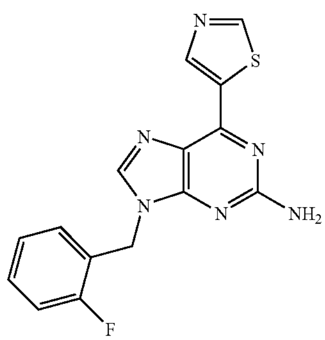 | 9-(2-Fluorobenzyl)-6-(thiazol-5-yl)-9H-purine-2-amine |
| 268 (AC) | 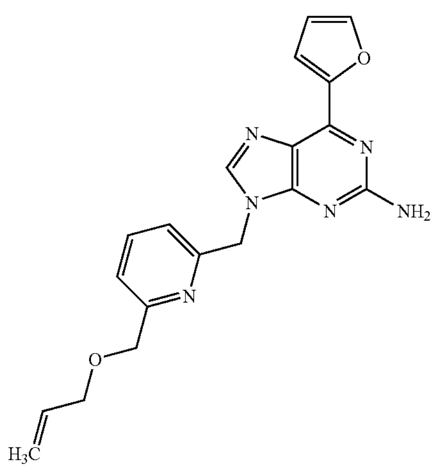 | 9-(6-Allyloxymethyl-2-pyridyl)-6-(2-furyl)-9H-purine-2-amine |
| 269 (AC) | 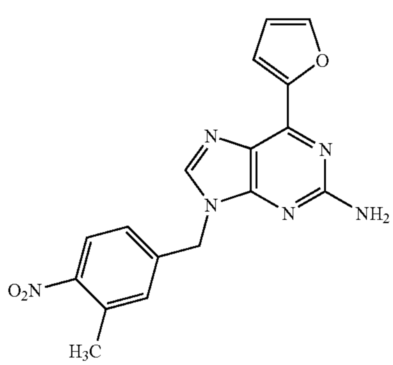 | 9-(3-Methyl-4-nitrobenzyl)-6-(2-furyl)-9H-purine-2-amine |

TABLE 1-continued
| Example | Structure | Compound Name |
|---|---|---|
| 270 (AC) | 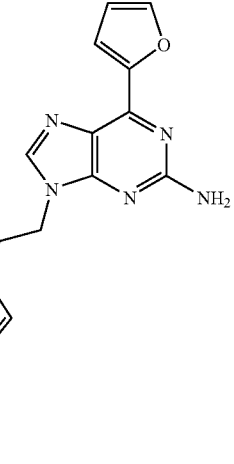 | tert-butyl 4-(2-amino-6-(2-furyl)-1H-purine-9-ylmethyl)indole-1-carboxylate |
| 271 (AQ) | 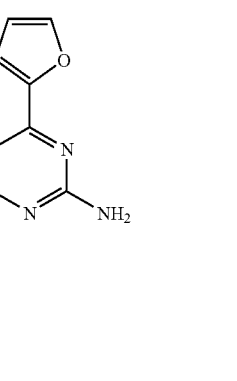 | 6-(2-Furyl)-9-(4-indolylmethyl)-9H-purine-2-amine |
| 272 (AQ) | 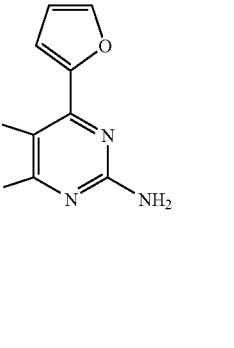 | 6-(2-Furyl)-9-(5-indolylmethyl)-9H-purine-2-amine |
| 273 (AC) | 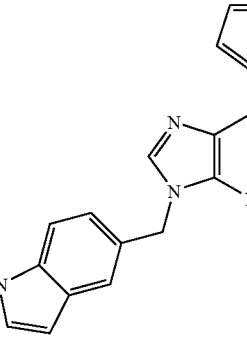 | tert-butyl 5-(2-amino-6-(2-furyl)-1H-purine-9-ylmethyl)indole-1-carboxylate |

Method A

2-Chloro-6-(2-furyl)-9-(2-trimethylsilylethoxymethyl)-9H-purine (Example 1)

A solution of 2,6-dichloro-9-(2-trimethylsilylethoxymethyl)-9H-purine (957 mg, 3 mmol) in DMF (2.5 mL) was treated with $PdCl_2(PPh_3)_2$ (105 mg, 0.15 mmol) and 2-(tributylstannyl)furan (944 µL, 3 mmol), stirred at room temperature for 16 h, diluted with EtOAc, washed with water, dried ($MgSO_4$) and concentrated in vacuo, purified by chromatography [$SiO_2$; EtOAc: Heptane, (1:2)] and the resulting cream solid recrystallised (heptane) to give the title compound (738 mg, 70%) as a white solid.

Method B

N,N-Dimethyl-6-(2-furyl)-9-(2-trimethylsilylethoxymethyl)-9H-purine-2-amine (Example 2)

A solution of 2-chloro-6-(2-furyl)-9-(2-trimethylsilylethoxymethyl)-9H-purine (488 mg, 1.4 mmol) in isopropanol (5 mL) was treated with 40% dimethylamine in water (1 mL), refluxed for 2 h, concentrated in vacuo and purified by chromatography [$SiO_2$; EtOAc Heptane, (1:1)] to give the title compound (431 mg, 86%) as a white solid.

Method C

N,N-Dimethyl-6-(2-furyl)-1H-purine-2-amine (Example 3)

A solution of N,N-dimethyl-6-(2-furyl)-9-(2-trimethylsilylethoxymethyl)-9H-purine-2-amine (200 mg, 0.56 mmol) in THF (5 mL) was treated with tetra-n butylammonium fluoride (1-M in THF, 0.67 mL, 0.67 mmol), refluxed for 4 h, cooled, poured into water and extracted with EtOAc. The combined organic phase was dried ($MgSO_4$), concentrated in vacuo and purified by chromatography ($SiO_2$; EtOAc) to give the title compound (98 mg, 76%) as a pale yellow solid.

Method D

6-(2-Furyl)-1H-purine-2-amine (Example 11)

A solution of N-(3,4-dimethoxybenzyl)-6-(2-furyl)-1H-purine-2-amine (194 mg, 0.55 mmol) in TFA (1 mL) was heated at 60° C. for 30 min, poured into water, extracted with EtOAc and the combined organic phase was dried ($MgSO_4$), concentrated in vacuo and purified by chromatography ($SiO_2$; 5% MeOH in EtOAc). The resulting yellow solid was dissolved in MeOH, treated with HCl (1-M in $Et_2O$) and filtered to give the title compound (75 mg, 57%) as a yellow solid.

Method E tert-Butyl 6-(2-furyl)-2-thiomethoxy-9H-purine-9-carboxylate (Example 12)

A solution of tert-butyl 2-chloro-6-(2-furyl)-9H-purine-9-carboxylate (320 mg, 1 mmol) in 1-methyl-2-pyrrolidinone (2 mL) was treated with NaSMe (140 mg, 2 mmol), heated at 110° C. for 48 h, cooled, poured into water, extracted with $CHCl_3$ and the combined organic phase dried ($MgSO_4$) and concentrated in vacuo. The resulting crude intermediate was dissolved in THF (2 mL), treated with di-tert-butyl dicarbonate (218 mg, 1 mmol), $Et_3N$ (139 µL, 1 mmol) and a catalytic amount of DMAP, stirred for 1 h, poured into water, extracted with $CHCl_3$ and the combined organic phase dried ($MgSO_4$), concentrated in vacuo and purified by chromatography [$SiO_2$; Heptane:EtOAc (4:1)] to give the title compound (106 mg, 32%) as a cream solid.

Method F

6-(2-Furyl)-2-thiomethoxy-1H-purine (Example 13)

A solution of tert-butyl 6-(2-furyl)-2-thiomethoxy-9H-purine-9-carboxylate (75 mg, 0.23 mmol) in dioxan (0.5 mL) was treated with HCl in dioxan (4-M, 0.5 mL, 2 mmol), stirred at room temperature for 30 min, poured into sat. $NaHCO_3$, extracted with EtOAc and the combined organic phase dried $MgSO_4$), concentrated in vacuo and the resulting cream solid triturated with EtOAc and filtered to give the title compound (46 mg, 86%) as a cream solid.

Method G

2-Amino-N-n-butyl-6-(2-furyl)-9H-purine-9-carboxamide (Example 36)

A solution of 6-(2-furyl)-1H-purine-2-amine (0.050 g, 0.25 mmol) and DMAP (5 mg, 0.03 mmol) in anhydrous DMF (1 µL) was treated with n-butylisocyanate (0.029 g, 0.30 mmol), shaken at 65° C. for 1 h, poured onto ice-cold water (10 mL), cooled at 0° C. for 15 min and the resulting precipitate filtered and dried in vacuo over $P_2O_5$ to give the title compound (74 mg, 100%) as a white solid.

Method H

9-(4-tert-Butylphenylsulphonyl)-6-(2-furyl)-9H-purine-2-amine (Example 27)

A solution of 6-(2-furyl)-1H-purine-2-amine (100 mg, 0.5 mmol) in THF (2 mL) and DMF (0.5 mL) was treated with 4-tert-butylbenzenesulphonyl chloride (116 mg, 0.5 mmol) and $Et_3N$ (69 µL, 0.6 mmol), heated at 60° C. for 2 h, cooled, diluted with water and the resulting solid filtered and washed with EtOAc to give the title compound (106 mg, 53%) as a cream solid.

Method I

6-(2-Furyl)-9-(1-pyrrolidinylcarbonyl)-9H-purine-2-amine (Example 29)

A solution of pyrrolidine (50 mL, 0.6 mmol) in toluene (2 mL) was treated with a solution of phosgene in toluene (0.31 mL, 1.93-M, 0.6 mmol), heated at 80° C. for 30 mins, cooled and concentrated in vacuo. The residue was dissolved in THF (2 mL) and added to a solution of 6-(2-furyl)-1H-purine-2-amine (100 mg, 0.5 mmol) and $Et_3N$ (83 mL, 0.6 mmol) in DMP (0.5 mL), stirred at 60° C. for 16 h, poured into water and extracted with EtOAc. The combined organic phase was dried ($MgSO_4$), concentrated in vacuo and the resulting solid triturated with EtOAc/heptane and filtered to give the title compound (92 mg, 62%) as a cream solid.

Method K

9-(2-Cyclohexylethyl)-6-(2-furyl)-9H-purine-2-amine (Example 54)

A solution of 6-(2-furyl)-1H-purine-2-amine (25 mg, 0.12 mmol) in anhydrous DMF (0.5 mL) and anhydrous THF (2 mL) was treated with triphenylphosphine polystyrene (65 mg, 0.25 mmol) and 2-cyclohexylethanol (35 mg, 0.25 mmol), shaken at room temperature for 10 min, treated with di-tert-butyl azodicarboxylate (0.058 g, 0.25 mmol), shaken at room temperature for 16 h, filtered and concentrated in vacuo. The resulting oil was dissolved in $CH_2Cl_2$ (2 mL) and TFA (1 mL), shaken for 2 h and concentrated in vacuo. The resulting oil was dissolved in $CH_2Cl_2$ (3 mL), shaken with 1-M aq HCl (1 mL) for 15 min and the organic phase concentrated in vacuo and purified by chromatography ($SiO_2$; EtOAc) to give the title compound (22 mg, 57%) as a yellow solid.

Method L

Isopropyl 2-dimethylamino-6-(2-furyl)-9H-purine-9-acetate (Example 70)

A solution of ethyl 2-chloro-6-(2-furyl)-9H-purine-9-acetate (100 mg, 0.33 mol) in isopropanol (1 mL) was treated with 40% dimethylamine in water, refluxed for 2 h, cooled, poured into water, extracted with EtOAc and the combined organic phase dried (MgSO$_4$), concentrated in vacuo and purified by chromatography [SiO$_2$; Heptane:EtOAc, (1:1)] to give the title compound (20 mg, 19%) as a white solid.

Method M

2-Amino-6-(2-furyl)-9H-purine-9-acetic acid (Example 73)

A solution of ethyl 2-amino-6-(2-furyl)-9H-purine-9-acetate (200 mg, 0.69 mmol) in MeOH (3 mL) was treated with aq NaOH (2-M, 0.5 mL, 1 mmol), refluxed for 10 min, cooled, diluted with water, acidified with aq HCl (1-M) and the resulting solid filtered, washed with water and dried to give the title compound (129 mg, 72%) as a yellow solid.

Method N

6(2-Furyl)-2-methoxy-9-(2-trimethylsilylethoxymethyl)-9H-purine (Example 74)

A solution of 2-chloro-6-(2-furyl)-9-(2-trimethylsilylethoxymethyl)-9H-purine (0.35 g, 1.0 mmol) and sodium methoxide (60 mg, 1.1 mmol) in methanol (5 mL) was refluxed for 23 h, cooled, concentrated in vacuo and the resulting solid treated with water, acidified to pH 4 with acetic acid, extracted with EtOAc, dried (Na$_2$SO$_4$), concentrated in vacuo and purified by chromatography [SiO$_2$; EtOAc:heptane (1:1)] to give the title compound (232 mg, 67%) as a pale yellow solid.

Method O

6(5-Chloro-2-thienyl)-1H-purine-2-amine (Example 129)

A solution of N,9-bis(tetrahydropyran-2-yl)-6-chloro-9H-purine-2-amine (1.01 g, 3.0 mmol) and Pd(PPh$_3$)$_4$ (250 mg, 10 mol %) in THF (20 mL) was treated with 5-chloro-2-thiophene acid (536 mg, 3.3 mmol) and saturated aq NaHCO$_3$ (10 mL), refluxed for 1 h, diluted with H$_2$O, extracted with EtOAc and the organic phase dried (MgSO$_4$), concentrated in vacuo and purified by chromatography [SiO$_2$; heptane:EtOAc (2:1)] to give the coupled product as a pale-yellow syrup. This material was dissolved in MeOH (20 mL) and stirred vigorously at 50° C. with Amberlyst-15 resin for 1 hr. The resin was filtered off, washed once with MeOH, and then re-suspended in fresh MeOH (20 mL), treated with NH$_3$ solution (2-M in MeOH, 2.0 mL), stirred vigorously at 50° C. for 1 h, filtered, the resin washed twice with MeOH, and the filtrate concentrated in vacuo to give the title compound (230 mg, 36%) as a yellow solid.

Method P

2-Amino-6-(2-furyl)-N-phenyl-9H-purine-9-acetamide (Example 85)

A solution of 2-amino-6-(2-furyl)-9H-purine-9-acetic acid (129 mg, 0.5 mmol) in DCM (2 mL) was treated with EDCI (96 mg, 0.5 mmol) and aniline (45 µL, 0.5 mmol), stirred at room temperature for 3 days, diluted with DCM, washed with water, dried (MgSO$_4$), concentrated in vacuo and purified by chromatography (SiO$_2$; 1% MeOH in EtOAc) to give the title compound (51 mg, 31%) as a white solid.

Method Q

2-Amino-N-benzyl-6-(2-furyl)-9H-purine-9-acetamide (Example 86)

A suspension of 2-amino-6-(2-furyl)-9H-purine-9-acetic acid (129 mg, 0.5 mmol) in DMF (2 mL) was treated with carbonyl diimidazole (81 mg, 0.5 mmol), stirred at room temperature for 1 h, treated with benzylamine (55 µL, 0.5 mmol), stirred at room temperature for 2 h, diluted with water, filtered and dried to give the title compound (115 mg, 66%) as a white solid.

Method R 6-(5-Methyl-[1,2,4]-oxadiazol-3-yl)-1H-purine-2-amine (Example 90)

A mixture of hydroxylamine hydrochloride (847 mg, 12.2 mmol) and potassium hydroxide (855 mg, 15.3 mmol) in EtOH was refluxed for 30 min, cooled, filtered to remove solid potassium chloride, treated with 9-(2-tetrahydropyranyl)-2-(2-tetrahydropyranylamino)-9H-purine-6-carbonitrile (1.0 g, 3.05 mmol), refluxed for 1 h, concentrated in vacuo and the residue triturated with Et$_2$O to give a pale yellow solid (1.12 g). A portion (600 mg) of this material was stirred with N,N-dimethylacetamide dimethylacetal at 100° C. for 1 h, concentrated in vacuo and purified by chromatography (SiO$_2$; EtOAc) to give a pale yellow syrup (212 mg). This material was dissolved in MeOH and stirred vigorously at 50° C. with Amberlyst-15 resin for 1 hr and the resin filtered off and washed once with MeOH. The resin was then re-suspended in fresh MeOH, treated with a solution of NH$_3$ in MeOH (2-M, 2 mL), stirred vigorously at 60° C. for 1 h, filtered, washed twice with MeOH, and the filtrate concentrated in vacuo to give the title compound (73 mg, 21%) as a pale grey solid.

Method S 6-(2-Furyl)-9-(2-(2-pyridyl)ethyl)-9H-purine-2-amine (Example 102)

A mixture of 6-(2-furyl)-1H-purine-2-amine (50 mg, 0.25 mmol) and triphenylphosphine polystyrene (0.21 g, 0.62 mmol) in anhydrous DMF (0.5 mL) and anhydrous THF (2 mL) was treated with 2-(2-hydroxyethyl)pyridine (61 mg, 0.50 mmol), shaken at room temperature for 10 min, treated with di-tert-butyl azodicarboxylate (0.115 g, 0.50 mmol), shaken for 16 h, filtered and the filtrate concentrated in vacuo and purified by chromatography [SiO$_2$; CH$_2$Cl$_2$-MeOH (100:5)] to give the title compound (36 mg, 47%) as an off-white solid.

Method T

Benzyl 2-amino-6-(2-furyl)-9H-purine-9-carboxylate (Example 106)

A solution of 6-(2-furyl)-1H-purine-2-amine (0.201 g, 1.0 mmol), benzyl chloroformate (0.20 mL, 1.1 mmol), triethylamine (0.21 mL, 1.5 mmol) and DMAP (15 mg) in DMF (10 mL) was stirred at room temperature for 4 h, poured into cold water, cooled for 30 min at 5° C. and the resulting solid filtered and dried at 40° C. to give the title compound (0.327 g, 98%) as a cream solid.

Method X

Ethyl 2,6-dichloro-9H-purine-9-acetate

An ice-cold solution of 2,6-dichloro-1H-purine (1.89 g, 10 mmol) in THF (10 mL) was treated with NaH (60% in oil, 440 mg, 11 mmol), stirred at 0° C. for 30 min, treated with ethyl bromoacetate (1.22 mL, 11 mmol), stirred at room temperature for 2 h, poured into sat. NaHCO$_3$, extracted with EtOAc and the combined organic phase dried (MgSO$_4$), concentrated in vacuo and purified by chromatography [SiO$_2$; Heptane:EtOAc (2:1)] to give the title compound (1.46 g, 53%) as a white solid: IR v$_{max}$ (Nujol)/cm$^{-1}$ 3106, 2985, 2955, 2924, 2854, 1734, 1598, 1557, 1374, 1341, 1298, 1156 and 884; NMR δ$_H$ (400 MHz, CDCl$_3$) 1.31 (3H, t, J7.0 Hz), 4.29 (2H, q, J7.0 Hz), 5.01 (2H, s), 8.17 (1H, s).

Method Y 6-(5-Methyl-2-furyl)-1H-purine-2-amine (Example 195)

A solution of N,9-bis(tetrahydropyran-2-yl)-4-chloro-9H-purine-2-amine (338 mg, 1 mmol), 5-methyl-2-(tributylstannyl)furan and Pd(PPh$_3$)$_2$Cl$_2$ (70 mg) in DMN was heated at 80° C. for 5 h, cooled, diluted with H$_2$O, extracted with EtOAc and the organic phase dried (MgSO$_4$), concentrated in vacuo and purified by chromatography [SiO$_2$; heptane:EtOAc (6:1)] to give the coupled product. This material was dissolved in MeOH (20 mL), stirred vigorously at 50° C. with Amberlyst-15 resin for 1 h then the resin was filtered off and washed once with MeOH. The resin was then re-suspended in fresh MeOH (20 mL), treated with NH$_3$ solution (2-M in MeOH, 1.0 mL) stirred vigorously at 50° C. for 1 h, filtered, washed twice with MeOH, and the filtrate concentrated in vacuo to give the title compound (45 mg, 21%) as a pale-yellow solid.

Method Z 6-(5-Methyl-2-pyridinyl)-1H-purine-2-amine (Example 241)

A stirred solution of 5-methyl-2-pyridylzinc bromide (0.5 M, 8 mL, 4 mmol) was treated with Pd(PPh$_3$)$_4$ (250 mg) and N,9-bis(tetrahydropyran-2-yl)$_4$-chloro-9H-purine-2-amine (676 mg, 2 mmol), refluxed for 1 h, cooled, diluted with H$_2$O, extracted with EtOAc, the extracts dried (MgSO$_4$), concentrated in vacuo and purified by chromatography [SiO$_2$; heptane:EtOAc (1:2), then EtOAc] to give the coupled product (498 mg). A portion of this material (100 mg) was suspended in MeOH, treated with a solution of HCl (4-M in dioxan, 0.5 mL), stirred for 17 h, diluted with Et$_2$O and filtered to afford the title compound (37 mg, 35%) as a yellow solid Method AA Methyl 3-(2-amino-6-(2-furyl)-9H-purine-9-yl)propionate (Example 151)

A solution of 6-(2-furyl)-1H-purine-2-amine (0.70 g, 3.48 mmol) and K$_2$CO$_3$ (0.48 g, 3.48 mmol) in DMF (20 mL) was treated with methyl acrylate (3.3 g, 38.3 mmol), stirred for 40 h, diluted with EtOAc, filtered to remove polymeric acrylate, washed with water, dried (MgSO$_4$), concentrated in vacuo and purified by chromatography [SiO$_2$: EtOAc-heptane, (4:1)] to give the title compound (114 mg, 11%) as a white solid.

Method AB 6.(2-Furyl)-2-methyl-1H-purine (Example 153)

A solution of 2-chloro-6-(2-furyl)-1H-purine (1.1 g, 5.0 mmol) and Pd(PPh$_3$)$_4$ (0.58 g, 0.5 mmol) in 1,2-dichloroethane (50 mL) at room temperature was treated dropwise with trimethylaluminium (3.3 mL, 2.0 M hexane), refluxed for 16 h, treated with water (100 mL) then EtOAc (100 mL), stirred for 60 h and filtered through glass microfibre paper. The organic phase was separated, dried (MgSO$_4$), concentrated in vacuo and the resulting solid recrystallised from 90% ethanol to give the title compound (0.30 g, 30%) as a pale brown solid.

Method AC 6-(2-Furyl)-9-(3-nitrobenzyl)-9H-purine-2-amine (Example 158)

An ice-cold solution of 6-(2-furyl)1H-purine-2-amine (201 mg, 1 mmol) in DMF (6 mL) was treated with NaH (44 mg, 1.1 mmol), stirred for 30 min, treated with 3-nitrobenzyl bromide (238 mg, 1.1 mmol), stirred at room temperature for 3 h, treated with water and the resulting solid filtered, suspended in methanol, stilled for 30 min, and filtered to give the title compound (201 mg, 60%) as a yellow solid.

Method AD 9-(3-Aminobenzyl)-6-(2-furyl)-9H-purine-2-amine Example 192)

A solution of 6-(2-furyl)-9-(3-nitrobenzyl)-9H-purine-2-amine (400 mg, 1.12 mmol) in EtOH (10 mL) at 50° C. was treated with a solution of SnCl$_2$.2H$_2$O (808 mg, 3.58 mmol) in conc.HCl (1.8 mL, 21.42 mmol), stirred for 1.5 h, cooled, basified to pH 10 (1-M NaOH) and the resulting solid was filtered, suspended in methanol, treated with HCl in dioxane (4-M, 2 mL), diluted with diethyl ether and filtered to give the title compound (90 mg, 22%) as a yellow solid.

Method AF 9-(3-Acetamidobenzyl)-6-(2-furyl)-9H-purine-2-amine (Example 205)

An ice-cold solution of 9-(3-aminobenzyl)-6-(2-furyl)-9H-purine-2-amine (145 mg, 0.48 mmol) in pyridine (3 mL) was treated with acetyl chloride (38 μL, 0.53 mmol), stirred for 1 h, quenched with water, extracted with EtOAc, dried (MgSO$_4$), concentrated in vacuo and purified by chromatography (SiO$_2$: Hexane:EtOAc (1:3) to EtOAc:MeOH (99:1)) to give the title compound (71 mg, 43%) as a yellow solid.

Method AG 6-(2-Furyl)-9-(3-hydroxybenzyl)-9H-purine-2-amine (Example 221)

An ice-cold solution of 6-(2-furyl)-9-(3-methoxybenzyl)-9H-purine-2-amine (160 mg, 0.5 mmol) in DCM (3 mL) was treated with BBr$_3$ (1 mL, 1-M in DCM, 1 mmol), stirred at 0° C. for 3 h, treated with more BBr$_3$ (2 ml, 1-M in DCM, 2 mmol), stirred for 16 h, treated with NH$_4$Cl solution, extracted with EtOAc, dried (MgSO$_4$), concentrated in vacuo, triturated with ether and filtered. The resulting solid was suspended in aqueous sodium bicarbonate, extracted with ether, the aqueous phase was acidified to pH 7 and the resulting solid filtered, suspended in methanol, treated with HCl in dioxane (4-M, 2 mL), diluted with ether and filtered to give the title compound (82 mg, 48%) as a yellow solid.

Method AH 6-(2-Furyl)-9-(4-methylbenzyl)-9H-purine-2-carbonitrile (Example 173)

A solution of 2-chloro-6-(2-furyl)-9-(4-methylbenzyl)-9H-purine (0.10 g, 0.31 mmol) and Et$_4$NCN (0.10 g, 0.62 mmol) in acetonitrile (10 mL) was treated with DABCO (0.07 g, 0.62 mmol), stirred for 48 h, concentrated in vacuo, dissolved in chloroform (50 mL), washed with water (2×30 mL), dried (MgSO$_4$) and concentrated in vacuo to give the title compound (56 mg, 57%) as a pale green solid.

Method AI

2-Amino-9-(2-fluorobenzyl)-9H-purine-6-thiocarboxamide

A suspension of 2-amino-9-(2-fluorobenzyl)-9H-purine-6-carbonitrile (680 mg, 1.85 mmol) in isopropanol (50 mL) was treated with H$_2$S gas for 15 min, then treated with Et$_3$N (0.51 mL, 3.7 mmol), heated at 50° C. for 1 h, concentrated in vacuo, diluted with Et$_2$O and filtered to give the title compound (757 mg, 100%) as a yellow solid; NMR $\delta_H$ (400 MHz, DMSO) 5.36 (2H, s), 6.66 (2H, br s), 7.06-7.43 (4H, m), 8.15 (1H, s), 9.81 (1H, br s) and 10.22 (1H, br s).

Method AJ 9-(2-Fluorobenzyl)-6-(4-methyl-2-thiazolyl)-9H-purine-2-amine (Example 244)

A stirred suspension of 2-amino-9-(2-fluorobenzyl)-9H-purine-6-thiocarboxamide (200 mg, 0.5 mmol) and chloroacetone (1 mL) in isopropanol (5 mL) was heated at 80° C. for 2 h, filtered and the filtrate concentrated in vacuo and purified by chromatography [SiO$_2$; EtOAc] to give the title compound (26 mg, 12%) as a yellow solid.

Method AK

2-Amino-N-benzyl-6-(2-furyl)-9H-purine-9-acetimidamide (Example 245)

A solution of 2-amino-6-(2-furyl)-9H-purine-9-acetonitrile (0.24 g, 1.0 mmol) in dry toluene (5 mL) under argon was treated with N-benzylmethylchloroaluminium amide in toluene (1.2-M, 5 mL, 6.0 mmol), heated to 80° C. for 3 h, stirred at room temperature for 16 h, poured into a slurry of SiO$_2$ (5 g) and CHCl$_3$ (25 mL) and stirred for 5 min. The slurry was filtered, the filtrate concentrated in vacuo and the resulting solid purified by chromatography [SiO$_2$; CH$_2$Cl$_2$-MeOH—NH$_4$OH (100:10:1)] to give the title compound (0.16 g, 46%) as a white solid.

Method AL (2S)-9-(2-Amino-1-propyl)-6-(2-furyl)-9H-purine-2-amine (Example 251)

A solution of the 6-(2-furyl)-1H-purine-2-amine (0.1 g, 0.5 mmol) in DMSO was treated with freshly ground KOH (112 mg, 2 mmol), shaken for 10 min, treated with N-butoxycarbonyl-L-alaninol mesylate (316 mg, 3 mmol), shaken at 40° C. for a further 17 h, treated with di-tert-butyl dicarbonate (655 mg, 3 mmol), shaken for a further 30 min, diluted with H$_2$O, extracted with EtOAc and the extracts dried (MgSO$_4$), concentrated in vacuo and purified by chromatography [SiO$_2$; (EtOAc)]. The resulting gelatinous solid was dissolved in MeOH (3 mL), treated with HCl solution (4-M in dioxan, 0.5 mL), stirred for 17 h, diluted with Et$_2$O and filtered to give the title compound (67 mg, 45%) as a yellow solid.

Method AM 9-(2-Fluorobenzyl)-6-(1H-pyrazol-3-yl)-9H-purine-2-amine (Example 262)

A mixture of 1-(2-trimethylsilylethoxymethyl)-1H-pyrazole-5-boronic acid, Pd(PPh$_3$)$_4$ and saturated aqueous NaHCO$_3$ in TBF was refluxed with vigorous stirring for 1 h, cooled, diluted with EtOAc, washed with water, dried (MgSO$_4$), concentrated in vacuo and purified by chromatography [SiO$_2$; isohexane:EtOAc (2:1)] to give the coupled product. This material was dissolved in MeOH (2 mL), treated with HCl solution (4-M in dioxan, 2 mL), stirred for 17 h, diluted with Et$_2$O and filtered to give the title compound (161 mg, 46%) as a cream solid.

Method AO 9-(3-Aminobenzyl)-6-(5-methyl-1H-pyrazol-3-yl)-1H-purine-2-amine (Example 265)

A mixture of 6-chloro-9-(3-nitrobenzyl)-1H-purine-2-amine (304 mg, 1 mmol), 1-((2-trimethylsilylethoxy)methyl)-1H-pyrazole-5-boronic acid (2.4 mmol), Pd(PPh$_3$)$_4$ (110 Mg, 10 mol %) and saturated NaHCO$_3$ (5 mL) in THF (20 mL) was refluxed for 3 h, treated with more Pd(PPh$_3$)$_4$ (50 mg, 5 mol %) and refluxed for a further 17 h. The mixture was diluted with H$_2$O (50 mL), extracted with EtOAc (2×25 mL), dried (MgSO$_4$), concentrated in vacuo and purified by chromatography [SiO$_2$; iso-hexane:EtOAc (1:2)] to afford a brown gum. This material was treated with MeOH (10 mL) and 10% Pd/C, stirred under an atmosphere of hydrogen for 30 min, filtered through a pad of Celite and concentrated in vacuo. The resulting gum was dissolved in MeOH (5 mL), treated with HCl solution (4-M in dioxane, 1 mL), stirred for 17 h and the filtered to give the title compound (25 mg, 7%) as a grey solid.

Method AP

2-Allyloxymethyl-6-bromomethylpyridine

A solution of 6-allyloxymethylpyridine-2-methanol (1.56 g, 8.72 mmol) and triphenylphosphine (2.74 g, 10.5 mmol) in dichloromethane (40 mL) at 0° C. was treated portionwise with CBr$_4$ (4.34 g, 13.1 mmol), stirred for 1 h, concentrated in vacuo and purified by chromatography [SiO$_2$; isohexane:EtOAc (3:1)] to give the title compound (1.99 g, 94%) as a colourless oil: NMR $\delta_H$ (400 MHz, CDCl$_3$) 7.71 (1H, t, J 7.5 Hz), 7.40 (1H, d, J 7.5 Hz), 7.34 (1H, d, J 7.5 Hz), 6.03-5.93 (1H, m), 5.37-5.32 (1H, m), 5.26-5.22 (1H, m), 4.64 (2H, s), 4.54 (2H, s) and 4.14-4.12 (2H, m).

Method AQ 6-(2-Furyl)-9-(5-indolylmethyl)-1H-purine-2-amine (Example 272)

A solution of tert-butyl 5-(2-amino-6-(2-furyl)-1H-purine-9-ylmethyl)indole-1-carboxylate (352 mg, 0.82 mmol) in MeOH (3 mL) was treated with NaOMe (221 mg, 4.1 mmol), refluxed for 17 h, diluted with water (10 mL) and filtered to give the title compound (168 mg, 62%) as a brown powder.

Method AR tert-Butyl 5-bromomethylindole-1-carboxylate

A solution of tert-butyl 5-methylindole-1-carboxylate (2.07 g, 9.0 mmol) in CCl$_4$ (50 mL) was treated with N-bromosuccinimide (1.60 g, 9.0 mmol) and benzoyl peroxide (75% in H$_2$O, 276 mg, 9.0 mmol), refluxed for 3 h, concentrated in vacuo and purified by chromatography [SiO$_2$; iso-hexane:EtOAc (20:1)] to give the title compound (1.67 g, 60%) as an orange oil: NMR $\delta_H$ (400 MHz, CDCl$_3$) 8.11 (1H, br d, J 8.5 Hz), 6.72 (1H, d, J 3.5 Hz), 7.59 (1H, d, J 1.5 Hz), 7.35 (1H, dd, J 8.5, 1.5 Hz), 6.54 (1H, d, J 4.0 Hz), 4.64 (2H, s) and 1.67 (9H, s).

Method AS

6-Allyloxymethyl-2-pyridinemethanol

A solution of 2,6-pyridinedimethanol (5.0 g, 35.9 mmol) in DMF (30 mL) at 0° C. was treated with sodium hydride (1.44 g, 35.9 mmol), stirred for 30 min, treated with allyl bromide (3.42 ml, 39.5 mmol), stirred for 16 h at room temperature, poured into water (150 mL), extracted with EtOAc (3×30 mL) and the combined organic phase was dried (MgSO$_4$), concentrated in vacuo and purified by chromatography [SiO$_2$; iso-hexane:EtOAc (3:1 to 1:1)] to give the title compound (1.56 g, 24%) as a colourless oil: NMR $\delta_H$ (400 MHz, CDCl$_3$) 7.69 (1H, t, J 7.5 Hz), 7.37 (1H, d, J 7.5 Hz), 7.13 (1H, d, J 7.5 Hz) 6.04-5.93 (1H, m), 5.38-5.21 (2H, m), 4.74 (2H, d, J 5.0 Hz), 4.65 (2H, s), 4.15-4.09 (2H, m) and 3.76 (1H, t, J 5.0 Hz).

The following intermediates were synthesised by the methods described above.

6-Chloro-9-(3-nitrobenzyl)-1H-purine-2-amine

This was prepared from 6-chloro-1H-purine-2-amine by method AC: NMR $\delta_H$ (400 Mz, DMSO) 8.82 (1H, s), 8.20-8.13 (2H, m), 7.73-7.61 (2H, m), 6.94 (2H, br s) and 5.45 (2H, s).

6-Chloro-9-(3-methoxybenzyl)-1H-purine-2-amine

This was prepared from 6-chloro-1H-purine-2-amine by method AC: NMR $\delta_H$ (400 MHz, DMSO) 8.22 (1H, s), 7.25 (1H, t, J 7.5 Hz), 6.91 (2H, br s), 6.89-6.84 (2H, m), 6.79 (1H, d, J 7.5 Hz), 5.25 (2H, s) and 3.72 (3H, s).

6-Chloro-9-(2-fluorobenzyl)-1H-purine-2-amine

This was prepared from 6-chloro-1H-purine-2-amine by method AC: IR (Nujol)/cm$^{-1}$ 3488, 3379, 2926, 1569, 1568, 1465, 1378, 918 and 756; NMR $\delta_H$ (400 MHz, DMSO) 8.17 (1H, s), 7.43-7.33 (1H, m), 7.29-7.21 (1H, m), 7.20-7.07 (2H, m), 6.91 (2H, br s) and 5.35 (2H, s).

2,6-Dichloro-9-(2-trimethylsilylethoxymethyl)-9H-purine

This was prepared from 2,6-dichloro-1H-purine by method X to give the title compound (1.77 g, 78%) as a pale yellow oil; NMR $\delta_H$ (400 Mz, CDCl$_3$) 0.00 (9H, s), 0.94 (2H, t, J 8.3 Hz), 3.63 (2H, t, J 8.3 Hz), 5.63 (2H, s) and 8.25 (1H, s).

tert-Butyl 2-amino-6-chloro-9H-purine-9-carboxylate

This was prepared from 6-chloro-1H-purine-2-amine and di-tert-butyl dicarbonate by method G to give title compound (862 mg, 64%) as a white solid; mp>350° C.; IR $v_{max}$ (Nujol)/mc$^{-1}$ 3521, 3304, 3193, 3129, 2955, 2925, 2854, 1772, 1730, 1632, 1561, 1511, 1367, 1308 and 1155; NMR $\delta_H$ (400 MHz, DMSO) 1.58 (9H, s), 7.06 (2H, s), 8.36 (1H, s). Anal. Calcd for $C_{10}H_{12}ClN_5O_2$: C, 44.54; H, 4.48; N, 25.96. Found: C, 44.27; H, 4.54; N, 25.88.

Isobutyl 2-amino-6-chloro-9H-purine-9-carboxylate

This was prepared from 6-chloro-1H-purine-2-amine by method T to give the title compound (528 mg, 98%) as a white solid; IR $v_{max}$ (Nujol)/cm$^{-1}$ 3519, 3310, 3201, 3124, 2955, 2925, 2854, 1778, 1624, 1560, 1469, 1367, 1301 and 1186; NMR $\delta_H$ (400 MHz, CDCl$_3$) 1.07 (6H, d, J 7.0 Hz), 2.10-2.25 (1H, m), 4.29 (2H, d, J 6.6 Hz), 5.48 (2H, s) and 8.25 (1H, s).

2-Amino-N-tert-butyl-6-chloro-9H-purine-9-carboxamide

This was prepared from 6-chloro-1H-purine-2-amine by method G to give the title compound (286 mg, 53%) as a white solid; IR $v_{max}$ (Nujol)/cm$^{-1}$ 3501, 3299, 3190, 3156, 2993, 2955, 2924, 2854, 1742, 1627, 1563, 1506 and 1369; NMR $\delta_H$ (400 Mz, CDCl$_3$) 1.46 (9H, s), 7.40 (1H, s), 8.45 (1H, s) and 8.57 (1H, s).

Phenyl 2-amino-6-chloro-9H-purine-9-carboxylate

This was prepared from 6-chloro-1H-purine-2-amine by method T to give the crude title compound (625 mg, 100%) as a white solid.

2-Amino-6-chloro-N-phenyl-9H-purine-9-carboxamide

This was prepared from 6-chloro-1H-purine-2-amine by method G to give the title compound (424 mg, 73%) as a white solid; IR $v_{max}$ (Nujol)/cm$^{-1}$ 3506, 3333, 3292, 3191, 3140, 2925, 2854, 1740, 1653, 1637, 1562, 1481 and 1367; NMR $\delta_H$ (400 MH, DMSO) 7.20 (1H, m), 7.44-7.50 (2H, m), 7.61 (2H, s), 7.75-7.81 (2H, m), 8.60 (1H, s), 10.86 (1H, s).

2-Amino-6-chloro-N-ethyl-9H-purine-9-carboxamide

This was prepared from 6-chloro-1H-purine-2-amine by method G to give the title compound (449 mg, 93%) as a white solid; IR $v_{max}$ (Nujol)/cm$^{-1}$ 3404, 3324, 3304, 3222, 3125, 2925, 2854, 1730, 1646, 1614, 1547, 1514, 1484, 1460, 1370 and 1228; NMR $\delta_H$ (400 z, DMSO) 1.25 (3H, t, J 7.0 Hz), 3.37-3.46 (2H, m), 7.37 (2H, s), 8.47 (1H, s), 8.64 (1H, t, J5.5 Hz).

2-Amino-6-chloro-N-cyclohexyl-9H-purine-9-carboxamide

This was prepared from 6-chloro-1H-purine-2-amine by method G to give the title compound (1.66 g, 53%) as a white solid; NMR $\delta_H$ (400 MHz, CDCl$_3$) 1.29-1.41 (1H, m), 1.42-1.54 (4H, m), 1.60-1.70 (1H, m), 1.74-1.86 (2H, m), 2.00-2.10 (2H, m), 3.88-4.00 (1H, m), 8.13 (1H, d, J6.7 Hz) and 8.81 (1H, s).

2-Amino-9-(2-fluorobenzyl)-9H-purine-6-carbonitrile

This was prepared from 6-chloro-9-(2-fluorobenzyl)-9H-purine-2-amine by method AH to give the title compound (450 mg, 84%) as a cream solid; NMR $\delta_H$ (400 MHz, DMSO) 5.39 (2H, s), 7.12 (2H, br s), 7.1207.45 (4H, m) and 8.41 (1H, s).

Table 2—Analytical data

HPLC is carried out using the following conditions: Column. Waters Xterra RP 18 (50×4.6 mm); Particle size 5 μM; Mobile phase MeOH: 10 mM aq NH$_4$OAc (pH 7 buffer); Gradient 50:50 isocratic for 1 min. then linear gradient 50:50 to 80:20 over 5 min. then 80:20 isocratic for 3 min.; Flow rate 2.0 mL/min.; Detection wavelength λ=230 nM. Retention times are provided in Table 2.

Alternatively HPLC is carried out using the following conditions: Column. Supelcosil ABZ$^+$ (170×4.6 mm), particle size 5 μM, mobile phase MeOH: 10 mM aq NH$_4$OAc (80:20), (80:50), (70:30), (60:40) or (50:20) (specified in Table 2), flow rate 1.0 mL/min., detection wavelength λ230 nM. Retention times and mobile phase ratio are provided in Table 2.

| Example | Method | Yield(%) | Data |
|---|---|---|---|
| 1 | A | 70 | mp 105.8-106.2° C.; IR $v_{max}$(Nujol)/cm$^{-1}$ 3552, 3146, 3892, 3082, 2954, 2924, 2854, 1589, 1566, 1484, 1370, 1319, 1250, 1219, 1162, 1095 and 841; NMR $\delta_H$ (400 MHz, CDCl$_3$) 0.0(9H, s), 0.97(2H, t, J 8.3 Hz), 3.66(2H, t, J 8.3 Hz), 5.66 (2H, s), 6.69-6.73(1H, m), 7.82(1H, s), 7.92(1H, d, J 3.5 Hz) and 8.24(1H, s); Anal. Calcd for $C_{15}H_{19}ClN_4O_2Si$: C, 51.35; H, 5.46; N, 15.96. Found: C, 51.39; H, 5.45; N, 15.97. |
| 2 | B | 86 | mp 81.5-82.2° C.; IR $v_{max}$ (Nujol)/cm$^{-1}$ 3142, 3109, 2927, 2854, 1601, 1585, 1560, 1465, 1397, 1372 and 1106; NMR $\delta_H$ (400 MHz, DMSO) −0.04(9H, s), 0.95(2H, t, J 8.3 Hz), 3.29(6H, s), 3.64(2H, t, J 8.3 Hz), 5.51(2H, s), 6.60-6.63 (1H, m), 7.67(1H, d, J 2.5 Hz), 7.73-7.74(1H, m) and 7.87(1H, s); Anal. Calcd for $C_{17}H_{25}N_5O_2Si$: C, 56.80; H, 7.01; N, 19.47. Found: C, 56.40; H, 6.98; N, 19.27. |
| 3 | C | 76 | IR $v_{max}$ (Nujol)/cm$^{-1}$ 3132, 3105, 2924, 2854, 1631, 1588, 1563, 1538, 1466, 1401, 1364, 832 and 780; NMR $\delta_H$ (400 MHz, DMSO) 3.21(6H, s), 6.74-6.80 |

-continued

| Example | Method | Yield(%) | Data |
|---|---|---|---|
| | | | (1H, m), 7.77(1H, d, J 2.9 Hz), 8.00(1H, s), 8.11(1H, s), 12.76(1H, s); Anal. Calcd for $C_{11}H_{11}N_5O \cdot 0.1\ H_2O$: C, 57.18; H, 4.89; N, 30.31. Found: C, 57.14; H, 4.81; N, 30.26. |
| 4 | B | 60 | mp 125.9-126.4° C.; IR $\nu_{max}$ (Nujol)/cm$^{-1}$ 3376, 3327, 2955, 2924, 2854, 1605, 1588, 1537, 1462, 1410, 1367, 1356, 1248, 1094 and 835; NMR $\delta_H$ (400 MHz, CDCl$_3$) −0.03(9H, s), 0.94(2H, t, J 8.3 Hz), 1.21(1H, d, J 6.5 Hz), 3.61(2H, t, J 8.3 Hz), 3.69(4H, q, J 5.6 Hz), 3.90(2H, q, J 4.8 Hz), 5.49(2H, s), 5.56-5.64 (1H, m), 6.62-6.66(1H, m), 7.72(1H, d, J 5.6 Hz) and 7.79(1H, d, J 3.5 Hz). |
| 5 | C | 86 | mp 227.1-228.1° C.; IR $\nu_{max}$ (Nujol)/cm$^{-1}$ 3428, 3113, 2924, 2854, 1626, 1588, 1576, 1541, 1485, 1457, 1404 and 1371; NMR $\delta_H$ (400 MHz, DMSO) 3.41(2H, q, J 6.0 Hz), 3.53-3.62(2H, m), 4.67-4.76(1H, s), 6.74-6.79(1H, m), 6.81-6.94 (1H, s), 7.69-7.78(1H, s), 7.98(1H, s), 8.05-8.15(1H, s) and 12.68-12.81 (1H, s). |
| 7 | A | 48 | mp >305° C. dec.; IR $\nu_{max}$ (Nujol)/cm$^{-1}$ 3130, 3111, 2925, 2854, 1776, 1755, 1596, 1558, 1467, 1373, 1302, 1288, 1153 and 1135; NMR $\delta_H$ (400 MHz, CDCl$_3$) 1.71(9H, s), 6.63-6.72(1H, m), 7.78-7.81(1H, m), 7.90(1H, d, J 3.5 Hz) and 8.50 (1H, s); Anal. Calcd for $C_{14}H_{13}ClN_4O_3$: C, 52.43; H, 4.09; N, 17.46. Found: C, 52.68; H, 4.08; N, 17.50. |
| 8 | A | 61 | mp >303° C. dec.; IR $\nu_{max}$ (Nujol)/cm$^{-1}$ 3101, 3042, 2927, 2854, 1628, 1556, 1448, 1364, 1283, 1166, 1023, 921, 837 and 752; NMR $\delta_H$ (400 MHz, DMSO) 6.84-6.91 (1H, m), 7.73-7.93(1H, s), 8.13(1H, s), 8.65-8.75(1H, s) and 13.71-13.84 (1H, s); Anal. Calcd for $C_9H_5ClN_4O$: C, 49.00; H, 2.28; N, 25.38. Found: C, 48.78; H, 2.54; N, 25.10. |
| 9 | B | 64 | mp 130.9-131.5° C.; IR $\nu_{max}$ (Nujol)/cm$^{-1}$ 3526, 3218, 3111, 3070, 2924, 2855, 2733, 1629, 1600, 1560, 1518, 1463, 1375 and 835; NMR $\delta_H$ (400 MHz, DMSO) 1.85-2.08(4H, m), 3.42-3.66(3H, m), 3.67-3.78(1H, m), 4.15-4.25(1H, s), 4.81-5.09(1H, s), 6.76-6.80(1H, m), 7.73-7.79(1H, s), 8.01(1H, s), 8.09-8.16 (1H, s) and 12.78-12.87(1H, s); Anal. Calcd for $C_{14}H_{15}N_5O_2$: C, 56.27; H, 5.57; N, 23.44. Found: C, 56.35; H, 5.52; N, 23.18. |
| 10 | B | 50 | mp 206.5-207.4° C.; IR $\nu_{max}$ (Nujol)/cm$^{-1}$ 3389, 3121, 2924, 2854, 1620, 1590, 1570 1539, 1515, 1465 and 1026; NMR $\delta_H$ (400 MHz, DMSO) 3.71(3H, s), 3.73 (3H, s), 4.49(2H, d, J 5.9 Hz), 6.77(1H, s), 6.82-6.94(2H, m), 7.06(1H, s), 7.41-7.56(1H, s), 7.76(1H, s), 7.98(1H, s), 8.08(1H, s) and 12.72(1H, s); Anal. Calcd for $C_{14}H_{15}N_5O_2 \cdot 0.5\ H_2O$: C, 59.99; H, 5.03; N, 19.43. Found: C, 59.81; H, 4.75; N, 19.07. |
| 11 | D | 57 | mp >230° C. dec.; IR $\nu_{max}$ (Nujol)/cm$^{-1}$ 3370, 3134, 3085, 2924, 2854, 2481, 1674, 1616 and 1465; NMR $\delta_H$ (400 MHz, DMSO) 6.91-6.97(1H, m), 7.91(1H, s), 8.25(1H, s) and 8.71(1H, s); M/Z 202(M + H)$^+$. |
| 12 | E | 32 | mp 112.0-113.0° C.; IR $\nu_{max}$ (Nujol)/cm$^{-1}$ 3113, 2925, 2854, 1775, 1749, 1596, 1460, 1374, 1303, 1139 and 762; NMR $\delta_H$ (400 MHz, CDCl$_3$) 1.72(9H, s), 2.68 (3H, s), 6.63-6.68(1H, m), 7.77(1H, s), 7.82(1H, d, J 3.6 Hz) and 8.44(1H, s). |
| 13 | F | 86 | mp 239.5-239.9° C.; IR $\nu_{max}$ (Nujol)/cm$^{-1}$ 3371, 3044, 2924, 2854, 2703, 1624, 1606, 1584, 1563, 1465, 1307 and 843; NMR $\delta_H$ (400 MHz, DMSO) 2.61(3H, s), 3.93-5.45(2H, m), 6.80-6.86(1H, m), 7.79(1H, d, J 3.6 Hz), 8.07-8.09(1H, m) and 8.53(1H, s); Anal. Calcd for $C_{10}H_8N_4OS \cdot 0.25\ HCl \cdot 0.5\ H_2O$: C, 48.26; H, 3.71; N, 22.14. Found: C, 47.97; H, 3.72; N, 22.38. |
| 14 | A | 69 | mp 143.2-144.1° C.; IR $\nu_{max}$ (Nujol)/cm$^{-1}$ 3512, 3394, 3324, 3215, 2955, 2925, 2854, 1769, 1749, 1639, 1587, 1565, 1372, 1298 and 1143; NMR $\delta_H$ (400 MHz, CDCl$_3$) 1.68(9H, s), 5.38(2H, s), 6.62-6.66(1H, m), 7.71-7.73(1H, m), 7.82 (1H, d, J 3.6 Hz) and 8.17(1H, s); Anal. Calcd for $C_{14}H_{15}N_5O_3$: C, 55.81; H, 5.02; N, 23.23. Found: C, 55.73; H, 5.06; N, 22.84. |
| 15 | B | 45 | mp 185.5-186° C.; IR $\nu_{max}$ (Nujol)/cm$^{-1}$ 3307, 3141, 3077, 2954, 2924, 2854, 1604, 1542, 1460, 1368, 1247 and 1093; NMR $\delta_H$ (400 MHz, CDCl$_3$) 0.00(9H, s), 0.97(2H, t, J 8.3 Hz), 3.66(2H, t, J 8.3 Hz), 4.19(2H, t, J 5.8 Hz), 5.15-5.20 (1H, m), 5.30-5.37(1H, m), 5.54(2H, s), 5.96-6.09(1H, m), 6.63-6.69(1H, m), 7.74-7.76(1H, m), 7.81(1H, d, J 3.5 Hz) and 7.92(1H, s); Anal. Calcd for $C_{18}H_{25}N_5O_2Si$: C, 58.19; H, 6.78; N, 18.84. Found: C, 58.14; H, 6.80; N, 18.73. |
| 16 | B | 82 | mp 160.1-160.8° C.; IR $\nu_{max}$ (Nujol)/cm$^{-1}$ 3312, 3143, 3095, 2924, 2854, 1605, 1580, 1552, 1467, 1396, 1367, 1249 and 1092; NMR $\delta_H$ (400 MHz, CDCl$_3$) 0.00 (9H, s), 0.99(2H, t, J 8.3 Hz), 3.11(3H, d, J 5.0 Hz), 3.68(2H, t, J 8.3 Hz), 5.21-5.29 (1H, s), 5.56(2H, s), 6.64-6.69(1H, m), 7.74(1H, s), 7.81(1H, d, J 2.9 Hz) and 7.91(1H, s); Anal. Calcd for $C_{16}H_{23}N_5O_2Si \cdot 0.2\ H_2O$: C, 55.05; H, 6.76; N, 20.06. Found: C, 55.03; H, 6.60; N, 20.12. |
| 17 | C | 58 | mp 158.7-160.1° C.; IR $\nu_{max}$ (Nujol)/cm$^{-1}$ 3397, 3528, 3084, 2924, 2854, 1626, 1592, 1536 and 1460; NMR $\delta_H$ (400 MHz, DMSO) 3.99 (2H, t, J 4.9 Hz), 5.06 (1H, d, J 10.2 Hz), 5.21(1H, d, J 18.9 Hz), 5.91-6.03(1H, m), 6.72-6.79(1H, m), 7.12-7.20(1H, s), 7.76(1H, d, J 3.0 Hz), 7.97(1H, s) and 8.08(1H, s). |
| 18 | C | 81 | mp 235-236° C. dec.; IR $\nu_{max}$ (Nujol)/cm$^{-1}$ 3311, 3102, 2924, 2854, 1630, 1587, 1555, 1460, 1400 and 1370; NMR $\delta_H$ (400 MHz, DMSO) 2.87(3H, d, J 4.8 Hz), 6.74-6.78(1H, m), 6.90-7.01(1H, m), 7.76(1H, d, J 3.5 Hz), 7.96(1H, s) and 8.07(1H, s). |
| 19 | A | 41 | mp 177.6-178.2° C.; IR $\nu_{max}$ (Nujol)/cm$^{-1}$ 3511, 3406, 3289, 3254, 3164, 3132, 2924, 2854, 1723, 1636, 1600, 1588, 1549, 1467 and 1403; NMR $\delta_H$ (400 MHz, DMSO) 1.23-1.34(1H, m), 1.36-1.54(4H, m), 1.58-1.68(1H, m), 1.73-1.81 (2H, m), 1.94-2.06(2H, m), 3.73-3.84(1H, m), 6.75-6.81(1H, m), 6.91 (1H, s), 7.76(1H, d, J 2.6 Hz), 7.99(1H, s), 8.44(1H, s) and 8.80(1H, d, J 7.5 Hz). |

-continued

| Example | Method | Yield(%) | Data |
|---|---|---|---|
| 20 | A | 24 | mp >300° C. dec.; IR $v_{max}$ (Nujol)/cm$^{-1}$ 3368, 3323, 3217, 3140, 3128, 2956, 2925, 2855, 1750, 1641, 1590, 1565, 1468, 1400, 1371, 1274 and 995; NMR $\delta_H$ (400 MHz, DMSO) 1.04(6H, d, J 6.3 Hz), 2.03-2.19(1H, m), 4.23(2H, d, J 7.0 Hz), 6.77-6.81(1H, m), 6.85(2H, s), 7.74(1H, d, J 3.6 Hz), 8.01(1H, s) and 8.46 (1H, s); Anal. Calcd for $C_{14}H_{15}N_5O_3$: C, 55.81; H, 5.02; N, 23.23. Found: C, 55.84; H, 5.08; N, 23.24. |
| 21 | A | 73 | mp 295° C. dec.; IR $v_{max}$ (Nujol)/cm$^{-1}$ 3517, 3310, 3269, 3190, 3127, 3082, 2924, 2854, 1734, 1644, 1627, 1603, 1561, 1468 and 1369; NMR $\delta_H$ (400 MHz, CDCl$_3$) 1.52(9H, s), 5.14(2H, s), 6.62-6.70(1H, m), 7.72-7.74(1H, m), 7.86(1H, d, J 3.5 Hz), 8.47(1H, s) and 8.59(1H, s); Anal. Calcd for $C_{14}H_{16}N_6O_2$: C, 55.99; H, 5.37; N, 27.97. Found: C, 55.78; H, 5.35; N, 27.79. |
| 22 | A | 75 | mp >300° C. dec.; IR $v_{max}$ (Nujol)/cm$^{-1}$ 3499, 3298, 3179, 3117, 2924, 2854, 1790, 1635, 1589, 1373, 1302 and 1193; NMR $\delta_H$ (400 MHz, DMSO) 6.78-6.82(1H, m), 6.96(2H, s), 7.37-7.44(1H, m), 7.44-7.50(2H, m), 7.50-7.59(2H, m), 7.75-7.77(2H, m), 8.02-8.03(1H, m) and 8.65(1H, s); Anal. Calcd for $C_{16}H_{11}N_5O_3 \cdot 0.25\ H_2O$: C, 58.99; H, 3.56; N, 21.50. Found: C, 58.79; H, 3.32; N, 21.82. |
| 23 | A | 26 | mp >330° C. dec.; IR $v_{max}$ (Nujol)/cm$^{-1}$ 2924, 2854, 1678, 1613, 1597, 1568, 1355, 1288 and 751; NMR $\delta_H$ (400 MHz, DMSO) 6.88-6.93(1H, m), 7.09(1H, t, J 7.4 Hz), 7.41(2H, t, J 8.1 Hz), 7.75(1H, d, J 8.0 Hz), 7.92(1H, s), 8.24(1H, s), 8.48 (1H, s), 10.02(1H, s), 12.35(1H, s) and 13.42(1H, s); Anal. Calcd for $C_{16}H_{12}N_6O_2$: C, 60.00; H, 3.78; N, 26.22. Found: C, 59.60; H, 3.75; N, 26.01; M/Z 321(M + H)$^+$. |
| 24 | A | 74 | mp >280° C. dec.; IR $v_{max}$ (Nujol)/cm$^{-1}$ 3510, 3292, 3161, 3112, 3053, 2955, 2925, 2854, 1749, 1725, 1645, 1603, 1591, 1567, 1468, 1401, 1372 and 748; NMR $\delta_H$ (400 MHz, DMSO) 1.26(3H, t, J 7.2 Hz), 3.38-3.49(2H, m), 6.78-6.83(1H, m), 7.05(2H, s), 7.77(1H, d, J 3.5 Hz), 8.02-8.04(1H, m), 8.48(1H, s) and 8.86 (1H, t, J 5.5 Hz); Anal. Calcd for $C_{12}H_{12}N_6O_2$: C, 52.94; H, 4.44; N, 30.85. Found: C, 52.94; H, 4.59; N, 30.65. |
| 25 | A | 21 | mp >300° C. dec.; IR $v_{max}$ (Nujol)/cm$^{-1}$ 3392, 3315, 3193, 3135, 3114, 2924, 2854, 1728, 1641, 1601, 1557, 1509, 1479, 1468, 1405, 1377, 1270, 1240 and 763; NMR $\delta_H$ (400 MHz, DMSO) 6.80-6.85(1H, m), 7.23(1H, t, J 7.4 Hz), 7.31 (2H, s), 7.48(2H, t, J 8.0 Hz), 7.78-7.85(3H, m), 8.04-8.07(1H, m), 8.60(1H, s) and 11.13(1H, s); Anal. Calcd for $C_{16}H_{12}N_6O_2 \cdot 0.5\ H_2O$: C, 58.36; H, 3.98; N, 25.52. Found: C, 58.38; H, 3.70; N, 25.61. |
| 26 | G | 84 | mp >300° C. dec.; IR $v_{max}$ (Nujol)/cm$^{-1}$ 3515, 3279, 3187, 3131, 2924, 2854, 1725, 1631, 1600, 1552, 1465, 1400 and 1373; NMR $\delta_H$ (400 MHz, DMSO) 4.66(2H, d, J 6.2 Hz), 6.79-6.83(1H, m), 7.06(2H, s), 7.29-7.45(5H, m), 7.78(1H, d, J 3.5 Hz), 8.03(1H, s), 8.53(1H, s) and 9.34(1H, t, J 6.2 Hz); Anal. Calcd for $C_{17}H_{14}N_6O_2 \cdot 0.1\ H_2O$: C, 60.74; H, 4.26; N, 25.00. Found: C, 60.94; H, 4.25; N, 24.67. |
| 27 | H | 53 | mp 238.7-239.2° C.; IR $v_{max}$ (Nujol)/cm$^{-1}$ 3500, 3343, 3221, 3135, 3064, 2925, 2854, 1628, 1593, 1566, 1478, 1383, 1349, 1146 and 1065; NMR $\delta_H$ (400 MHz, DMSO) 1.29(9H, s), 6.65-6.79(1H, m), 7.05(2H, s), 7.69(1H, d, J 3.5 Hz), 7.73(2H, d, J 9.1 Hz), 7.98-8.01(1H, m), 8.19(2H, d, J 8.6 Hz) and 8.53(1H, s); Anal. Calcd for $C_{19}H_{19}N_5O_3S \cdot 0.1\ H_2O$: C, 57.16; H, 4.85; N, 17.54. Found: C, 57.04; H, 4.86; N, 17.22. |
| 28 | H | 65 | mp >300° C. dec.; IR $v_{max}$ (Nujol)/cm$^{-1}$ 3497, 3283, 3158, 3129, 2931, 2854, 1720, 1627, 1593, 1467, 1392, 1360, 1259, 1180 and 746; NMR $\delta_H$ (400 MHz, DMSO) 1.23-1.35(1H, m), 1.39-1.58(4H, m), 1.69-1.82(3H, m), 1.95-2.04(2H, m), 3.94-4.03(1H, m), 6.77-6.80(1H, m), 6.91(2H, m), 7.74(1H, d, J 3.5 Hz), 7.99-8.09(1H, m) and 8.56(1H, s). |
| 29 | I | 62 | mp >300° C. dec.; IR $v_{max}$ (Nujol)/cm$^{-1}$ 3414, 3312, 3206, 3137, 3118, 2922, 2854, 1681, 1629, 1588, 1565, 1464, 1403, 1368 and 1194; NMR $\delta_H$ (400 MHz, DMSO) 1.82-2.01(4H, m), 3.49-3.63(4H, m), 6.76-6.80(1H, m), 6.81(2H, s), 7.72-7.77 (1H, m), 8.06(1H, s) and 8.31(1H, s). |
| 30 | G | 92 | mp >300° C. dec.; IR $v_{max}$ (Nujol)/cm$^{-1}$ 3550, 3378, 3309, 3242, 3139, 3054, 2924, 2854, 1715, 1640, 1603, 1588, 1543, 1465 and 1377; NMR $\delta_H$ (400 MHz, DMSO) 1.32(6H, d, J 6.6 Hz), 3.98-4.10(1H, m), 6.78-6.81(1H, m), 7.08(2H, s), 7.76(1H, d, J 3.5 Hz), 8.01-8.04(1H, m), 8.47(1H, s) and 8.79(1H, d, J 7.4 Hz); Anal. Calcd for $C_{13}H_{14}N_6O_2 \cdot 0.9\ H_2O$: C, 51.62; H, 5.26; N, 27.78. Found: C, 51.80; H, 5.04; N, 27.51. |
| 31 | A | 38 | mp 177.4-177.8° C.; IR $v_{max}$ (Nujol)/cm$^{-1}$ 3304, 3126, 3106, 2926, 2854, 1726, 1597, 1567, 1548, 1465, 1377 and 768; NMR $\delta_H$ (400 MHz, DMSO) 1.29-1.41 (1H, m), 1.44-1.53(4H, m), 1.60-1.69(1H, m), 1.75-1.85(2H, m), 2.00-2.10 (2H, m), 3.89-4.00(1H, m), 6.67-6.72(1H, m), 7.80-7.82(1H, m) and 7.94(1H, d, J 3.5 Hz). |
| 33 | H | 17 | mp 175.4-176.1° C.; IR $v_{max}$ (Nujol)/cm$^{-1}$ 3497, 3294, 3173, 3122, 2924, 2854, 1729, 1623, 1595, 1463, 1392, 1376 and 1359; NMR $\delta_H$ (400 MHz, CDCl$_3$) 1.09 (6H, d, J 6.5 Hz), 2.27-2.42(1H, m), 3.24(2H, d, J 6.3 Hz), 5.16(1H, s), 6.62-6.66 (1H, m), 7.70-7.73(1H, m), 7.82(1H, d, J 3.5 Hz) and 8.48(1H, s); Anal. Calcd for $C_{14}H_{15}N_5O_2$: C, 58.94; H, 5.30; N, 24.54. Found: C, 58.84; H, 5.30; N, 24.19. |
| 34 | H | 14 | mp >300° C. dec.; NMR $\delta_H$ (400 MHz, CDCl$_3$) 2.94(3H, s), 5.21(2H, s), 6.62-6.69 (1H, m), 7.72(1H, s), 7.83(1H, d, J 3.6 Hz) and 8.48(1H, s). |
| 35 | G | 82 | mp 175.5° C.; IR $v_{max}$ (Nujol)/cm$^{-1}$ 3282, 3131, 3116, 3033, 2924, 2854, 1735, 1587, 1576, 1538, 1478, 1462, 1375, 1294 and 1201; NMR $\delta_H$ (400 MHz, CDCl$_3$) |

-continued

| Example | Method | Yield(%) | Data |
|---|---|---|---|
| | | | 2.35(3H, s), 4.69(2H, d, J 5.5 Hz), 6.63-6.67(1H, m), 7.33-7.44(5H, m), 7.77-7.78(1H, m), 7.84(1H, d, J 3.4 Hz), 8.65(1H, s) and 8.96-9.03(1H, s); Anal. Calcd for $C_{18}H_{15}N_5O_2S$: C, 59.17; H, 4.14; N, 19.16. Found: C, 59.00; H, 4.14; N, 18.95. |
| 36 | G | 100 | IR $\nu_{max}$ (Nujol)/cm$^{-1}$ 3399, 3317, 3204, 1717, 1643, 1603, 1557, 1510, 1403, 1268 and 1232; NMR $\delta_H$ (400 MHz, DMSO) 0.94(3H, t, J 7.3 Hz), 1.39(2H, sextet, J 7.4 Hz), 1.61(2H, quintet, J 7.3 Hz), 3.38(2H, q, J 6.5 Hz), 6.78(1H, dd, J 1.5, 3.5 Hz), 7.02(2H, br s), 7.74(1H, dd, J 1.0, 3.5 Hz), 8.00(1H, dd, J 1.0, 1.5 Hz), 8.46(1H, s) and 8.83(1H, t, J 5.4 Hz); Retention time: 4.12 min |
| 37 | G | 100 | NMR $\delta_H$ (400 MHz, DMSO) 3.74(3H, s), 4.55(2H, d, J 5.9 Hz), 6.78(1H, dd, J 1.5, 3.5 Hz), 6.93(2H, d, J 8.5 Hz), 7.01(2H, br s), 7.33(2H, d, J 8.5 Hz), 7.75 (1H, dd, J 1.0, 3.5 Hz), 8.01(1H, m), 8.49(1H, s) and 9.23(1H, t, J 6.3 Hz); Retention time: 4.62 min |
| 38 | G | 97 | NMR $\delta_H$ (400 MHz, DMSO) 2.29(3H, s), 4.58(2H, d, J 6.1 Hz), 6.78(1H, dd, J 1.5, 3.5 Hz), 7.01(2H, br s), 7.17(2H, d, J 8.0 Hz), 7.29(2H, d, J 8.0 Hz), 7.75 (1H, dd, J 1.0, 3.5 Hz), 8.01(1H, dd, J 1.0, 1.5 Hz), 8.50(1H, s) and 9.26(1H, t, J 6.3 Hz); Retention time: 5.55 min |
| 39 | G | 100 | NMR $\delta_H$ (400 MHz, DMSO) 4.69(2H, d, J 6.6 Hz), 6.79(1H, dd, J 1.5, 3.5 Hz), 7.00(2H, br s), 7.36(2H, m), 7.51(2H, m), 7.76(1H, dd, J 1.0, 3.5 Hz), 8.02(1H, m), 8.50(1H, s) and 9.41(1H, t, J 6.4 Hz); Retention time: 5.63 min |
| 40 | G | 96 | NMR $\delta_H$ (400 MHz, DMSO) 6.77(1H, dd, J 1.5, 3.5 Hz), 7.00(2H, br s), 7.42-7.68 (7H, m), 7.75(1H, dd, J 1.0, 3.5 Hz), 8.01(1H, dd, J 1.0, 1.5 Hz), 8.22(1H, s) and 9.21(1H, s); Retention time: 6.94 min; (80:50). |
| 41 | G | 70 | NMR $\delta_H$ (400 MHz, DMSO) 0.86(3H, t, J 6.8 Hz), 1.22-1.39(10H, m), 3.37 (2H, q, J 6.7 Hz), 6.78(1H, dd, J 1.5, 3.5 Hz), 7.02(2H, br s), 7.74(1H, dd, J 1.0, 3.5 Hz), 8.01(1H, dd, J 1.0, 1.5 Hz), 8.46(1H, s) and 8.84(1H, t, J 5.7 Hz); Retention time: 6.96 min |
| 42 | G | 100 | NMR $\delta_H$ (400 MHz, DMSO) 2.44(3H, s), 6.81(1H, dd, J 2.0, 3.5 Hz), 7.10(2H, br s), 7.16(2H, m), 7.29(1H, m), 7.34(1H, m), 7.78(1H, m), 8.03(1H, m), 8.60 (1H, s) and 10.64(1H, s); Retention time: 3.82 min |
| 43 | G | 90 | NMR $\delta_H$ (400 MHz, DMSO) 2.37(3H, s), 6.80(1H, dd, J 1.5, 3.5 Hz), 7.02(1H, m), 7.32(3H, m), 7.61(2H, m), 7.77(1H, br d, J 3.5 Hz), 8.03(1H, d, J 1.0 Hz), 8.57(1H, s) and 11.05(1H, s); Retention time: 6.54 min |
| 44 | G | 91 | NMR $\delta_H$ (400 MHz, DMSO) 6.81(1H, dd, J 1.5, 3.5 Hz), 7.03(2H, br s), 7.07 (1H, m), 7.27(1H, m), 7.46(1H, m), 7.79(1H, dd, J 1.0, 3.5 Hz), 8.04(1H, m), 8.27(1H, m), 8.62(1H, s) and 11.12(1H, s); Retention time: 6.65 min |
| 45 | G | 87 | NMR $\delta_H$ (400 MHz, DMSO) 1.60(3H, d, J 7.0 Hz), 5.11(1H, quintet, J 7.2 Hz), 6.78(1H, dd, J 1.5, 3.5 Hz), 7.13(2H, br s), 7.29(1H, m), 7.38(2H, m), 7.45(2H, m), 7.75(1H, dd, J 1.0, 3.5 Hz), 8.02(1H, m), 8.45(1H, s) and 9.34(1H, d, J 8.0 Hz); Retention time: 5.11 min |
| 46 | G | 91 | NMR $\delta_H$ (400 MHz, DMSO) 1.60(3H, d, J 7.0 Hz), 5.12(1H, quintet, J 7.1 Hz), 6.79(1H, dd, J 1.5, 3.5 Hz), 7.13(2H, br s), 7.29(1H, m), 7.38(2H, m), 7.46(2H, m), 7.75(1H, dd, J 1.0, 3.5 Hz), 8.01(1H, dd, J 1.0, 1.5 Hz), 8.44(1H, s) and 9.34(1H, d, J 8.0 Hz); Retention time: 5.14 min |
| 47 | G | 96 | NMR $\delta_H$ (400 MHz, DMSO) 2.30(3H, s), 4.59(2H, d, J 16.2 Hz), 6.79(1H, dd, J 2.0, 3.5 Hz), 7.02(2H, br s), 7.09(1H, m), 7.20(2H, m), 7.26(1H, m), 7.75(1H, br d, J 3.5 Hz), 8.01(1H, m), 8.50(1H, s) and 9.28(1H, d, J 6.1 Hz); Retention time: 5.63 min |
| 48 | G | 89 | NMR $\delta_H$ (400 MHz, DMSO) 2.32(3H, s), 6.80(1H, dd, J 2.0, 3.5 Hz), 7.25(2H, d, J 8.0 Hz), 7.28(2H, br s), 7.68(2H, d, J 8.0 Hz), 7.77(1H, br d, J 3.1 Hz), 8.03 (1H, m), 8.57(1H, s) and 11.02(1H, s); Retention time: 6.66 min |
| 49 | G | 100 | NMR $\delta_H$ (400 MHz, DMSO) 3.99(3H, s), 6.80(1H, dd, J 1.5, 3.5 Hz), 6.89(2H, br s), 7.01(1H, m), 7.17(2H, m), 7.79(1H, dd, J 1.0, 3.5 Hz), 8.04(1H, m), 8.16 (1H, m), 8.60(1H, s) and 10.98(1H, s); Retention time: 6.28 min |
| 50 | G | 77 | NMR $\delta_H$ (400 MHz, DMSO) 3.78(3H, s), 6.80(1H, dd, J 1.5, 3.5 Hz), 7.02(2H, d, J 9.1 Hz), 7.26(2H, br s), 7.69(2H, d, J 9.0 Hz), 7.77(1H, dd, J 1.0, 3.5 Hz), 8.03(1H, dd, J 1.0, 1.5 Hz), 8.56(1H, s) and 10.93(1H, s); Retention time: 5.70 min |
| 51 | G | 100 | NMR $\delta_H$ (400 MHz, DMSO) 6.38(2H, br s), 6.80(1H, dd, J 2.0, 3.5 Hz), 7.52 (2H, d, J 9.0 Hz), 7.77(1H, br d, J 3.5 Hz), 7.84(2H, m, J 9.0 Hz), 8.03(1H, m), 8.58(1H, s) and 11.21(1H, s); Retention time: 7.19 min |
| 52 | G | 62 | NMR $\delta_H$ (400 MHz, DMSO) 0.90(3H, t, J 7.1 Hz), 1.35(4H, m), 1.63(2H, quintet, J 7.2 Hz), 3.37(2H, q, J 6.7 Hz), 6.78(1H, dd, J 1.5, 3.5 Hz), 7.02(2H, br s), 7.74(1H, dd, J 0.5, 3.5 Hz), 8.01(1H, m), 8.46(1H, s) and 8.84(1H, t, J 5.8 Hz); Retention time: 5.27 min |
| 53 | G | 81 | NMR $\delta_H$ (400 MHz, DMSO) 0.83(3H, t, J 6.8 Hz), 1.19-1.38(18H, m), 1.62 (2H, quintet, J 7.0 Hz), 3.37(2H, q, J 6.4 Hz), 6.78(1H, dd, J 1.5, 3.5 Hz), 7.02 (2H, br s), 7.75(1H, dd, J 0.5, 3.5 Hz), 8.01(1H, m), 8.46(1H, s) and 8.84(1H, t, J 5.9 Hz); Retention time: 10.76 min |
| 54 | K | 57 | IR $\nu_{max}$ (Nujol)/cm$^{-1}$ 3431, 3384, 3334, 3220, 3122, 1665, 1648, 1587, 1564, 1302, 1210 and 1130; NMR $\delta_H$ (400 MHz, CDCl$_3$) 1.01(2H, m), 1.17-1.32(4H, m), 1.66-1.82(7H, m), 4.14(1H, t, J 7.5 Hz), 6.32(3H, m), 6.69(1H, m), 7.81 (1H, m), 7.89(1H, m) and 7.99(1H, m); M/Z 312(M + H)$^+$; Retention time: 5.09 min |
| 55 | G | 63 | IR $\nu_{max}$ (Nujol)/cm$^{-1}$ 3320, 3218, 3109, 3029, 2926, 2854, 1734, 1601, 1587, 1550, 1464 and 1375; NMR $\delta_H$ (400 MHz, DMSO) 3.31(6H, s), 4.66(2H, d, J 5.5 Hz), 6.80-6.82(1H, m), 7.30-7.36(1H, m), 7.38-7.43(2H, m), 7.44-7.50(2H, m), 7.80(1H, d, J 3.5 Hz), 8.05-8.07(1H, m), 8.53(1H, s) and 9.11(1H, t, J 5.0 Hz); |

-continued

| Example | Method | Yield(%) | Data |
|---|---|---|---|
| | | | Anal. Calcd for C$_{19}$H$_{18}$N$_6$O$_2$•0.25 H$_2$O: C, 62.20; H, 5.08; N, 22.91. Found: C, 62.42; H, 5.01; N, 22.58. |
| 56 | H | 86 | mp 212.6-213° C.; IR ν$_{max}$ (Nujol)/cm$^{-1}$ 3138, 2925, 2854, 1601, 1555, 1463, 1372, 1352, 1183, 670 and 584; NMR δ$_H$ (400 MHz, DMSO) 2.41(3H, s), 3.21 (6H, s), 6.76-6.80(1H, m), 7.53(2H, d, J 7.9 Hz), 7.72(1H, d, J 3.5 Hz), 8.02-8.04 (1H, m), 8.12-8.16(2H, m) and 8.54(1H, s); Anal. Calcd for C$_{18}$H$_{17}$N$_5$O$_3$S: C, 56.39; H, 4.47; N, 18.26. Found: C, 56.20; H, 4.48; N, 18.23. |
| 57 | K | 21 | NMR δ$_H$ (400 MHz, CDCl$_3$) 4.89(2H, dd, J 1.5, 6.0 Hz), 5.09(2H, br s), 6.37 (1H, dt, J 6.0, 16.0 Hz), 6.59(1H, dt, J 1.5, 16.0 Hz), 6.64(1H, dd, J 1.5, 3.5 Hz), 7.28-7.38(5H, m), 7.72(1H, dd, J 1.0, 1.5 Hz), 7.82(1H, dd, J 1.0, 3.5 Hz) and 7.84(1H, s); M/Z 318(M + H)$^+$; Retention time: 3.82 min |
| 58 | K | 18 | NMR δ$_H$ (400 MHz, CDCl$_3$) 1.74(3H, m), 4.65(2H, m), 5.06(2H, br s), 5.71 (2H, m), 6.63(1H, dd, J 1.5, 3.5 Hz), 7.71(1H, dd, J 1.0, 1.5 Hz), 7.78(1H, s) and 7.80(1H, dd, J 1.0, 3.5 Hz); M/Z 256(M + H)$^+$; Retention time: 1.19 min |
| 59 | K | 40 | M/Z 258(M + H)$^+$; Retention time: 1.40 min |
| 60 | K | 20 | M/Z 270(M + H)$^+$; Retention time: 1.43 min |
| 61 | K | 18 | M/Z 244(M + H)$^+$; Retention time: 0.87 min |
| 62 | K | 34 | NMR δ$_H$ (400 MHz, CDCl$_3$) 1.68(2H, quintet, J 7.5 Hz), 1.92(2H, quintet, J 7.5 Hz), 2.67(2H, t, J 7.5 Hz), 4.12(2H, t, J 7.1 Hz), 5.63(2H, br s), 6.67(1H, br s), 7.12-7.30(5H, m), 7.77(2H, m) and 7.89(1H, m); Retention time: 4.60 min |
| 63 | K | 43 | NMR δ$_H$ (400 MHz, CDCl$_3$) 3.79(2H, t, J 5.0 Hz), 4.30(2H, t, J 4.8 Hz), 4.51 (2H, s), 6.17(2H, br s), 6.69(1H, dd, J 1.5, 3.5 Hz), 7.20-7.32(5H, m), 7.80 (1H, m), 7.98(1H, m) and 8.00(1H, s); Retention time: 1.88 min |
| 64 | K | 19 | NMR δ$_H$ (400 MHz, CDCl$_3$) 0.99(6H, d, J 6.5 Hz), 1.62(1H, septet, J 6.6 Hz), 1.78(2H, q, J 7.4 Hz), 4.13(2H, t, J 7.2 Hz), 5.15(2H, br s), 6.63(1H, m), 7.71 (1H, m) and 7.80(2H, m); Retention time: 2.21 min |
| 65 | K | 31 | NMR δ$_H$ (400 MHz, CDCl$_3$) 1.82(6H, d, J 6.6 Hz), 4.68(2H, d, J 7.0 Hz), 5.41 (1H, t, J 7.0 Hz), 6.24(2H, br s), 6.69(1H, m), 7.80(1H, m), 7.87(1H, m) and 7.98(1H, m); Retention time: 1.82 min |
| 66 | K | 22 | NMR δ$_H$ (400 MHz, CDCl$_3$) 5.29(2H, s), 5.85(2H, br s), 6.63(1H, m), 7.33-7.46 (4H, m), 7.57-7.72(3H, m) and 8.22(1H, m); Retention time: 1.87 min |
| 67 | K | 21 | NMR δ$_H$ (400 MHz, CDCl$_3$) 5.27(2H, s), 5.97(2H, br s), 6.55(1H, m), 7.29-7.60 (6H, m) and 8.21(1H, s); Retention time: 3.93 min |
| 68 | K | 23 | NMR δ$_H$ (400 MHz, CDCl$_3$) 2.26(2H, quintet, J 7.2 Hz), 2.71(2H, t, J 7.4 Hz), 4.14(2H, t, J 7.3 Hz), 6.72(1H, m), 6.83(2H, br s), 7.15-7.33(5H, m), 7.86 (1H, m), 7.92(1H, m) and 8.06(1H, m); Retention time: 3.48 min |
| 69 | X | 55 | mp 184.3-184.5° C.; IR ν$_{max}$ (Nujol)/cm$^{-1}$ 3458, 3316, 3200, 3069, 2955, 2924, 2854, 1749, 1728, 1631, 1606, 1592, 1462 and 1210; NMR δ$_H$ (400 MHz, DMSO) 1.24(3H, t, J 7.1 Hz), 4.19(2H, q, J 7.1 Hz), 5.01(2H, s), 6.61(2H, s), 6.75-6.79 (1H, m), 7.75(1H, d, J 2.5 Hz), 7.98(1H, s) and 8.11(1H, s); Anal. Calcd for C$_{18}$H$_{17}$N$_5$O$_3$S: C, 56.39; H, 4.47; N, 18.26. Found: C, 56.20; H, 4.48; N, 18.23. |
| 70 | L | 19 | IR ν$_{max}$ (Nujol)/cm$^{-1}$ 3139, 3109, 2924, 2854, 1740, 1610, 1583, 1561, 1547, 1403, 1235 and 1114; NMR δ$_H$ (400 MHz, DMSO) 1.25(6H, d, J 6.1 Hz), 3.21(6H, s), 5.00(2H, s), 6.77-6.80(1H, m), 7.76(1H, d, J 3.5 Hz), 7.99-8.03(1H, m) and 8.14(1H, s); Anal. Calcd for C$_{18}$H$_{17}$N$_5$O$_3$S: C, 56.39; H, 4.47; N, 18.26. Found: C, 56.20; H, 4.48; N, 18.23. |
| 71 | B | 47 | mp 180.6-181.8° C.; IR ν$_{max}$ (Nujol)/cm$^{-1}$ 3387, 3139, 3116, 2925, 2854, 1744, 1611, 1588, 1559, 1464, 1401, 1376, 1220, 1008 and 764; NMR δ$_H$ (400 MHz, CDCl$_3$) 1.28(3H, t, J 7.0 Hz), 4.26(2H, q, J 7.0 Hz), 4.86(2H, s), 6.58-6.62 (1H, m), 7.65-7.67(1H, m), 7.71-7.73(1H, m) and 7.79(1H, s); Anal. Calcd for C$_{15}$H$_{17}$N$_5$O$_3$: C, 57.14; H, 5.43; N, 22.20. Found: C, 56.88; H, 5.43; N, 22.05. |
| 72 | A | 12 | mp 314° C.; IR ν$_{max}$ (Nujol)/cm$^{-1}$ 3142, 3106, 3064, 2924, 2854, 1736, 1587, 1567, 1487, 1402, 1347, 1230 and 768; NMR δ$_H$ (400 MHz, CDCl$_3$) 1.31(3H, t, J 7.0 Hz), 4.30(2H, q, J 7.0 Hz), 5.10(2H, s), 6.56-6.59(1H, m), 6.66-6.68(1H, m), 7.40(1H, d, J 3.7 Hz), 7.64-7.65(1H, m), 7.79-7.81(1H, m), 7.89(1H, d, J 3.5 Hz) and 8.15(1H, s); Anal. Calcd for C$_{17}$H$_{14}$N$_4$O$_4$: C, 60.35; H, 4.17; N, 16.56. Found: C, 59.91; H, 4.25; N, 16.36. |
| 73 | M | 72 | mp >300° C. dec.; IR ν$_{max}$ (Nujol)/cm$^{-1}$ 3320, 3129, 3107, 2924, 2854, 2776, 1908, 1690, 1636, 1597, 1465, 1383, 1312, 782, 768, 686 and 676; NMR δ$_H$ (400 MHz, DMSO) 4.90(2H, s), 6.60(2H, s), 6.75-6.79(1H, m), 7.73-7.75(1H, m), 7.97-7.98 (1H, s), 8.11(1H, s), 13.02-13.48(1H, s); Anal. Calcd for C$_{11}$H$_9$N$_5$O$_3$: C, 50.97; H, 3.50; N, 27.00. Found: C, 50.75; H, 3.53; N, 26.80. |
| 74 | N | 67 | mp 79.6° C. dec; IR ν$_{max}$ (Nujol)/cm$^{-1}$ 3094, 2924, 2855, 1600, 1466, 1380, 1248, 1092 and 839; NMR δ$_H$ (400 MHz, CDCl$_3$) −0.04(9H, s), 0.95(2H, m), 3.65(2H, m), 4.10(3H, s), 5.60(2H, s), 6.65(1H, dd, J 3.5, 1.7 Hz), 7.78(2H, m) and 8.08 (1H, s). Retention time: 5.82 min(80:50) |
| 75 | C | 43 | IR ν$_{max}$ (Nujol)/cm$^{-1}$ 2924, 2854, 1636, 1599, 1569, 1466, 1357 and 756; NMR δ$_H$ (400 MHz, DMSO) 3.99(3H, s), 6.81(1H, dd, J 3.5, 1.7 Hz), 7.85(1H, d, J 3.5 Hz), 8.05(1H, m), 8.38(1H, s) and 13.3(1H, br s); M/Z 217(M + H)$^+$; Retention time: 0.81 min(80:50) |
| 77 | G | 79 | mp >200° C. dec; IR ν$_{max}$ (Nujol)/cm$^{-1}$ 3458, 3360, 2925, 1721, 1611, 1549, 1465, 1386, 1046 and 702; NMR δ$_H$ (400 MHz, DMSO) 4.64(2H, d, J 6.5 Hz), 6.97 (2H, br s), 7.23-7.44(6H, m), 7.88(1H, dd, J 5.0, 1.5 Hz) 8.53(1H, s) 8.55(1H, dd, J 3.5, 1.0 Hz) and 9.33(1H, br t, J 6.0 Hz); Retention time: 6.08 min |
| 78 | A | 5 | mp >250° C. dec; IR ν$_{max}$ (Nujol)/cm$^{-1}$ 3332, 3215, 3144, 2925, 1741, 1651, 1576, 1378, 1292, 1143, 993 and 713; NMR δ$_H$ (400 MHz, DMSO) 1.69(9H, s), 5.22 |

-continued

| Example | Method | Yield(%) | Data |
|---|---|---|---|
| | | | (2H, br. s), 7.22(1H, dd, J 5.0, 3.5 Hz), 7.57(1H, dd, J 5.0, 1.0 Hz), 8.10(1H, s) and 8.58(1H, dd, J 4.5, 1.5 Hz); Retention time: 3.95 min |
| 79 | G | 59 | NMR $\delta_H$ (400 MHz, DMSO) 4.61(2H, d, J 5.9 Hz), 6.78(1H, dd, J 1.5, 3.5 Hz), 7.01(2H, br s), 7.22(2H, m), 7.45(2H, m), 7.75(1H, dd, J 1.0, 3.5 Hz), 8.01(1H, dd, J 1.0, 1.5 Hz), 8.50(1H, s) and 9.31(1H, t, J 6.2 Hz); Retention time: 5.07 min |
| 80 | G | 100 | NMR $\delta_H$ (400 MHz, DMSO) 4.63(2H, d, J 6.1 Hz), 6.78(1H, dd, J 1.5, 3.5 Hz), 6.99(2H, br s), 7.41(1H, dd, J 2.0, 8.5 Hz), 7.63(1H, d, J 8.5 Hz), 7.69(1H, d, J 2.0 Hz), 7.75(1H, br d, J 3.5 Hz), 8.01(1H, m), 8.49(1H, s) and 9.35(1H, t, J 6.1 Hz); Retention time: 7.12 min |
| 81 | K | 66 | NMR $\delta_H$ (400 MHz, CDCl$_3$) 3.16(2H, t, J 7.0 Hz), 4.35(2H, t, J 7.0 Hz), 5.05 (2H, br s), 6.62(1H, m), 7.09(2H, m), 7.22-7.31(3H, m), 7.40(1H, s), 7.70 (1H, m) and 7.76(1H, m); Retention time: 2.13 min |
| 82 | K | 10 | NMR $\delta_H$ (400 MHz, CDCl$_3$) 1.95(3H, d, J 7.0 Hz), 5.03(2H, br s), 5.81(1H, q, J 7.0 Hz), 6.63(1H, dd, J 1.5, 3.5 Hz), 7.04(2H, m), 7.30(2H, m), 7.71(1H, m), 7.75(1H, m) and 7.79(1H, m); Retention time: 2.94 min |
| 83 | K | 48 | NMR $\delta_H$ (400 MHz, CDCl$_3$) 1.23(6H, d, J 6.6 Hz), 2.89(1H, septet, J 6.9 Hz), 5.06(2H, br s), 5.25(2H, s), 6.63(1H, dd, J 1.5, 3.5 Hz), 7.21(4H, s), 7.71(1H, dd, J 1.0, 1.5 Hz), 7.74(1H, s) and 7.79(1H, br d, J 3.5 Hz); Retention time: 5.23 min |
| 84 | K | 12 | NMR $\delta_H$ (400 MHz, CDCl$_3$) 5.06(2H, br s), 5.19(2H, s), 6.64(1H, dd, J 1.5, 3.5 Hz), 6.99-7.16(3H, m), 7.72(1H, m), 7.75(1H, s) and 7.80(1H, br d, J 3.5 Hz); Retention time: 3.22 min |
| 85 | P | 31 | mp 289.1-289.7° C.; IR $\nu_{max}$ (Nujol)/cm$^{-1}$ 3499, 3477, 3314, 3264, 3199, 3139, 3076, 2926, 2854, 1673, 1662, 1634, 1606, 1590, 1467 and 750; NMR $\delta_H$ (400 MHz, DMSO) 5.03(2H, s), 6.55(2H, s), 6.76-6.79(1H, m), 7.09(1H, t, J 7.5 Hz), 7.34(2H, t, J 8.1 Hz), 7.60(2H, d, J 7.6 Hz), 7.76(1H, d, J 4.0 Hz), 7.97-7.99 (1H, s), 8.12(1H, s) and 10.43(1H, s); Anal. Calcd for C$_{17}$H$_{14}$N$_6$O$_2$ .0.4 H$_2$O: C, 59.78; H, 4.37; N, 24.61. Found: C, 59.92; H, 4.08; N, 24.36. |
| 86 | Q | 66 | mp 287.2-287.8° C.; IR $\nu_{max}$ (Nujol)/cm$^{-1}$ 3479, 3464, 3279, 3182, 3076, 2924, 2854, 1656, 1631, 1608, 1539, 1567 and 1464; NMR $\delta_H$ (400 MHz, DMSO) 4.34 (2H, d, J 5.9 Hz), 4.86(2H, s), 6.53(2H, s), 6.75-6.78(1H, m), 7.24-7.39(5H, m), 7.75(1H, d, J 3.0 Hz), 7.97(1H, s), 8.09(1H, s) and 8.72(1H, t, J 5.9 Hz). |
| 87 | Q | 100 | mp 321.5-321.6° C.; IR $\nu_{max}$ (Nujol)/cm$^{-1}$ 3379, 3296, 3220, 2924, 2854, 1689, 1662, 1593, 1463 and 1378; NMR $\delta_H$ (400 MHz, DMSO) 4.75(2H, s), 6.53(2H, s), 6.74-6.78(1H, m), 7.29(1H, s), 7.69(1H, s), 7.74(1H, d, J 2.5 Hz), 7.96-7.98 (1H, m) and 8.05(1H, s). |
| 88 | Q | 74 | mp 283.6-283.7° C.; IR $\nu_{max}$ (Nujol)/cm$^{-1}$ 3368, 3332, 3215, 3098, 2925, 2854, 1648, 1585, 1566, 1467, 1408 and 1298; NMR $\delta_H$ (400 MHz, DMSO) 1.83(2H, quin, J 6.8 Hz), 1.98(2H, quin, J 6.8 Hz), 3.34(2H, t, J 6.8 Hz), 3.57(2H, t, J 6.8 Hz), 4.97(2H, s), 6.52(2H, s), 6.75-6.78(1H, m), 7.75(1H, d, J 2.5 Hz), 7.96-7.99 (1H, m) and 8.01(1H, s). Anal. Calcd for C$_{15}$H$_{16}$N$_6$O$_2$•0.5 H$_2$O: C, 56.07; H, 5.33; N, 26.15. Found: C, 56.26; H, 5.08; N, 26.13. |
| 89 | Q | 67 | mp 290.2-291.6° C.; IR $\nu_{max}$ (Nujol)/cm$^{-1}$ 3558, 3471, 3324, 3113, 2924, 2854, 1664, 1626, 1598 and 1460; NMR $\delta_H$ (400 MHz, DMSO) 2.64(3H, d, J 4.5 Hz), 4.76(2H, s), 6.53(2H, s), 6.75-6.78(1H, m), 7.74(1H, d, J 3.2 Hz), 7.96-7.98 (1H, m), 8.06(1H, s) and 8.09-8.15(1H, m). |
| 90 | R | 21 | mp >200° C. dec; IR $\nu_{max}$ (Nujol)/cm$^{-1}$ 3499, 3394, 2925, 1628, 1598, 1455, 1378, 1249, 950, 878 and 628; NMR $\delta_H$ (400 MHz, DMSO) 2.73(3H, s), 6.58(1H, br s), 8.24(1H, br s) and 12.76(1H, br s); M/Z 217(M + H)$^+$; Retention time: 0.6 min |
| 91 | G | 72 | mp >250° C. dec; IR $\nu_{max}$ (Nujol)/cm$^{-1}$ 3505, 3255, 3089, 2925, 1735, 1622, 1465, 1278, 887 and 725; NMR $\delta_H$ (400 MHz, DMSO) 2.73(3H, s) 4.65(2H, d, J 6.0 Hz), 7.18-7.45(5H, m), 8.56(1H, s) and 9.22(1H, br t, J 6.0 Hz); Retention time: 1.99 min |
| 92 | G | 89 | NMR $\delta_H$ (400 MHz, DMSO) 2.96(2H, t, J 7.2 Hz), 3.63(2H, q, J 6.9 Hz), 6.78 (1H, dd, J 1.9, 3.5 Hz), 6.94(2H, br s), 7.17-7.30(5H, m), 7.74(1H, br d, J 3.5 Hz), 8.01(1H, dd, J 1.0, 1.5 Hz), 8.46(1H, s) and 8.92(1H, t, J 5.5 Hz); Retention time: 4.89 min |
| 93 | G | 100 | NMR $\delta_H$ (400 MHz, DMSO) 4.66(2H, d, J 6.1 Hz), 6.79(1H, dd, J 1.5, 3.5 Hz), 7.00(2H, br s), 7.44(1H, m), 7.54(1H, m), 7.66(1H, m), 7.75(1H, dd, J 1.0, 3.5 Hz), 8.01(1H, dd, J 1.0, 1.5 Hz), 8.49(1H, s) and 9.40(1H, t, J 6.1 Hz); Retention time: 7.06 min |
| 94 | G | 100 | NMR $\delta_H$ (400 MHz, DMSO) 1.74(3H, d, J 7.0 Hz), 5.92(1H, quintet, J 7.0 Hz), 6.79(1H, dd, J 1.5, 3.5 Hz), 7.16(2H, br s), 7.47-7.68(5H, m), 7.76(1H, dd, J 1.0, 3.5 Hz), 7.79-7.99(2H, m), 8.02(1H, dd, J 1.0, 1.5 Hz), 8.45(1H, s) and 9.52(1H, t, J 8.2 Hz); Retention time: 7.12 min |
| 95 | G | 85 | NMR $\delta_H$ (400 MHz, DMSO) 1.81(6H, s), 2.09(3H, s), 5.08(1H, m), 5.38(1H, m), 6.79(1H, dd, J 1.5, 3.5 Hz), 7.09(2H, br s), 7.37(3H, m), 7.56(1H, m), 7.76 (1H, dd, J 1.0, 3.5 Hz), 8.02(1H, dd, J 1.0, 1.5 Hz), 8.39(1H, s) and 9.33(1H, t, J 5.8 Hz); Retention time: 7.14 min |
| 96 | Q | 84 | mp >250° C. dec.; IR $\nu_{max}$ (Nujol)/cm$^{-1}$ 3462, 3279, 3212, 3097, 2924, 2854, 1660, 1591 and 1465; NMR $\delta_H$ (400 MHz, DMSO) 3.13-3.24(2H, m), 3.41-3.49 (2H, m), 4.73(1H, s), 4.79(2H, s), 6.53(2H, s), 6.74-6.79(1H, m), 7.74(1H, d, J 2.6 Hz), 7.97(1H, s), 8.05(1H, s) and 8.24-8.34(1H, m). |
| 97 | Q | 52 | mp >270° C. dec.; IR $\nu_{max}$ (Nujol)/cm$^{-1}$ 3386, 3327, 3214, 3087, 2924, 2854, 1668, 1640, 1585, 1565, 1466, 1408 and 1376; NMR $\delta_H$ (400 MHz, DMSO) 2.24(3H, s), 2.29-2.35(2H, m), 2.39-2.46(2H, m), 3.44-3.51(2H, m), 3.54-3.61(2H, m), 5.08(2H, s), 6.52(2H, s), 6.75-6.79(1H, m), 7.74(1H, d, J 3.7 Hz), 7.97 (1H, s) and 8.01(1H, s). |

-continued

| Example | Method | Yield(%) | Data |
|---|---|---|---|
| 98 | G | 39 | NMR δ$_H$ (400 MHz, DMSO) 3.74(2H, q, J 5.9 Hz), 3.85(2H, t, J 6.0 Hz), 6.78 (1H, dd, J 1.5, 3.5 Hz), 6.99(2H, br s), 7.75(1H, dd, J 1.0, 3.5 Hz), 8.02(1H, dd, J 1.0, 1.5 Hz), 8.49(1H, s) and 9.12(1H, t, J 5.8 Hz); Retention time: 2.16 min |
| 99 | G | 80 | NMR δ$_H$ (400 MHz, DMSO) 2.10(2H, quintet, J 6.7 Hz), 3.52(2H, q, J 6.5 Hz), 3.77(2H, t, J 6.5 Hz), 6.78(1H, dd, J 2.0, 3.5 Hz), 7.02(2H, br s), 7.74(1H, dd, J 1.0, 3.5 Hz), 8.01(1H, dd, J 1.0, 2.0 Hz), 8.47(1H, s) and 8.90(1H, t, J 5.7 Hz); Retention time: 3.08 min |
| 100 | G | 70 | NMR δ$_H$ (400 MHz, DMSO) 1.18(3H, t, J 6.9 Hz), 2.70(2H, t, J 6.7 Hz), 3.61 (2H, q, J 6.5 Hz), 4.10(2H, t, J 7.2 Hz), 6.78(1H, dd, J 1.5, 3.5 Hz), 6.96(2H, br s), 7.74(1H, br d, J 3.5 Hz), 8.01(1H, dd, J 1.0, 1.5 Hz), 8.47(1H, s) and 8.98 (1H, t, J 5.8 Hz); Retention time: 2.19 min |
| 101 | G | 46 | NMR δ$_H$ (400 MHz, DMSO) 1.17(3H, t, J 7.0 Hz), 3.19(1H, dd, J 8.5, 14.0 Hz), 3.29(1H, dd, J 6.0, 14.0 Hz), 4.15(2H, q, J 7.0 Hz), 4.70(1H, m), 6.78(1H, dd, J 1.5, 3.5 Hz), 7.03(2H, br s), 7.15-7.39(5H, m), 7.74(1H, dd, J 1.0, 3.5 Hz), 8.02(1H, dd, J 1.0, 2.0 Hz), 8.43(1H, s) and 9.23(1H, d, J 6.9 Hz). |
| 102 | S | 47 | NMR δ$_H$ (400 MHz, CDCl$_3$) 3.34(2H, t, J 6.6 Hz), 4.60(2H, t, J 6.7 Hz), 5.05 (2H, br s), 6.61(1H, dd, J 1.5, 3.5 Hz), 6.98(1H, d, J 7.5 Hz), 7.15(1H, m), 7.53 (1H, m), 7.53(1H, s), 7.69(1H, m), 7.74(1H, dd, J 1.0, 3.5 Hz) and 8.60(1H, m); Retention time: 0.76 min |
| 103 | S | 44 | NMR δ$_H$ (400 MHz, DMSO) 3.36-3.42(10H, m), 4.49(2H, m), 6.90(1H, dd, J 1.5, 3.5 Hz), 7.91(1H, br d, J 3.5 Hz), 8.18(1H, m), 8.52(1H, s) and 9.62(2H, br s); Retention time: 0.80 min,(50:20) |
| 104 | S | 66 | NMR δ$_H$ (400 MHz, CDCl$_3$) 1.44(2H, m), 1.57(4H, m), 2.45(4H, m), 2.69(2H, t, J 6.0 Hz), 4.18(2H, t, J 6.0 Hz), 5.02(2H, br s), 6.63(1H, m), 7.71(1H, m), 7.79(1H, m) and 7.99(1H, s); M/Z 313(M + H)$^+$; Retention time: 3.69 min, (50:20) |
| 105 | S | 53 | NMR δ$_H$ (400 MHz, CDCl$_3$) 1.78(4H, m), 2.58(4H, m), 2.90(2H, t, J 6.3 Hz), 4.22(2H, t, J 6.2 Hz), 5.03(2H, br s), 6.63(1H, dd, J 1.5, 3.5 Hz), 7.71(1H, m), 7.79(1H, br d, J 3.5 Hz) and 7.93(1H, s); Retention time: 1.50 min,(50:20) |
| 106 | T | 98 | mp 161.7° C. dec; NMR δ$_H$ (400 MHz, CDCl$_3$) 5.36(2H, br s), 5.52(2H, s), 6.64 (1H, dd, J 3.5, 1.7 Hz), 7.35-7.75(5H, m), 7.72(1H, nm), 7.81(1H, m) and 8.26 (1H, s); Retention time: 3.95 min(80:50) |
| 112 | G | 35 | mp 139.3° C.; NMR δ$_H$ (400 MHz, CDCl$_3$) 3.99(3H, s), 4.70-4.71(2H, s, rotamers), 6.67(1H, dd, J 3.5, 1.7 Hz), 7.27-7.44(5H, m), 7.79(1H, m), 7.84 (1H, m), 8.66(1H, s) and 8.95(1H, br); Retention time: 5.13 min(80:50) |
| 113 | S | 37 | NMR δ$_H$ (400 MHz, CDCl$_3$) 3.14(2H, t, J 6.8 Hz), 4.33(2H, t, J 7.0 Hz), 5.06 (2H, br s), 6.63(1H, dd, J 1.5, 3.5 Hz), 7.02(2H, d, J 8.1 Hz), 7.25(2H, m), 7.41 (1H, s), 7.72(1H, m) and 7.76(1H, br d, J 3.5 Hz); Retention time: 4.02 min |
| 114 | S | 64 | NMR δ$_H$ (400 MHz, CDCl$_3$) 2.91(6H, s), 3.04(2H, t, J 6.8 Hz), 4.29(2H, t, J 6.8 Hz), 5.05(2H, br s), 6.62(1H, dd, J 2.0, 3.5 Hz), 6.65(2H, d, J 8.6 Hz), 6.95(2H, d, J 8.7 Hz), 7.40(1H, s), 7.70(1H, dd, J 1.0, 1.5 Hz) and 7.76(1H, dd, J 1.0, 3.5 Hz); Retention time: 2.58 min |
| 115 | S | 15 | NMR δ$_H$ (400 MHz, CDCl$_3$) 4.30(2H, t, J 5.0 Hz), 4.52(2H, t, J 5.0 Hz), 5.08 (2H, br s), 6.64(1H, dd, J 1.5, 3.5 Hz), 6.87(2H, m), 6.96(1H, m), 7.27(2H, m), 7.71(1H, m), 7.80(1H, br d, J 3.5 Hz) and 7.79(1H, s); Retention time: 2.37 min |
| 116 | S | 66 | NMR δ$_H$ (400 MHz, CDCl$_3$) 1.01(2H, m), 1.21(4H, m), 1.69(4H, m), 1.89(1H, m), 3.39(2H, d, J 7.8 Hz), 5.04(2H, br s), 6.64(1H, dd, J 1.5, 3.5 Hz), 7.71(1H, m), 7.74(1H, s) and 7.79(1H, br d, J 3.5 Hz); Retention time: 3.78 min |
| 117 | S | 84 | NMR δ$_H$ (400 MHz, CDCl$_3$) 0.87(2H, m), 1.09-1.27(6H, m), 1.61-1.72(5H, m), 1.88(2H, quintet, J 7.0 Hz), 4.08(2H, t, J 7.1 Hz), 5.04(2H, br s), 6.64(1H, dd, J 2.0, 3.5 Hz), 7.72(1H, dd, J 1.0, 2.0 Hz), 7.78(1H, s) and 7.79(1H, dd, J 1.0, 3.5 Hz); Retention time: 6.06 min |
| 118 | I | 20 | NMR δ$_H$ (400 MHz, CDCl$_3$) 3.04(3H, s), 4.72(2H, br s), 5.18(2H, br s), 6.64 (1H, dd, J 3.5, 1.7 Hz), 7.29-7.42(5H, m), 7.72(1H, m), 7.83(1H, m), 8.10(1H, s); M/Z 349(M + H)$^+$; Retention time: 1.66 min(80:50) |
| 119 | Q | 85 | mp 238.3-238.4° C.; IR ν$_{max}$ (Nujol)/cm$^{-1}$ 3444, 3325, 3181, 3083, 2925, 2855, 1651, 1696, 1591, 1567, 1523, 1467, 1414, 1376, 1355, 1300, 1182, 1017 and 754; NMR δ$_H$ (400 MHz, DMSO) 4.41(2H, d, J 5.4 Hz), 4.88(2H, s), 6.53(2H, s), 6.72-6.77(1H, m), 7.25-7.31(1H, m), 7.36(2H, d, J 8.0 Hz), 7.72(1H, d, J 3.6 Hz), 7.75-7.81(1H, m), 7.94(1H, s), 8.08(1H, s), 8.51(1H, d, J 4.5 Hz) and 8.80(1H, t, J 5.8 Hz). |
| 120 | O | 12 | mp 310.0-310.3° C.; IR ν$_{max}$ (Nujol)/cm$^{-1}$ 3322, 2925, 1636, 1586, 1464, 1378, 1297, 1026, 734 and 630; NMR δ$_H$ (400 MHz, DMSO) 6.53(2H, br s), 7.34(1H, t, J 7.5 Hz), 7.45(1H, t, J 8.0 Hz), 7.72(1H, d, J 8.5 Hz), 7.83(1H, d, J 7.5 Hz), 8.17(1H, br s), 8.21(1H, br s) and 12.78(1H, br s); Retention time: 1.48 min |
| 122 | Q | 46 | mp 242.5-243.6° C.; IR ν$_{max}$ (Nujol)/cm$^{-1}$ 3485, 3442, 3312, 3203, 3072, 2924, 2854, 1697, 1652, 1633, 1605, 1580, 1462, 1442, 1412 and 1303; NMR δ$_H$ (400 MHz, DMSO) 5.07(2H, s), 6.53(2H, s), 6.73-6.77(1H, m), 7.09-7.14(1H, m), 7.73(1H, d, J 2.8 Hz), 7.77(1H, t, J 7.0 Hz), 7.90-8.04(2H, m), 8.08(1H, s), 8.35(1H, d, J 4.0 Hz) and 10.96(1H, s). |
| 123 | Q | 57 | mp 247.3-247.4° C.; IR ν$_{max}$ (Nujol)/cm$^{-1}$ 3500, 3308, 3187, 3092, 3022, 2924, 2854, 1656, 1636, 1609, 1590, 1567 and 1466; NMR δ$_H$ (400 MHz, DMSO) 2.72 (2H, t, J 7.3 Hz), 3.24-3.35(2H, m), 4.73(2H, s), 6.49(2H, s), 6.71-6.77(1H, m), 7.15-7.23(3H, m), 7.25-7.32(2H, m), 7.71(2H, d, J 3.5 Hz), 7.93-7.95 (1H, m), 8.01(1H, s) and 8.29(1H, t, J 5.5 Hz). |
| 124 | Q | 46 | mp 258.7-260.1° C.; IR ν$_{max}$ (Nujol)/cm$^{-1}$ 3487, 3470, 3293, 3172, 3098, 2925, 2854, 1659, 1629, 1605, 1594, 1568, 1461 and 1409; NMR δ$_H$ (400 MHz, DMSO) |

-continued

| Example | Method | Yield(%) | Data |
|---|---|---|---|
| | | | 0.86(3H, t, J 7.6 Hz), 1.39-1.48(2H, m), 3.05(2H, q, J 6.5 Hz), 4.75(2H, s), 6.49(2H, s), 6.72-6.77(1H, m), 7.72(1H, d, J 3.5 Hz), 7.93-7.96(1H, m), 8.04(1H, s) and 8.19(1H, t, J 5.5 Hz). |
| 125 | S | 12 | NMR $\delta_H$ (400 MHz, CDCl$_3$) 5.07(2H, br s), 5.27(2H, s), 6.64(1H, dd, J 1.5, 3.5 Hz), 7.14(1H, m), 7.25-7.30(3H, m), 7.72(1H, m), 7.76(1H, s) and 7.80(1H, dd, J 1.0, 3.5 Hz); Retention time: 2.66 min |
| 126 | S | 33 | NMR $\delta_H$ (400 MHz, CDCl$_3$) 2.32(3H, s), 5.07(2H, br s), 5.25(2H, s), 6.63(1H, dd, J 2.0, 3.5 Hz), 7.06(2H, m), 7.13(1H, d, J 7.6 Hz), 7.23(1H, d, J 7.6 Hz), 7.71(1H, m), 7.74(1H, s) and 7.79(1H, dd, J 1.0, 3.5 Hz); Retention time: 2.12 min |
| 127 | S | 17 | NMR $\delta_H$ (400 MHz, CDCl$_3$) 2.34(3H, s), 5.06(2H, br s), 5.24(2H, s), 6.63(1H, dd, J 2.0, 3.5 Hz), 7.16(4H, m), 7.71(1H, dd, J 1.0, 2.0 Hz), 7.73(1H, s) and 7.79(1H, dd, J 1.0, 3.5 Hz); Retention time: 2.21 min |
| 128 | G | 53 | mp >250° C. dec; IR $\nu_{max}$ (Nujol)/cm$^{-1}$ 3296, 3181, 2925, 1717, 1629, 1467, 1390, 1228 and 754; NMR $\delta_H$ (400 MHz, DMSO) 4.66(2H, d, J 6.0 Hz), 7.18(2H, br s), 7.21-7.51(7H, m), 7.74(1H, d, J 8.0 Hz), 7.87(1H, d, J 7.5 Hz), 8.25(1H, s), 8.59(1H, s) and 9.30(1H, br t, J 6.0 Hz); Retention time: 6.85 min |
| 129 | O | 36 | mp >250° C. dec; IR $\nu_{max}$ (Nujol)/cm$^{-1}$ 3492, 3331, 3196, 2924, 1618, 1569, 1442, 1377, 1301, 1180, 1030 and 784; NMR $\delta_H$ (400 MHz, DMSO) 6.39(2H, br s), 7.27(1H, d, J 4.0 Hz), 8.12(1H, s), 8.33(1H, d, J 4.0 Hz) and 12.68(1H, br s); Retention time: 2.74 min |
| 130 | G | 67 | mp 194-195° C. dec; IR $\nu_{max}$ (Nujol)/cm$^{-1}$ 3460, 3360, 2923, 1722, 1608, 1465, 1386, 1218, 1013 and 792; NMR $\delta_H$ (400 MHz, DMSO) 4.64(2H, d, J 6.0 Hz), 7.02(2H, br s), 7.25-7.44(6H, m), 8.35(1H, d, J 4.0 Hz) and 9.28(1H, t, J 6.0 Hz); Retention time: 7.81 min |
| 131 | I | 17 | IR $\nu_{max}$ (Nujol)/cm$^{-1}$ 4332, 4258, 3421, 3299, 3193, 3105, 2924, 2854, 1682, 1631, 1596, 1465, 1376, 747; NMR $\delta_H$ (400 MHz, CDCl$_3$) 3.09(2H, m), 3.86(2H, br m), 4.80(2H, s), 5.10(2H, s), 6.66(1H, dd, J 3.5, 1.7 Hz), 7.18-7.25(4H, m), 7.74(1H, m), 7.85(1H, m) and 8.12(1H, s); Retention time: 2.25 min(80:50) |
| 132 | I | 81 | IR $\nu_{max}$ (Nujol)/cm$^{-1}$ 4331, 3293, 3164, 2924, 2854, 1694, 1638, 1467, 746; NMR $\delta_H$ (400 MHz, CDCl$_3$) 3.23(2H, m), 4.33(2H, m), 5.13(2H, s), 6.67(1H, dd, J 3.5, 1.7 Hz), 7.10-7.31(4H, m), 7.74(1H, s), 7.74(1H, m), 7.86(1H, m) and 8.16(1H, s); M/Z 369(M+Na)$^+$; Retention time: 2.80 min(80:50) |
| 133 | A | 11 | mp >240° C. dec; IR $\nu_{max}$ (Nujol)/cm$^{-1}$ 3465, 3321, 2925, 1619, 1567, 1460, 1384, 1304, 1056, 832 and 740; NMR $\delta_H$ (400 MHz, DMSO) 4.11(3H, s), 6.15(3H, m), 6.98(1H, t, J 2.0 Hz), 7.60(1H, br s), 7.96(1H, s) and 12.43(1H, br s); Retention time: 1.67 min |
| 134 | G | 68 | mp >230° C. dec; IR $\nu_{max}$ (Nujol)/cm$^{-1}$ 3465, 3364, 2924, 1722, 1609, 1549, 1462, 1062 and 732; NMR $\delta_H$ (400 MHz, DMSO) 4.12(3H, s), 4.67(2H, d, J 6.0 Hz), 6.20(1H, dd, J 4.0, 2.5 Hz), 6.80(2H, br s), 7.08(1H, t, J 2.0 Hz), 7.25-7.33 (1H, m), 7.34-7.43(4H, m), 7.68(1H, dd, J 4.0, 2.0 Hz), 8.41(1H, s) and 9.43 (1H, t, J 6.0 Hz); Retention time: 5.26 min |
| 137 | Y | 39 | mp 300° C.(dec); IR $\nu_{max}$ (Nujol)/cm$^{-1}$ 3423, 3313, 2924, 1622, 1580, 1464, 1389, 1305, 1114, 888 and 633; NMR $\delta_H$ (400 MHz, DMSO) 6.46(2H, br s), 8.15(1H, s), 9.11(1H, s), 9.27(1H, s) and 12.72(1H, br s); Retention time: 1.24 min |
| 139 | G | 76 | mp 188° C.; IR $\nu_{max}$ (Nujol)/cm$^{-1}$ 3313, 3195, 2924, 1718, 1629, 1558, 1467, 1392, 1254, 890, 792 and 702; NMR $\delta_H$ (400 MHz, DMSO) 4.65(2H, d, J 6.5 Hz), 7.09 (2H, br s), 7.25-7.32(1H, m), 7.34-7.44(4H, m), 8.59(1H, s), 9.11(1H, s), 9.27(1H, s) and 9.35(1H, t, J 6.5 Hz); Retention time: 4.34 min |
| 140 | Q | 80 | Mp 299.2-299.3° C.; IR $\nu_{max}$ (Nujol)/cm$^{-1}$ 3483, 3259, 3187, 2923, 2854, 1661, 1631, 1603, 1570, 1537, 1462, 1416 and 1378; NMR $\delta_H$ (400 MHz, DMSO) 9.69 (1H, br s), 8.11(1H, s), 7.95(1H, s), 7.73(1H, d, J 3.3 Hz), 7.43(1H, d, J 7.6 Hz), 7.23-7.07(3H, m), 6.75(1H, dd, J 3.3, 1.7 Hz), 6.49(2H, br s), 5.04(2H, s) and 2.25(3H, s); Anal. Calcd for C$_{18}$H$_{16}$N$_6$O$_2$•0.8 H$_2$O: C, 59.59; H, 4.89; N, 20.17. Found: C, 59.43; H, 4.60; N, 20.27. |
| 141 | Q | 60 | Mp 278° C.(dec); IR $\nu_{max}$ (Nujol)/cm$^{-1}$ 3480, 3257, 3179, 2924, 2854, 1678, 1661, 1627, 1592, 1545, 1463 and 1415; NMR $\delta_H$ (400 MHz, DMSO) 10.59(1H, br s), 8.10(1H, s), 7.95(1H, s), 7.76-7.73(2H, m), 7.45(1H, d, J 9.2 Hz), 7.36(1H, t, J 8.0 Hz), 7.13(1H, m), 6.75(1H, dd, J 3.6, 2.0 Hz), 6.50(2H, s) and 5.01(2H, s); Anal. Calcd for C$_{17}$H$_{13}$ClN$_6$O$_2$•0.25 H$_2$O: C, 54.70; H, 3.65; N, 23.51. Found: C, 54.53; H, 3.50; N, 23.50. |
| 142 | Q | 20 | Mp 281.3-283.2° C.; IR $\nu_{max}$ (Nujol)/cm$^{-1}$ 3185, 2923, 2854, 1704, 1638, 1591, 1571, 1541, 1464, 1416, 1377 and 1297; NMR $\delta_H$ (400 MHz, DMSO) 10.80(1H, br s), 8.45(2H, d, J 5.6 Hz), 8.10(1H, s), 7.95(1H, s), 7.73(1H, d, J 3.2 Hz), 7.54 (2H, d, J 6.4 Hz), 6.75(1H, dd, J 3.2, 1.6 Hz), 6.51(2H, br s) and 5.05(2H, s). |
| 143 | Q | 63 | Mp 285.6-286.4° C.; IR $\nu_{max}$ (Nujol)/cm$^{-1}$ 3472, 3176, 2924, 2854, 1698, 1640, 1591, 1560, 1460, 1415, 1377 and 1297; NMR $\delta_H$ (400 MHz, DMSO) 10.63(1H, br s), 8.74(1H, d, J 2.4 Hz), 8.29(1H, d, J 3.6 Hz), 8.11(1H, s), 8.00(1H, m), 7.95(1H, s), 7.74(1H, d, J 3.2 Hz), 7.36(1H, dd, J 8.4, 4.8 Hz), 6.75(1H, dd, J 3.2, 1.6 Hz), 6.51(2H, br s) and 5.04(2H, s); Anal. Calcd for C$_{16}$H$_{13}$N$_7$O$_2$•2.2 H$_2$O: C, 51.25; H, 4.68; N, 26.15. Found: C, 51.33; H, 4.51; N, 26.18. |
| 144 | Q | 51 | Mp 277° C.(dec); IR $\nu_{max}$ (Nujol)/cm$^{-1}$ 3486, 3272, 3181, 2924, 2854, 1650, 1633, 1594, 1555, 1492, 1463, 1412 and 1377; NMR $\delta_H$ (400 MHz, DMSO) 8.70(1H, br t, J 6.0 Hz), 8.07(1H, s), 7.94(1H, s), 7.72(1H, d, J 3.2 Hz), 7.42-7.30(4H, m), 6.74(1H, dd, J 3.2, 1.6 Hz), 6.50(2H, br s), 4.84(2H, s) and 4.30(2H, d, J 5.6 Hz). |
| 145 | Q | 64 | Mp 224.0-224.1° C.; IR $\nu_{max}$ (Nujol)/cm$^{-1}$ 3476, 3317, 3196, 3072, 2924, 2854, 1654, 1628, 1607, 1592, 1570, 1515, 1490, 1458, 1413, 1360, 1304 and 1292; |

| Example | Method | Yield(%) | Data |
|---|---|---|---|
| | | | NMR δ$_H$ (400 MHz, DMSO) 8.04(1H, s), 7.94(1H, d, J 1.0 Hz), 7.73(1H, d, J 2.9 Hz), 7.48-7.25(5H, m), 6.75(1H, dd, J 3.4, 1.8 Hz), 6.48(2H, br s), 5.13 (2H, s), 4.53(2H, s) and 3.07(3H, s). |
| 146 | S | 16 | NMR δ$_H$ (400 MHz, CDCl$_3$) 3.19(2H, t, J 7.0 Hz), 4.38(2H, t, J 7.0 Hz) 5.08 (2H, br s), 6.63(1H, dd, J 1.5, 3.5 Hz), 7.04(2H, dd, J 1.5, 4.5 Hz), 7.49(1H, s), 7.72(1H, dd, J 1.0, 2.5 Hz), 7.78(1H, dd, J 1.5, 3.5 Hz) and 8.52(2H, dd, J 1.5, 4.5 Hz); Retention time: 2.71 min,(50:20). |
| 147 | S | 9 | NMR δ$_H$ (400 MHz, CDCl$_3$) 2.52(4H, t, J 4.7 Hz), 2.76(2H, t, J 6.0 Hz), 3.69 (4H, t, J 4.7 Hz), 4.10(2H, t, J 6.0 Hz), 5.04(2H, br s), 6.64(1H, dd, J 1.5, 3.5 Hz), 7.71(1H, dd, J 1.0, 1.5 Hz), 7.79(1H, dd, J 1.0, 3.5 Hz) and 7.94(1H, s); Retention time: 1.96 min,(50:20). |
| 148 | S | 17 | NMR δ$_H$ (400 MHz, CDCl$_3$) 5.06(2H, br s), 5.31(2H, s), 6.63(1H, dd, J 2.0, 3.5 Hz), 7.28(1H, m), 7.60(1H, m), 7.72(1H, dd, J 1.0, 2.5 Hz), 7.77(1H, s), 7.80 (1H, dd, J 1.0, 3.5 Hz), 8.59(1H, dd, J 1.5, 5.0 Hz) and 8.67(1H, d, J 2.5 Hz); Retention time: 2.51 min,(50:20). |
| 150 | A | 10 | mp 247-248° C.; NMR δ$_H$ (400 MHz, DMSO) 2.66(3H, s), 6.28(2H, br s), 7.03 (1H, d, J 5.0 Hz), 7.63(1H, d, J 5.0 Hz), 8.03(1H, s) and 12.57(1H, br s); Retention time: 2.91 min |
| 151 | AA | 11 | IR ν$_{max}$ (Nujol)/cm$^{-1}$ 3317, 3194, 2923, 2854, 1732, 1456; NMR δ$_H$ (400 MHz, CDCl$_3$) 2.92(2H, t, J 6.4 Hz), 3.67(3H, s), 4.40(2H, t, J 6.4 Hz), 5.30(2H, br s), 6.62(1H, dd, J 1.6, 3.4 Hz), 7.70(1H, dd, J 0.7, 1.6 Hz), 7.79(1H, dd, J 0.7, 3.4 Hz and 7.87(1H, s). |
| 152 | M | 99 | IR ν$_{max}$ (Nujol)/cm$^{-1}$ 3500-2800 br, 2923, 2855, 1715, 1644, 1588, 1520, 1465, 1412 and 1378; NMR δ$_H$ (400 MHz, DMSO) 8.07(1H, s), 7.94(1H, m), 7.70(1H, m), 6.73(1H, dd, J 3.5, 1.5 Hz), 6.55(2H, br s), 4.25(2H, t) and 2.85(2H, t, J 6.5 Hz); M/Z 274(M + H)$^+$. |
| 153 | AB | 30 | Mp. 342° C. dec.; IR ν$_{max}$ (Nujol)/cm$^{-1}$ 2925, 2855, 1587, 1463, 1377, 846; NMR δ$_H$ (400 MHz, DMSO) 2.68(3H, s), 6.78(1H, m), 7.80(1H, m), 8.00(1H, m), 8.40(1H, m) and 13.32(1H, br). |
| 154 | G | 46 | Mp 152° C.(dec); IR ν$_{max}$ (Nujol)/cm$^{-1}$ 3273, 3109, 2920, 2854, 1727, 1600, 1588, 1551, 1481, 1455, 1401 and 1374; NMR δ$_H$ (400 MHz, DMSO) 9.26(1H, t, J 5.9 Hz), 8.92(1H, s), 8.09(1H, m), 7.85(1H, m), 7.30-7.50(5H, m), 6.84(1H, dd, J 3.5, 1.5 Hz), 4.68(2H, d, J 5.9 Hz) and 2.76(3H, s); Retention time 5.38 min. (80:50) |
| 155 | H | | NMR δ$_H$ (400 MHz, CDCl$_3$) 8.25(1H, s), 8.09(1H, d, J 6.8 Hz), 7.84(1H, d, J 3.6 Hz), 6.66(1H, dd, J 3.6, 1.6 Hz), 5.15(2H, br s), 4.07(1H, m) and 1.44(6H, d, J 6.8 Hz). |
| 156 | AC | 6 | IR ν$_{max}$ (Nujol)/cm$^{-1}$ 2923, 2854, 1588, 1564, 1486, 1462, 1376, 1352, 1309 and 1236; NMR δ$_H$ (400 MHz, CDCl$_3$) 7.96(1H, m), 7.88(1H, m), 7.75(1H, m), 7.20 (4H, m), 6.50(1H, m), 5.35(2H, s) and 2.35(3H, s). |
| 157 | AC | | NMR δ$_H$ (400 MHz, DMSO) 5.38(2H, s), 6.56(2H, br s), 6.75(1H, dd, J 1.5, 3.5 Hz), 7.10(1H, m), 7.16(1H, m), 7.25(1H, m), 7.37(1H, m), 7.72(1H, d, J 3.5 Hz), 7.95(1H, dd, J 1.0, 2.0 Hz) and 8.15(1H, s); Retention time: 1.58 min, (80:50). |
| 158 | AC | 60 | mp 284.5-285.3° C.; IR ν$_{max}$ (Nujol)/cm$^{-1}$ 3319, 3195, 3139, 3091, 1641, 1590, 1557, 1530, 1463, 1377 and 1349; NMR δ$_H$ (400 MHz, DMSO) 5.47(2H, s), 6.58 (2H, s), 6.72-6.78(1H, m), 7.65(1H, dt, J 7.5, 1.0 Hz), 7.69-7.76(2H, m), 7.95 (1H, t, J 1.0 Hz), 8.15-8.16(1H, m), 8.17(1H, s), 8.26(1H, s); Anal. Calcd for C$_{16}$H$_{12}$N$_6$O$_3$•0.35 H$_2$O: C, 56.09; H, 3.74; N, 24.53. Found: C, 56.10; H, 3.72; N, 24.40. |
| 159 | AC | 46 | mp 212.8-212.9° C.; NMR δ$_H$ (400 MHz, DMSO) 5.43(2H, s), 6.57(2H, s), 6.73-6.78 (1H, m), 7.45(2H, d, J 8.0 Hz), 7.70-7.75(3H, m), 7.95-7.97(1H, m), 8.24(1H, s); Anal. Calcd for C$_{17}$H$_{12}$N$_5$OF$_3$•0.1 H$_2$O: C, 56.54; H, 3.41; N, 19.39. Found: C, 56.65; H, 3.62; N, 19.01. |
| 160 | H | 95 | NMR δ$_H$ (400 MHz, DMSO) 6.76(1H, dd, J 2.0, 3.5 Hz), 7.05(2H, br s), 7.67 (1H, d, J 3.5 Hz), 7.99(2H, m), 8.56(1H, s), 8.62(1H, dd, J 1.5, 8.0 Hz), 8.72 (1H, d, J 8.0 Hz) and 8.89(1H, t, J 2.0 Hz); Retention time: 4.15 min,(80:50). |
| 161 | H | 55 | IR ν$_{max}$ (Nujol)/cm$^{-1}$ 3493, 3405, 3309, 3192, 2924, 2854, 1624, 1586, 1565, 1467 and 1351; NMR δ$_H$ (400 MHz, DMSO) 6.77(1H, dd, J 2.0, 3.5 Hz), 6.86(2H, br s), 7.70(1H, d, J 3.5 Hz), 7.72-7.76(2H, m), 7.90(1H, dd, J 2.0, 7.0 Hz), 8.00 (1H, dd, J 1.5, 3.5 Hz), 8.39(1H, dd, J 2.5, 7.5 Hz) and 8.62(1H, s); Retention time 4.54 min,(80:50). |
| 162 | H | 69 | IR ν$_{max}$ (Nujol)/cm$^{-1}$ 3503, 3324, 3202, 3115, 2924, 2854, 1634, 1587, 1569, 1467, 1392 and 1350; NMR δ$_H$ (400 MHz, DMSO) 6.76(1H, dd, J 2.0, 3.5 Hz), 7.04(2H, br s), 7.67(1H, dd, J 0.5, 3.5 Hz), 7.92(2H, d, J 8.5 Hz), 7.98(1H, dd, J 1.0, 2.0 Hz), 8.17(2H, d, J 9.0 Hz) and 8.50(1H, s); Retention time 2.01 min, (80:50). |
| 163 | H | 36 | IR ν$_{max}$ (Nujol)/cm$^{-1}$ 3505, 3327, 3206, 2924, 2854, 1634, 1593, 1567, 1480, 1465, 1384 and 1348; NMR δ$_H$ (400 MHz, DMSO) 6.76(1H, dd, J 1.5, 3.5 Hz), 7.04(2H, br s), 7.54(2H, t, J 9.0 Hz), 7.67(1H, dd, J 0.5, 3.5 Hz), 7.98(1H, dd, J 1.0, 2.0 Hz), 8.34(1H, dd, J 5.0, 9.0 Hz) and 8.50(1H, s); Retention time 3.89 min,(80:50). |
| 164 | H | 29 | IR ν$_{max}$ (Nujol)/cm$^{-1}$ 3484, 3301, 3184, 3107, 2924, 2854, 1661, 1633, 1588, 1465, 1376, 1356 and 1166; NMR δ$_H$ (400 MHz, DMSO) 3.78(3H, s), 6.78(1H, dd, J 2.0 3.5 Hz), 7.05(2H, br s), 7.72(1H, m), 8.01(1H, m) and 8.31(1H, s); Retention time 3.22 min,(80:50). |

-continued

| Example | Method | Yield(%) | Data |
|---|---|---|---|
| 165 | H | 34 | NMR δ$_H$ (400 MHz, DMSO) 0.84(3H, t, J 7.2 Hz), 1.36(2H, sextet, J 7.2 Hz), 1.65(2H, m), 3.93(2H, m), 6.78(1H, dd, J 2.0, 3.5 Hz), 7.05(2H, br s), 7.73(1H, dd, J 1.0, 3.5 Hz), 8.01(1H, dd, J 1.0, 1.5 Hz) and 8.32(1H, s); Retention time 2.27(80:50). |
| 166 | H | 55 | NMR δ$_H$ (400 MHz, DMSO) 6.74(1H, dd, J 1.5, 3.5 Hz), 6.76(2H, br s), 7.66 (2H, m), 7.92(1H, t, J 8.0 Hz), 7.95(1H, dd, J 1.0, 2.0 Hz), 8.48(1H, dd, J 1.5, 8.0 Hz), 8.55(1H, dd, J 1.5, 8.5 Hz), 8.72(1H, dd, J 1.5, 7.5 Hz), 8.75(1H, s) and 8.95(1H, dd, J 1.5, 4.5 Hz); Retention time 3.29 min,(80:50). |
| 167 | H | 26 | NMR δ$_H$ (400 MHz, DMSO) 2.38(3H, s), 2.87(3H, s), 6.77(1H, dd, J 1.5 3.5 Hz), 6.97(2H, br s), 7.70(1H, dd, J 1.0, 3.5 Hz), 8.00(1H, dd, J 1.0, 1.5 Hz) and 8.57(1H, s); Retention time: 3.70 min,(80:50). |
| 168 | H | 58 | NMR δ$_H$ (400 MHz, DMSO) 6.76(1H, dd, J 1.5, 3.5 Hz), 7.43(1H, ddd, J 1.0, 5.0, 7.5 Hz), 7.68(1H, dd, J 1.0, 3.5 Hz), 7.93(1H, dt, J 1.5, 7.5 Hz), 7.97(1H, d, J 4.5 Hz), 7.99(1H, dd, J 1.0, 1.5 Hz), 8.09(1H, dt, J 1.0, 8.0 Hz), 8.24(1H, d, J 4.0 Hz), 8.52(1H, s) and 8.59(1H, ddd, J 1.0, 5.0, 5.5 Hz); Retention time 5.71 min, (80:50). |
| 169 | Q |  | Mp 287.1-288.2° C.; IR ν$_{max}$ (Nujol)/cm$^{-1}$ 3200, 2920, 2854, 1666, 1651, 1591, 1568, 1538, 1503, 1453, 1416, 1378, 1282 and 1233; NMR δ$_H$ (400 MHz, DMSO) 9.60(1H, br s), 8.11(1H, s), 7.96(1H, s), 7.73(1H, d, J 3.2 Hz), 7.25(1H, d, J 8.4 Hz), 6.80(1H, d, J 2.8 Hz), 6.76-6.71(2H, m), 6.52(2H, br s), 5.00(2H, s), 3.71(3H, s) and 2.20(3H, s). |
| 170 | Q |  | NMR δ$_H$ (400 MHz, DMSO) 9.63(1H, br s), 8.11(1H, s), 7.95(1H, s), 7.73(1H, s), 7.28(1H, d, J 8.0 Hz), 7.03(1H, s), 6.97(1H, m), 6.75(1H, s), 6.52(2H, br s), 5.02(2H, s), 2.24(3H, s) and 2.20(3H, s). |
| 171 | I | 57 | Mp 134.6° C.; NMR δ$_H$ (400 MHz, DMSO) 8.35(1H, s), 7.88(1H, m), 7.65(1H, m), 7.30-7.40(5H, m), 6.67(1H, dd, J 3.5, 1.5 Hz), 4.75(2H, br m), 3.09(3H, br m) and 2.86(3H, br m); Retention time 2.56 min(80:50) |
| 172 | AC | 28 | mp 245.6-246.0° C.; IR ν$_{max}$ (Nujol)/cm$^{-1}$ 3393, 3318, 3189, 3091, 1794, 1740, 1646, 1592, 1519, 1466, 1408, 1342 and 1310; NMR δ$_H$ (400 MHz, DMSO) 5.49 (2H, s), 6.58(2H, s), 6.74-6.79(1H, m), 7.47-7.51(2H, m), 7.75(1H, dd, J 3.5 Hz, 1.0 Hz), 7.96-7.98(1H, m), 8.19-8.24(2H, m) and 8.26(1H, m). |
| 173 | AH | 57 | Mp. 196.5° C. dec.; IR ν$_{max}$ (Nujol)/cm$^{-1}$ 2923, 2852, 2243, 1596, 1463, 1378, 1144; NMR δ$_H$ (400 MHz, CDCl$_3$) 2.35(3H, s), 5.42(2H, s), 6.69(1H, dd J 1.8, 3.5 Hz), 7.19(2H, m), 7.25(2H, m), 7.82(1H, m), 7.90(1H, m) and 8.19(1H, br s). |
| 174 | X | 43 | Mp 160° C.(dec); IR ν$_{max}$ (Nujol)/cm$^{-1}$ 3347, 2924, 2854, 1771, 1718, 1607, 1593, 1562, 1460, 1403 and 1378; NMR δ$_H$ (400 MHz, DMSO) 8.07(1H, s), 7.93(1H, d, J 2.0 Hz), 7.80(4H, s), 7.67(1H, d, J 4.0 Hz), 6.72(1H, dd, J 3.5, 2.0 Hz), 6.19 (2H, br s), 4.37-4.30(2H, m), 4.04-3.96(2H, m) and 3.30(3H, m). |
| 175 | Q |  | NMR δ$_H$ (400 MHz, DMSO) 10.55(1H, br s), 8.10(1H, s), 7.96(1H, s), 7.74(1H, s), 7.60(2H, m), 7.39(2H, m), 6.76(1H, s), 6.53(2H, br s) and 5.01(2H, s). |
| 176 | Q |  | NMR δ$_H$ (400 MHz, DMSO) 10.72(1H, br s), 8.10(1H, s), 7.96(1H, s), 7.94(1H, s), 7.74(1H, s), 7.59(1H, d, J 8.8 Hz), 7.49(1H, d, J 8.4 Hz), 6.76(1H, s), 6.54 (2H, s) and 5.02(2H, s). |
| 177 | AC | 50 | mp 302.5-304.8° C.; IR ν$_{max}$ (Nujol)/cm$^{-1}$ 3356, 3314, 3198, 2232, 1636, 1618, 1591, 1557, 1515 and 1463; NMR δ$_H$ (400 MHz, DMSO) 5.38(2H, s), 6.58(2H, s), 6.73-6.78(1H, m), 7.54-7.61(2H, m), 7.73(1H, d, J 3.5 Hz), 7.76-7.80 (2H, m), 7.94-7.96(1H, m), 8.23(1H, s); Anal. Calcd for C$_{17}$H$_{12}$N$_6$O•0.4 H$_2$O: C, 63.11; H, 3.99; N, 25.98. Found: C, 63.18; H, 3.92; N, 26.02. |
| 178 | AC | 32 | IR ν$_{max}$ (Nujol)/cm$^{-1}$ 1644, 1584, 1463, 1408 and 1377; NMR δ$_H$ (400 MHz, DMSO) 5.44(3H, s), 6.92-6.95(1H, m), 7.03-7.06(1H, m), 7.32(1H, dt, J 7.5 Hz, 1.5 Hz), 7.39(1H, dt, J 7.5 Hz, 1.5 Hz), 7.55(1H, dd, J 8.0 Hz, 1.0 Hz), 7.98 (1H, d, J 3.5 Hz), 8.23(1H, s) and 8.51(1H, s). |
| 179 | H | 38 | NMR δ$_H$ (400 MHz, DMSO) 4.67(2H, d, J 5.5 Hz), 6.76(1H, dd, J 1.5, 3.5 Hz), 7.05(2H, br s), 7.23(1H, d, J 4.0 Hz), 7.55(2H, d, J 8.5 Hz), 7.67(1H, d, J 3.5 Hz), 7.87(1H, d, J 8.5 Hz), 7.99(1H, dd, J 1.0 1.5 Hz), 8.10(1H, d, J 4.5 Hz), 8.48(1H, s) and 9.34(1H, t, J 6.0 Hz); Retention time 5.38 min,(80:50). |
| 180 | H | 34 | NMR δ$_H$ (400 MHz, DMSO) 6.75(1H, dd, J 2.0, 3.5 Hz), 6.95(2H, br s), 7.66 (1H, dd, J 1.0, 3.5 Hz), 7.89(1H, dd, J 7.0, 9.0 Hz), 7.97(1H, dd, J 1.0, 1.5 Hz), 8.55(1H, dd, J 1.0, 9.0 Hz) and 8.64(2H, t, J 3.5 Hz); Retention time 3.82 min, (80:50). |
| 181 | H |  | IR ν$_{max}$ (Nujol)/cm$^{-1}$ 3480, 3317, 3203, 2923, 2854, 1723, 1626, 1588, 1566, 1466, 1378, 1350 and 1268; NMR δ$_H$ (400 MHz, DMSO) 3.83(3H, s), 6.77(1H, dd, J 1.5, 3.5 Hz), 6.89(2H, br s), 7.70(1H, dd, J 1.5, 3.5 Hz), 7.80(1H, d, J 5.5 Hz), 7.99(1H, dd, J 0.5, 1.5 Hz), 8.12(1H, d, J 5.0 Hz) and 8.49(1H, s); Retention time 2.71 min,(80:50). |
| 182 | H | 61 | NMR δ$_H$ (400 MHz, DMSO) 4.39(2H, br s), 6.77(1H, dd, J 1.5, 3.5 Hz), 7.20 (1H, d, J 2.0 Hz), 7.69(1H, dd, J 1.0, 3.5 Hz), 7.87(1H, d, J 4.0 Hz), 8.01(1H, dd, J 1.0, 1.5 Hz), 8.29(1H, d, J 4.0 Hz), 8.54(1H, s) and 8.76(1H, d, J 2.0 Hz); Retention time 4.72 min,(80:50). |
| 183 | H |  | IR ν$_{max}$ (Nujol)/cm$^{-1}$ 3424, 3323, 3208, 2924, 2854, 1634, 1586, 1565, 1502, 1464, 1378 and 1352; NMR δ$_H$ (400 MHz, DMSO) 2.56(3H, s), 3.75(3H, s), 6.76(1H, dd, J 1.5, 3.5 Hz), 6.88(2H, br s), 7.69(1H, dd, J 1.0, 3.5 Hz), 7.99 (1H, dd, J 0.5, 2.0 Hz) and 8.49(1H, s); Retention time 2.98 min,(80:50). |
| 184 | H | 47 | NMR δ$_H$ (400 MHz, DMSO) 2.62(3H, s), 6.76(1H, dd, J 1.5, 0.5 Hz), 7.06(2H, br s), 7.68(1H, dd, J 1.0, 3.5 Hz), 7.99(1H, dd, J 1.0, 1.5 Hz), 8.18(2H, d, J 8.5 Hz), 8.38(2H, d, J 8.5 Hz) and 8.54(1H, s); Retention time 3.27 min,(80:50). |

-continued

| Example | Method | Yield(%) | Data |
|---|---|---|---|
| 185 | H | 59 | IR ν$_{max}$ (Nujol)/cm$^{-1}$ 3493, 3334, 2924, 2854, 1627, 1591, 1565, 1469, 1378, 1346, 1156 and 1145; NMR δ$_H$ (400 MHz, DMSO) 6.76(1H, dd, J 1.5, 3.5 Hz), 6.98(2H, br s), 7.46-7.53(3H, m), 7.70(1H, dd, J 1.0, 3.5 Hz), 7.73(1H, d, J 15.5 Hz), 7.81(2H, dd, J 1.5, 8.5 Hz), 7.99(1H, dd, J 1.0, 2.0 Hz), 8.06(1H, J 15.5 Hz) and 8.39(1H, s); Retention time 4.77 min,(80:50). |
| 186 | H | 18 | NMR δ$_H$ (400 MHz, DMSO) 1.25(3H, t, J 7.5 Hz), 3.92(2H, q, J 7.5 Hz), 6.78 (1H, dd, J 1.5, 3.5 Hz), 7.05(2H, br s), 7.73(1H, d, J 3.5 Hz), 8.01(1H, dd, J 1.0, 2.0 Hz) and 8.32(1H, s); Retention time 1.0,(80:50). |
| 187 | S | 34 | NMR δ$_H$ (400 MHz, CDCl$_3$) 5.10(2H, br s), 5.42(2H, s), 6.64(1H, dd, J 1.5, 3.5 Hz), 7.20(1H, d, J 8.0 Hz), 7.23(1H, m), 7.65(1H, dt, J 2.0, 7.5 Hz), 7.71(1H, m), 7.82(1H, d, J 4.0 Hz), 7.96(1H, s) and 8.58(1H, m); Retention time 2.66 min, (50:20). |
| 188 | S | 30 | IR ν$_{max}$ (Nujol)/cm$^{-1}$ 3315, 3190, 2924, 1586, 1567, 1513, 1462, 1408 and 1377; NMR δ$_H$ (400 MHz, CDCl$_3$) 1.75(2H, br s), 5.11(2H, br s), 6.65(1H, dd, J 1.5, 2.5 Hz), 7.12(2H, dd, J 1.0, 4.5 Hz), 7.73(1H, dd, J 1.0, 2.0 Hz), 7.78(1H, s), 7.83(1H, dd, J 1.0, 3.5 Hz), and 8.60(2H, dd, J 1.5, 4.5 Hz); Retention time 2.27 min, (50:20). |
| 189 | S | 43 | IR ν$_{max}$ (Nujol)/cm$^{-1}$ 3501, 3303, 3176, 3150, 2933, 2855, 1640, 1604, 1587, 1568, 1515, 1466, 1411 and 1378; NMR δ$_H$ (400 MHz, CDCl$_3$) 2.26(2H, quintet, J 7.5 Hz), 2.69(2H, t, J 7.5 Hz), 4.16(2H, t, J 7.0 Hz), 5.12(2H, br s), 6.64(1H, dd, J 1.5, 3.5 Hz), 7.24(1H, ddd, J 1.0, 5.0, 8.0 Hz), 7.51(1H, dt, J 2.0, 8.0, 8.1 Hz), 7.74(1H, dd, J 1.0, 2.0 Hz), 7.76(1H, s), 7.80(1H, dd, J 1.0, 3.5 Hz), 8.48 (1H, dd, J 1.5, 5.0 Hz) and 8.51(1H, d, J 2.0 Hz); Retention time 4.15 min, (50:20). |
| 190 | S | 31 | NMR δ$_H$ (400 MHz, CDCl$_3$) 2.26(2h, quintet, J 7.5 Hz), 2.68(2H, t, J 7.5 Hz), 4.16(2H, t, J 7.0 Hz), 5.08(2H, br s), 6.64(1H, dd, J 1.5, 3.5 Hz), 7.12(2H, dd, J 1.5, 4.5 Hz), 7.72(1H, dd, J 1.0, 1.5 Hz), 7.75(1H, s), 7.80(1H, dd, J 1.0, 3.5 Hz) and 8.52(2H, dd, J 1.5, 4.5 Hz); Retention time 3.95 min,(50:20). |
| 191 | G | 39 | NMR δ$_H$ (400 MHz, DMSO) 1.58(3H, d, J 7.0 Hz), 5.09(1H, m), 6.78(1H, dd, J 1.5, 3.5 Hz), 7.13(2H, br s), 7.42(2H, d, J 8.5 Hz), 7.57(2H, d, J 8.5 Hz), 7.75 (1H, dd, J 1.0, 3.5 Hz), 8.01(1H, dd, J 1.0, 2.0 Hz), 8.44(1H, s) and 1.33(1H, d, J 7.5 Hz); Retention time 6.28 min,(80:50). |
| 192 | AD | 22 | IR ν$_{max}$ (Nujol)/cm$^{-1}$ 3404, 3347, 3137, 3089, 1661, 1647, 1628, 1535, 1517, 1466, 1420 and 1377; NMR δ$_H$ (400 MHz, DMSO) 3.51-4.43(6H, s), 5.37(2H, s), 6.84-6.86(1H, m), 7.03(1H, s), 7.16(2H, t, J 10.0 Hz), 7.40(1H, t, J 7.5 Hz), 7.86(1H, d, J 3.0 Hz), 8.10(1H, s) and 8.42(1H, s). |
| 193 | AC | 36 | mp 216.5-216.6° C.; IR ν$_{max}$ (Nujol)/cm$^{-1}$ 3483, 3298, 3186, 3096, 1721, 1624, 1595, 1514, 1489, 1456, 1409, 1379, 1287 and 1202; NMR δ$_H$ (400 MHz, DMSO) 3.83(3H, s), 5.40(2H, s), 6.74-6.76(1H, m), 7.49-7.58(2H, m), 7.72-7.74 (1H, m), 7.85-7.91(2H, m), 7.96(1H, t, J 1.0 Hz) and 8.25(1H, s); Anal. Calcd for $C_{18}H_{15}N_5O_3$: C, 61.89; H, 4.33; N, 20.55. Found: C, 61.77; H, 4.38; N, 19.96. |
| 194 | AC | 45 | IR ν$_{max}$ (Nujol)/cm$^{-1}$ 3309, 3089, 2231, 1645, 1517, 1466, 1410, 1378 and 1304; NMR δ$_H$ (400 MHz, DMSO) 5.45(2H, s), 6.85-6.90(1H, m), 7.45(2H, d, J 8.5 Hz), 7.84(2H, d, J 8.5 Hz), 7.88(1H, d, J 3.5 Hz), 8.15(1H, s) and 8.48(1H, s). |
| 195 | Y | 21 | mp >190° C.(dec) IR ν$_{max}$ (Nujol)/cm$^{-1}$ 3492, 3302, 3085, 2918, 1629, 1580, 1456, 1031, 817 and 627; NMR δ$_H$ (400 MHz, DMSO) 2.40(3H, s), 6.42-6.31 (3H, m), 7.66(1H, d, J 3.0 Hz), 8.02(1H, s) and 12.54(1H, br s); Retention time (80:50) 0.65 min |
| 196 | H | 27 | NMR δ$_H$ (400 MHz, DMSO) 0.82(3H, t, J 7.5 Hz), 1.15-1.30(6H, m), 1.66(2H, quintet, J 7.5 Hz), 3.92(2H, t, J 7.5 Hz), 6.78(1H, dd, J 1.5, 3.5 Hz), 7.05(2H, br s), 7.72(1H, d, J 3.5 Hz), 8.01(1H, dd, J 1.0, 1.5 Hz) and 8.32(1H, s); Retention time 7.72(80:50). |
| 197 | AC | 74 | mp 290.6-290.7° C.; NMR δ$_H$ (400 MHz, DMSO) 5.69(2H, s), 6.58(2H, s), 6.75-6.79 (1H, m), 6.87(1H, d, J 7.5 Hz), 7.60(1H, t, J 7.5 Hz), 7.68(1H, d, J 3.5 Hz), 7.97(1H, s) and 8.14-8.20(2H, m). |
| 198 | AC | 17 | mp 19.7-201.5° C.; NMR δ$_H$ (400 MHz, DMSO) 3.72(3H, s), 5.28(2H, s), 6.56 (2H, s), 6.73-6.76(1H, m), 6.79-6.91(3H, m), 7.25(1H, t, J 7.5 Hz), 7.72(1H, dd, J 3.5 Hz, 1.0 Hz), 7.94-7.96(1H, m) and 8.20(1H, s). |
| 199 | M | 77 | mp 294.0-294.3° C.; NMR δ$_H$ (400 MHz, DMSO) 5.40(2H, s), 5.75(1H, s), 6.57 (2H, s), 6.74-6.77(1H, m), 7.45-7.56(2H, m), 7.74(1H, dd, J 3.5, 1.0 Hz), 7.80-7.83(1H, m), 7.86(1H, dt, J 7.5, 1.5 Hz), 7.95-7.97(1H, m), 8.25(1H, s) and 12.83-13.12(1H, s). |
| 201 | G | 62 | Mp. 350° C. dec.; NMR δ$_H$ (400 MHz, CDCl$_3$) 4.62(2H, m), 6.45(2H, m), 6.80 (1H, m), 7.05(1H, br s), 7.63(1H, m), 7.77(1H, m), 8.03(1H, m), 8.50(1H, s) and 9.20(1H, m). |
| 202 | G | 20 | Mp 296.3° C.; IR ν$_{max}$ (Nujol)/cm$^{-1}$ 3291, 3167, 3119, 2927, 1715, 1633, 1596, 1567, 1401 and 1376; NMR δ$_H$ (400 MHz, DMSO) 9.32(1H, t, J 6.0 Hz), 8.46 (1H, s), 8.05(1H, m), 7.75(1H, m), 7.45(1H, m), 7.15(1H, m), 7.00(3H, m), 6.78(1H, m) and 4.79(2H, d, J 6.0 Hz); Retention time 3.52 min(80:50) |
| 203 | AC | 20 | mp 218.2-218.5° C.; IR ν$_{max}$ (Nujol)/cm$^{-1}$ 3335, 3201, 1654, 1586, 1520, 1470 and 1412; NMR δ$_H$ (400 MHz, DMSO) 5.35(2H, s), 6.57(2H, s), 6.74-6.77 (1H, m), 7.07-7.17(3H, m), 7.36-7.44(1H, m), 7.73(1H, d, J 3.5 Hz), 7.96 (1H, s) and 8.22(1H, s). |
| 204 | G | 50 | Mp 160° C.(dec); IR ν$_{max}$ (Nujol)/cm$^{-1}$ 3540, 3300, 3188, 3123, 2920, 2854, 1708, 1628, 1603, 1584, 1561, 1461, 1395 and 1377; NMR δ$_H$ (400 MHz, DMSO) 9.33 (1H, br t, J 6.5 Hz), 8.47(1H, s), 7.70(1H, d, J 3.5 Hz), 7.44-7.33(4H, m), 7.32-7.25 |

-continued

| Example | Method | Yield(%) | Data |
|---|---|---|---|
| | | | (1H, m), 7.00(2H, br s), 6.42(1H, dd, J 3.5, 1.0 Hz), 4.63(2H, d, J 6.5 Hz) and 2.42(3H, s). |
| 205 | AF | 43 | IR ν$_{max}$ (Nujol)/cm$^{-1}$ 3516, 3294, 3170, 3144, 3075, 1655, 1629, 1589, 1540, 1464, 1410 and 1368; NMR δ$_H$ (400 MHz, DMSO) 1.98(3H, s), 5.30(2H, s), 6.55(2H, s), 6.74-6.77(1H, m), 6.92(1H, d, J 8.5 Hz), 7.23-7.31(2H, m), 7.54(1H, d, J 8.0 Hz), 7.72-7.75(1H, m), 7.95-7.96(1H, m), 8.18(1H, s) and 9.88(1H, s). |
| 206 | AC | 19 | mp 201.9-203.0° C.; NMR δ$_H$ (400 MHz, DMSO) 3.18(3H, s), 5.45(2H, s), 6.57 (2H, s), 6.47-6.77(1H, m), 7.48(2H, d, J 8.5 Hz), 7.74(1H, d, J 3.5 Hz), 7.90 (2H, d, J 8.5 Hz), 7.95-7.97(1H, m) and 8.25(1H, s). |
| 207 | AD | 92 | IR ν$_{max}$ (Nujol)/cm$^{-1}$ 3314, 1644, 1464, 1378, 1311, 1256 and 1117; NMR δ$_H$ (400 MHz, DMSO) 5.31(2H, s), 6.84-6.89(1H, m), 6.91-7.01(1H, m), 7.14(2H, t, J 7.5 Hz), 7.24(1H, t, J 7.0 Hz), 7.87(1H, d, J 3.5 Hz), 8.14(1H, s), 8.47(1H, s). |
| 208 | AC | 34 | Mp 210-220° C.(dec); NMR δ$_H$ (400 MHz, DMSO) 7.77(1H, d, J 3.0 Hz), 7.69 (1H, s), 7.19-7.12(4H, m), 6.26-6.22(1H, m), 5.22(2H, s), 5.04(2H, br s), 2.49(3H, s) and 2.33(2H, s). |
| 209 | Y | 58 | Mp 300° C.(dec); NMR δ$_H$ (400 MHz, DMSO) 8.24(1H, s), 8.02(1H, s), 7.82 (1H, s), 6.31(2H, br s) and 4.11(3H, s). |
| 210 | AF | 16 | mp 254.7-255.3° C.; NMR δ$_H$ (400 MHz, DMSO) 3.12(3H, s), 5.42(2H, s), 6.53 (2H, s), 6.74-6.77(1H, m), 6.96(1H, d, J 7.0 Hz), 7.21(1H, dt, J 7.5 Hz, 1.0 Hz), 7.34(1H, dt, J 7.0 Hz, 1.5 Hz), 7.39-7.43(1H, m), 7.74(1H, dd, J 3.5 Hz, 1.0 Hz), 7.96-7.97(1H, m), 8.17(1H, s). |
| 211 | AC | 53 | IR ν$_{max}$ (Nujol)/cm$^{-1}$ 3325, 3194, 1650, 1589, 1519, 1467, 1411, 1377, 1305 and 1016; NMR δ$_H$ (400 MHz, DMSO) 5.37(2H, s), 6.51(2H, s), 6.72-6.75(1H, m), 7.15(2H, t, J 8.0 Hz), 7.43-7.52(1H, m), 7.69(1H, dd, J 3.5 Hz, 1.0 Hz), 7.93-7.95(1H, m) and 8.05(1H, s). |
| 212 | S | 43 | NMR δ$_H$ (400 MHz, CDCl$_3$) 2.55(3H, s), 5.08(2H, br s), 5.37(2H, s), 6.63(1H, dd, J 1.5, 3.5 Hz), 6.93(1H, d, J 7.8 Hz), 7.07(1H, d, J 7.8 Hz), 7.52(1H, t, J 7.5 Hz), 7.71(1H, dd, J 1.0, 1.5 Hz), 7.81(1H, dd, J 1.0, 3.5 Hz) and 7.98(1H, s); Retention time 4.68 min,(50:20). |
| 213 | S | 11 | NMR δ$_H$ (400 MHz, CDCl$_3$) 5.05(2H, br s), 5.14(2H, s), 6.38(1H, dd, J 1.0, 2.0 Hz), 6.63(1H, dd, J 2.0, 3.0 Hz), 7.41(1H, dd, J 1.5, 2.0 Hz), 7.48(1H, dd, J 1.0, 2.0 Hz), 7.71(1H, dd, J 1.0, 2.0 Hz), 7.76(1H, s) and 7.79(1H, dd, J 1.0, 3.5 Hz); Retention time 0.88 min,(80:50). |
| 214 | H | 17 | NMR δ$_H$ (400 MHz, DMSO) 5.27(2H, s), 6.78(1H, dd, J 1.5, 3.5 Hz), 7.12-7.18 (3H, m), 7.33-7.38(2H, m), 7.68(1H, dd, J 1.0, 3.5 Hz), 7.96(1H, s) and 8.04(1H, dd, J 1.0, 1.5 Hz); Retention time 2.16 min,(80:50). |
| 215 | AC | 56 | mp 219.5-219.7° C.; NMR δ$_H$ (400 MHz, DMSO) 3.86(3H, s), 5.42(2H, s), 6.57 (2H, s), 6.74-6.77(1H, m), 7.36(2H, d, J 8.0 Hz), 7.74(1H, d, J 3.0 Hz), 7.91-7.98 (3H, m) and 8.23(1H, s). |
| 216 | M | 98 | mp 301.1-302.1° C.; NMR δ$_H$ (400 MHz, DMSO) 5.42(2H, s) 6.80-6.84(1H, m), 7.36(2H, d, J 8.5 Hz), 7.82(1H, d, J 3.0 Hz), 7.93(2H, d, J 8.0 Hz), 8.06 (1H, s) and 8.38(1H, s). |
| 217 | AF | 95 | mp 171.2-171.3° C.; NMR δ$_H$ (400 MHz, DMSO) 5.42(2H, s), 6.80-6.84(1H, m), 7.36(2H, d, J 8.5 Hz), 7.82(1H, d, J 3.0 Hz), 7.89-7.94(2H, m), 8.06(1H, s) and 8.38(1H, s). |
| 218 | Q | 52 | mp 276.4-276.9° C.; NMR δ$_H$ (400 MHz, DMSO) 4.31(2H, d, J 5.5 Hz), 4.81 (2H, s), 6.29(1H, d, J 3.5 Hz), 6.41(1H, m), 6.52(2H, s), 6.74-6.76(1H, m), 7.59-7.61(1H, m), 7.73(1H, d, J 3.0 Hz), 7.95(1H, s), 8.06(1H, s) and 8.72 (1H, t, J 5.5 Hz). |
| 219 | AC | 45 | mp 205.3-205.4° C.; IR ν$_{max}$ (Nujol)/cm$^{-1}$ 3571, 3384, 3328, 3215, 3081, 1645, 1394, 1523, 1480, 1466, 1409, 1364 and 1312; NMR δ$_H$ (400 MHz, DMSO) 3.69 (6H, s), 5.22(2H, s), 6.41-6.46(2H, m), 6.56(2H, s), 6.73-6.76(1H, m), 7.72 (1H, d, J 2.5 Hz), 7.95(1H, d, J 1.0 Hz) and 8.19(1H, s). |
| 220 | AF | 10 | NMR δ$_H$ (400 MHz, DMSO) 2.12(3H, s), 5.27(2H, s), 6.55(2H, s), 6.74-6.77 (1H, m), 6.90(1H, d, J 7.0 Hz), 7.13(1H, t, J 7.5 Hz), 7.28(1H, dt, J 7.5 Hz, 1.0 Hz), 7.36-7.41(1H, m), 7.73(1H, d, J 3.5 Hz), 7.95-7.97(1H, m), 8.10(1H, s) and 9.69(1H, s); Retention time 0.87 min(80:20) |
| 221 | AG | 48 | IR ν$_{max}$ (Nujol)/cm$^{-1}$ 4328, 1643, 1463, 1410, 1378 and 1284; NMR δ$_H$ (400 MHz, DMSO) 5.27(2H, s), 6.66(1H, t, J 1.5 Hz), 6.68-6.74(2H, m), 6.90-6.96(1H, m), 7.15(1H, t, J 7.5 Hz), 7.97(1H, d, J 3.5 Hz), 8.23(1H, s) and 8.59(1H, s). |
| 222 | S | 4 | NMR δ$_H$ (400 MHz, CD$_3$OD) 3.83(2H, t, J 5.6 Hz), 4.43(2H, t, J 5.6 Hz), 6.69 (1H, dd, J 1.5, 3.5 Hz), 7.63(2H, dd, J 1.5, 4.5 Hz), 7.66(1H dd, J 1.0, 3.5 Hz), 7.82(1H, dd, J 1.0, 2.0 Hz), 8.06(1H, s) and 8.63(2H, dd, J 2.0, 4.5 Hz). |
| 223 | S | 9 | IR ν$_{max}$ (Nujol)/cm$^{-1}$ 3336, 3204, 3090, 2923, 2854, 1651, 1588, 1567, 1519, 1468, 1408, 1376 and 1302; NMR δ$_H$ (400 MHz, CDCl$_3$) 5.07(2H, br s), 5.29 (2H, s), 6.63(1H, dd, J 1.5, 3.5 Hz), 7.04(1H, dd, J 1.5, 5.0 Hz), 7.22(1H, dd, J 1.0, 3.0 Hz), 7.33(1H, dd, J 3.0, 5.0 Hz), 7.71(1H, dd, J 1.0, 1.5 Hz), 7.75(1H, s) and 7.80(1H, dd, J 1.0, 3.5 Hz); Retention time 1.47 min,(80:50). |
| 224 | S | 15 | NMR δ$_H$ (400 MHz, CDCl$_3$) 5.01(2H, br s), 5.24(2H, s), 5.33(2H, s), 6.62(1H, dd, J 2.0, 3.5 Hz), 6.85(2H, dd, J 1.5, 8.0 Hz), 6.93(1H, dd, J 1.5, 3.5 Hz), 7.10(1H, d, J 1.5 Hz), 7.12-7.21(3H, m), 7.69(1H, dd, J 1.0, 1.5 Hz), 7.73(1H, dd, J 1.0, 3.5 Hz) and 7.82(1H, s); Retention time 1.07 min,(80:50). |
| 225 | AD | 86 | IR ν$_{max}$ (Nujol)/cm$^{-1}$ 4330, 4259, 1642, 1579, 1513, 1464 and 1378; NMR δ$_H$ (400 MHz, DMSO) 5.34(2H, s), 6.84-6.87(1H, m), 7.25(2H, d, J 8.5 Hz), 7.35(2H, d, J 8.5 Hz), 7.88(1H, d, J 3.5 Hz), 8.12(1H, s) and 8.45(1H, s). |

-continued

| Example | Method | Yield(%) | Data |
|---|---|---|---|
| 226 | P | 92 | mp 243.2-243.8° C.; IR ν$_{max}$ (Nujol)/cm$^{-1}$ 3481, 3266, 3190, 1639, 1626, 1544, 1514, 1463, 1409 and 1378; NMR δ$_H$ (400 MHz, DMSO) 4.47(2H, d, J 6.0 Hz), 5.37(2H, s), 6.54(2H, s), 6.75(1H, s), 7.19-7.25(1H, m), 7.26-7.33(4H, m), 7.37-7.49(2H, m), 7.73(1H, d, J 2.5 Hz), 7.79-7.83(2H, m), 7.95(1H, s), 8.22(1H, s) and 8.99-9.05(1H, m). |
| 227 | P | 47 | mp 170.0-171.9° C.; IR ν$_{max}$ (Nujol)/cm$^{-1}$ 3474, 3286, 3179, 1634, 1591, 1548, 1462, 1408, 1377 and 1308; NMR δ$_H$ (400 MHz, DMSO) 4.46(2H, d, J 6.0 Hz), 5.38(2H, s), 6.56(2H, s), 6.73-6.77(1H, m), 7.19-7.26(1H, m), 7.28-7.36 (5H, m), 7.73(1H, d, J 3.0 Hz), 7.86(2H, d, J 8.5 Hz), 7.96(1H, s), 8.23(1H, s) and 8.96(1H, t, J 6.0 Hz); Anal. Calcd for C$_{24}$H$_{20}$N$_6$O$_2$•1.0 H$_2$O: C, 65.15; H, 5.01; N, 18.99. Found: C, 65.51; H, 4.66; N, 18.63. |
| 228 | H | 54 | IR ν$_{max}$ (Nujol)/cm$^{-1}$ 3504, 3299, 3184, 3138, 1630, 1596, 1468, 1376 and 1353; NMR δ$_H$ (400 MHz, DMSO) 2.39(3H, s), 6.76(1H, s), 7.01(2H, s), 7.50(2H, d, J 7.0 Hz), 7.67(1H, s), 7.98(1H, s), 8.13(2H, d, J 7.0 Hz), 8.49(1H, s); Anal. calcd for C$_{16}$H$_{13}$N$_5$O$_3$S•0.8 H$_2$O: C, 51.97; H 3.98; N, 18.94. Found: C, 52.21; H, 3.79; N, 18.60. M/Z 355(M + H)$^+$. |
| 229 | AC | 40 | mp 282.4-282.6° C.; NMR δ$_H$ (400 MHz, DMSO) 2.19(3H, s), 2.49(3H, s), 5.08 (2H, s), 6.53(2H, s), 6.73-6.75(1H, m), 6.70(1H, d, J 2.5 Hz), 7.94(1H, s) and 8.16(1H, s). |
| 230 | P | 3 | IR ν$_{max}$ (Nujol)/cm$^{-1}$ 3390, 3325, 3215, 1640, 1586, 1518, 1467, 1410 and 1379; NMR δ$_H$ (400 MHz, DMSO) 2.85(3H, s), 2.95(3H, s), 5.35(2H, s), 6.57(2H, s), 6.73-6.76(1H, m), 7.29-7.35(3H, m), 7.41(1H, t, J 7.0 Hz), 7.73(1H, d, J 3.5 Hz), 7.94-7.97(1H, m) and 8.23(1H, s). |
| 231 | Q | 45 | mp 278.5-280.4° C.; IR ν$_{max}$ (Nujol)/cm$^{-1}$ 3458, 3273, 3185, 1679, 1604, 1551, 1495, 1466 and 1378; NMR δ$_H$ (400 MHz, DMSO) 3.71(3H, s), 5.00(2H, s), 6.53(2H, s), 6.65(1H, dd, J 8.0 Hz, 2.0 Hz), 6.74-6.77(1H, m), 7.11(1H, d, J 8.0 Hz), 7.23(1H, t, J 8.5 Hz), 7.28(1H, t, J 2.0 Hz), 7.74(1H, d, J 4.0 Hz), 7.95-7.96 (1H, m), 8.10(1H, s) and 10.41(1H, s); Anal. calcd for C$_{18}$H$_{16}$N$_6$O$_3$•0.7 H$_2$O: C, 57.35; H, 4.65; N, 22.29. Found: C, 57.27; H, 4.30; N, 22.29. |
| 232 | AF | 10 | IR ν$_{max}$ (Nujol)/cm$^{-1}$ 3466, 3331, 3210, 1705, 1634, 1591, 1515, 1465, 1408, 1378, 1331, 1225 and 1152; NMR δ$_H$ (400 MHz, DMSO) 2.95(3H, s), 5.26(2H, s), 6.55(2H, s), 6.73-6.76(1H, m), 7.17(2H, d, J 8.5 Hz), 7.27(2H, d, J 8.5 Hz), 7.72(1H, d, J 3.0 Hz), 7.95(1H, d, J 1.0 Hz), 8.18(1H, s) and 9.73(1H, s). |
| 233 | P | 45 | mp 223.1-226.9° C.; NMR δ$_H$ (400 MHz, DMSO) 2.87(3H, s), 2.94(3H, s), 5.36 (2H, s), 6.57(2H, s), 6.73-6.77(1H, m), 7.30(2H, d, J 8.5 Hz), 7.37(2H, d, J 3.5 Hz), 7.73(1H, d, J 3.5 Hz), 7.94-7.97(1H, m) and 8.20-8.24(1H, m); Anal. calcd for C$_{19}$H$_{18}$N$_6$O$_2$•1.2 H$_2$O: C, 59.43; H, 5.35; N, 21.89. Found: C, 59.70; H, 5.16; N, 21.50. |
| 234 | AF | 8 | NMR δ$_H$ (400 MHz, DMSO) 0.83(4H, d, J 6.0 Hz), 5.28(2H, s), 6.54(2H, s), 6.74-6.77(1H, m), 6.85(1H, d, J 7.5 Hz), 7.12(1H, t, J 7.5 Hz), 7.27(1H, t, J 7.5 Hz), 7.42(1H, d, J 3.5 Hz), 7.74(1H, d, J 3.5 Hz), 7.94-7.98(1H, m), 8.10 (1H, s) and 9.93(1H, s); Anal. calcd for C$_{20}$H$_{18}$N$_6$O$_2$•0.8 H$_2$O: C, 61.78; H, 5.08; N, 21.61. Found: C, 61.92; H, 4.81; N, 21.60. |
| 235 | AF | 48 | mp 253.1-257.1° C.; NMR δ$_H$ (400 MHz, DMSO) 3.68(3H, s), 5.36(2H, s), 6.59 (2H, s), 6.72-6.80(1H, m), 6.97(1H, d, J 7.5 Hz), 7.08-7.15(1H, m), 7.19-7.23 (2H, m), 7.74(1H, d, J 3.5 Hz), 7.77(1H, s), 7.84(1H, s), 7.97(1H, s), 8.08 (1H, s) and 10.42(1H, s). |
| 236 | Q | 54 | mp 279.9-281.0° C.; NMR δ$_H$ (400 MHz, DMSO) 3.83(3H, s), 4.30(2H, d, J 4.5 Hz), 4.82(2H, s), 6.23(2H, s), 6.72(1H, s), 6.88-7.00(2H, m), 7.24(1H, s), 7.70(1H, s), 7.89(1H, s), 8.03(1H, s) and 8.32(1H, s). |
| 237 | Q | 60 | mp 291.9-292.1° C.; NMR δ$_H$ (400 MHz, DMSO) 4.35(2H, s), 4.83(2H, s), 6.52 (2H, s), 6.74(1H, s), 7.13-7.23(2H, m), 7.27-7.43(2H, m), 7.72(1H, s), 7.95 (1H, s), 8.06(1H, s) and 8.71(1H, s). |
| 238 | AF | 52 | mp 265.6-266.0° C.; NMR δ$_H$ (400 MHz, DMSO) 5.27(2H, s), 6.56(2H, s), 6.76 (1H, s), 6.94(2H, t, J 6.5 Hz), 7.13-7.28(3H, m), 7.51-7.55(1H, m), 7.72-7.76 (1H, m), 7.95-8.00(2H, m), 8.03(1H, s) and 10.39(1H, s); Anal. calcd for C$_{20}$H$_{16}$N$_6$O$_3$S$_2$•1.0 H$_2$O: C, 51.05; H, 3.86; N, 17.86. Found: C, 50.72; H, 3.48; N, 17.98. |
| 239 | AF | 50 | mp 251.4-253.1° C.; NMR δ$_H$ (400 MHz, DMSO) 2.13(3H, s), 2.31(3H, s), 5.37 (2H, s), 6.52(2H, s), 6.74-6.77(1H, m), 6.90-6.94(1H, m), 6.99-7.03(1H, m), 7.25-7.32(2H, m), 7.74(1H, d, J 3.5 Hz), 7.97(1H, s), 8.08(1H, s) and 10.28(1H, s). |
| 240 | AC | 19 | mp 210.9-211.5° C.; NMR δ$_H$ (400 MHz, DMSO) 5.42(2H, s), 6.61(2H, s), 6.72-6.78 (1H, m), 6.99-7.03(2H, m), 7.71(1H, d, J 3.5 Hz), 7.95(1H, t, J 1.0 Hz) and 8.19(1H, s); Anal. Calcd for C$_{14}$H$_{10}$ClN$_5$OS: C, 50.68; H, 3.04; N, 21.10. Found: C, 50.57; H, 3.15; N, 21.11. M/Z 332(M + H)$^+$. |
| 241 | Z | 35 | mp 246.2-248.0° C.; IR ν$_{max}$ (Nujol)/cm$^{-1}$ 3410, 3325, 2924, 1689, 1463, 1377, 1289, 654 and 620; NMR δ$_H$ (400 MHz, DMSO) 2.49(3H, s), 7.76(1H, br s), 8.02(1H, d, J 8.5 Hz), 8.76(1H, s), 8.81(1H, d, J 7.5 Hz) and 8.87(1H, s); Retention time(20/50): 1.89 min |
| 242 | AF | 42 | IR ν$_{max}$ (Nujol)/cm$^{-1}$ 4330, 4259, 3239, 1716, 1665, 1597, 1518, 1464, 1404 and 1378; NMR δ$_H$ (400 MHz, DMSO) 1.11(3H, s), 1.12(3H, s), 1.15(3H, s), 1.16 (3H, s), 5.36(2H, s), 6.79-6.83(1H, m), 7.16-7.22(1H, m), 7.22-7.26(1H, m), 7.30(2H, d, J 3.5 Hz), 7.36-7.40(1H, m), 7.84(1H, d, J 3.0 Hz), 8.05(1H, s), 8.56(1H, s), 9.71(1H, s), 10.71(1H, s). |
| 243 | AC | 33 | Mp 299.8° C.; IR ν$_{max}$ (Nujol)/cm$^{-1}$ 3470, 3356, 2922, 2854, 1621, 1607, 1592, 1567, 1492, 1462 and 1377; NMR δ$_H$ (400 MHz, DMSO) 9.20-7.85(3H, br m), |

-continued

| Example | Method | Yield(%) | Data |
|---|---|---|---|
| | | | 7.46-7.36(1H, m), 7.33-7.16(3H, m), 7.11(2H, br s), 5.48(2H, s) and 2.45 (3H, s). |
| 244 | AJ | 12 | mp 259.2° C.; NMR $\delta_H$ (400 MHz, DMSO) 3.29(3H, s), 5.40(2H, s), 6.69(2H, br s), 7.06-7.20(2H, m), 7.21-7.31(1H, m), 7.33-7.42(1H, m), 7.56(1H, s) and 8.23(1H, s); Retention time(80:50): 2.15 min |
| 245 | AK | 46 | IR $\nu_{max}$ (Nujol)/cm$^{-1}$ 3643, 3464, 3263, 3099, 1636, 1601, 1567, 1413, 1311, 1221 and 1170; NMR $\delta_H$ (400 MHz, DMSO) 4.17(2H, br s), 4.76(2H, s), 6.52(2H, br s), 6.74(1H, dd, J 1.5, 3.5 Hz), 7.15-7.24(5H, m), 7.72(1H, dd, J 1.0, 3.5 Hz), 7.94(1H, dd, J 1.0, 1.5 Hz) and 8.08(1H, s); Retention time: 0.70 min. |
| 246 | Q | 42 | IR $\nu_{max}$ (Nujol)/cm$^{-1}$ 3486, 3281, 3182, 3075, 1657, 1605, 1563, 1460, 1409 and 1377; NMR $\delta_H$ (400 MHz, DMSO) 0.85(3H, t, J 7.5 Hz), 1.05(3H, d, J 6.5 Hz), 1.37-1.46(2H, m), 3.63-3.72(1H, m), 4.74(2H, s), 6.48(2H, s), 6.75(1H, s), 7.72(1H, d, J 2.5 Hz), 7.95(1H, s) and 8.02-8.09(2H, m). |
| 247 | Q | 13 | NMR $\delta_H$ (400 MHz, DMSO) 1.05(3H, t, J 7.0 Hz), 3.07-3.16(2H, m), 4.74 (2H, s), 6.50(2H, s), 6.74-6.76(1H, m), 7.72(1H, dd, J 3.5 Hz, 1.0 Hz), 7.94-7.95 (1H, m), 8.04(1H, s) and 8.20(1H, t, J 5.0 Hz); Anal. calcd for $C_{13}H_{14}N_6O_2 \cdot 0.35$ $H_2O$: C, 53.36; H, 5.06; N, 28.72. Found: C, 53.39; H, 5.03; N, 28.38. |
| 248 | Q | 42 | NMR $\delta_H$ (400 MHz, DMSO) 3.70-3.77(2H, m), 4.80(2H, s), 5.10(1H, d, J 9.5 Hz), 5.21(1H, d, J 17.0 Hz), 5.75-5.88(1H, m), 6.50(2H, s), 6.75(1H, s), 7.72 (1H, d, J 2.5 Hz), 7.95(1H, s), 8.05(1H, s) and 8.39(1H, t, J 5.0 Hz); Anal. calcd for $C_{14}H_{14}N_6O_2 \cdot 0.7$ $H_2O$: C, 54.08; H, 4.99; N, 27.03. Found: C, 53.96; H, 4.64; N, 26.78. |
| 249 | Q | 43 | NMR $\delta_H$ (400 MHz, DMSO) 5.01(2H, s), 6.54(2H, s), 6.76(1H, s), 7.27-7.33 (1H, m), 7.36-7.45(1H, m), 7.70-7.77(2H, m), 7.96(1H, s), 8.10(1H, s) and 10.66(1H, s); Anal. calcd for $C_{17}H_{12}N_6O_2F_2 \cdot 1.8$ $H_2O$: C, 50.70; H, 3.90; N, 20.87. Found: C, 50.87; H, 3.75; N, 20.58. |
| 250 | AF | 54 | IR $\nu_{max}$ (Nujol)/cm$^{-1}$ 3552, 3397, 3336, 3224, 1644, 1589, 1567, 1464, 1409, 1377, 1331 and 1300; NMR $\delta_H$ (400 MHz, DMSO) 2.15(3H, s), 2.35(3H, s), 5.28(2H, s), 6.74-6.77(1H, m), 6.92(1H, s), 6.97(1H, d, J 8.0 Hz), 7.04(1H, d, J 7.5 Hz), 7.28(1H, t, J 8.0 Hz) 7.74(1H, d, J 3.0 Hz), 7.96(1H, s), 8.14(1H, s) and 10.46(1H, s). |
| 251 | AL | 45 | mp 247-252° C.; IR $\nu_{max}$ (Nujol)/cm$^{-1}$ 3328, 2922, 1661, 1586, 1464, 1378 and 767; NMR $\delta_H$ (400 MHz, DMSO) 1.28(3H, d, J 6.5 Hz), 3.74-3.87(1H, m), 4.30(1H, dd, J 14, 5.5 Hz), 4.43(1H, dd, J 14, 7.5 Hz), 6.91-6.95(1H, m), 7.99 (1H, d, J 3.5 Hz), 8.23(1H, s) and 8.46-8.60(4H, m); Retention time(50:20): 0.81 min |
| 252 | Q | 44 | IR $\nu_{max}$ (Nujol)/cm$^{-1}$ 3480, 3275, 3189, 3086, 1660, 1608, 1568, 1462, 1414, 1378 and 1359; NMR $\delta_H$ (400 MHz, DMSO) 2.20(6H, s), 2.37(2H, t, J 6.0 Hz), 3.21 (2H, q, J 6.0 Hz), 4.76(2H, s), 6.50(2H, s), 6.73-6.77(1H, m), 7.72(1H, d, J 3.0 Hz), 7.95(1H, s), 8.04(1H, s), 8.19(1H, t, J 5.0 Hz); Anal. calcd for $C_{15}H_{19}N_7O_2 \cdot 0.6$ $H_2O$: C, 52.96; H, 5.99; N, 28.82. Found: C, 52.84; H, 5.83; N, 28.58. |
| 253 | AC | 42 | IR $\nu_{max}$ (Nujol)/cm$^{-1}$ 2923, 1651, 1463; NMR $\delta_H$ (400 MHz, DMSO) 8.37(1H, s), 8.07-8.06(1H, m), 7.81-7.79(1H, m), 7.40-7.35(2H, m), 7.21-7.16(2H, m), 6.83-6.81(1H, m) and 5.32(2H, s). |
| 254 | AL | 37 | IR $\nu_{max}$ (Nujol)/cm$^{-1}$ 3500-2500 br, 2923, 2853, 1659, 1585, 1463 and 1378; NMR $\delta_H$ (400 MHz, DMSO) 8.52(1H, s), 8.48(1H, br s), 8.21(1H, s), 7.96(1H, d, J 3.5 Hz), 6.91(1H, d, J 3.5 Hz), 4.42(1H, dd, J 14.5, 7.5 Hz), 4.29(1H, dd, J 14.5, 5.5 Hz), 3.88-3.73(1H, m) and 2.33(2H, s). |
| 255 | X | 32 | Mp 181.6-181.7° C.; NMR $\delta_H$ (400 MHz, DMSO) 7.98-7.95(1H, m), 7.95-7.93 (1H, m), 7.71(1H, d, J 3.5 Hz), 7.00-6.94(1H, br m), 6.74(1H, dd, J 3.5, 2.0 Hz), 6.49(2H, br s), 4.10(2H, br t, J 5.5 Hz), 3.34(2H, br q, J 6.0 Hz) and 1.33(9H, s). |
| 256 | AC | 12 | IR $\nu_{max}$ (Nujol)/cm$^{-1}$ 3318, 2922, 2854, 1604, 1588, 1538, 1456, 1406, 1377, 1356 and 1308; NMR $\delta_H$ (400 MHz, DMSO) 8.20(1H, s), 7.97-7.94(1H, m), 7.70 (1H, d, J 3.5 Hz), 7.25(2H, d, J 8.0 Hz), 7.18(2H, d, J 8.0 Hz), 7.06(4H, d, J 8.0 Hz), 6.76-6.71(1H, m), 5.21(2H, s), 4.50(2H, br d, J 6.0 Hz), 2.26(3H, s) and 2.25(3H, s). |
| 257 | F | 99 | Mp 190° C.(dec); IR $\nu_{max}$ (Nujol)/cm$^{-1}$ 3379, 2923, 2854, 1679, 1649, 1626, 1600, 1585, 1462 and 1377; NMR $\delta_H$ (400 MHz, DMSO) 8.49(1H, s), 8.39-8.25(3H, m), 8.19(1H, s), 7.93(1H, d, J 3.5 Hz), 6.90(1H, dd, J 3.5, 1.5 Hz), 4.42(2H, t, J 6.0 Hz) and 3.41-3.31(2H, m). |
| 258 | AC | 2 | NMR $\delta_H$ (400 MHz, DMSO) 7.74(1H, s), 7.71(1H, s), 7.57(1H, d, J 3.5 Hz), 7.22(5H, d, J 7.5 Hz), 7.15-7.01(7H, m), 6.57(1H, dd, J 3.5, 1.5 Hz), 5.17(2H, s), 4.93(4H, br s), 2.33(6H, s) and 2.31(3H, s). |
| 259 | AC | 29 | IR $\nu_{max}$ (Nujol)/cm$^{-1}$ 3324, 3189, 3085, 1649, 1587, 1568, 1527, 1463, 1411, 1377 and 1347; NMR $\delta_H$ (400 MHz, DMSO) 5.48(2H, s), 6.58(2H, s), 6.73-6.77 (1H, m), 7.57(1H, t, J 9.5 Hz), 7.72(1H, d, J 2.5 Hz), 7.96(1H, s), 8.06-8.10 (1H, m), 8.21(1H, s) and 8.26-8.31(1H, m). |
| 260 | AG | 55 | IR $\nu_{max}$ (Nujol)/cm$^{-1}$ 2924, 2854, 1587, 1516, 1462; NMR $\delta_H$ (400 MHz, DMSO) 9.44(1H, s), 8.17(1H, s), 7.96-7.95(1H, m), 7.73-7.72(1H, m), 7.15(2H, d, J 8.5 Hz), 6.76-6.74(1H, m), 6.72(2H, d, J 8.5 Hz), 6.60(2H, br s) and 5.17(2H, s). |
| 261 | AC | 70 | IR $\nu_{max}$ (Nujol)/cm$^{-1}$ 3290, 2922, 2854, 1644, 1514, 1464; NMR $\delta_H$ (400 MHz, DMSO) 8.17(1H, s), 7.95-7.94(1H, m), 7.72-7.70(1H, m), 7.26(2H, d, J 8.5 Hz), 6.90(2H, d, J 8.5 Hz), 6.75-6.73(1H, m), 6.54(2H, br s), 5.23(2H, s) and 3.72(3H, s). |

-continued

| Example | Method | Yield(%) | Data |
|---|---|---|---|
| 262 | AM | 46 | Mp 257-259° C.; IR $v_{max}$ (Nujol)/cm$^{-1}$ 3326, 3147, 3111, 1654, 1640, 1615, 1587, 1461, 1415 and 1376; NMR $\delta_H$ (400 MHz, DMSO) 8.62(1H, s), 8.10(1H, d, J 2.0 Hz), 7.48(1H, d, J 2.5 Hz), 7.45-7.36(1H, m), 7.31-7.24(2H, m), 7.23-7.16 (1H, m) and 5.43(1H, s). |
| 263 | AM | 28 | NMR $\delta_H$ (400 MHz, DMSO) 5.65(2H, s), 7.18-7.31(2H, m), 7.36-7.45(1H, m), 7.55-7.62(1H, m), 8.64(1H, s), 8.87(1H, s) and 9.58(2H, s); Retention time: 0.98 min(80:50) |
| 264 | AM | 76 | IR $v_{max}$ (Nujol)/cm$^{-1}$ 3500-2500 br, 2921, 1650, 1609, 1584, 1526, 1462, 1415 and 1377; NMR $\delta_H$ (400 MHz, DMSO) 8.75(1H, s), 8.14(1H, d, J 2.0 Hz), 7.51 (1H, d, J 2.5 Hz), 7.43(1H, t, J 8.0 Hz), 7.29-7.20(3H, m) and 5.43(2H, s). |
| 265 | AO | 7 | IR $v_{max}$ (DR)/cm$^{-1}$ 3311, 2919, 1646, 1463, 1378, 999 and 738; NMR $\delta_H$ (400 MHz, DMSO) 8.74(1H, s), 7.69-7.59(1H, m), 7.58-7.51(1H, m), 7.48(1H, t, J 7.5 Hz), 7.34-7.24(4H, m), 5.42(2H, s) and 2.40(3H, s). |
| 266 | AC | 26 | NMR $\delta_H$ (400 MHz, DMSO) 8.16(1H, s), 7.67(1H, d, J 3.5 Hz), 7.25(1H, t, J 8.0 Hz), 6.91-6.83(2H, m), 6.81(1H, d, J 7.5 Hz), 6.54(2H, br s), 6.38(1H, d, J 3.5 Hz), 5.26(2H, s), 3.72(3H, s) and 2.40(3H, s). |
| 267 | AC | 38 | mp 190.5-190.6° C.; IR $v_{max}$ (DR)/cm$^{-1}$ 3502, 3306, 3192, 3089, 2710, 1766, 1633 and 1228; NMR $\delta_H$ (400 MHz, DMSO) 9.29(1H, s), 9.12(1H, s), 8.24(1H, s), 7.43-7.33(1H, m), 7.28-7.21(1H, m), 7.20-7.10(2H, m), 6.61(2H, br s) and 5.40(2H, s). |
| 268 | AC | 37 | mp 183.0-183.1° C.; IR $v_{max}$ (DR)/cm$^{-1}$ 3328, 3209, 3091, 2855, 1598, 1519, 1466; NMR $\delta_H$ (400 MHz, DMSO) 8.21(1H, s), 7.96-7.95(1H, m), 7.80-7.76 (1H, m), 7.75-7.74(1H, m), 7.35(1H, d, J 7.5 Hz), 7.00(1H, d, J 7.5 Hz), 6.76-6.75 (1H, m), 6.53(2H, br s), 5.97-5.87(1H, m), 5.41(2H, s), 5.31-5.25(1H, m), 5.18-5.14(1H, m), 4.50(2H, s) and 4.05-4.03(2H, m); Anal. Calcd for $C_{19}H_{18}N_6O_2 \cdot 0.1$ $H_2O$: C, 62.66; H, 5.04; N, 23.08. Found: C, 62.45; H, 4.98; N, 22.91. |
| 269 | AC | 75 | IR $v_{max}$ (Nujol)/cm$^{-1}$ 3332, 3204, 2923, 1648, 1588, 1515, 1464, 1342, 1166, 1010, 842 and 738; NMR $\delta_H$ (400 MHz, DMSO) 5.40(2H, s), 6.57(2H, s), 6.75-6.76 (1H, m), 7.26(1H, dd, J 8.5, 1.5 Hz), 7.38-7.41(1H, m), 7.74(1H, d, J 3.5 Hz), 7.94-7.98(2H, m) and 8.24(1H, s); Anal. calcd for $C_{17}H_{14}N_6O_3 \cdot 0.5$ $H_2O$: C, 56.82; H, 4.21; N, 23.39. Found: C, 57.07; H, 4.13; N, 22.99. |
| 270 | AC | 29 | mp 190.4-190.5° C.; IR $v_{max}$ (Nujol)/cm$^{-1}$ 3457, 3311, 2923, 1724, 1586, 1456, 1348, 1129, 849, 757, 523 and 516; NMR $\delta_H$ (400 MHz, DMSO) 8.15(1H, s), 8.02(1H, d, J 8.5 Hz), 7.97-7.94(1H, m), 7.72(2H, t, J 3.5 Hz), 7.29(1H, t, J 7.5 Hz), 7.04(1H, d, J 7.0 Hz), 6.95(1H, d, J 4.0 Hz), 6.75-6.72(1H, m), 6.57 (2H, s), 5.56(2H, s) and 1.64(9H, s). |
| 271 | AQ | 69 | mp 305.4-306.8° C.; IR $v_{max}$ (Nujol)/cm$^{-1}$ 3324, 3209, 2923, 1639, 1592, 1465, 1411, 1303, 1166, 1015, 851 and 750; NMR $\delta_H$ (400 MHz, DMSO) 11.21(1H, s), 8.10(1H, s), 7.96-7.94(1H, m), 7.71(1H, d, J 4.0 Hz), 7.35(2H, t, J 3.0 Hz), 7.03(1H, t, 7.5 Hz), 6.78(1H, d, J 8.0 Hz), 6.75-6.72(1H, m), 6.56(3H, s) and 5.53(2H, s). |
| 272 | AQ | 62 | IR $v_{max}$ (DR)/cm$^{-1}$ 3482, 3201, 1595, 1461, 1208, 1141, 1100, 1023, 949, 887, 840, 793, 738, 655, 595 and 505; NMR $\delta_H$ (400 MHz, DMSO) 11.08(1H, s), 8.17 (1H, s), 7.95-7.93(1H, m), 7.71(1H, d, J 4.0 Hz), 7.48(1H, s), 7.35-7.32(2H, m), 7.09(1H, d, J 8.0 Hz), 6.75-6.73(1H, m), 6.54(2H, s), 6.39(1H, s) and 5.34 (2H, s). |
| 273 | AC | 82 | NMR $\delta_H$ (400 MHz, DMSO) 8.29(1H, s), 8.07(1H, s), 7.81(1H, d, J 8.5 Hz), 7.57(2H, d, J 4.0 Hz), 7.51(1H, d, J 3.5 Hz), 7.39(1H, s), 6.79-6.76(1H, m), 6.66(1H, s), 6.52(1H, s), 6.44(1H, d, J 3.5 Hz), 5.50(2H, s) and 1.59(9H, d, J 7.5 Hz). |

Adenosine Receptor Binding

Binding Affinities at $hA_{2A}$ Receptors

The compounds were examined in an assay measuring in vitro binding to human adenosine $A_{2A}$ receptors by determining the displacement of the adenosine $A_{2A}$ receptor selective radioligand [$^3$H]-CGS 21680 using standard techniques. The results are summarised in Table 3.

TABLE 3

| Example | $K_i$ (nM) |
|---|---|
| Example 3 | 23 |
| Example 13 | 12 |
| Example 26 | 1 |
| Example 36 | 7 |
| Example 37 | 4 |
| Example 38 | 1 |
| Example 39 | 1 |
| Example 45 | 2 |

TABLE 3-continued

| Example | $K_i$ (nM) |
|---|---|
| Example 47 | 1 |
| Example 52 | 5 |
| Example 57 | 12 |
| Example 68 | 9 |
| Example 79 | 1 |
| Example 80 | 5 |
| Example 83 | 13 |
| Example 92 | 6 |
| Example 93 | 4 |
| Example 106 | 1 |
| Example 112 | 8 |
| Example 118 | 3 |
| Example 125 | 6 |
| Example 126 | 7 |
| Example 127 | 9 |
| Example 141 | 36 |
| Example 157 | 4 |

TABLE 3-continued

| Example | $K_i$ (nM) |
|---|---|
| Example 159 | 10 |
| Example 162 | 8 |
| Example 185 | 7 |
| Example 189 | 21 |
| Example 192 | 24 |
| Example 198 | 7 |
| Example 201 | 2 |
| Example 202 | 1 |
| Example 208 | 6 |
| Example 211 | 3 |
| Example 212 | 35 |
| Example 235 | 4 |
| Example 240 | 7 |
| Example 244 | 7 |
| Example 259 | 11 |

Evaluation of Potential Anti-Parkinsonian Activity in Vivo

Haloperidol-induced Hypolocomotion Model

It has previously been demonstrated that adenosine antagonists, such as theophylline, can reverse the behavioural depressant effects of dopamine antagonists, such as haloperidol, in rodents (Mandhane S. N. et al., Adenosine $A_2$ receptors modulate haloperidol-induced catalepsy in rats. *Eur. J. Pharmacol.* 1997, 328, 135-141). This approach is also considered a valid method for screening drugs with potential antiparkinsonian effects. Thus, the ability of novel adenosine antagonists to block haloperidol-induced deficits in locomotor activity in mice can be used to assess both in vivo and potential antiparkinsonian efficacy.

Method

Female TO mice (25-30 g) obtained from TUCK, UK, are used for all experiments. Animals are housed in groups of 8 [cage size—40 (width)×40 (length)×20 (height)cm] under 12 hr light/dark cycle (lights on 08:00 hr), in a temperature (20±2° C.) and humidity (55±15%) controlled environment. Animals have free access to food and water, and are allowed at least 7 days to acclimatize after delivery before experimental use.

Drugs

Liquid injectable haloperidol (1 ml Serenance ampoules from Baker Norton, Harlow, Essex, each containing haloperidol BP 5 mg, batch # P424) are diluted to a final concentration of 0.02 mg/ml using saline. Test compounds are typically prepared as aqueous suspensions in 8% Tween. An compounds are administered intraperitoneally in a volume of 10 ml/kg.

Procedure 1.5 hours before testing, mice are administered 0.2 mg/kg haloperidol, a dose that reduces baseline locomotor activity by at least 50%. Test substances are typically administered 5-60 minutes prior to testing. The animals are then placed individually into clean, clear polycarbonate cages [20 (width)×40 (length)×20 (height) cm, with a flat perforated, Perspex lid]. Horizontal locomotor activity is determined by placing the cages within a frame containing a 3×6 array of photocells linked to a computer, which tabulates beam breaks. Mice are left undisturbed to explore for 1 hour, and the number of beams breaks made during this period serves as a record of locomotor activity which is compared with data for control animals for statistically significant differences.

6-OHDA Model

Parkinson's disease is a progressive neurodegenerative disorder characterised by symptoms of muscle rigidity, tremor, paucity of movement (hypokinesia), and postural instability. It has been established for some time that the primary deficit in PD is a loss of dopaminergic neurones in the substantia nigra which project to the striatum, and indeed a substantial proportion of striatal dopamine is lost (ca 80-85%) before symptoms are observed. The loss of striatal dopamine results in abnormal activity of the basal ganglia, a series of nuclei which regulate smooth and well co-ordinated movement (Blandini F. et al., Glutamate and Parkinson's Disease. *Mol. Neurobiol.* 1996, 12, 73-94). The neurochemical deficits seen in Parkinson's disease can be reproduced by local injection of the dopaminergic neurotoxin 6-hydroxydopamine into brain regions containing either the cell bodies or axonal fibres of the nigrostriatal neurones.

By unilaterally lesioning the nigrostriatal pathway on only one-side of the brain, a behavioural asymmetry in movement inhibition is observed. Although unilaterally-lesioned animals are still mobile and capable of self maintenance, the remaining dopamine-sensitive neurones on the lesioned side become supersenstive to stimulation. This is demonstrated by the observation that following systemic administration of dopamine agonists, such as apomorphine, animals show a pronounced rotation in a direction contralateral to the side of lesioning. The ability of compounds to induce contralateral rotations in 6-OHDA lesioned rats has proven to be a sensitive model to predict drug efficacy in the treatment of Parkinson's Disease.

Animals

Male Sprague-Dawley rats, obtained from Charles River, are used for all experiments. Animals are housed in groups of 5 under 12 hr light/dark cycle (lights on 08:00 hr), in a temperature (20±2° C.) and humidity (55±15%) controlled environment. Animals have free access to food and water, and are allowed at least 7 days to acclimatize after delivery before experimental use.

Drugs

Ascorbic acid, desipramine, 6-OHDA and apomorphine (Sigma-Aldrich, Poole, UK). 6-OHDA is freshly prepared as a solution in 0.2% ascorbate at a concentration of 4 mg/mL prior to surgery. Desipramine is dissolved in warm saline, and administered in a volume of 1 ml/kg. Apomorphine is dissolved in 0.02% ascorbate and administered in a volume of 2 mL/kg. Test compounds are suspended in 8% Tween and injected in a volume of 2 mL/kg.

Surgery 15 minutes prior to surgery, animals are given an intraperitoneal injection of the noradrenergic uptake inhibitor desipramine (25 mg/kg) to prevent damage to non-dopamine neurones. Animals are then placed in an anaesthetic chamber and anaesthetised using a mixture of oxygen and isoflurane. Once unconscious, the animals are transferred to a stereotaxic frame, where anaesthesia is maintained through a mask. The top of the animal's head is shaved and sterilised using an iodine solution. Once dry, a 2 cm long incision is made along the midline of the scalp and the skin retracted and clipped back to expose the skull. A small hole is then drilled through the skill above the injection site. In order to lesion the nigrostriatal pathway, the injection cannula is slowly lowered to position above the right medial forebrain bundle at −3.2 mm anterior posterior, −1.5 mm medial lateral from bregma, and to a depth of 7.2 mm below the duramater. 2 minutes after lowing the cannula, 2 µL of 6-OHDA is infused at a rate of 0.5

µL/min over 4 minutes, yeilding a final dose of 8 µg. The cannula is then left in place for a further 5 minutes to facilitate diffusion before being slowly withdrawn. The skin is then sutured shut using Ethicon W501 Mersilk, and the animal removed from the strereotaxic frame and returned to its homecage. The rats are allowed 2 weeks to recover from surgery before behavioural testing.

Apparatus

Rotational behaviour is measured using an eight station rotameter system provided by Med Associates, San Diego, USA. Each station is comprised of a stainless steel bowl (45 cm diameter×15 cm high) enclosed in a transparent Plexiglas cover running around the edge of the bowl, and extending to a height of 29 cm. To assess rotation, rats are placed in cloth jacket attached to a spring tether connected to optical rotameter positioned above the bowl, which assesses movement to the left or right either as partial (45°) or full (360°) rotations. All eight stations are interfaced to a computer that tabulated data.

Procedure

To reduce stress during drug testing, rats are initially habituated to the apparatus for 15 minutes on four consecutive days. On the test day, rats are given an intraperitoneal injection of test compound 30 minutes prior to testing. Immediately prior to testing, animals are given a subcutaneous injection of a subthreshold dose of apomorphine, then placed in the harness and the number of rotations recorded for one hour. The total number of full contralatral rotations during the hour test period serves as an index of antiparkinsonian drug efficacy.

The invention claimed is:

1. Use of a compound of formula (I) or a pharmaceutically acceptable salt thereof:

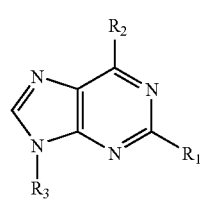

(I)

wherein
$R_1$ is selected from alkyl, aryl, alkoxy, aryloxy, alkylthio, arylthio, CN, halo, $NR_5R_6$, $NR_4COR_5$, $NR_4CONR_5R_6$, $NR_4CO_2R_7$, and $NR_4SO_2R_7$;
$R_2$ is selected from N, O or S-containing heteroaryl groups, wherein the heteroaryl group is attached via an unsaturated carbon atom of said heteroaryl group which is adjacent to one or two N, O, or S-heteroatom(s), other than heteroaryl groups substituted at both positions adjacent the point of attachment of the heteroaryl group to the purine moiety;
$R_3$ is selected from H, alkyl, $COR_8$, $CONR_9R_{10}$, $CONR_8NR_9R_{10}$, $CO_2R_{11}$, and $SO_2R_{11}$; wherein:
  alkyl is substituted by a substituent $R_{12}$, wherein $R_{12}$ is selected from the group consisting of hydroxy, alkoxy, dialkylamino, $NH_2$, aryloxy, CN, halo, cycloalkyl, $Ar(R_{18})_a(R_{19})_b(R_{20})_c$, non-aromatic heterocyclyl, $CO_2R_{13}$, $CONR_{14}R_{15}$, $CONR_8NR_9R_{10}$, $C(=NR_{13})NR_{14}R_{15}$, $NR_{13}COR_{14}$, $NR_{13}CO_2R_{11}$, trialkylsilyl, and phthalimido, wherein:
  (a) $R_{13}$, $R_{14}$ and $R_{15}$ are selected from the group consisting of hydrogen, alkyl, and aryl, or (b) where $R_{14}$ and $R_{15}$ are in an ($NR_{14}R_{15}$)group, $R_{14}$ and $R_{15}$ may be linked to form a heterocyclic ring;
  Ar is an aryl group;
  $R_{18}$, $R_{19}$ and $R_{20}$ are selected from $NR_5R_6$, substituted alkyl, alkoxy, halogen, $NO_2$, CN, hydroxy, NHOH, CHO, $CONR_5R_6$, $CO_2R_5$, $NR_4COR_5$, $NR_4CO_2R_7$, $NR_4SO_2R_7$, $OCO_2R_7$ and aryl; and
  a, b and c are 0 or 1 such that a+b+c≧1;
$R_4$, $R_5$ and $R_6$ are independently selected from H, alkyl, and aryl, or where $R_5$ and $R_6$ are in an ($NR_5R_6$) group then $R_5$ and $R_6$ may be linked to form a heterocyclic ring;
$R_7$ is alkyl or aryl;
$R_8$, $R_9$ and $R_{10}$ are independently selected from H, alkyl, and aryl, or $R_9$ and $R_{10}$ may be linked to form a heterocyclic ring, or where $R_8$, $R_9$, and $R_{10}$ are in a ($CONR_8NR_9R_{10}$) group, $R_8$ and $R_9$ may be linked to form a heterocyclic group;
wherein said heterocylic ring or group is a saturated, partially unsaturated or aromatic 5, 6 or 7 membered ring optionally containing one or more further heteroatoms selected from N, O and S; and
$R_{11}$ is alkyl or aryl,
other than compounds wherein $R_3$ is H, $R_1$ is $NH_2$ and $R_2$ is thienyl.

2. The compound of claim 1, wherein $R_1$ is selected from the group consisting of $NR_5R_6$, alkoxy, and alkylthio.

3. The compound of claim 1, wherein $R_1$ is $NH_2$.

4. The compound of claim 1, wherein $R_1$ is selected from the group consisting of $NR_4COR_5$, $NR_4CONR_5R_6$, $NR_4CO_2R_7$, and $NR_4SO_2R_7$, and $R_4$ is H or alkyl.

5. The compound of claim 1, wherein $R_1$ is selected from the group consisting of $NHCOR_5$, $NHCONR_5R_6$, $NHCO_2R_7$, and $NHSO_2R_7$.

6. The compound of claim 1, wherein $R_2$ is unsubstituted at either position adjacent the point of attachment of $R_2$ to the purine moiety.

7. The compound of claim 1, wherein $R_2$ is an unsubstituted heteroaryl group.

8. The compound of claim 1, wherein $R_2$ is selected from the group consisting of 2-furyl, 2-thienyl, 2-pyridyl, 2-thiazolyl, and 3-pyrazolyl.

9. The compound of claim 1, wherein $R_2$ is 2-furyl.

10. The compound of claim 1, wherein $R_3$ is selected from the group consisting of H, alkyl and $CONR_9R_{10}$ wherein:
alkyl is substituted by a substituent $R_{12}$, wherein $R_{12}$ is selected from the group consisting of hydroxy, alkoxy, dialkylamino, $NH_2$, aryloxy, CN, halo, cycloalkyl, $Ar(R_{18})_a(R_{19})_b(R_{20})_c$, non-aromatic heterocyclyl, $CO_2R_{13}$, $CONR_{14}R_{15}$, $CONR_8NR_9R_{10}$, $C(=NR_{13})NR_{14}R_{15}$, $NR_{13}COR_{14}$, $NR_{13}CO_2R_{11}$, trialkylsilyl, and phthalimido, wherein:
(a) $R_{13}$, $R_{14}$ and $R_{15}$ are selected from the group consisting of hydrogen, alkyl, and aryl, or (b) where $R_{14}$ and $R_{15}$ are in an ($NR_{14}R_{15}$) group, $R_{14}$ and $R_{15}$ may be linked to form a heterocyclic ring;
a heterocyclic ring is a saturated, partially unsaturated or aromatic 5, 6 or 7 membered ring optionally containing one or more further heteroatoms selected from N, O and S;
Ar is an aryl group;
$R_{18}$, $R_{19}$ and $R_{20}$ are selected from $NR_5R_6$, substituted alkyl, alkoxy, halogen, $NO_2$, CN, hydroxy, NHOH, CHO, $CONR_5R_6$, $CO_2R_5$, $NR_4COR_5$, $NR_4CO_2R_7$, $NR_4SO_2R_7$, $OCO2R_7$ and aryl; and
a,b and c are 0 or 1 1 such that a+b+c≧1.

11. The compound of claim 10, wherein $R_3$ is selected to be alkyl, and the alkyl is substituted by $R_{12}$, wherein $R_{12}$ is selected from $Ar(R_{18})_a(R_{19})_b(R_{20})_c$ or $CONR_{14}R_{15}$.

12. The compound of claim 1, wherein $R_3$ is $COR_8$ and $R_8$ is alkyl or aryl.

13. The compound of claim 1, wherein $R_3$ is $CONR_9R_{10}$ and $R_9$ is hydrogen.

14. The compound of claim 13, wherein $R_3$ is $CONR_9R_{10}$, $R_9$ is hydrogen, and $R_{10}$ is alkyl.

15. The compound of claim 13, wherein $R_3$ is $CONR_9R_{10}$, $R_9$ is hydrogen, and $R_{10}$ is an alkyl substituted by aryl.

16. The compound of claim 13, wherein $R_3$ is $CONR_9R_{10}$, $R_9$ is hydrogen, and $R_{10}$ is methyl substituted by aryl.

17. The compound of claim 15, wherein $R_{10}$ is an alkyl substituted by an said aryl group selected from the group consisting of phenyl, thienyl, furyl, and pyridyl.

18. The compound of claim 1, wherein $R_3$ is selected to be alkyl and the alkyl is substituted by a substituent $R_{12}$, wherein $R_{12}$ is selected from the group consisting of hydroxy, alkoxy, dialkylamino, $NH_2$, aryloxy, CN, halo, cycloalkyl, $Ar(R_{18})_a(R_{19})_b(R_{20})_c$, non-aromatic heterocyclyl, $CO_2R_{13}$, $CONR_{14}R_{15}$, $CONR_8NR_9R_{10}$, $C(=NR_{13})NR_{14}R_{15}$, $NR_{13}COR_{14}$, $NR_{13}CO_2R_{11}$, trialkylsilyl, and phthalimido, wherein:
   (a) $R_{13}$, $R_{14}$ and $R_{15}$ are selected from the group consisting of hydrogen, alkyl, and aryl, or (b) where $R_{14}$ and $R_{15}$ are in an ($NR_{14}R_{15}$) group, $R_{14}$ and $R_{15}$ may be linked to form a heterocyclic ring;
   a heterocylic ring is a saturated, partially unsaturated or aromatic 5, 6 or 7 membered ring optionally containing one or more further heteroatoms selected from N, O and S;
   Ar is an aryl group;
   $R_{18}$, $R_{19}$ and $R_{20}$ are selected from $NR_5R_6$, substituted alkyl, alkoxy, halogen, $NO_2$, CN, hydroxy, NHOH, CHO, $CONR_5R_6$, $CO_2R_5$, $NR_4COR_5$, $NR_4CO_2R_7$, $NR_4SO_2R_7$, $OCO_2R_7$ and aryl; and
   a, b and c are 0 or 1 such that $a+b+c \geq 1$.

19. The compound of claim 18, wherein $R_{12}$ is $Ar(R_{18})_a(R_{19})_b(R_{20})_c$ or $CONR_{14}R_{15}$.

20. The compound of claim 18, wherein $R_{12}$ is $Ar(R_{18})_a(R_{19})_b(R_{20})_c$ and Ar selected from the group consisting of phenyl, thienyl, furyl, indolyl, and pyridyl.

21. The compound of claim 18, wherein $R_{12}$ is $Ar(R_{18})_a(R_{19})_b(R_{20})_c$.

22. The compound of claim 18, wherein $R_{12}$ is $Ar(R_{18})_a(R_{19})_b(R_{20})_c$ and $R_{18}$, $R_{19}$ and $R_{20}$ are selected from $NR_5R_6$, substituted alkyl or halogen.

23. The compound of claim 18, wherein $R_{12}$ is $Ar(R_{18})_a(R_{19})_b(R_{20})_c$ and $R_{18}$, $R_{19}$ and $R_{20}$ are substituted alkyl selected from the group consisting of alkoxyalkyl, hydroxyalkyl, aminoalkyl, and haloalkyl.

24. The compound of claim 18, wherein $R_{12}$ is $Ar(R_{18})_a(R_{19})_b(R_{20})_c$ and $R_{18}$, $R_{19}$ and $R_{20}$ are selected from the group consisting of substituted alkyl, $NH_2$, and fluoro.

25. The compound of claim 18, wherein $R_{12}$ is $CONR_{14}R_{15}$ and $R_{14}$ is hydrogen.

26. The compound of claim 18, wherein $R_{12}$ is $CONR_{14}R_{15}$ and $R_{15}$ is an alkyl substituted by one or more substituent group(s) selected from the group consisting of hydroxy, alkoxy, and dialkylamino.

27. The compound of claim 1, wherein $R_4$ is selected from the group consisting of H and alkyl.

28. The compound of claim 1, wherein the compound of formula (I) is selected from the group consisting of:

N,N-Dimethyl-6-(2-furyl)-1H-purine-2-amine;
6-(2-Furyl)-1H-purine-2-amine:
6-(2-Furyl)-2-methylthio-1H-purine;
2-Amino-N-benzyl-6-(2-furyl)-9H-purine-9-carboxamide;
2-Amino-N-n-butyl-6-(2-furyl)-9H-purine-9-carboxamide;
2-Amino-6-(2-furyl)-N-(4-methoxybenzyl)-9H-purine-9-carbaxamide;
2-Amino-6-(2-furyl)-N-(4-methylbenzyl)-9H-purine-9-carboxamide;
2-Amino-N-(2-chlorobenzyl)-6-(2-furyl)-9H-purine-9-carboxamide;
(1S)-2-Amino-6-(2-furyl)-N-(1-phenylethyl)-9H-purine-9-carboxamide;
2-Amino-6-(2-furyl)-N-(3-methylbenzyl)-9H-purine-9-carboxamide;
2-Amino-6-(2-furyl)-N-n-pentyl-9H-purine-9-carboxamide;
2-Amino-N-(4-fluorobenzyl)-6-(2-furyl)-9H-purine-9-carboxamide;
2-Amino-N-(3,4-dichlorobenzyl)-6-(2-furyl)-9H-purine-9-carboxamide;
2-Amino-6-(2-furyl)-N-(2-phenylethyl)-9H-purine-9-carboxamide;
2-Amino-N-(2,4-dichlorobenzyl)-6-(2-furyl)-9H-purine-9-carboxamide;
Benzyl 2-amino-6-(2-furyl)-9H-purine-9-carboxylate;
N-Benzyl-2-methoxy-6-(2-furyl)-9H-purine-9-carboxamide;
2-Amino-N-benzyl-6-(2-furyl)-N-methyl-9H-purine-9-carboxamide;
9-(3-Chlorobenzyl)-6-(2-furyl)-9H-purine-2-amine;
2-Amino-N-(3-chlorophenyl)-6-(2-furyl)-9H-purine-9-acetamide;
9-(2-Fluorobenzyl)-6-(2-furyl)-9H-purine-2-amine;
6-(2-Furyl)-9-(4-trifluoromethylbenzyl)-9H-purine-2-amine;
9-(4-Bromophenyl)sulphonyl-6-(2-furyl)-9H-purine-2-amine;
6-(2-Furyl)-9-(2-phenylethenyl)sulphonyl-9H-purine-2-amine;
9-(3-Aminobenzyl)-6-(2-furyl)-9H-purine-2-amine;
6-(2-Furyl)-9-(3-methoxybenzyl)-9H-purine-2-amine;
2-Amino-6-(2-furyl )-N-(2-furylmethyl)-9H-purine-9-carboxamide;
2-Amino-6-(2-furyl)-N-(2-thienylmethyl)-9H-purine-9-carboxamide;
9-(2,6-Difluorobenzyl)-6-(2-furyl)-9H-purine-2-amine;
6-(2-Furyl)-9-(2-(1-methyl-1H-imidazol-4-ylsulphonylamino)benzyl)-9H-purine-2-amine;
9-(5-Chloro-2-thienylmethyl)-6-(2-furyl)-9H-purine-2-amine;
9-(2-Fluorobenzyl)-6-(4-methyl-2-thiazolyl)-9H-purine-2-amine; and
9-(2-Fluoro-5-nitrobenzyl)-6-(2-furyl)-9H-purine-2-amine.

29. A pharmaceutical composition comprising a compound of claim 1 and at least one pharmaceutically acceptable carrier.

30. The compound of claim 1 wherein $R_1$ is $NR_5R_6$.

31. The compound of claim 18, wherein $R_{13}$ is selected from the group consisting of H and alkyl.

* * * * *